(12) United States Patent
Baker et al.

(10) Patent No.: US 8,252,792 B2
(45) Date of Patent: *Aug. 28, 2012

(54) PYRIMIDINE DERIVATIVES AS PI3K INHIBITORS

(75) Inventors: Stewart James Baker, Slough (GB);
Paul John Goldsmith, Slough (GB);
Timothy Colin Hancox, Slough (GB);
Neil Anthony Pegg, Slough (GB);
Stephen Price, Harlow (GB); Stephen Joseph Shuttleworth, Slough (GB);
Sukhjit Sohal, Slough (GB)

(73) Assignee: F. Hoffman-La Roche AG, Basel (CH)

( * ) Notice: Subject to any disclaimer, the term of this patent is extended or adjusted under 35 U.S.C. 154(b) by 596 days.

This patent is subject to a terminal disclaimer.

(21) Appl. No.: 12/298,507

(22) PCT Filed: Apr. 25, 2007

(86) PCT No.: PCT/GB2007/001504
§ 371 (c)(1),
(2), (4) Date: Aug. 26, 2009

(87) PCT Pub. No.: WO2007/122410
PCT Pub. Date: Nov. 1, 2007

(65) Prior Publication Data
US 2010/0016306 A1      Jan. 21, 2010

(30) Foreign Application Priority Data

Apr. 26, 2006 (GB) .................................... 0608264.8
Apr. 27, 2006 (GB) .................................... 0608397.6

(51) Int. Cl.
*A61K 31/535* (2006.01)
*C07D 413/14* (2006.01)
(52) U.S. Cl. ..................................... 514/234.5; 544/116
(58) Field of Classification Search .................. 544/116; 514/234.5
See application file for complete search history.

(56) References Cited

U.S. PATENT DOCUMENTS 7,776,856 B2 * 8/2010 Shuttleworth et al. ..... 514/234.5
2003/0220365 A1   11/2003 Stewart et al.

FOREIGN PATENT DOCUMENTS

| EP | 1 067 123 A1 | 1/2001 |
| EP | 1 277 738 A1 | 1/2003 |
| WO | WO 2004/017950 A2 | 3/2004 |
| WO | WO 2006/046035 A1 | 5/2006 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stae Alzheimer's [online], [retrieved on Sep. 23, 2003]. Retrieved from the Internet, URL; http://www.cnn.com/2003/HEALTH/conditions/09/24/alzheimers.drug.ap/index.html>.*
Huff, Joel R., "HIV Protease: A Novel Chemotherapeutic Target for AIDS,"Journal fo Medicinal Chemistry, vol. 34, No. 8, Aug. 1991, p. 2305-2314.*
EP International Searching Authority, "Notification of Transmittal of the International Search Report and the Written Opinion of the International Searching Authority, or the Declaration," dated Jul. 4, 2007, pp. 1-16.

* cited by examiner

*Primary Examiner* — Rebecca Anderson
(74) *Attorney, Agent, or Firm* — Viksnins Harris & Padys PLLP

(57) ABSTRACT

Thienopyrimidines of formula (Ia) or (Ib):

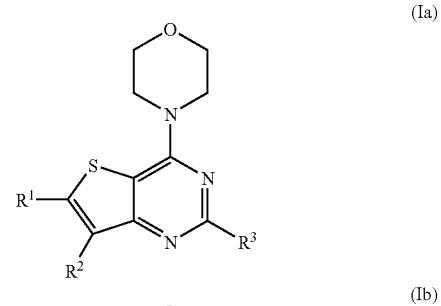

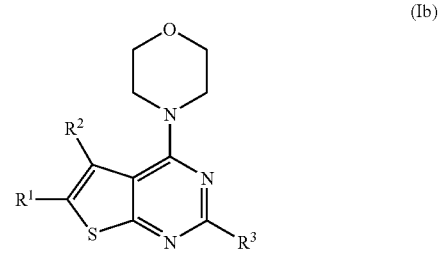

wherein $R^1$-$R^3$ have any of the values described herein, and the pharmaceutically acceptable salt thereof have activity as inhibitors of PI3K and may thus be used to treat diseases and disorders arising from abnormal cell growth, function or behaviour associated with PI3 kinase, in particular the p110 delta subtype, such as immune disorders, cardiovascular disease, viral infection, inflammation, metabolism/endocrine disorders and neurological disorders. Processes for synthesizing the compounds are also described.

16 Claims, No Drawings

PYRIMIDINE DERIVATIVES AS PI3K INHIBITORS

RELATED APPLICATIONS

This application is a National Stage application under 35 U.S.C. §371 and claims the benefit of priority of International Application No. PCT/GB2007/001504 having an International Filing Date of Apr. 25, 2007 which claims the benefit of priority of United Kingdom Application Ser. No. 0608264.8 filed on Apr. 26, 2006 and 0608397.6 filed on Apr. 27, 2006, which are hereby incorporated by reference herein in their entireties.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI(4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β, and C2γ subtypes, which are characterized by containing C2 domains at the C terminus. The substrate for class III PI3 Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis, immune disorders and conditions involving inflammation.

WO 01/083456 describes a series of condensed heteroaryl derivatives which have activity as inhibitors of PI3 K and which suppress cancer cell growth.

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3Ks over class Ib, in particular for the P110δ (delta) subtype.

Accordingly, the present invention provides a compound which is a thienopyrimidine of formula (Ia) or (Ib):

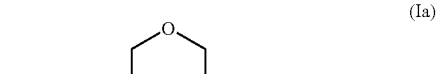

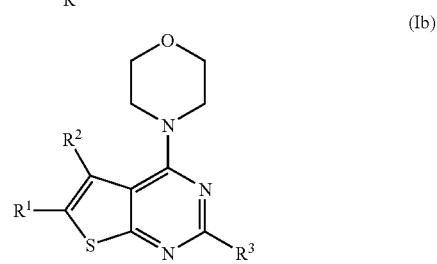

wherein
$R^1$ is a group of formula:

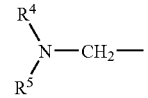

$R^2$ is H, halo or $C_1$-$C_6$ alkyl;
$R^3$ is an indole group which is unsubstituted or substituted;
$R^4$ and $R^5$ form, together with the N atom to which they are attached, a group selected from piperazine, piperidine and pyrrolidine, which group is unsubstituted or substituted by one or more groups selected from $C_1$-$C_6$ alkyl, —S(O)$_2$R$^{10}$, —S(O)$_2$-(alk)$_q$-NR$^{11}$R$^{12}$, oxo (=O), -alk-OR$^{10}$, -(alk)$_q$-Het, a heterocyclyl group and —NR$^{13}$R$^{14}$;
or one of $R^4$ and $R^5$ is $C_1$-$C_6$ alkyl and the other is a piperazine, piperidine or pyrrolidine group, which group is unsubstituted or substituted;
$R^{10}$ is H or $C_1$-$C_6$ alkyl which is unsubstituted;
$R^{11}$ and $R^{12}$ are each independently selected from H and $C_1$-$C_6$ alkyl which is unsubstituted, or $R^{11}$ and $R^{12}$ together form, with the N atom to which they are attached, a 5- or 6-membered saturated heterocyclic group;
$R^{13}$ and $R^{14}$ are each independently selected from $C_1$-$C_6$ alkyl, —S(O)$_2$R$^{10}$, alk-OR$^{10}$, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof;
with the proviso that, in formula (Ia) only, when $R^2$ is H and $R^3$ is unsubstituted indole, then —NR$^4$R$^5$ is other than (i) piperazine which is unsubstituted or substituted by one substituent selected from methyl, —S(O)₂Me and —CH₂CH₂OH; and (ii) piperidine which is substituted by one substituent selected from —NMe₂, —N(Me)(CH₂CH₂OMe) and morpholino.

In one embodiment the invention provides a compound which is a thienopyrimidine of formula (Ia'):

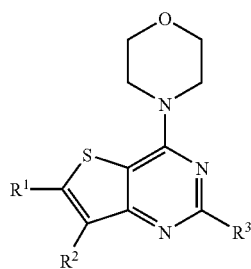

(Ia')

wherein

R¹ is a group of formula:

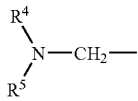

R² is halo or $C_1$-$C_6$ alkyl;

R³ is an indole group which is unsubstituted or substituted;

R⁴ and R⁵ form, together with the N atom to which they are attached, a group selected from piperazine, piperidine and pyrrolidine, which group is unsubstituted or substituted by one or more groups selected from $C_1$-$C_6$ alkyl, —S(O)₂R¹⁰, —S(O)₂-(alk)$_q$-NR¹¹R¹², oxo (=O), -alk-OR¹⁰, -(alk)$_q$-Het, a heterocyclyl group and —NR¹³R¹⁴; or one of R⁴ and R⁵ is $C_1$-$C_6$ alkyl and the other is a piperazine, piperidine or pyrrolidine group, which group is unsubstituted or substituted;

R¹⁰ is H or $C_1$-$C_6$ alkyl which is unsubstituted;

R¹¹ and R¹² are each independently selected from H and $C_1$-$C_6$ alkyl which is unsubstituted, or R¹¹ and R¹² together form, with the N atom to which they are attached, a 5- or 6-membered saturated heterocyclic group;

R¹³ and R¹⁴ are each independently selected from $C_1$-$C_6$ alkyl, —S(O)₂R¹⁰, alk-OR¹⁰, -(alk)$_q$-Ph and -(alk)$_q$-Het;

Ph is phenyl;

q is 0 or 1;

Het is a thiazole, imidazole, pyrrole, pyridine or pyrimidine group, which group is unsubstituted or substituted; and alk is $C_1$-$C_6$ alkylene;

or a pharmaceutically acceptable salt thereof.

In another embodiment the invention provides a compound which is a thienopyrimidine is of formula (Ia"):

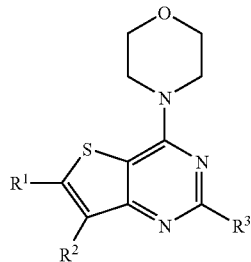

(Ia")

wherein

R¹ is a group of formula:

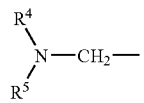

R² is H, halo or $C_1$-$C_6$ alkyl

R³ is an indole group which is substituted;

R⁴ and R⁵ form, together with the N atom to which they are attached, a group selected from piperazine, piperidine and pyrrolidine, which group is unsubstituted or substituted by one or more groups selected from $C_1$-$C_6$ alkyl, —S(O)₂R¹⁰, —S(O)₂-(alk)$_q$-NR¹¹R¹², oxo (=O), -alk-OR¹⁰, -(alk)$_q$-Het, a heterocyclyl group and —NR¹³R¹⁴; or one of R⁴ and R⁵ is $C_1$-$C_6$ alkyl and the other is a piperazine, piperidine or pyrrolidine group, which group is unsubstituted or substituted;

R¹⁰ is H or $C_1$-$C_6$ alkyl which is unsubstituted;

R¹¹ and R¹² are each independently selected from H and $C_1$-$C_6$ alkyl which is unsubstituted, or R¹¹ and R¹² together form, with the N atom to which they are attached, a 5- or 6-membered saturated heterocyclic group;

R¹³ and R¹⁴ are each independently selected from $C_1$-$C_6$ alkyl, —S(O)₂R¹⁰, alk-OR¹⁰, -(alk)$_q$-Ph and -(alk)$_q$-Het;

Ph is phenyl;

q is 0 or 1;

Het is a thiazole, imidazole, pyrrole, pyridine or pyrimidine group, which group is unsubstituted or substituted; and alk is $C_1$-$C_6$ alkylene;

or a pharmaceutically acceptable salt thereof.

In a further embodiment the invention provides a compound which is a thienopyrimidine is of formula (Ia'''):

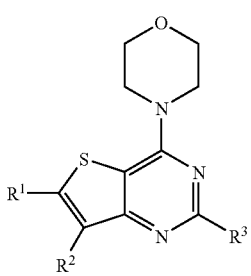

(Ia''')

wherein
R[1] is a group of formula:

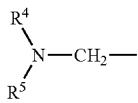

R[2] is H;
R[3] is an unsubstituted indole group;
R[4] and R[5] form, together with the N atom to which they are attached, a group selected from:
  piperazine which is substituted by —S(O)$_2$-(alk)$_q$-NR[11]R[12], C$_2$-C$_6$ alkyl, oxo (═O), -(alk)$_q$-Het, a heterocyclyl group or —NR[13]R[14]
  piperidine which is unsubstituted or substituted by —S(O)$_2$R[10], —S(O)$_2$-(alk)$_q$-NR[11]R[12], C$_1$-C$_6$ alkyl, oxo (═O), -alk-OR[10], -(alk)$_q$-Het or a heterocyclyl group;
  pyrrolidine which is unsubstituted or substituted by —S(O)$_2$R[10], —S(O)$_2$-(alk)$_q$-NR[11]R[12], C$_1$-C$_6$ alkyl, oxo (═O), -alk-OR[10], -(alk)$_q$-Het, a heterocyclyl group or —NR[13]R[14]
or one of R[4] and R[5] is C$_1$-C$_6$ alkyl and the other is a piperazine, piperidine or pyrrolidine group, which group is unsubstituted or substituted;
R[10] is H or C$_1$-C$_6$ allyl which is unsubstituted;
R[11] and R[12] are each independently selected from H and C$_1$-C$_6$ alkyl which is unsubstituted, or R[11] and R[12] together form, with the N atom to which they are attached, a 5- or 6-membered saturated heterocyclic group;
R[13] and R[14] are each independently selected from C$_1$-C$_6$ alkyl, —S(O)$_2$R[10], -alk-OR[10], -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is C$_1$-C$_6$ alkylene;
or a pharmaceutically acceptable salt thereof;
with the proviso that the thienopyrimidine is not selected from
{1-[2-(1H-Indol-4-yl)-4-morpholin-4-yl-thieno[3,2-d]pyrimidin-6-ylmethyl]-piperidin-4-yl}-(2-methoxy-ethyl)-methyl-amine;
2-{4-[2-(1H-Indol-4-yl)-4-morpholin-4-yl-thieno[3,2-d]pyrimidin-6-ylmethyl]-piperazin-1-yl}-ethanol; and
{1-[2-(1H-Indol-4-yl)-4-morpholin-4-yl-thieno[3,2-d]pyrimidin-6-ylmethyl]-piperidin-4-yl}-dimethyl-amine.

In a yet further embodiment the invention provides a compound which is a thienopyrimidine of formula (Ib'):

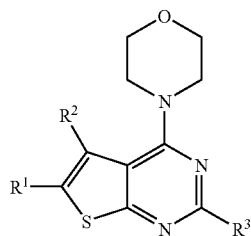

(Ib')

wherein
R[1] is a group of formula:

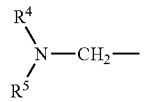

R[2] is H, halo or C$_1$-C$_6$ alkyl
R[3] is an indole group which is unsubstituted or substituted;
R[4] and R[5] form, together with the N atom to which they are attached, a group selected from piperazine, piperidine and pyrrolidine, which group is unsubstituted or substituted by —S(O)$_2$R[10], —S(O)$_2$-(alk)$_q$-NR[11]R[12], C$_1$-C$_6$ alkyl, oxo (═O), -alk-OR[10], -(alk)$_q$-Het, a heterocyclyl group or —NR[13]R[14];
or one of R[4] and R[5] is C$_1$-C$_6$ alkyl and the other is a piperazine, piperidine or pyrrolidine group, which group is unsubstituted or substituted;
R[10] is H or C$_1$-C$_6$ alkyl which is unsubstituted;
R[11] and R[12] are each independently selected from H and C$_1$-C$_6$ alkyl which is unsubstituted, or R[11] and R[12] together form, with the N atom to which they are attached, a 5- or 6-membered saturated heterocyclic group;
R[13] and R[14] are each independently selected from C$_1$-C$_6$ alkyl, —S(O)$_2$R[10], -alk-OR[10], -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is C$_1$-C$_6$ alkylene;
or a pharmaceutically acceptable salt thereof.

DETAILED DESCRIPTION OF THE INVENTION

Compounds of formulae Ia and Ib are regioisomers, i.e. they differ by the placement of atom S in the thienopyrimidine. The two possible regioisomeric forms of the ring systems encompassed by formulae Ia and Ib are:

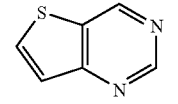

thieno[3,2-d]pyrimidine

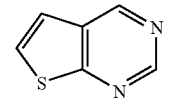

thieno[2,3-d]pyrimidine

Compounds of the invention thus include both regioisomers of each of the 4-morpholino thienopyrimidine compounds of formulae (Ia), (Ia'), (Ia''), (Ia'''), (Ib) and (Ib').

As specified herein, an alkyl group is a straight or branched chain saturated hydrocarbon radical which is unsubstituted or substituted. Typically it is C$_1$-C$_{20}$ alkyl, for instance C$_1$-C$_{10}$ alkyl, such as C$_1$-C$_6$ alkyl. C$_1$-C$_6$ alkyl is typically C$_1$-C$_4$ alkyl. It may be, for example, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), or 3,3-dimethyl-2-butyl (—$CH(CH_3)C(CH_3)_3$).

When an alkyl group is substituted it typically bears one or more substituents $R^{20}$ selected from halogen, alkoxy, carbocyclyl, a 5- or 6-membered saturated N-containing heterocyclic group as defined below, OH, SR, CN, nitro, $NR_2$, —COOR, —C(O)R, $S(O)_mR$ and —$CONR_2$, wherein each R is H, unsubstituted alkyl or $C_3$-$C_{10}$ cycloalkyl and m is 1 or 2. It is, for instance, a hydroxyalkyl group, a haloalkyl group or a group -alk-$N(R^4)(R^5)$ wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted.

Typically $R^{20}$ is selected from halogen, alkoxy, carbocyclyl, a 5- or 6-membered saturated N-containing heterocyclic group as defined below, OH, CN, $NR_2$, —COOR and —$CONR_2$, wherein each R is H or unsubstituted alkyl as defined above.

Substituted alkyl may be, for instance, a haloalkyl group or a group -alk-$N(R^4)(R^5)$ wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted. More typically it is a haloalkyl group or a group -alk-$N(R^4)(R^5)$ wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above or by alkyl which is unsubstituted or substituted by a group $R^{20}$ as defined above. It may, for instance, be $C_1$-$C_3$ alkylene, such as —$CH_2$—, —$CH_2CH_2$—, or —$CH_2CH_2CH_2$—.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is straight or branched chain. It is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated or unsaturated monocyclic hydrocarbon ring, typically having from 3 to 10 carbon atoms. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. Alternatively it may be a cycloalkenyl group, typically $C_4$-$C_8$ cycloalkenyl, for instance cylcopentenyl, cyclohexenyl, cyclohexadienyl, cycloheptenyl, cyclohepadienyl, cyclooctenyl or cyclooctadienyl. A carbocyclyl group may be unsubstituted or substituted, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR or —$CONR_2$, wherein each R is H or unsubstituted alkyl as defined above.

A 5- or 6-membered saturated N-containing heterocyclic group which includes 0 or 1 additional heteroatoms selected from N, S and O, which may be fused to a benzene ring and which is unsubstituted or substituted is typically selected from morpholine, piperidine, piperazine, pyrrolidine, thiomorpholine, tetrahydroquinoline and tetrahydroisoquinoline.

When a 5- or 6-membered saturated N-containing heterocyclic group as defined above is substituted it may be substituted by a group $R^{20}$ as defined above or by alkyl which is unsubstituted or substituted by a group $R^{20}$ as defined above. Typically it is substituted by alkyl which is unsubstituted or substituted, alkoxy which is unsubstituted or substituted, a second 5- or 6-membered saturated N-containing heterocyclic group as defined above, a 5- or 6-membered N-containing heteroaryl group which is unsubstituted or substituted and which may be fused to a benzene ring, —NR'R", -alk-OR, —C(O)NR'R", -alk-C(O)NR'R", -alk-N(R)C(O)R, —C(O)N(R)-alk-OR, —$S(O)_2$-alk-NR'R", —N(R)-alk-OR, —COOR, oxo (=O), OR, —$N(R)SO_2R$, —$SO_2NR_2$, —$SO_2R'''$ or —CO-alk-OR, wherein alk is an alkylene chain, R is H or alkyl, each of R' and R" is independently H, alkyl or alkoxy, or R' and R" together form a 5- or 6-membered saturated N-containing heterocyclic group as defined above, and R''' is alkyl which is unsubstituted or substituted, for instance by $NR_2$ or a 5- or 6-membered saturated N-containing heterocyclic group as defined above.

A 5-, 6- or 7-membered saturated heterocyclic group which contains 1 or 2 heteroatoms selected from N, S and O and which is unsubstituted or substituted is typically selected from tetrahydropyran, tetrahydrothiopyran, tetrahydrofuran and tetrahydrothiofuran.

When a 5-, 6- or 7-membered saturated heterocyclic group which contains 1 or 2 heteroatoms selected from N, S and O is substituted it may be substituted by a group $R^{20}$ as defined above or by alkyl which is unsubstituted or substituted by a group $R^{20}$ as defined above. Typically it is substituted by one or more substituents selected from alkyl which is unsubstituted or substituted, for instance by $R^{20}$ as defined above, haloalkyl as defined above, alkoxy as defined above which is unsubstituted or substituted, halogen, hydroxy, CN, nitro, amino, oxo (=O), and —NR'R'' wherein each of R' and R'' is independently H or alkyl.

Het is a thiazole, imidazole, pyrrole, pyridine or pyrimidine group, which group is unsubstituted or substituted. When substituted, Het may for instance be substituted by a group $R^{20}$ as specified above or by alkyl which is unsubstituted or substituted by a group $R^{20}$ as defined above. In particular, Het is unsubstituted or substituted by $C_1$-$C_6$ alkyl.

Examples of -(alk)$_q$-Het include —(CH$_2$)$_m$-pyridine, —(CH$_2$)$_m$-pyrimidine, —(CH$_2$)$_m$-pyrrole, —(CH$_2$)$_m$-imidazole and —(CH$_2$)$_m$-thiazole, wherein m is 0, 1, 2 or 3 and wherein the pyridine, pyrimidine, pyrrole, imidazole or thiazole group is unsubstituted or substituted as defined above. The Het group is bonded via any available ring carbon or heteroatom. Thus, for instance, pyrimidine may be linked as pyrimidin-2-yl or pyrimidin-4-yl. Pyridine may be linked as pyridine-2-yl, pyridin-3-yl or pyridine-4-yl. Pyrrole may be linked as pyrrol-1-yl, pyrrol-2-yl or pyrrol-3-yl. Imidazole may be linked as imidazol-1-yl, imidazol-2-yl, imidazol-3-yl, imidazol-4-yl or imidazol-5-yl.

Examples of —S(O)$_2$-(alk)$_q$-NR$^{11}$R$^{12}$ include —S(O)$_2$—N(Me)$_2$, —S(O)$_2$—NHMe, —S(O)$_2$—(CH$_2$)$_m$NMe$_2$, —S(O)$_2$—(CH$_2$)$_m$NHMe and —S(O)$_2$—(CH$_2$)$_m$NH$_2$ wherein m is 0, 1, 2 or 3. Specific examples include —S(O)$_2$—(CH$_2$)NMe$_2$, —S(O)$_2$—(CH$_2$)$_2$NMe$_2$ and —S(O)$_2$—(CH$_2$)$_3$NMe$_2$ Further examples include

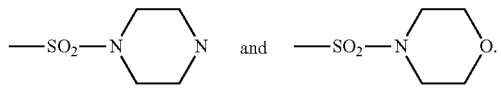

Examples of -alk-OR$^{10}$ include —CH$_2$OH, —CH$_2$OMe, —CH$_2$CH$_2$OMe, —CH$_2$CH$_2$OH, —CH$_2$CH$_2$CH$_2$OMe and —CH$_2$CH$_2$CH$_2$OH.

Examples of Heterocyclyl include piperidine, for instance piperidin-1-yl, piperidin-2-yl, piperidin-3-yl or piperidin-4-yl, in particular piperidin-4-yl; morpholine; and pyrrolidine, for instance pyrrolidin-2-yl or pyrrolidin-3-yl, groups.

In —S(O)$_2$R$^{10}$, R$^{10}$ is typically H, methyl or propyl (either n-propyl or i-propyl).

Examples of the —NR$^4$R$^5$ moiety in compounds of the invention as defined above include the following structures:

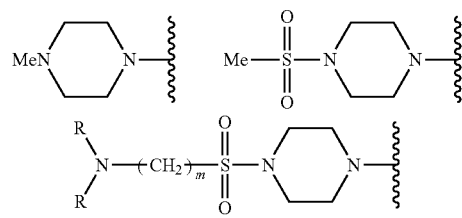

wherein m is 0, 1, 2 or 3, and each R is independently methyl or H, or the two groups R form a morpholine ring with the N atom to which they are attached.

Further examples of the —NR$^4$R$^5$ moiety include the following structures:

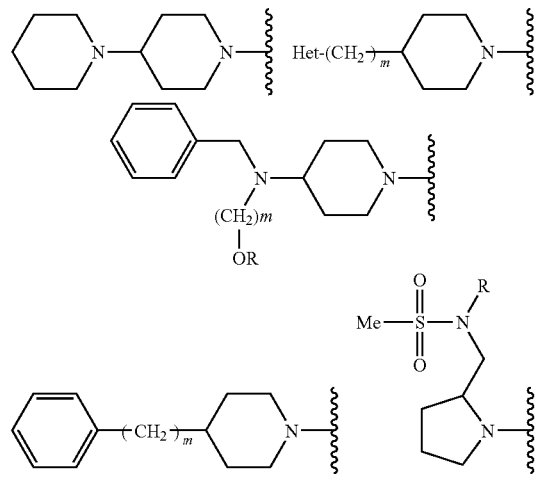

wherein m is 0, 1, 2 or 3, and each R is methyl or H.

R$^2$ is H, halo or $C_1$-$C_6$ alkyl. Typically it is H, F, Cl or Me.

The indole group in the definition of R$^3$ is bonded to the pyrimidine ring of the thienopyrimidine nucleus via any available ring N or C atom. Thus it may be an indol-1-yl, indol-2-yl, indol-3-yl, indol-4-yl, indol-5-yl, indol-6-yl, or indol-7-yl group.

The indole group is unsubstituted or substituted. If it is substituted it may be substituted by one or more substituents selected from: a group Z, wherein Z is selected from H, —OR, —SR, CH$_2$OR, —CO$_2$R, CF$_3$, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —N(R)C(O)R, —S(O)$_m$N(R)$_2$, —OC(O)R, OC(O)N(R)$_2$, —N(R)S(O)$_m$R, —NRC(O)N(R)$_2$, CN, halogen and —NO$_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2; and one or more substituents selected from halo, alkyl, alkenyl, alkynyl, CN, NO$_2$, OR, SR, NR$_2$, C(O)R, SOR, SO$_2$R, SO$_2$NR$_2$, NRC(O)R and CO$_2$R, wherein each R is independently H or alkyl.

Typically, if substituted, the indole group is substituted by —OR, $C_1$-$C_6$ alkyl, halo, cyano, NH$_2$ or an oxo group, wherein R is H or $C_1$-$C_6$ alkyl. In particular the indole group may be substituted by —OMe, —OEt, OH, —CN, F or Cl.

Specific examples of compounds of the invention include those listed in the following Table 1:

TABLE 1

| Compound No. | Structure | Name |
|---|---|---|
| 2 | 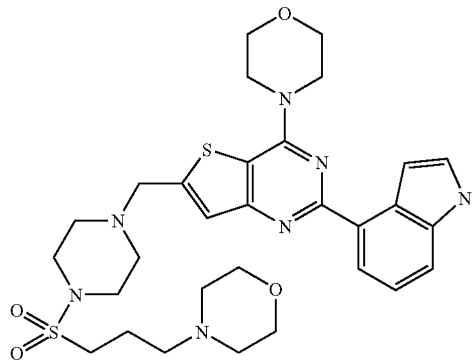 | 2-(1H-Indol-4-yl)-4-morpholin-4-yl-6-[4-(3-morpholin-4-yl-propane-1-sulfonyl)-piperazin-1-ylmethyl]-thieno[3,2-d]pyrimidine |
| 3 | 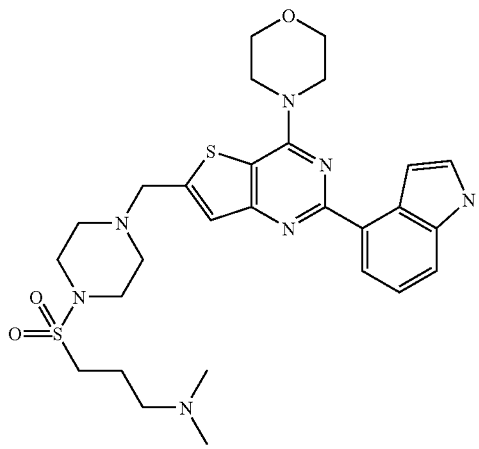 | (3-{4-[2-(1H-Indol-4-yl)-4-morpholin-4-yl-thieno[3,2-d]pyrimidin-6-ylmethyl]-piperazine-1-sulfonyl}-propyl)-dimethyl-amine |
| 4 | 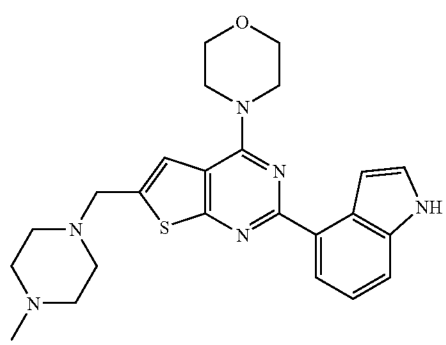 | 2-(1H-Indol-4-yl)-6-(4-methyl-piperazin-1-ylmethyl)-4-morpholin-4-yl-thieno[2,3-d]pyrimidine |
| 5 | 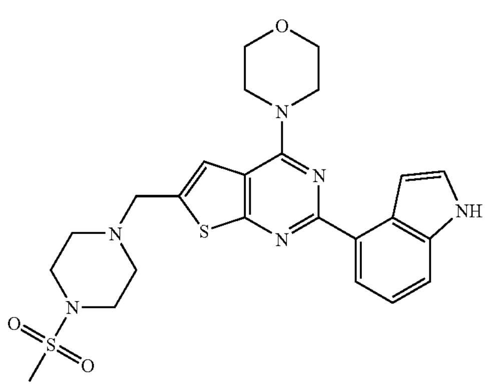 | 2-(1H-Indol-4-yl)-6-(4-methanesulfonyl-piperazin-1-ylmethyl)-4-morpholin-4-yl-thieno[2,3-d]pyrimidine |

TABLE 1-continued

| Compound No. | Structure | Name |
|---|---|---|
| 6 | 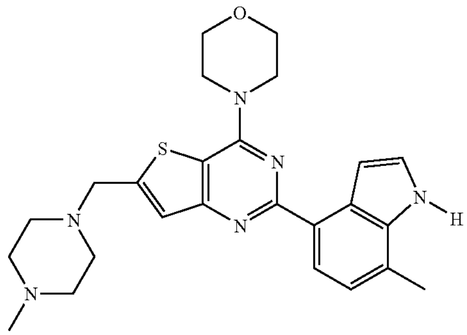 | 2-(7-Methyl-1H-indol-4-yl)-6-(4-methyl-piperazin-1-ylmethyl)-4-morpholin-4-yl-thieno[3,2-d]pyrimidine |
| 7 | 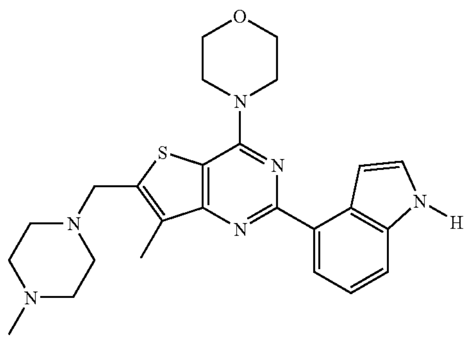 | 2-(1H-Indol-4-yl)-7-methyl-6-(4-methyl-piperazin-1-ylmethyl)-4-morpholin-4-yl-thieno[3,2-d]pyrimidine |
| 8 | 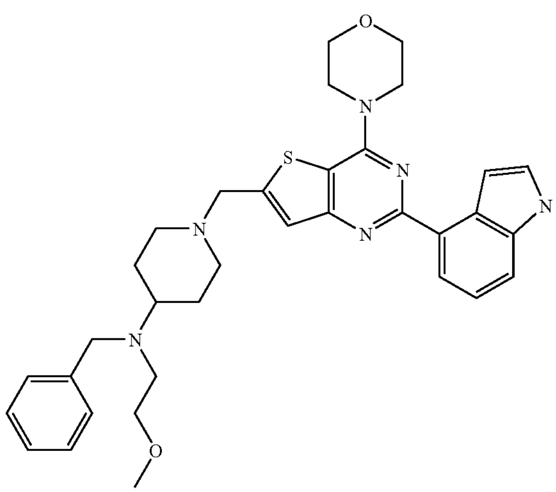 | Benzyl-{1-[2-(1H-indol-4-yl)-4-morpholin-4-yl-thieno[3,2-d]pyrimidine-6-ylmethyl]-piperidin-4-yl}-(2-methoxy-ethyl)-amine |
| 9 | 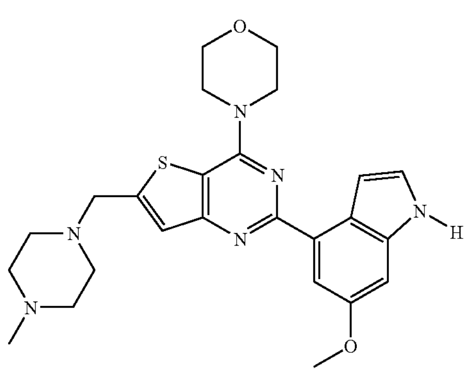 | 2-(6-Methoxy-1H-indol-4-yl)-6-(4-methyl-piperazin-1-ylmethyl)-4-morpholin-4-yl-thieno[3,2-d]pyrimidine |

TABLE 1-continued

| Compound No. | Structure | Name |
|---|---|---|
| 10 | 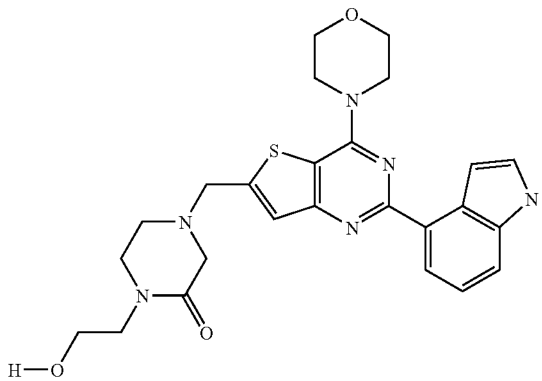 | 1-(2-hydroxy-ethyl)-4-[2-(1H-indol-4-yl)-4-morpholin-4-yl-thieno[3,2-d]pyrimidine-6-ylmethyl]-piperazin-2-one |
| 11 | 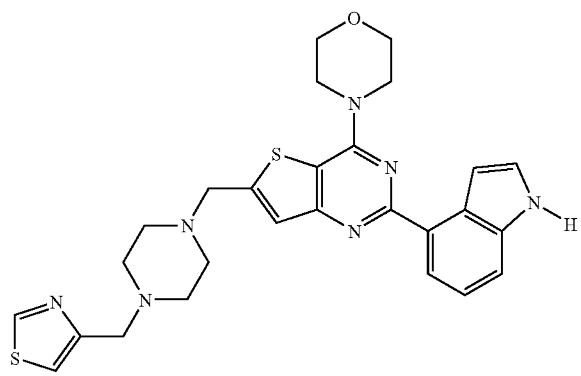 | 2-(1H-Indol-4-yl)-4-morpholin-4-yl-6-(4-thiazol-4-ylmethyl-piperazin-1-ylmethyl)-thieno[3,2-d]pyrimidine |
| 12 | 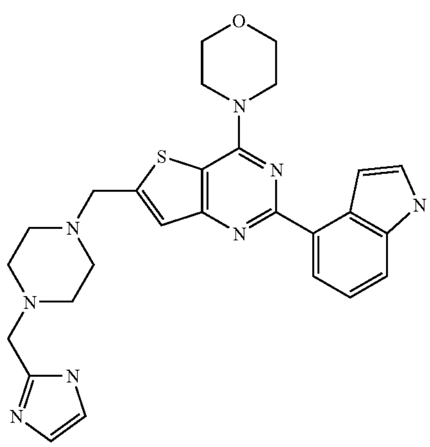 | 6-[4-(1H-Imidazol-2-ylmethyl)-piperazin-1-ylmethyl]-2-(1H-indol-4-yl)-4-morpholin-4-yl-thieno[3,2-d]pyrimidine |
| 13 | 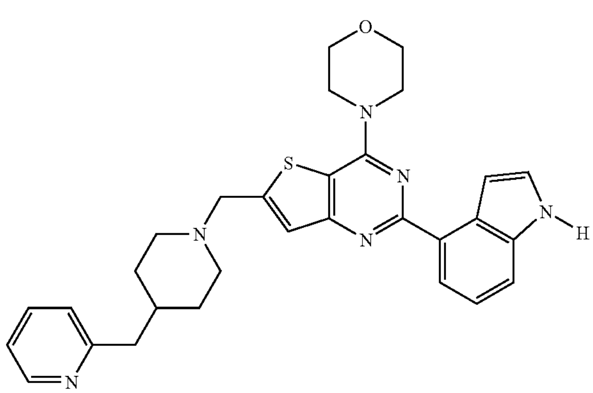 | 2-(1H-Indol-4-yl)-4-morpholin-4-yl-6-(4-pyridin-2-ylmethyl-piperidin-1-ylmethyl)-thieno[3,2-d]pyrimidine |

TABLE 1-continued

| Compound No. | Structure | Name |
|---|---|---|
| 14 | 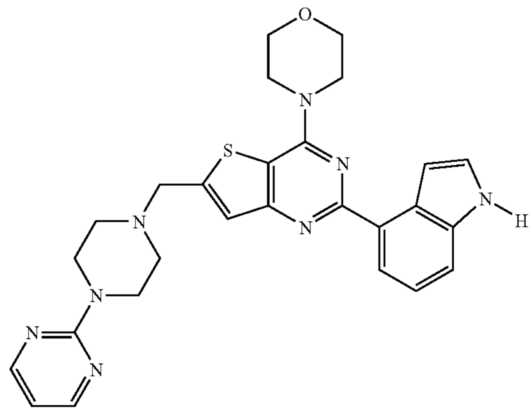 | 2-(1H-Indol-4-yl)-4-morpholin-4-yl-6-(4-pyrimidin-2-yl-piperazin-1-ylmethyl)-thieno[3,2-d]pyrimidine |
| 15 | 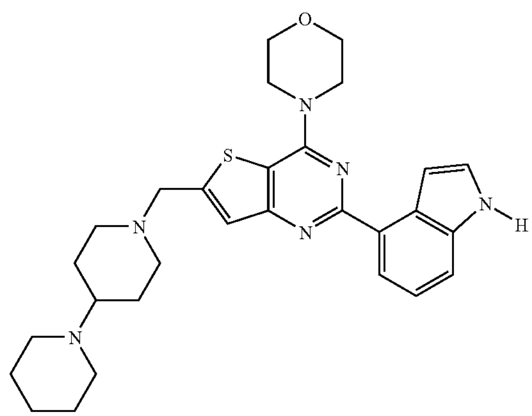 | 1'-[2-(1H-Indol-4-yl)-4-morpholin-4-yl-thieno[3,2-d]pyrimidin-6-ylmethyl]-[1,4']bipiperidinyl |
| 16 | 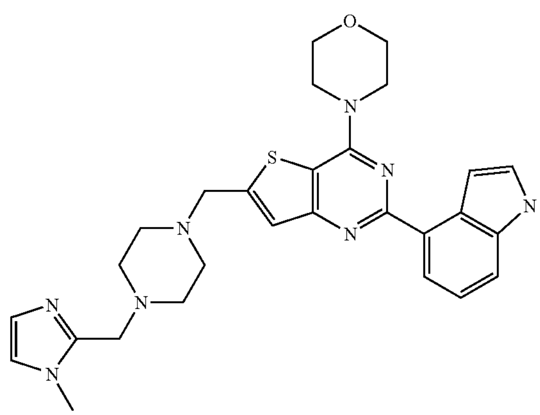 | 2-(1H-indol-4-yl)-6-[4-(1-methyl-1H-imidazol-2-ylmethyl)-piperazin-1-ylmethyl]-4-morpholin-4-yl-thieno[3,2-d]pyrimidine |
| 17 | 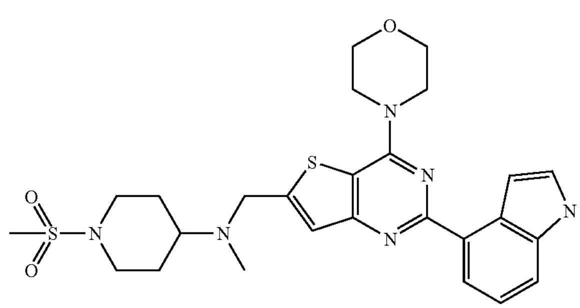 | [2-(1H-indol-4-yl)-4-morpholin-4-yl-thieno[3,2-d]pyrimidin-6-ylmethyl]-(1-methanesulphonyl-piperidin-4-yl)-methyl-amine |

TABLE 1-continued

| Compound No. | Structure | Name |
|---|---|---|
| 18 | 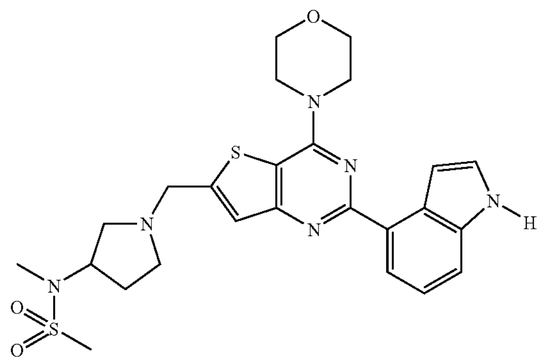 | N-{1-[2-(1H-Indol-4-yl)-4-morpholin-4-yl-thieno[3,2-d]pyrimidin-6-ylmethyl]-pyrrolidin-3-yl}-N-methyl-methanesulfonamide |
| 19 | 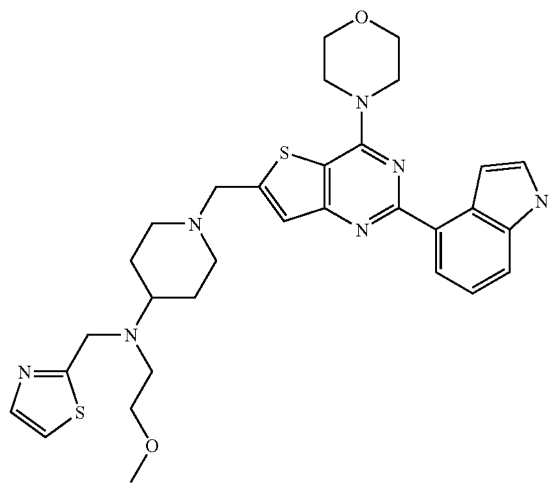 | {1-[2-(1H-Indol-4-yl)-4-morpholin-4-yl-thieno[3,2-d]pyrimidin-6-ylmethyl]piperidin-4-yl}-(2-methoxy-ethyl)-thiazol-2-ylmethyl-amine |
| 20. | 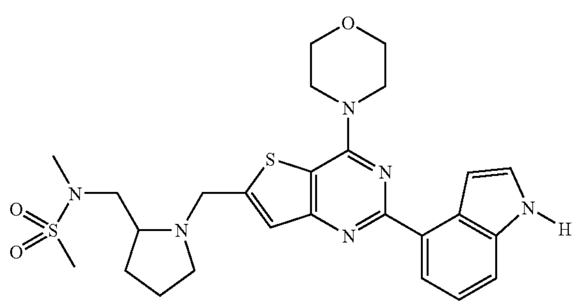 | N-{1-[2-(1H-Indol-4-yl)-4-morpholin-4-yl-thieno[3,2-d]pyrimidin-6-ylmethyl]-pyrrolidin-2-ylmethyl}-N-methyl-methanesulfonamide |
| 21 | 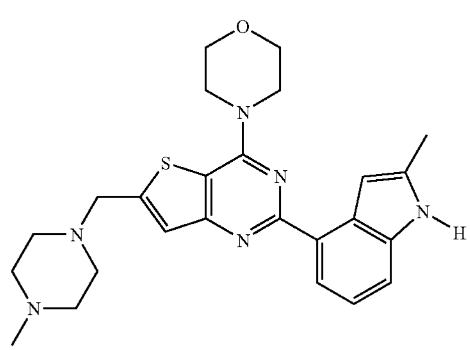 | 2-(2-Methyl-1H-indol-4-yl)-6-(4-methyl-piperazin-1-ylmethyl)-4-morpholin-4-yl-thieno[3,2-d]pyrimidin |

TABLE 1-continued

| Compound No. | Structure | Name |
|---|---|---|
| 22 | 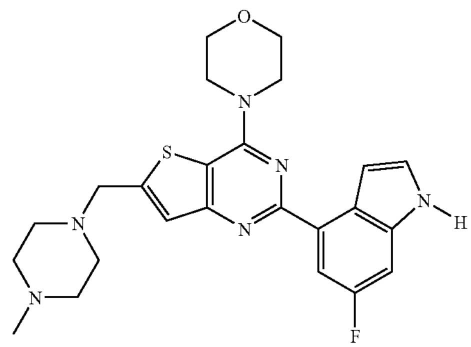 | 2-(6-Fluoro-1H-indol-4-yl)-6-(4-methyl-piperazin-1-ylmethyl)-4-morpholin-4-yl-thieno[3,2-d]pyrimidine |
| 23 | 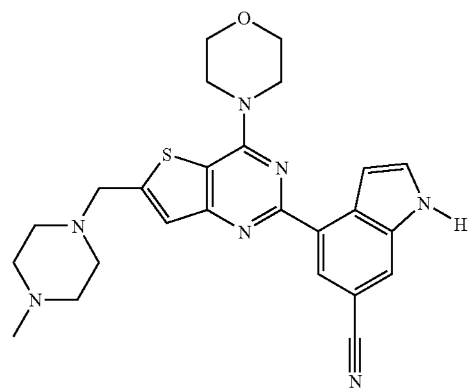 | 4-[6-(4-Methyl-piperazin-1-ylmethyl)-4-morpholin-4-yl-thieno[3,2-d]pyrimidin-2-yl]-1H-indole-6-carbonitrile |
| 24 | 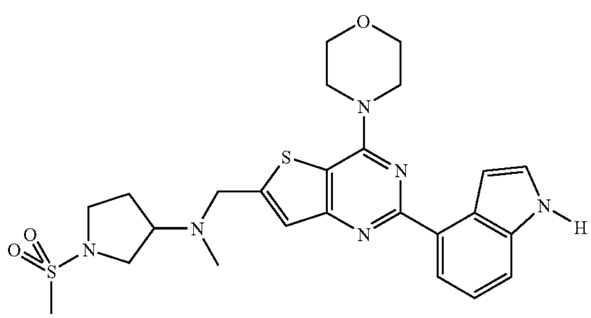 | [2-(1H-Indol-4-yl)-4-morpholin-4-yl-thieno[3,2-d]pyrimidin-6-ylmethyl]-(1-methanesulfonyl-pyrrolidin-3-yl)-methyl-amine |
| 25 | 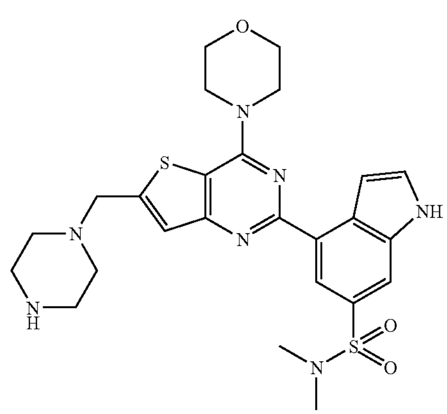 | 4-(4-Morpholin-4-yl-6-piperazin-1-ylmethyl-thieno[3,2-d]pyrimidin-2-yl)-1H-indole-6-sulfonic acid dimethylamide |

TABLE 1-continued

| Compound No. | Structure | Name |
|---|---|---|
| 26 | 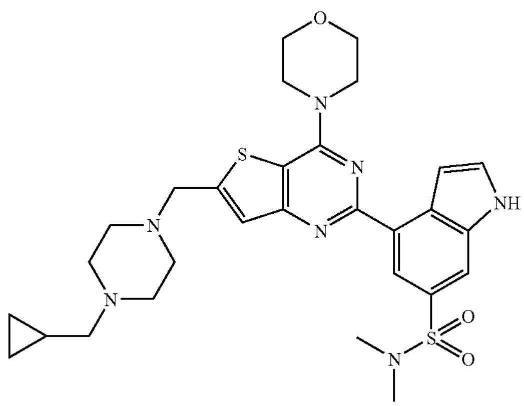 | 4-[6-(4-Cyclopropylmethyl-piperazin-1-ylmethyl)-4-morpholin-4-yl-thieno[3,2-d]pyrimidin-2-yl]-1H-indole-6-sulfonic acid dimethylamide |
| 27 | 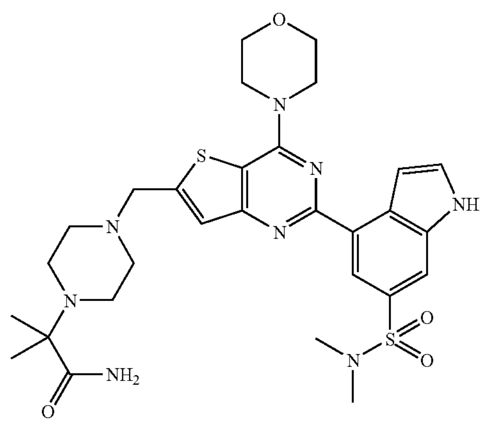 | 2-{4-[2-(6-Dimethylsulfamoyl-1H-indol-4-yl)-4-morpholin-4-yl-thieno[3,2-d]pyri-midin-6-ylmethyl]-piperazin-1-yl}-isobutyramide |
| 28 | 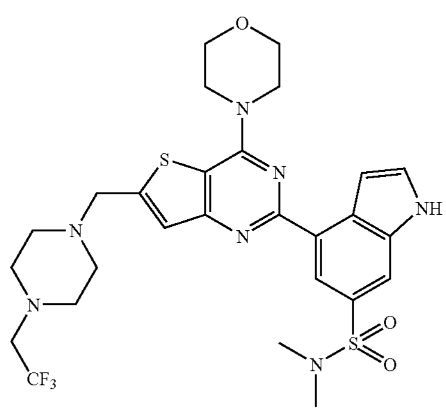 | 4-{4-Morpholin-4-yl-6-[4-(2,2,2-trifluoro-ethyl)-piperazin-1-ylmethyl]-thieno[3,2-d]pyrimidin-2-yl}-1H-indole 6-sulfonic acid dimethylamide |
| 29 | 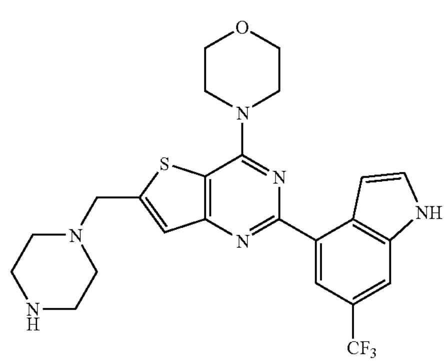 | 4-Morpholin-4-yl-6-piperazin-1-ylmethyl-2-(6-trifluoromethyl-1H-indol 4-yl)-thieno[3,2-d]pyrimidine |

TABLE 1-continued

| Compound No. | Structure | Name |
|---|---|---|
| 30 | 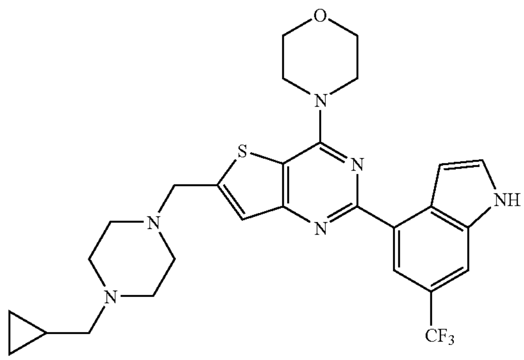 | 6-(4-Cyclopropylmethyl-piperazin-1-ylmethyl)-4-morpholin-4-yl-2-(6-trifluoro-methyl-1H-indol-4-yl)-thieno[3,2-d]pyrimidine |
| 31 | 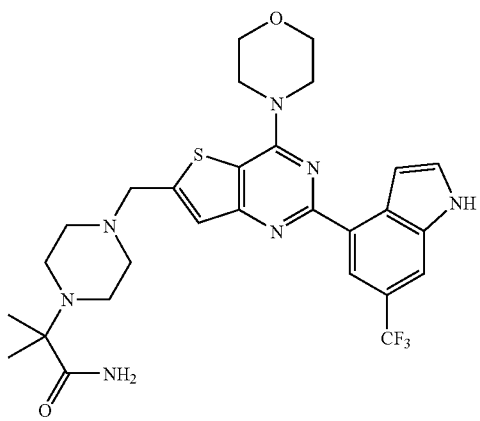 | 2-{4-[4-Morpholin-4-yl-2-(6-trifluoromethyl-1H-indol-4-yl)-thieno[3,2-d]pyri-midin-6-ylmethyl]-piperazin-1-yl}-isobutyramide |
| 32 | 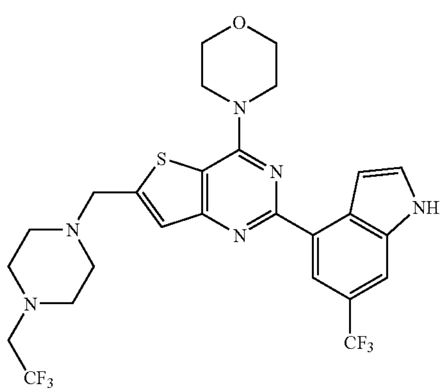 | 4-Morpholin-4-yl-6-[4-(2,2,2-trifluoro-ethyl)-piperazin-1-ylmethyl]-2-(6-trifluoromethyl-1H-indol-4-yl)-thieno[3,2-d]pyrimidine |
| 33 | 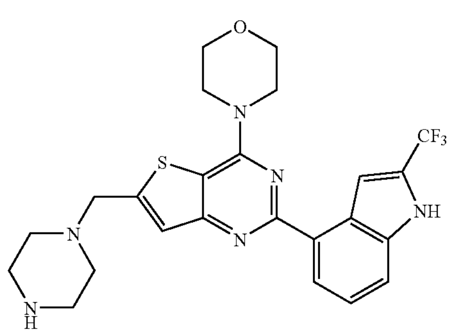 | 4-Morpholin-4-yl-6-piperazin-1-ylmethyl-2-(2-trifluoromethyl-1H-indol-4-yl)-thieno[3,2-d]pyrimidine |

TABLE 1-continued

| Compound No. | Structure | Name |
| --- | --- | --- |
| 34 | 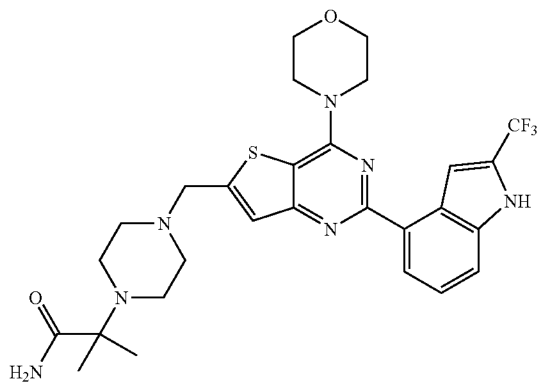 | 2-{4-[4-Morpholin-4-yl-2-(2-trifluoromethyl-1H-indol-4-yl)-thieno[3,2-d]pyrimidin-6-ylmethyl]-piperazin-1-yl}-isobutyramide |
| 35 | 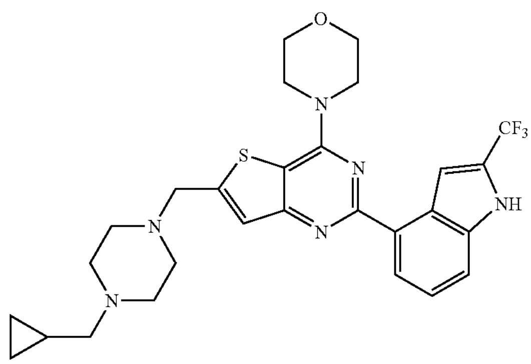 | 6-(4-Cyclopropylmethyl-piperazin-1-ylmethyl)-4-morpholin-4-yl-2-(2-trifluoro-methyl-1H-indol-4-yl)-thieno[3,2-d]pyrimidine |
| 36 | 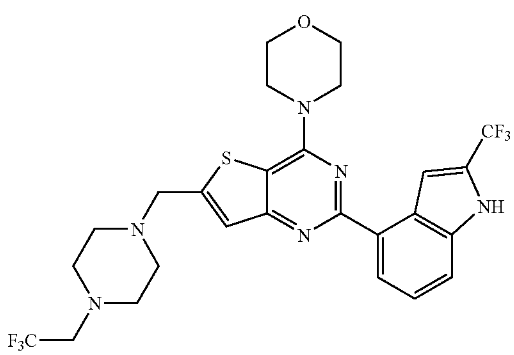 | 4-Morpholin-4-yl-6-[4-(2,2,2-trifluoro-ethyl)-piperazin-1-ylmethyl]-2-(2-trifluoromethyl-1H-indol-4-yl)-thieno[3,2-d]pyrimidine |
| 37 | 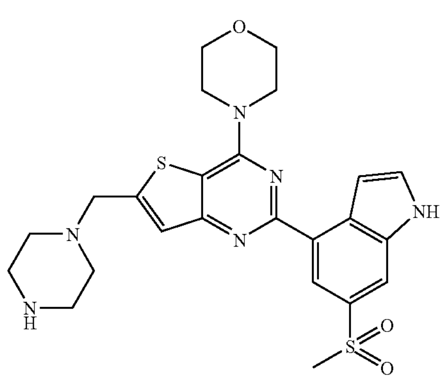 | 2-(6-Methanesulfonyl-1H-indol-4-yl)-4-morpholin-4-yl-6-piperazin-1-ylmethyl-thieno[3,2-d]pyrimidine |

TABLE 1-continued

| Compound No. | Structure | Name |
|---|---|---|
| 38 | 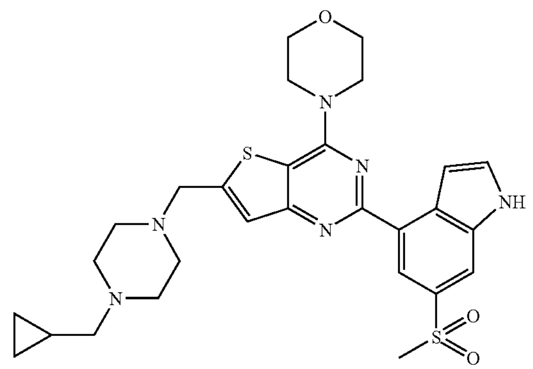 | 6-(4-Cyclopropylmethyl-piperazin-1-ylmethyl)-2-(6-methanesulfonyl-1H-indol-4-yl)-4-morpholin-4-yl-thieno[3,2-d]pyrimidine |
| 39 | 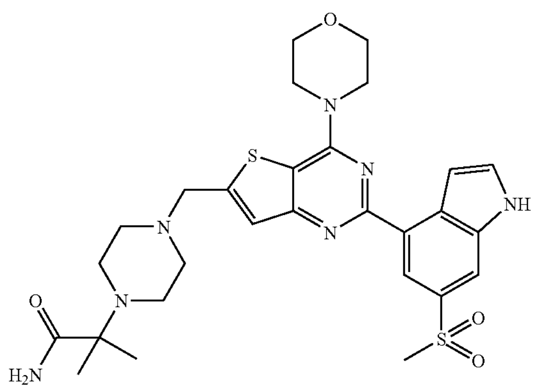 | 2-{4-[2-(6-Methanesulfonyl-1H-indol-4-yl)-4-morpholin-4-yl-thieno[3,2-d]pyrimidin-6-ylmethyl]-piperazin-1-yl}-isobutyramide |
| 40 | 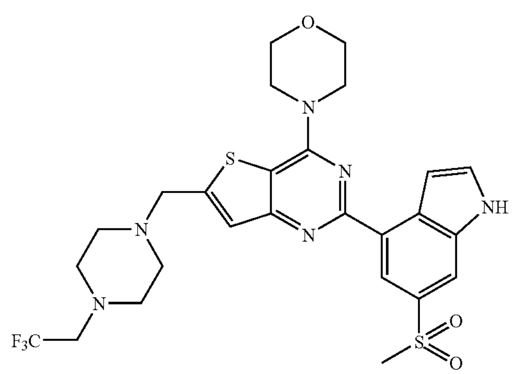 | 2-(6-Methanesulfonyl-1H-indol-4-yl)-4-morpholin-4-yl-6-[4-(2,2,2-trifluoro-ethyl)piperazin-1-ylmethyl]-thieno[3,2-d]pyrimidine |
| 41 | 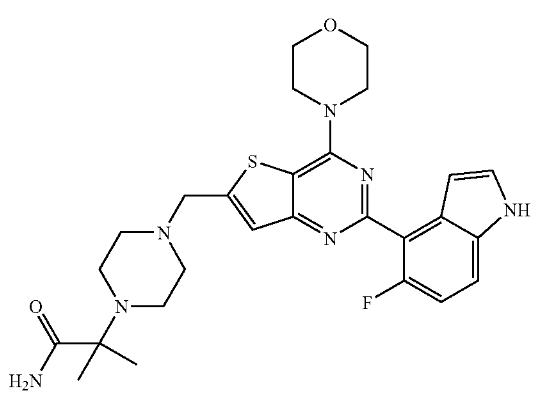 | 2-{4-[2-(5-Fluoro-1H-indol-4-yl)-4-morpholin-4-yl-thieno[3,2-d]pyrimidin-6-ylmethyl]-piperazin-1-yl}-isobutyramide |

TABLE 1-continued

| Compound No. | Structure | Name |
|---|---|---|
| 42 | 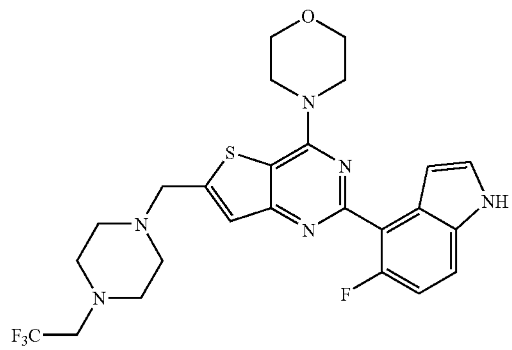 | 2-(5-Fluoro-1H-indol-4-yl)-4-morpholin-4-yl-6-[4-(2,2,2-trifluoro-ethyl)-piperazin-1-ylmethyl]-thieno[3,2-d]pyrimidine ( |
| 43 | 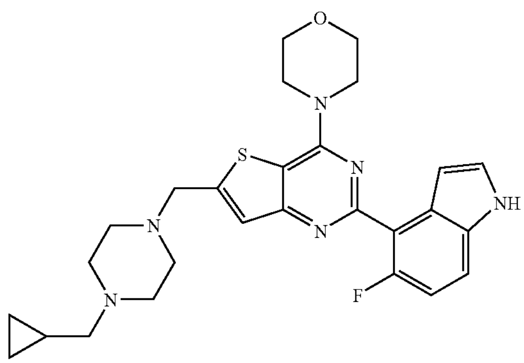 | 6-(4-Cyclopropylmethyl-piperazin-1-ylmethyl)-2-(5-fluoro-1H-indol-4-yl)-4-morpholin-4-yl-thieno[3,2-d]pyrimidine |
| 44 | 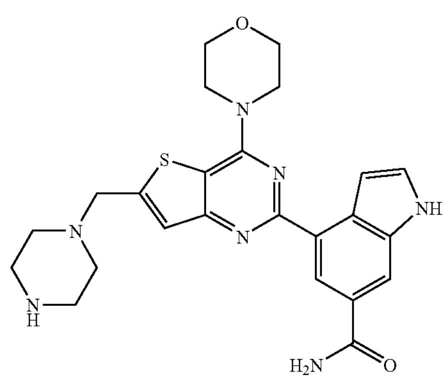 | 4-(4-Morpholin-4-yl-6-piperazin-1-ylmethyl-thieno[3,2-d]pyrimidin-2-yl)-1H-indole-6-carboxylic acid amide |
| 45 | 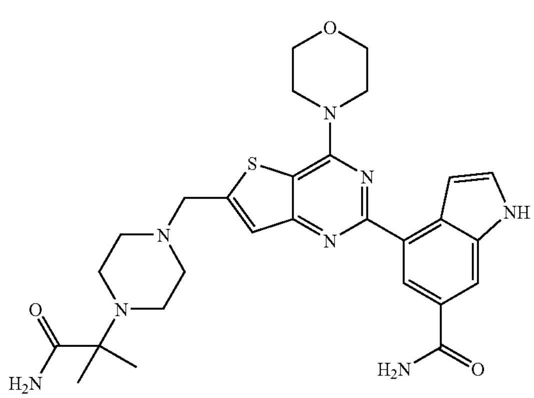 | 4-{6-[4-(1-Carbamoyl-1-methyl-ethyl)-piperazin-1-ylmethyl]-4-morpholin-4-yl-thieno[3,2-d]pyrimidin-2-yl}-1H-indole-6-carboxylic acid amide |

TABLE 1-continued

| Compound No. | Structure | Name |
|---|---|---|
| 46 | 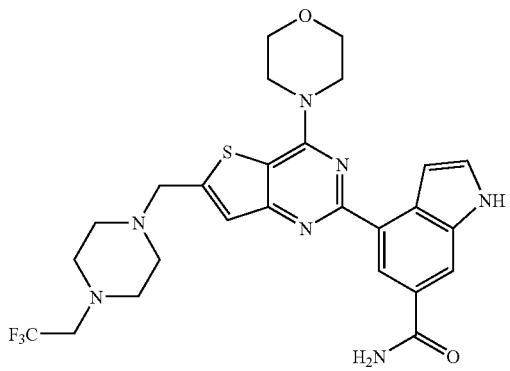 | 4-{4-Morpholin-4-yl-6-[4-(2,2,2-trifluoro-ethyl)-piperazin-1-ylmethyl]-thieno[3,2-d]pyrimidin-2-yl}-1H-indole 6-carboxylic acid amide |
| 47 | 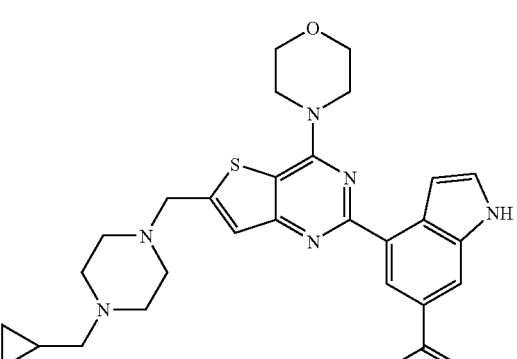 | 4-[6-(4-Cyclopropylmethyl-piperazin-1-ylmethyl)-4-morpholin-4-yl-thieno[3,2-d]pyrimidin-2-yl]-1H-indole-6-carboxylic acid amide |
| 48 | 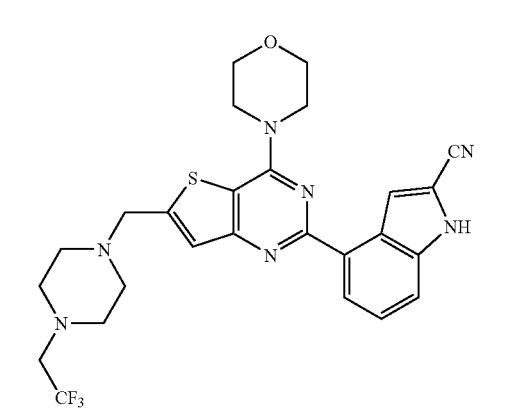 | 4-{4-Morpholin-4-yl-6-[4-(2,2,2-trifluoro-ethyl)-piperazin-1-ylmethyl]-thieno[3,2-d]pyrimidin-2-yl}-1H-indole-2-carbonitrile |
| 49 | 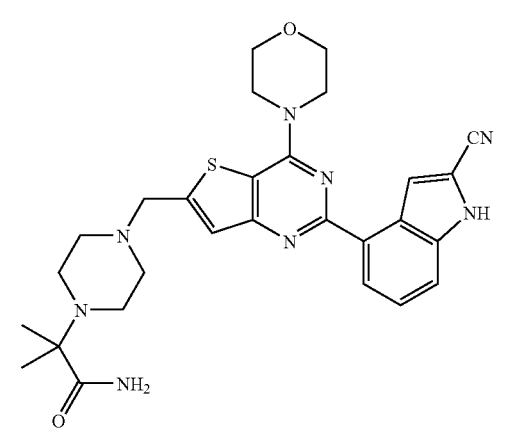 | 2-{4-[2-(2-Cyano-1H-indol-4-yl)-4-morpholin-4-yl-thieno[3,2-d]pyrimidin-6-ylmethyl]-piperazin-1-yl}-isobutyramide |

TABLE 1-continued

| Compound No. | Structure | Name |
|---|---|---|
| 50 | 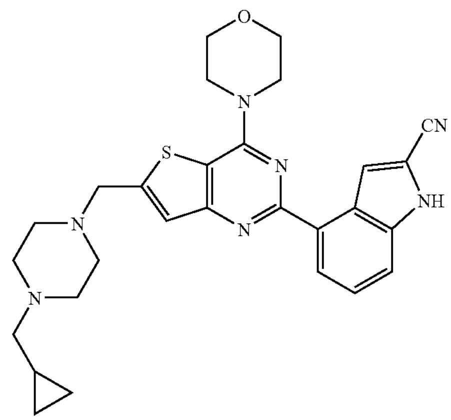 | 4-[6-(4-Cyclopropylmethyl-piperazin-1-ylmethyl)-4-morpholin-4-yl-thieno[3,2-d]pyrimidin-2-yl]-1H-indole-2-carbonitrile |
| 51 | 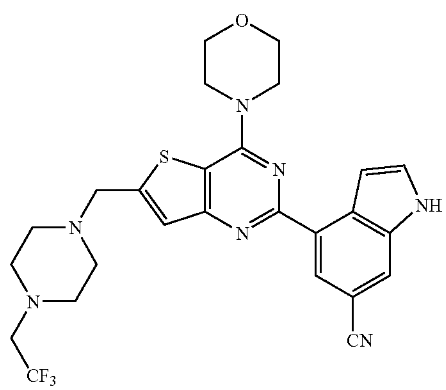 | 4-{4-Morpholin-4-yl-6-[4-(2,2,2-trifluoro-ethyl)-piperazin-1-ylmethyl]-thieno[3,2-d]pyrimidin-2-yl}-1H-indole-6-carbonitrile |
| 52 | 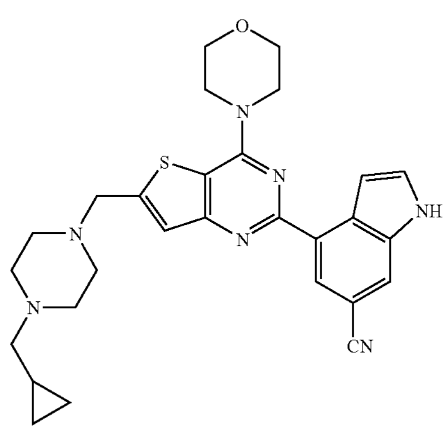 | 4-[6-(4-Cyclopropylmethyl-piperazin-1-ylmethyl)-4-morpholin-4-yl-thieno[3,2-d]pyrimidin-2-yl]-1H-indole-6-carbonitrile |

TABLE 1-continued

| Compound No. | Structure | Name |
|---|---|---|
| 53 | 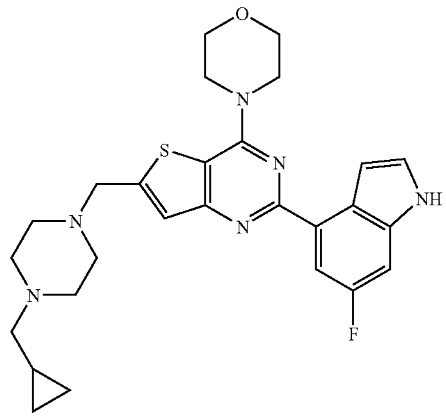 | 6-(4-Cyclopropylmethyl-piperazin-1-ylmethyl)-2-(6-fluoro-1H-indol-4-yl)-4-morpholin-4-yl-thienol[3,2-d]pyrimidine |
| 54 | 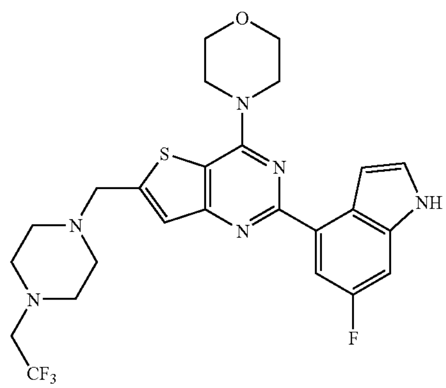 | 2-(6-Fluoro-1H-indol-4-yl)-4-morpholin-4-yl-6-[4-(2,2,2-trifluoro-ethyl)-piperazin-1-ylmethyl]-thieno[3,2-d]pyrimidine |
| 55 | 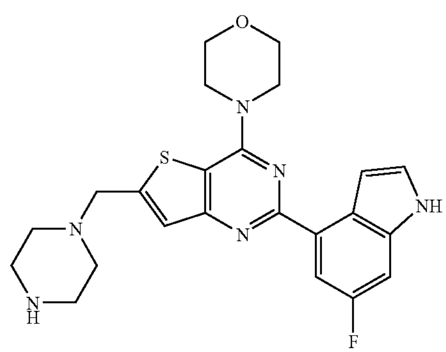 | 2-(6-Fluoro-1H-indol-4-yl)-4-morpholin-4-yl-6-piperazin-1-ylmethyl thieno[3,2-d]pyrimidine |
| 56 | 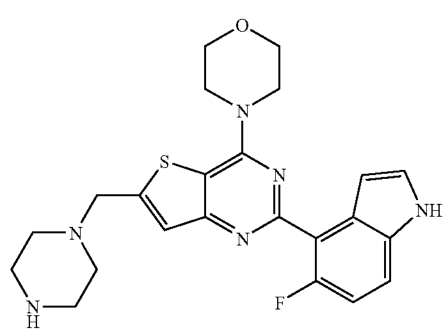 | 2-(5-Fluoro-1H-indol-4-yl)-4-morpholin-4-yl-6-piperazin-1-ylmethyl thieno[3,2-d]pyrimidine |

TABLE 1-continued

| Compound No. | Structure | Name |
|---|---|---|
| 57 | 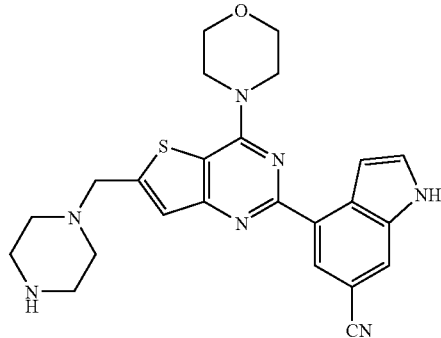 | 4-(4-Morpholin-4-yl-6-piperazin-1-ylmethyl-thieno[3,2-d]pyrimidin-2-yl)-1H-indole-6-carbonitrile |
| 58 | 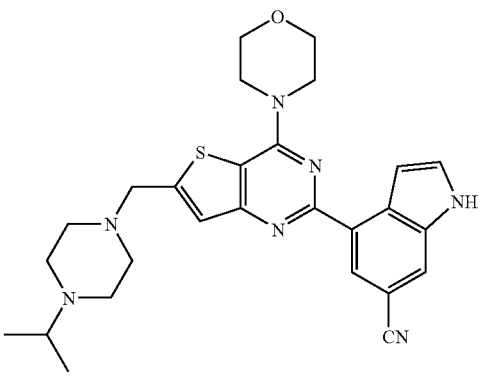 | 4-[6-(4-Isopropyl-piperazin-1-ylmethyl)-4-morpholin-4-yl-thieno[3,2-d]pyrimidin-2-yl]-1H-indole-6-carbonitrile |
| 59 | 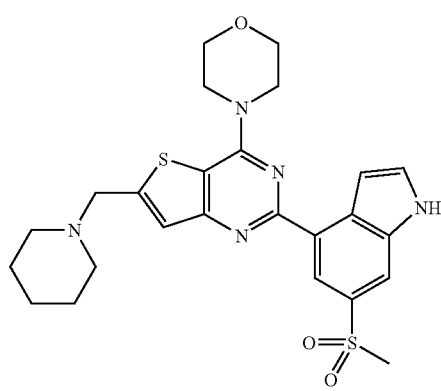 | 2-(6-Methanesulfonyl-1H-indol-4-yl)-4-morpholin-4-yl-6-piperidin-1-ylmethyl-thieno[3,2-d]pyrimidine |
| 60 | 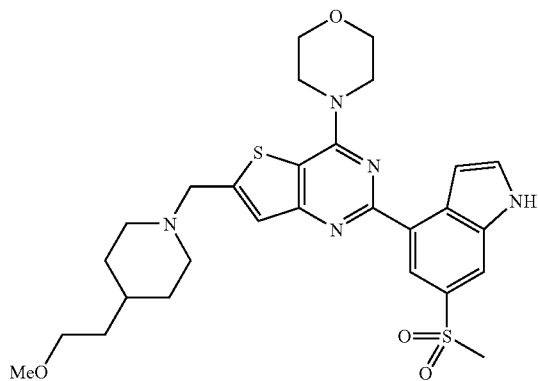 | 2-(6-Methanesulfonyl-1H-indol-4-yl)-6-[4-(2-methoxy-ethyl)-piperidin-1-ylmethyl]-4-morpholin-4-yl-thieno[3,2-d]pyrimidine |

TABLE 1-continued

| Compound No. | Structure | Name |
|---|---|---|
| 61 | 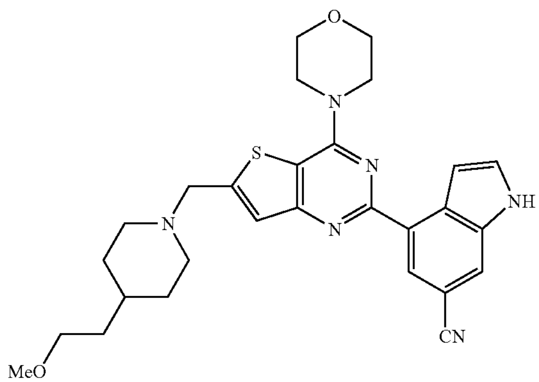 | 4-{6-[4-(2-Methoxy-ethyl)-piperidin-1-ylmethyl]-4-morpholin-4-yl-thieno[3,2-d]pyrimidin-2-yl}-1H-indole-6-carbonitrile |
| 62 | 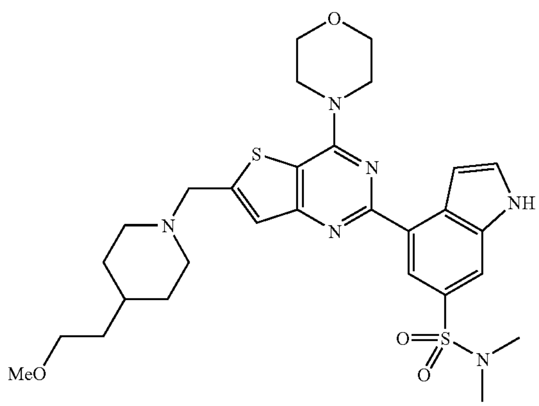 | 4-{6-[4-(2-Methoxy-ethyl)-piperidin-1-ylmethyl]-4-morpholin-4-yl-thieno[3,2-d]pyrimidin-2-yl}-1H-indole-6-sulfonic acid dimethylamide |
| 63 | 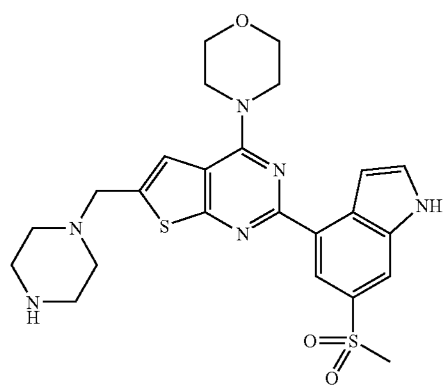 | 2-(6-Methanesulfonyl-1H-indol-4-yl)-4-morpholin-4-yl-6-piperazin-1-ylmethyl-thieno[2,3-d]pyrimidine |
| 64 | 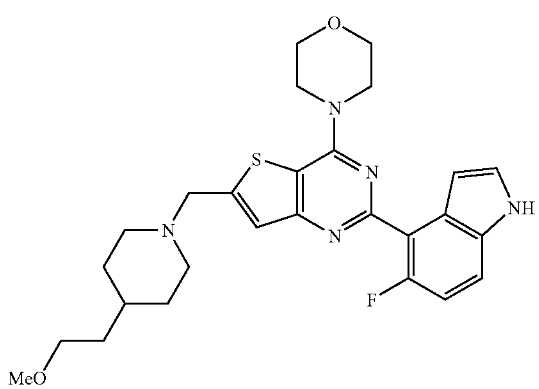 | 2-(5-Fluoro-1H-indol-4-yl)-6-[4-(2-methoxy-ethyl)-piperidin-1-ylmethyl]-4-morpholin-4-yl-thieno[3,2-d]pyrimidine |

TABLE 1-continued

| Compound No. | Structure | Name |
|---|---|---|
| 65 | 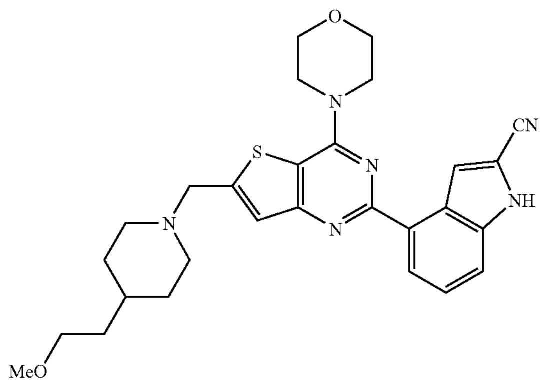 | 4-{6-[4-(2-Methoxy-ethyl)-piperidin-1-ylmethyl]-4-morpholin-4-yl-thieno[3,2-d]pyrimidin-2-yl}-1H-indole-2-carbonitrile |
| 66 | 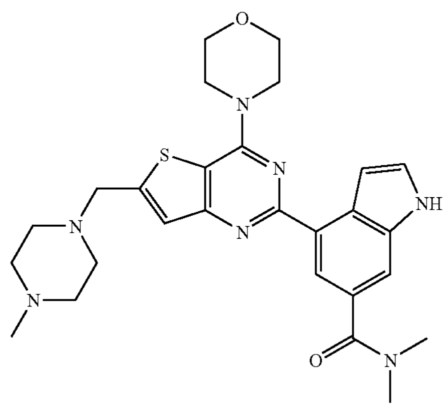 | 4-[6-(4-Methyl-piperazin-1-ylmethyl)-4-morpholin-4-yl-thieno[3,2-d]pyrimidin-2-yl]-1H-indole-6-carboxylic acid dimethylamide |
| 67 | 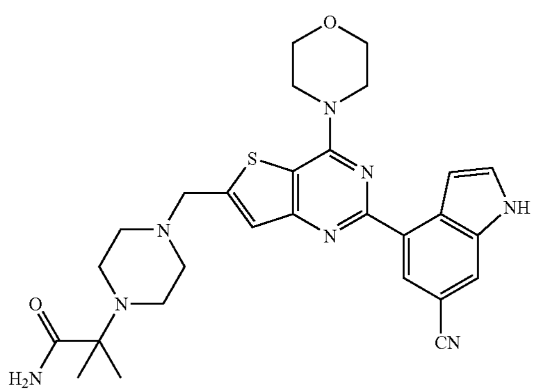 | 2-{4-[2-(6-Cyano-1H-indol-4-yl)-4-morpholin-4-yl-thieno[3,2-d]pyrimidin-6-ylmethyl]-piperazin-1-yl}-isobutyramide |
| 68 | 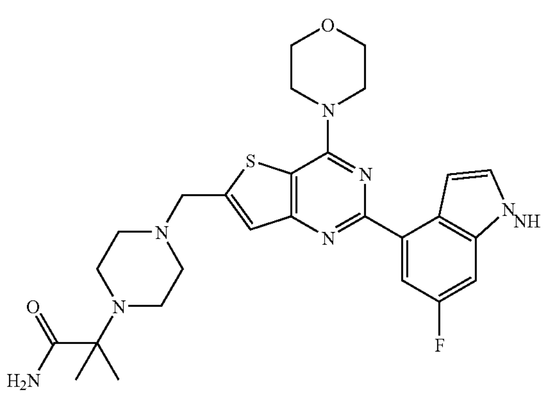 | 2-{4-[2-(6-Fluoro-1H-indol-4-yl)-4-morpholin-4-yl-thieno[3,2-d]pyrimidin-6-ylmethyl]-piperazin-1-yl}-isobutyramide |

TABLE 1-continued
| Compound No. | Structure | Name |
|---|---|---|
| 69 | 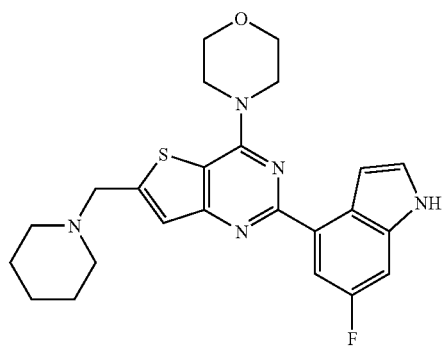 | 2-(6-Fluoro-1H-indol-4-yl)-4-morpholin-4-yl-6-piperidin-1-ylmethyl-thieno[3,2-d]pyrimidine ( |
| 70 | 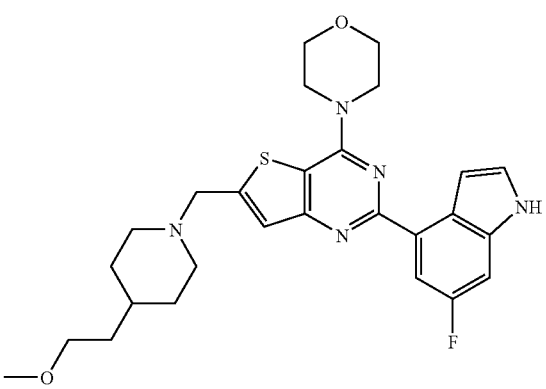 | 2-(6-Fluoro-1H-indol-4-yl)-6-[4-(2-methoxy-ethyl)-piperidin-1-ylmethyl]-4-morpholin-4-yl-thieno[3,2-d]pyrimidine |
| 71 | 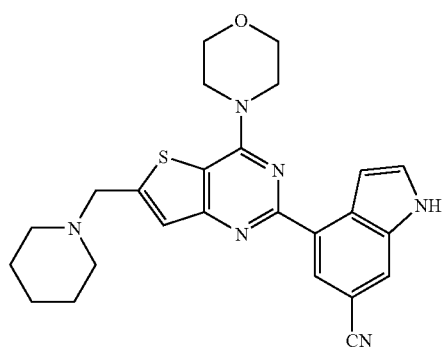 | 4-(4-Morpholin-4-yl-6-piperidin-1-ylmethyl-thieno[3,2-d]pyrimidin-2-yl)-1H-indole-6-carbonitrile |
| 72 | 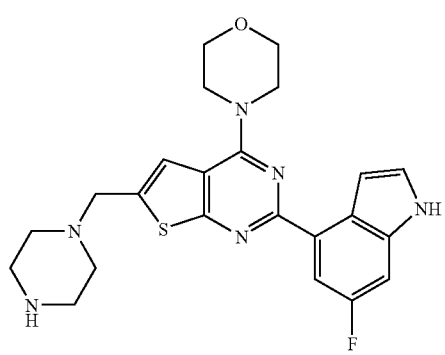 | 2-(6-Fluoro-1H-indol-4-yl)-4-morpholin-4-yl-6-piperazin-1-ylmethyl-thieno[2,3-d]pyrimidine |

TABLE 1-continued

| Compound No. | Structure | Name |
|---|---|---|
| 73 | 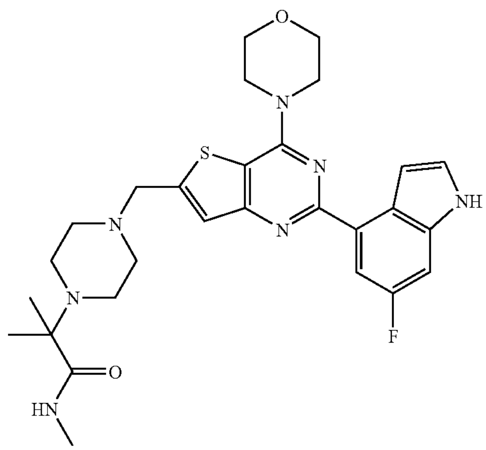 | 2-{4-[2-(6-Fluoro-1H-indol-4-yl)-4-morpholin-4-yl-thieno[3,2-d]pyrimidin-6-ylmethyl]-piperazin-1-yl}-N-methyl-isobutyramide |
| 74 | 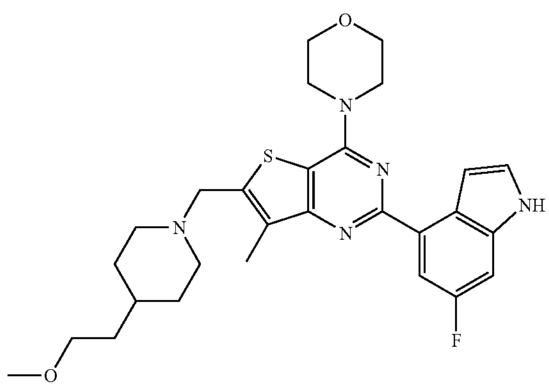 | 2-(6-Fluoro-1H-indol-4-yl)-6-[4-(2-methoxy-ethyl)-piperidin-1-ylmethyl]-7-methyl-4-morpholin-4-yl-thieno[3,2-d]pyrimidine |
| 75 | 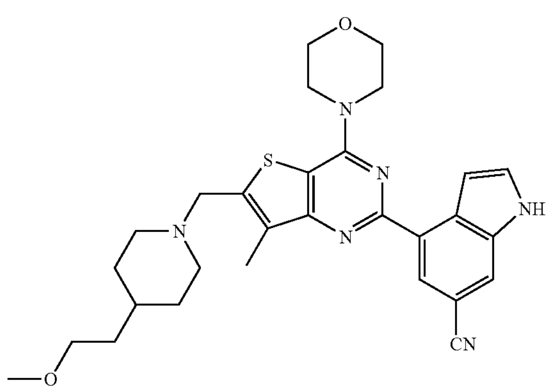 | 4-{6-[4-(2-Methoxy-ethyl)-piperidin-1-ylmethyl]-7-methyl-4-morpholin-4-yl-thieno[3,2-d]pyrimidin-2-yl}-1H-indole 6-carbonitrile |

TABLE 1-continued

| Compound No. | Structure | Name |
|---|---|---|
| 76 | 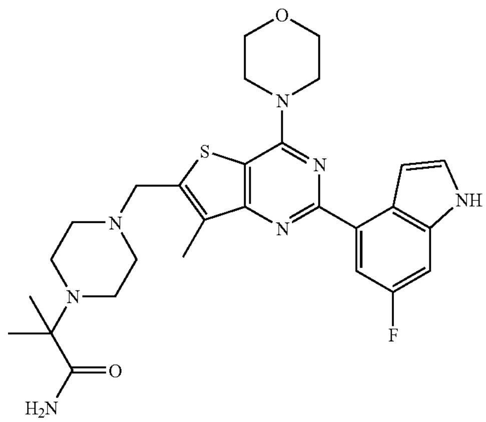 | 2-{4-[2-(6-Fluoro-1H-indol-4-yl)-7-methyl-4-morpholin-4-yl-thieno[3,2-d]pyrimidin-6-ylmethyl]-piperazin-1-yl}-isobutyramide |
| 77 | 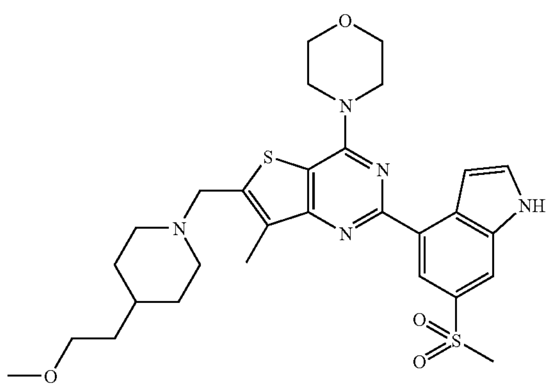 | 2-(6-Methanesulfonyl-1H-indol-4-yl)-6-[4-(2-methoxy-ethyl)-piperidin-1-ylmethyl]-7-methyl-4-morpholin-4-yl-thieno[3,2-d]pyrimidine |
| 78 | 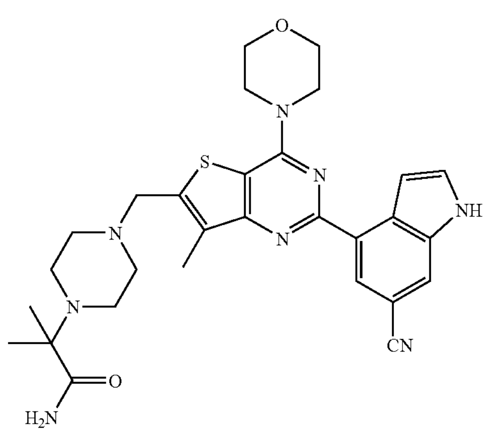 | 2-{4-[2-(6-Cyano-1H-indol-4-yl)-7-methyl-4-morpholin-4-yl-thieno[3,2-d]pyrimidin-6-ylmethyl]-piperazin-1-yl}-isobutyramide |

TABLE 1-continued

| Compound No. | Structure | Name |
|---|---|---|
| 79 | 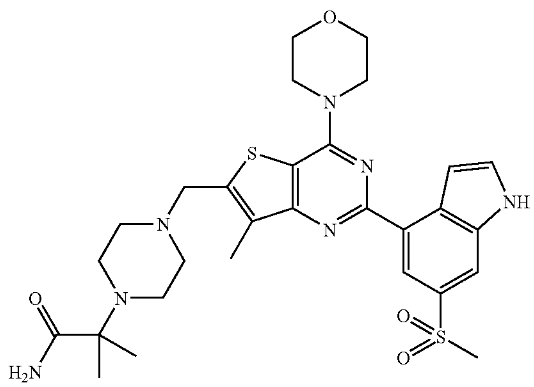 | 2-{4-[2-(6-Methanesulfonyl-1H-indol-4-yl)-7-methyl-4-morpholin-4-yl-thieno[3,2-d]pyrimidin-6-ylmethyl]-piperazin-1-yl}-isobutyramide |
| 80 | 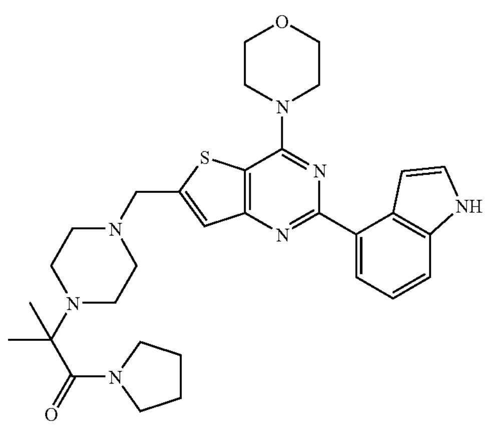 | 2-{4-[2-(1H-Indol-4-yl)-4-morpholin-4-yl-thieno[3,2-d]pyrimidin-6-ylmethyl]-piperazin-1-yl}-2-methyl-1-pyrrolidin-1-yl-propan-1-one |
| 81 | 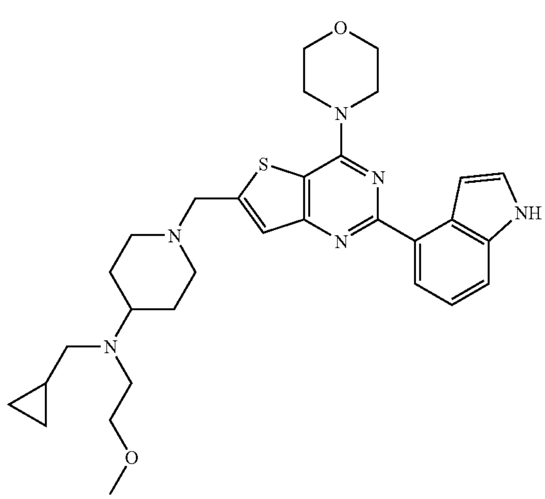 | Cyclopropylmethyl-{1-[2-(1H-indol-4-yl)-4-morpholin-4-yl-thieno[3,2-d]pyrimidin-6-ylmethyl]-piperidin-4-yl}-(2-methoxy-ethyl)-amine |

TABLE 1-continued

| Compound No. | Structure | Name |
|---|---|---|
| 82 | 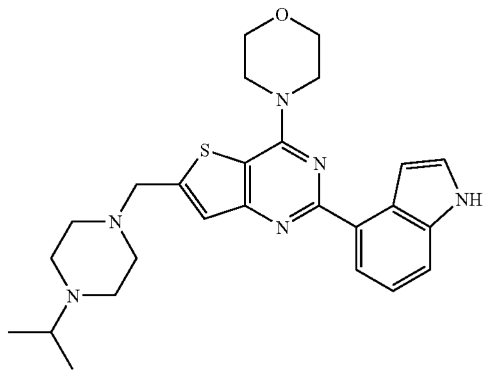 | 2-(1H-Indol-4-yl)-6-(4-isopropyl-piperazin-1-ylmethyl)-4-morpholin4yl-thieno[3,2-d]pyrimidine |
| 83 | 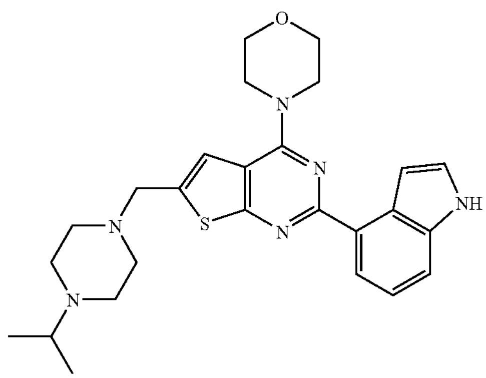 | 2-(1H-Indol-4-yl)-6-(4-isopropyl-piperazin-1-ylmethyl)-4-morpholin-4-yl-thienol-[2,3-d]pyrimidine |
| 84 | 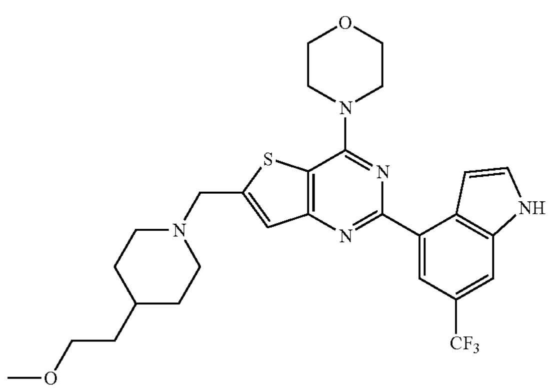 | 6-[4-(2-Methoxy-ethyl)-piperidin-1-ylmethyl]-4-morpholin-4-yl-2-(6-trifluoromethyl-1H-indol-4-yl)-thieno[3,2-d]pyrimidine |
| 85 | 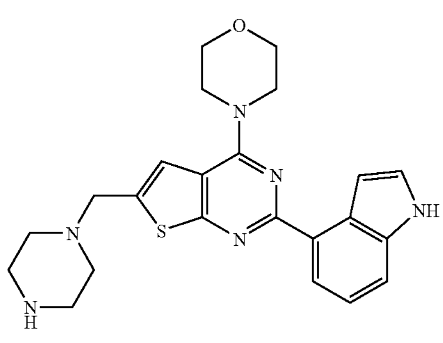 | 2-(1H-Indol-4-yl)-4-morpholin-4-yl-6-piperazin-1-ylmethyl-thieno[2,3-d]pyrimidine |

TABLE 1-continued

| Compound No. | Structure | Name |
|---|---|---|
| 86 | 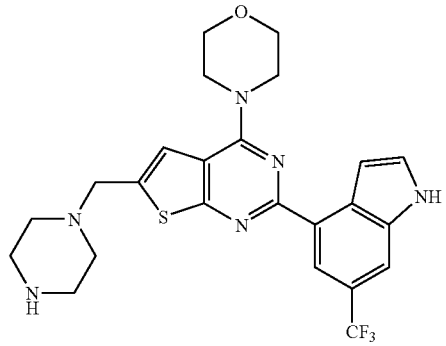 | 4-Morpholin-4-yl-6-piperazin-1-ylmethyl-2-(6-trifluoromethyl-1H-indol-4-yl)-thieno[2,3-d]pyrimidine |
| 87 | 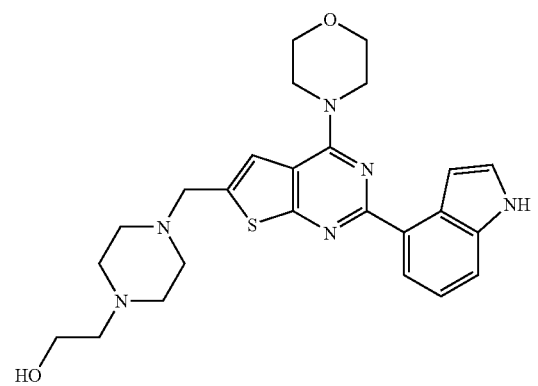 | 2-{4-[2-(1H-Indol-4-yl)-4-morpholin-4-yl-thieno[2,3-d]pyrimidin-6-ylmethyl]-piperazin-1-yl}-ethanol |
| 88 | 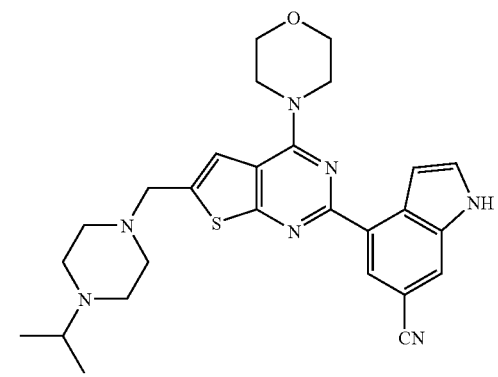 | 4-[6-(4-Isopropyl-piperazin-1-ylmethyl)-4-morpholin-4-yl-thieno[2,3-d]pyrimidin-2-yl]-1H-indole-6-carbonitrile |
| 89 | 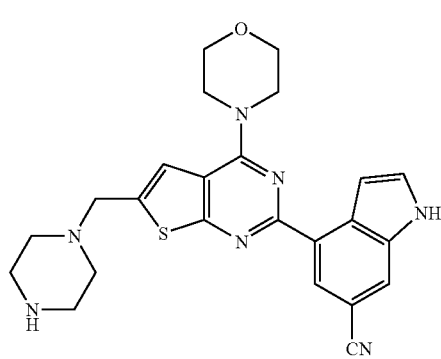 | 4-(4-Morpholin-4-yl-6-piperazin-1-ylmethyl-thieno[2,3-d]pyrimidin-2-yl)-1H-indole-6-carbonitrile |

TABLE 1-continued

| Compound No. | Structure | Name |
| --- | --- | --- |
| 90 | 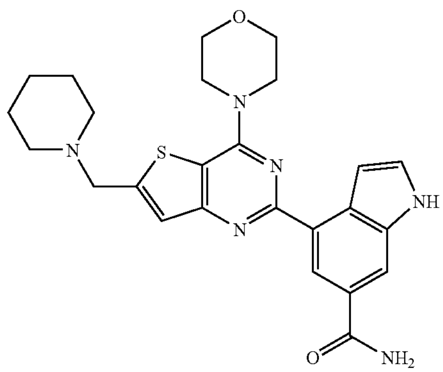 | 4-(4-Morpholin-4-yl-6-piperidin-1-ylmethyl-thieno[3,2-d]pyrimidin-2-yl)-1H-indole-6-carboxylic acid amide |
| 91 | 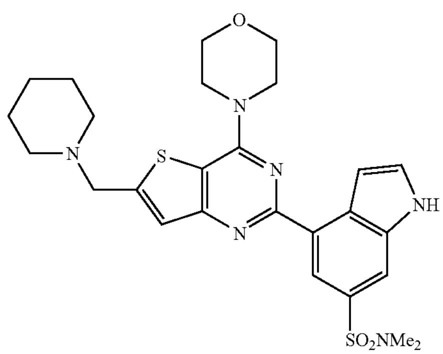 | 4-(4-Morpholin-4-yl-6-piperidin-1-ylmethyl-thieno[3,2-d]pyrimidin-2-yl)-1H-indole-6-sulfonic acid dimethylamide |
| 92 | 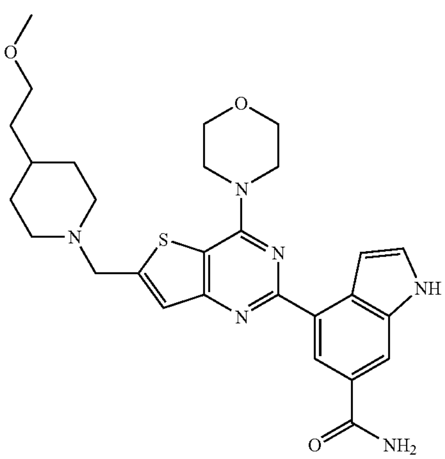 | 4-{6-[4-(2-Methoxy-ethyl)-piperidin-1-ylmethyl]-4-morpholin-4-yl-thieno[3,2-d]pyrimidin-2-yl}-1H-indole-6-carboxylic acid amide |
| 93 | 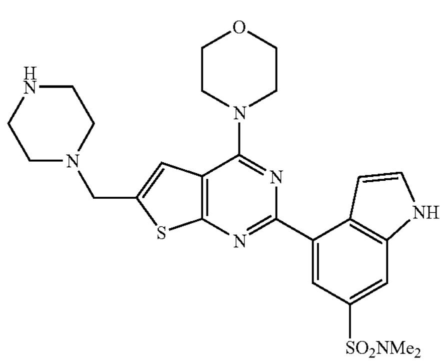 | 4-(4-Morpholin-4-yl-6-piperazin-1-ylmethyl-thieno[2,3-d]pyrimidin-2-yl)-1H-indole-6-sulfonic acid dimethylamide |

| Compound No. | Structure | Name |
|---|---|---|
| 94 | 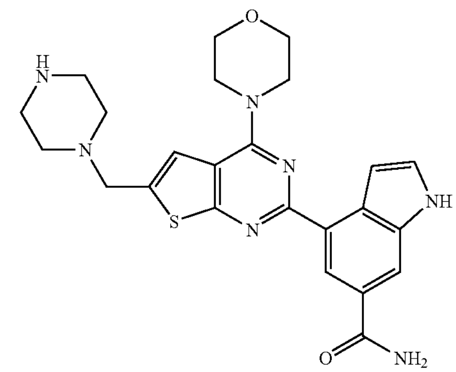 | 4-(4-Morpholin-4-yl-6-piperazin-1-ylmethyl-thieno[2,3-d]pyrimidin-2-yl)-1H-indole-6-carboxylic acid amide |
| 95 | 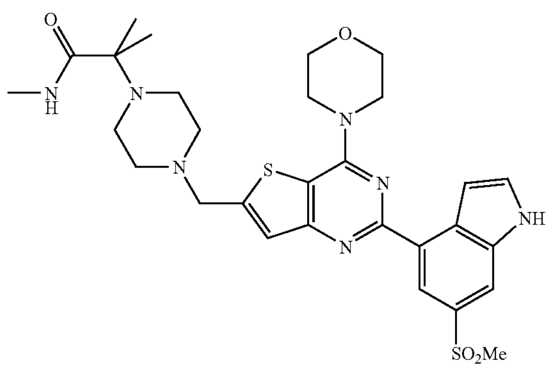 | 2-{4-[2-(6-Methanesulfonyl-1H-indol-4-yl)-4-morpholin-4-yl-thieno[3,2-d]pyrimidin-6-ylmethyl]-piperazin-1-yl}-N-methyl-isobutyramide |
| 96 | 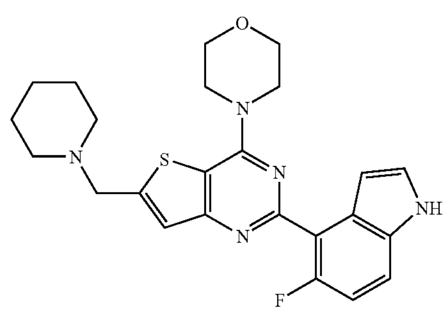 | 2-(5-Fluoro-1H-indol-4-yl)-4-morpholin-4-yl-6-piperidin-1-ylmethyl-thieno[3,2-d]pyrimidine |
| 97 | 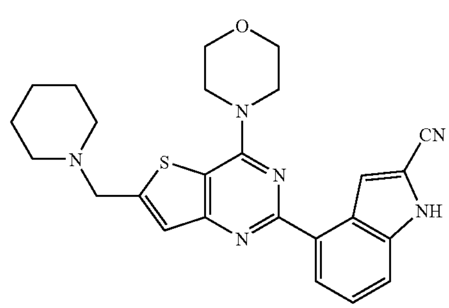 | 4-(4-Morpholin-4-yl-6-piperidin-1-ylmethyl-thieno[3,2-d]pyrimidin-2-yl)-1H-indole-2-carbonitrile |

TABLE 1-continued

| Compound No. | Structure | Name |
|---|---|---|
| 98 | 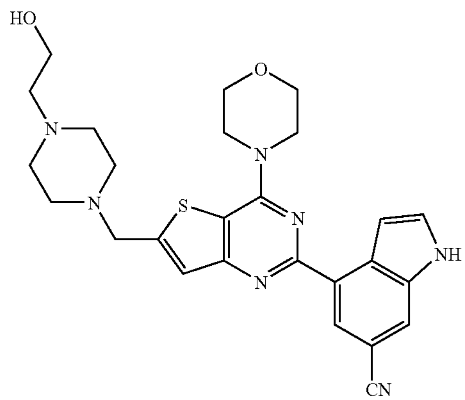 | 4-{6-[4-(2-Hydroxy-ethyl)-piperazin-1-ylmethyl]-4-morpholin-4-yl-thieno[3,2-d]pyrimidin-2-yl}-1H-indole-6-carbonitrile |
| 99 | 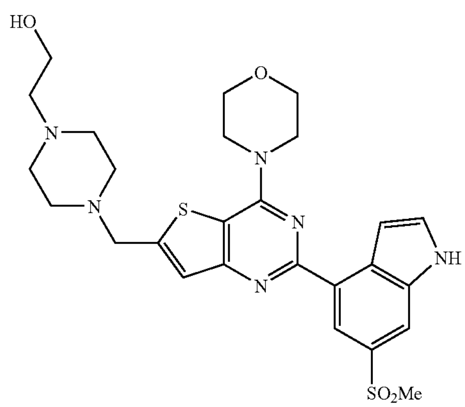 | 2-{4-[2-(6-Methanesulfonyl-1H-indol-4-yl)-4-morpholin-4-yl-thieno[3,2-d]pyrimidin-6-ylmethyl]-piperazin-1-yl}-ethanol |
| 100 | 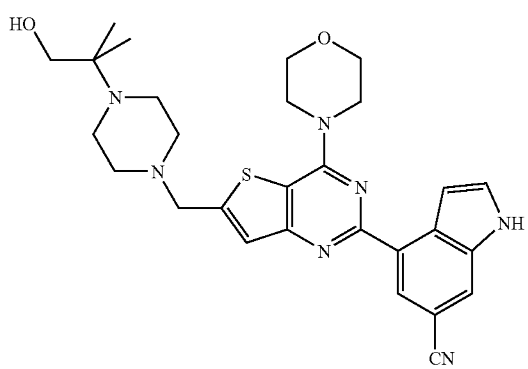 | 4-{6-[4-(2-Hydroxy-1,1-dimethyl-ethyl)-piperazin-1-ylmethyl]-4-morpholin-4-yl-thieno[3,2-d]pyrimidin-2-yl}-1H-indole-6-carbonitrile |
| 101 | 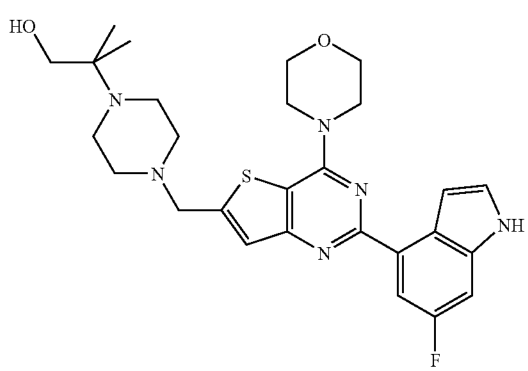 | 2-{4-[2-(6-Fluoro-1H-indol-4-yl)-4-morpholin-4-yl-thieno[3,2-d]pyrimidin-6-ylmethyl]-piperazin-1-yl}-2-methyl-propan-1-ol |

TABLE 1-continued

| Compound No. | Structure | Name |
|---|---|---|
| 102 | 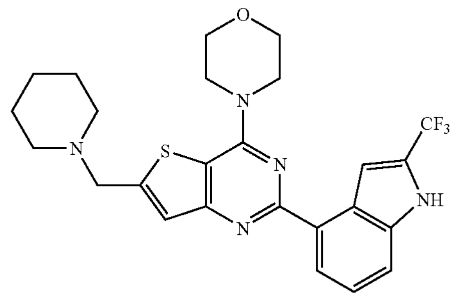 | 4-Morpholin-4-yl-6-piperidin-1-ylmethyl-2-(2-trifluoromethyl-1H-indol-4-yl)-thieno[3,2-d]pyrimidine |
| 103 | 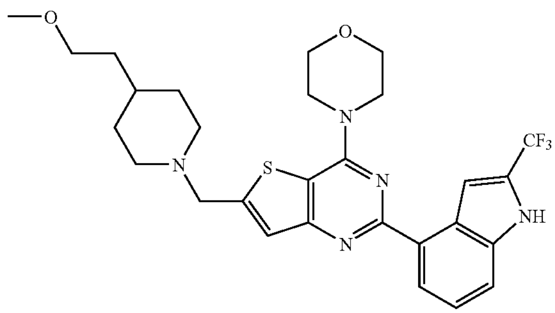 | 6-[4-(2-Methoxy-ethyl)-piperidin-1-ylmethyl]-4-morpholin-4-yl-2-(2-trifluoromethyl-1H-indol-4-yl)-thieno[3,2-d]pyrimidine |
| 104 | 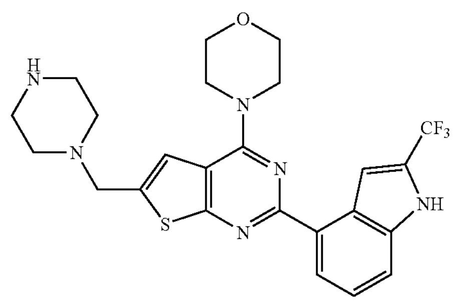 | 4-Morpholin-4-yl-6-piperazin-1-ylmethyl-2-(2-trifluoromethyl-1H-indol-4-yl)-thieno[2,3-d]pyrimidine |
| 105 | 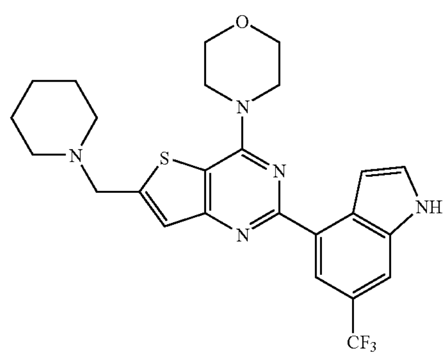 | 4-Morpholin-4-yl-6-piperidin-1-ylmethyl-2-(6-trifluoromethyl-1H-indol-4-yl)-thieno[3,2-d]pyrimidine |
| 106 | 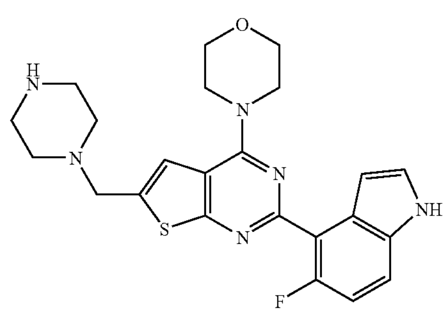 | 2-(5-Fluoro-1H-indol-4-yl)-4-morpholin-4-yl-6-piperazin-1-ylmethyl thieno[2,3-d]pyrimidine |

TABLE 1-continued

| Compound No. | Structure | Name |
|---|---|---|
| 107 | 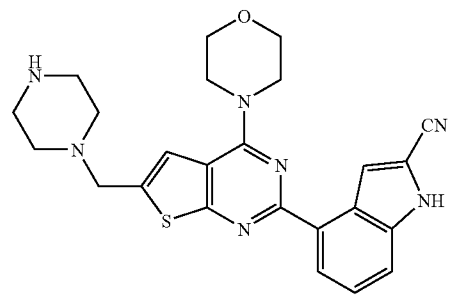 | 4-(4-Morpholin-4-yl-6-piperazin-1-ylmethyl-thieno[2,3-d]pyrimidin-2-yl)-1H-indole-2-carbonitrile |
| 108 | 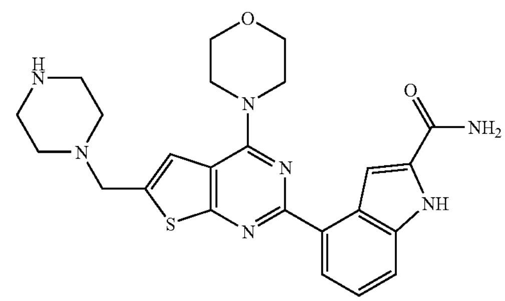 | 4-(4-Morpholin-4-yl-6-piperazin-1-ylmethyl-thieno[2,3-d]pyrimidin-2-yl)-1H-indole-2-carboxylic acid amide |
| 109 | 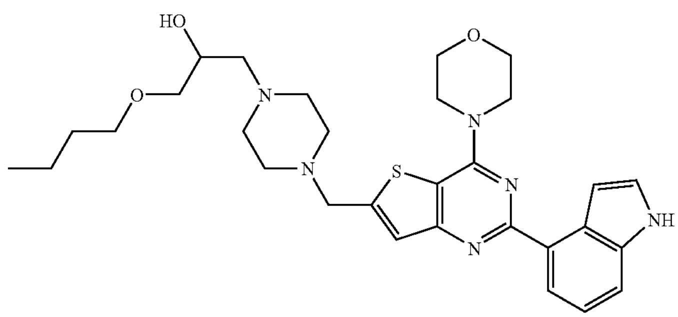 | 1-Butoxy-3-{4-[2-(1H-indol-4-yl)-4-morpholin-4-yl-thieno[3,2-d]pyrimidin-6-ylmethyl]-piperazin-1-yl}-propan-2-ol |
| 110 | 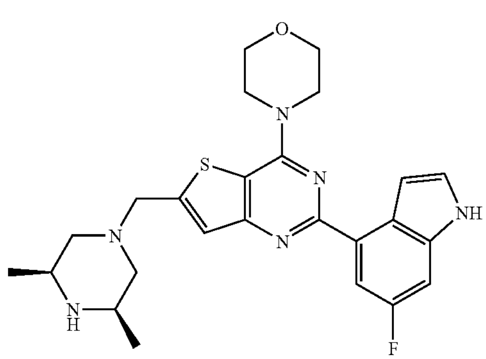 | 6-(cis-3,5-Dimethyl-piperazin-1-ylmethyl)-2-(6-fluoro-1H-indol-4-yl)-4-morpholin-4-yl-thieno[3,2-d]pyrimidine |

TABLE 1-continued

| Compound No. | Structure | Name |
| --- | --- | --- |
| 111 | 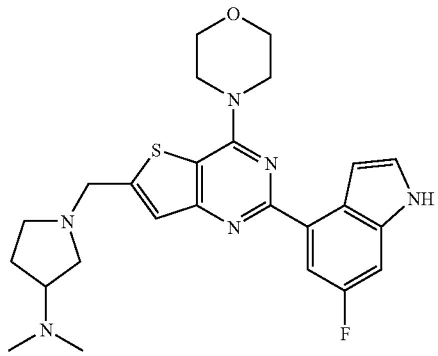 | {1-[2-(6-Fluoro-1H-indol-4-yl)-4-morpholin-4-yl-thieno[3,2-d]pyrimidin-6-ylmethyl]-pyrrolidin-3-yl}-dimethyl-amine |
| 112 | 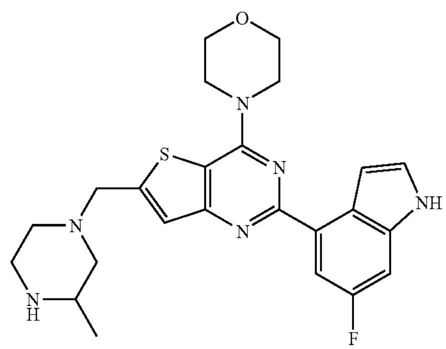 | 2-(6-Fluoro-1H-indol-4-yl)-6-(3-methyl piperazin-1-ylmethyl)-4-morpholin-4-yl-thieno[3,2-d]pyrimidine |
| 113 | 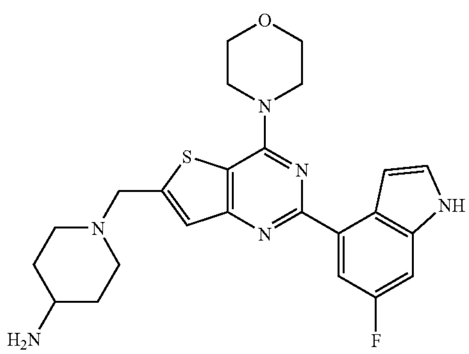 | 1-[2-(6-Fluoro-1H-indol-4-yl)-4-morpholin-4-yl-thieno[3,2-d]pyrimidin-6-ylmethyl]-piperidin-4-ylamine |
| 114 | 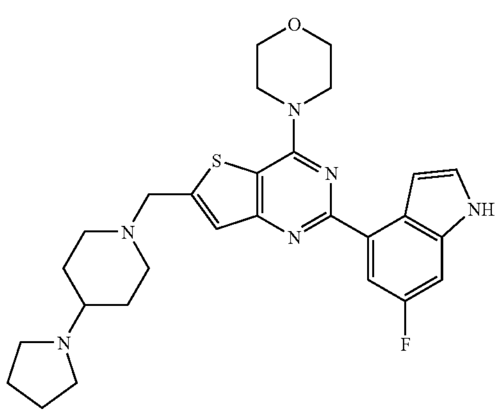 | 2-(6-Fluoro-1H-indol-4-yl)-4-morpholin-4-yl-6-(4-pyrrolidin-1-yl-piperidin-1-ylmethyl)-thieno[3,2-d]pyrimidine |

TABLE 1-continued

| Compound No. | Structure | Name |
|---|---|---|
| 115 | 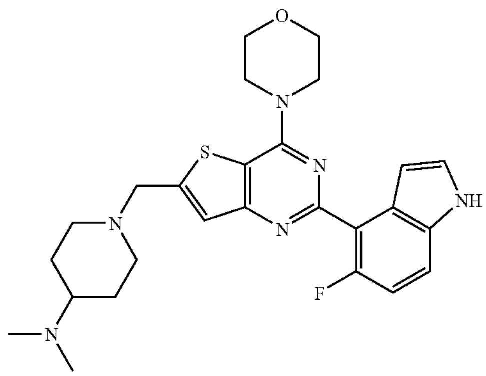 | {1-[2-(5-Fluoro-1H-indol-4-yl)-4-morpholin-4-yl-thieno[3,2-d]pyrimidin-6-ylmethyl]-piperidin-4-yl}-dimethyl-amine |
| 116 | 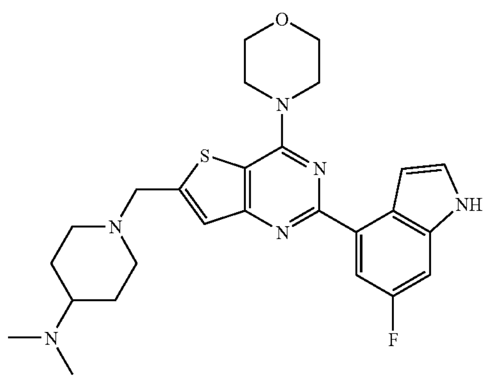 | {1-[2-(6-Fluoro-1H-indol-4-yl)-4-morpholin-4-yl-thieno[3,2-d]pyrimidin-6-ylmethyl]-piperidin-4-yl}-dimethyl-amine |
| 117 | 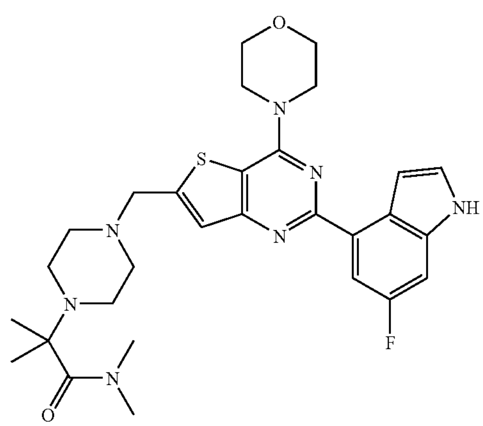 | 2-{4-[2-(6-Fluoro-1H-indol-4-yl)-4-morpholin-4-yl-thieno[3,2-d]pyrimidin-6-ylmethyl]-piperazin-1-yl}-N,N-dimethyl-isobutyramide |
| 118 | 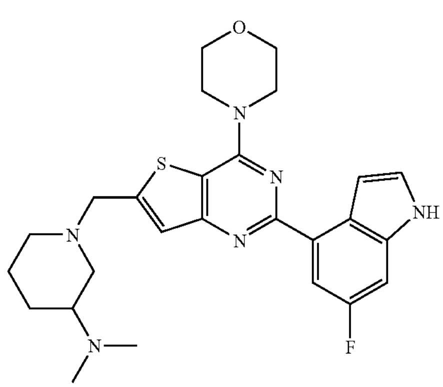 | {1-[2-(6-Fluoro-1H-indol-4-yl)-4-morpholin-4-yl-thieno[3,2-d]pyrimidin-6-ylmethyl]-piperidin-3-yl}-dimethyl-amine |

TABLE 1-continued

| Compound No. | Structure | Name |
| --- | --- | --- |
| 119 | 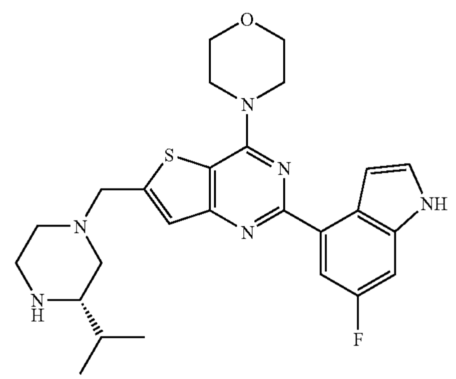 | 2-(6-Fluoro-1H-indol-4-yl-6-((S)-3-isopropyl-piperazin-1-ylmethyl)-4-morpholin-4-yl-thieno[3,2-d]pyrimidine |
| 120 | 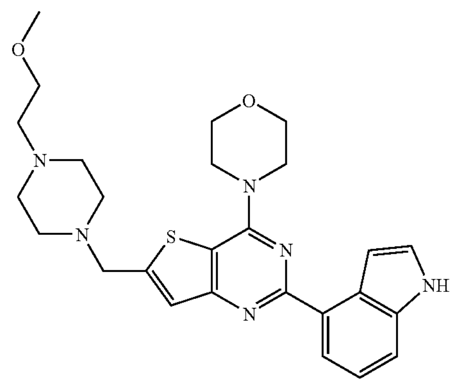 | 2-(1H-Indol-4-yl)-6-[4-(2-methoxy-ethyl)-piperazin-1-ylmethyl]-4-morpholin-4-yl-thieno[3,2-d]pyrimidine |
| 121 | 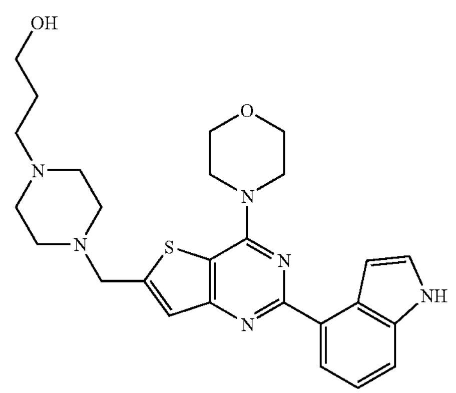 | 3-{4-[2-(1H-Indol-4-yl)-4-morpholin-4-yl-thieno[3,2-d]pyrimidin-6-ylmethyl]-piperazin-1-yl}-propan-1-ol |
| 122 | 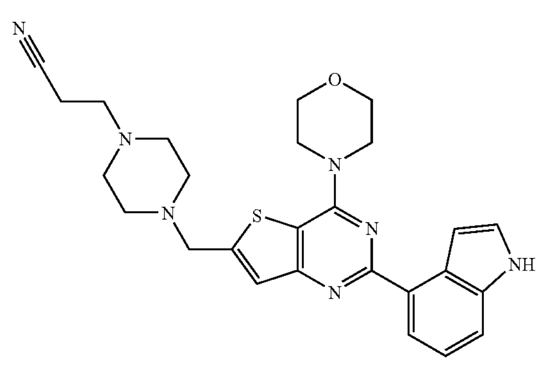 | 3-{4-[2-(1H-Indol-4-yl)-4-morpholin-4-yl-thieno[3,2-d]pyrimidin-6-ylmethyl]-piperazin-1-yl}-propionitrile |

TABLE 1-continued

| Compound No. | Structure | Name |
| --- | --- | --- |
| 123 | 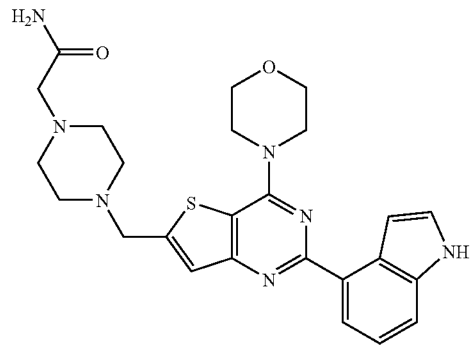 | 2-{4-[2-(1H-Indol-4-yl)-4-morpholin-4-yl-thieno[3,2-d]pyrimidin-6-ylmethyl]-piperazin-1-yl}-acetamide |
| 124 | 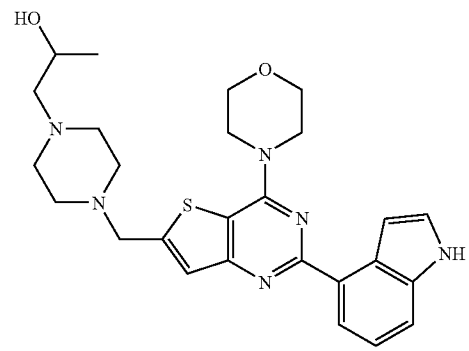 | 1-{4-[2-(1H-Indol-4-yl)-4-morpholin-4-yl-thieno[3,2-d]pyrimidin-6-ylmethyl]-piperazin-1-yl}-propan-2-ol |
| 125 | 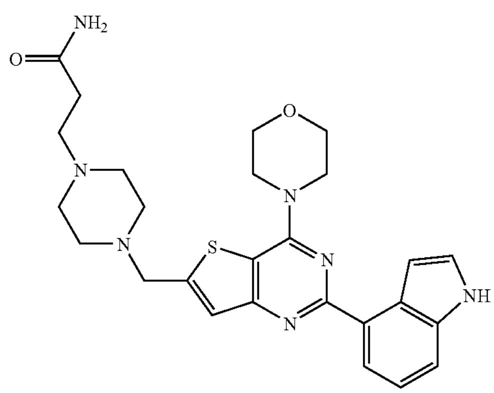 | 3-{4-[2-(1H-Indol-4-yl)-4-morpholin-4-yl-thieno[3,2-d]pyrimidin-6-ylmethyl]-piperazin-1-yl}-propionamide |
| 126 | 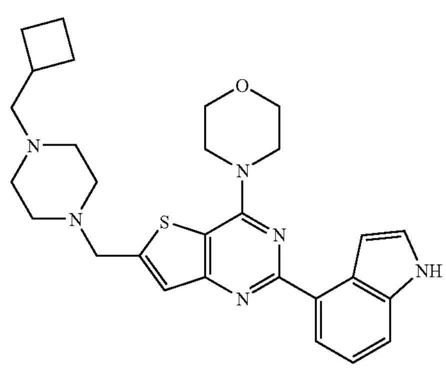 | 6-(4-Cyclobutylmethyl-piperazin-1-ylmethyl)-2-(1H-indol-4-yl)-4-morpholin-4-yl-thieno[3,2-d]pyrimidine |

TABLE 1-continued

| Compound No. | Structure | Name |
|---|---|---|
| 127 | 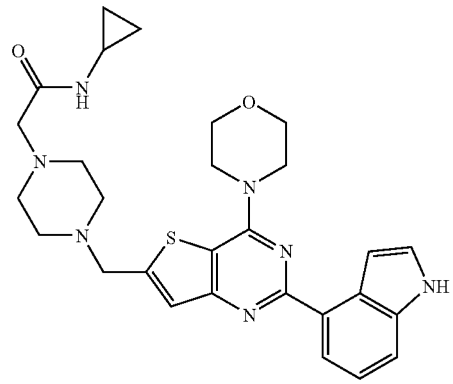 | N-Cyclopropyl-2-{4-[2-(1H-indol-4-yl)-4-morpholin-4-yl-thieno[3,2-d]pyrimidin-6-ylmethyl]-piperazin-1-yl}-acetamide |
| 128 | 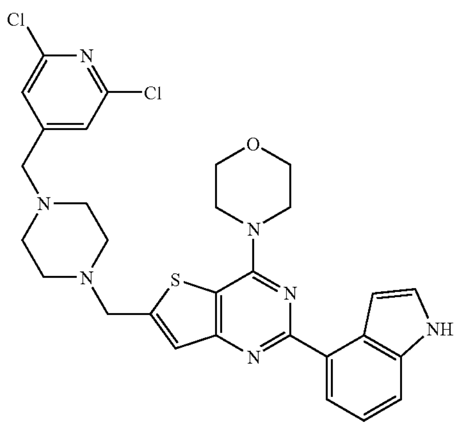 | 6-[4-(2,6-Dichloro-pyridin-4-ylmethyl)-piperazin-1-ylmethyl]-2-(1H-indol-4-yl)-4-morpholin-4-yl-thieno[3,2-d]pyrimidine |
| 129 | 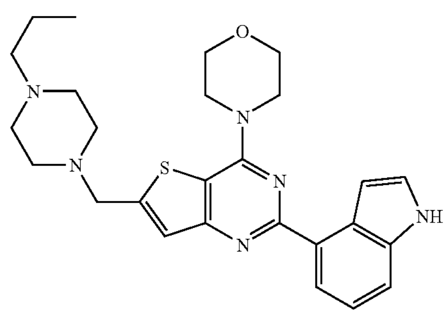 | 2-(1H-Indol-4-yl)-4-morpholin-4-yl-6-(4-propyl-piperazin-1-ylmethyl)-thieno[3,2-d]pyrimidine |
| 130 | 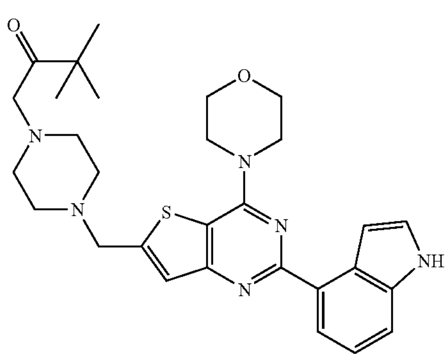 | 1-{4-[2-(1H-Indol-4-yl)-4-morpholin-4-yl-thieno[3,2-d]pyrimidin-6-ylmethyl]-piperazin-l-yl}-3,3-dimethyl-butan-2-one |

TABLE 1-continued

| Compound No. | Structure | Name |
|---|---|---|
| 131 | 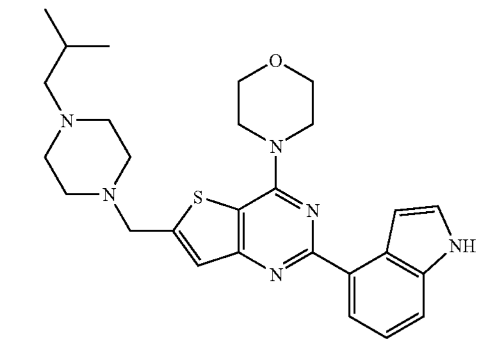 | 2-(1H-Indol-4-yl)-6-(4-isobutyl-piperazin-1-ylmethyl)-4-morpholin-4-yl-thieno[3,2-d]pyrimidine |
| 132 | 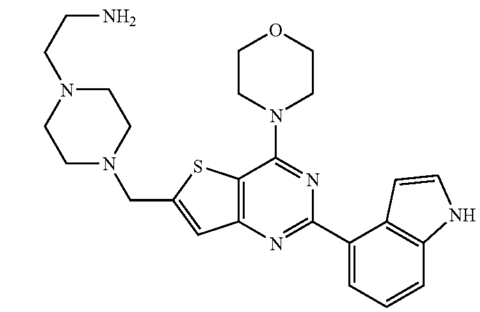 | 2-{4-[2-(1H-Indol-4-yl)-4-morpholin-4-yl-thieno[3,2-d]pyrimidin-6-ylmethyl]-piperazin-1-yl}-ethylamine |
| 133 | 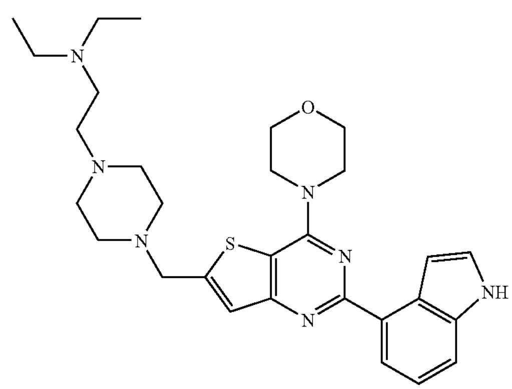 | Diethyl-(2-{4-[2-(1H-indol-4-yl)-4-morpholin-4-yl-thieno[3,2-d]pyrimidin-6-ylmethyl]-piperazin-1-yl}-ethyl)-amine |
| 134 | 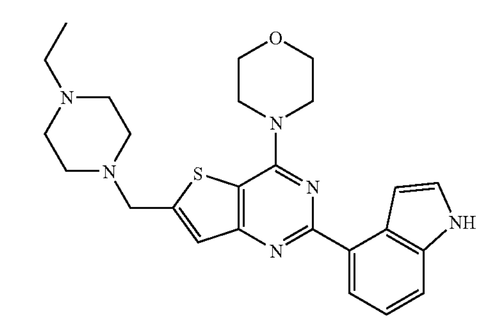 | 6-(4-Ethyl-piperazin-1-ylmethyl)-2-(1H-indol-4-yl)-4-morpholin-4-yl-thieno[3,2-d]pyrimidine |

TABLE 1-continued

| Compound No. | Structure | Name |
|---|---|---|
| 135 | 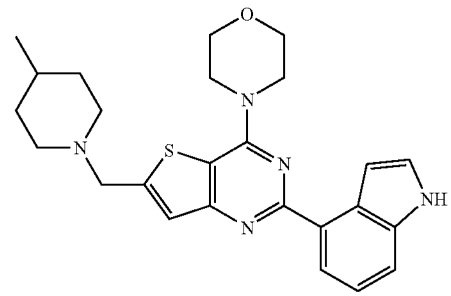 | 2-(1H-Indol-4-yl)-6-(4-methyl-piperidin-1-ylmethyl)-4-morpholin-4-yl thieno[3,2-d]pyrimidine |
| 136 | 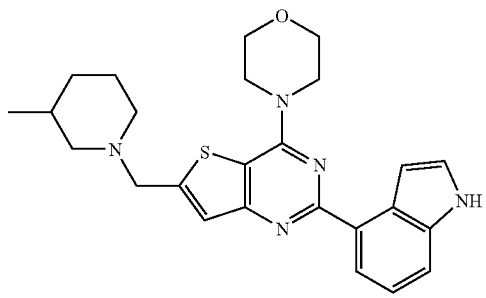 | 2-(1H-Indol-4-yl)-6-(3-methyl-piperidin-1-ylmethyl)-4-morpholin-4-yl thieno[3,2-d]pyrimidine |
| 137 | 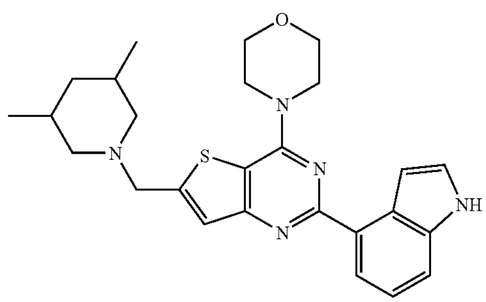 | 6-(3,5-Dimethyl-piperidin-1-ylmethyl)-2-(1H-indol-4-yl)-4-morpholin-4-yl-thieno[3,2-d]pyrimidine |
| 138 | 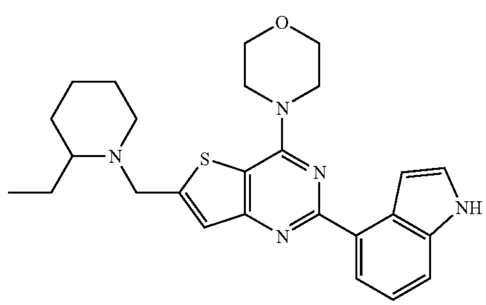 | 6-(2-Ethyl-piperidin-1-ylmethyl)-2-(1H indol-4-yl)-4-morpholin-4-yl-thieno[3,2-d]pyrimidine |
| 139 | 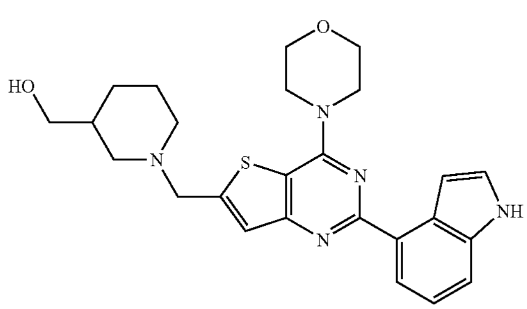 | {1-[2-(1H-Indol-4-yl)-4-morpholin-4-yl-thieno[3,2-d]pyrimidin-6-ylmethyl]-piperidin-3-yl}-methanol |

TABLE 1-continued

| Compound No. | Structure | Name |
|---|---|---|
| 140 | 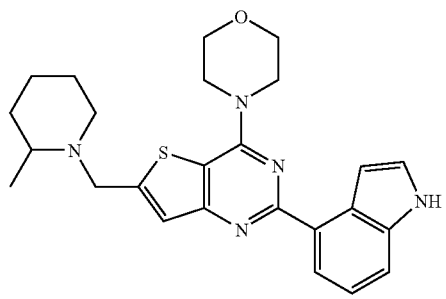 | 2-(1H-Indol-4-yl)-6-(2-methyl-piperidin-1-ylmethyl)-4-morpholin-4-yl thieno[3,2-d]pyrimidine |
| 141 | 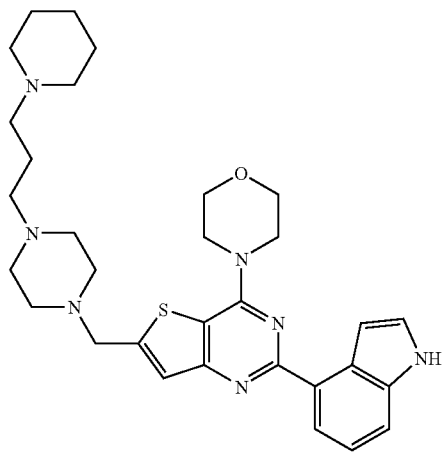 | 2-(1H-Indol-4-yl)-4-morpholin-4-yl-6-[4-(3-piperidin-1-yl-propyl)-piperazin-1-ylmethyl]-thieno[3,2-d]pyrimidine |
| 142 | 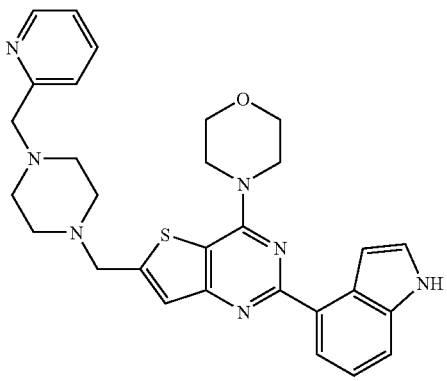 | 2-(1H-Indol-4-yl)-4-morpholin-4-yl-6-(4-pyridin-2-ylmethyl-piperazin-1-ylmethyl)-thieno[3,2-d]pyrimidine |
| 143 | 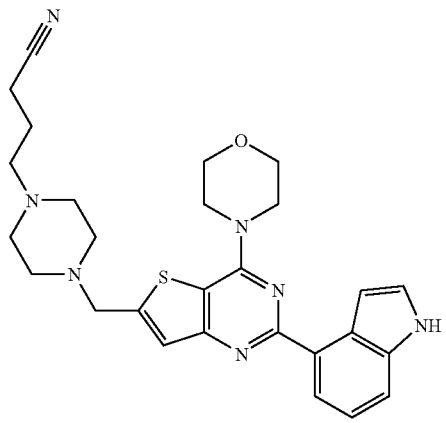 | 4-{4-[2-(1H-Indol-4-yl)-4-morpholin-4-yl-thieno[3,2-d]pyrimidin-6-ylmethyl]-piperazin-1-yl}-butyronitrile |

TABLE 1-continued

| Compound No. | Structure | Name |
|---|---|---|
| 144 | 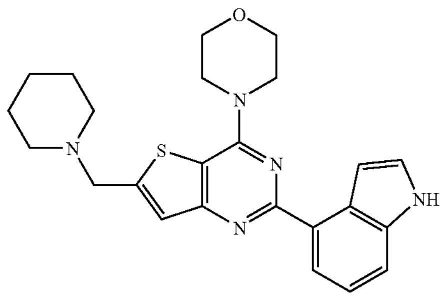 | 2-(1H-Indol-4-yl)-4-morpholin-4-yl-6-piperidin-1-ylmethyl-thieno[3,2-d]pyrimidine |
| 145 | 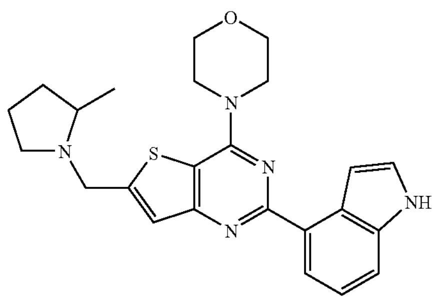 | 2-(1H-Indol-4-yl)-6-(2-methyl-pyrrolidin-1-ylmethyl)-4-morpholin-4-yl-thieno[3,2-d]pyrimidine |
| 146 | 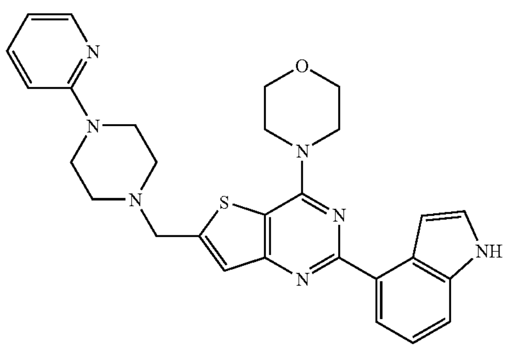 | 2-(1H-Indol-4-yl)-4-morpholin-4-yl-6-(4-pyridin-2-yl-piperazin-1-ylmethyl)-thieno[3,2-d]pyrimidine |
| 147 | 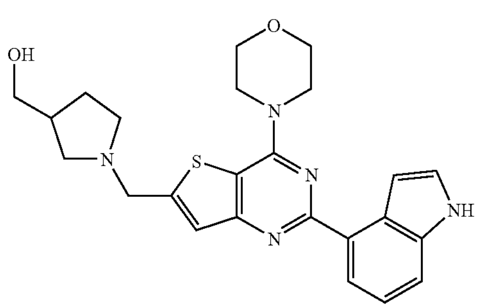 | {1-[2-(1H-Indol-4-yl)-4-morpholin-4-yl-thieno[3,2-d]pyrimidin-6-ylmethyl]-pyrrolidin-3-yl}-methanol |

TABLE 1-continued

| Compound No. | Structure | Name |
|---|---|---|
| 148 | 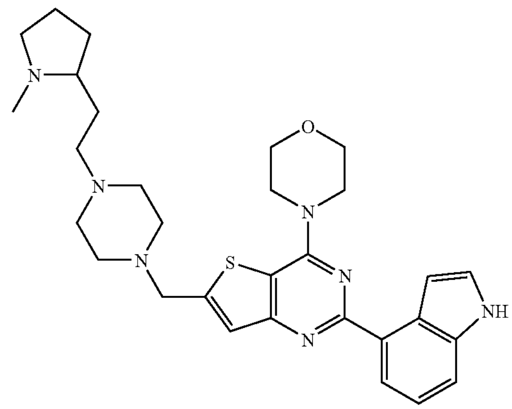 | 2-(1H-Indol-4-yl)-6-{4-[2-(1-methyl-pyrrolidin-2-yl)-ethyl]-piperazin-1-ylmethyl}-4-morpholin-4-yl-thieno[3,2-d]pyrimidine |
| 149 | 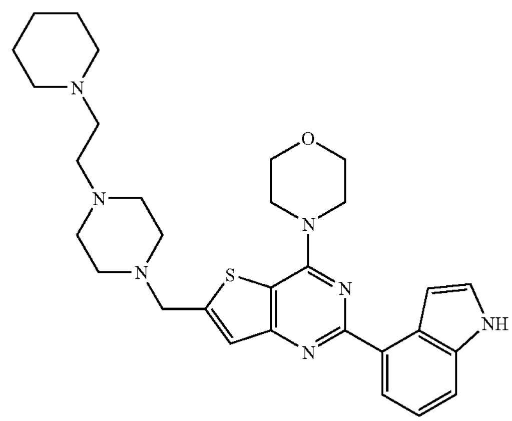 | 2-(1H-Indol-4-yl)-4-morpholin-4-yl-6-[4-(2-piperidin-1-yl-ethyl)-piperazin-1-ylmethyl]-thieno[3,2-d]pyrimidine |
| 150 | 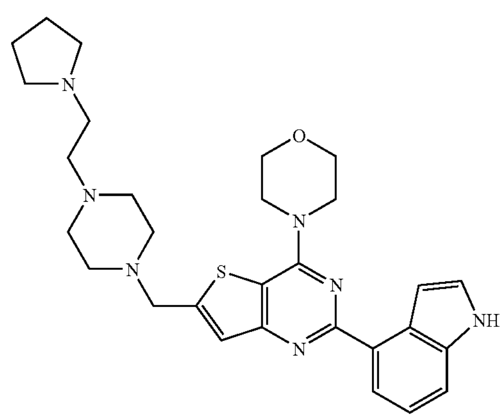 | 2-(1H-Indol-4-yl)-4-morpholin-4-yl-6-[4-(2-pyrrolidin-1-yl-ethyl)-piperazin-1-ylmethyl]-thieno[3,2-d]pyrimidine |
| 151 | 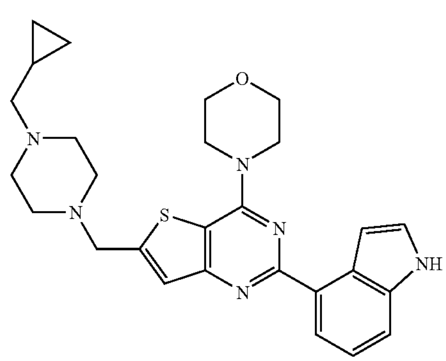 | 6-(4-Cyclopropylmethyl-piperazin-1-ylmethyl)-2-(1H-indol-4-yl)-4-morpholin-4-yl-thieno[3,2-d]pyrimidine |

TABLE 1-continued

| Compound No. | Structure | Name |
|---|---|---|
| 152 | 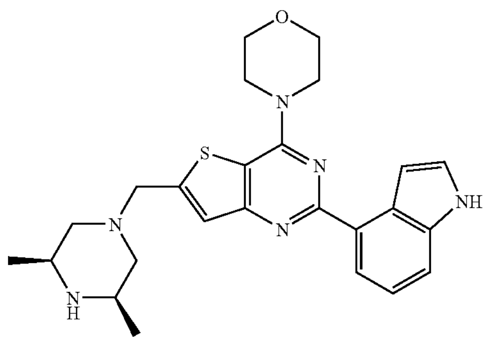 | 6-(cis-3,5-Dimethyl-piperazin-1-ylmethyl)-2-(1H-indol-4-yl)-4-morpholin-4-yl-thieno[3,2-d]pyrimidine |
| 153 | 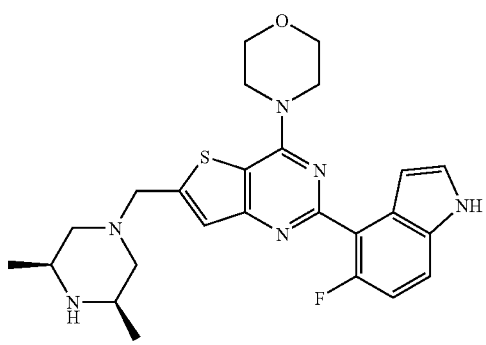 | 6-(cis-3,5-Dimethyl-piperazin-1-ylmethyl)-2-(5-fluoro-1H-indol-4-yl)-4-morpholin-4-yl-thieno[3,2-d]pyrimidine |
| 154 | 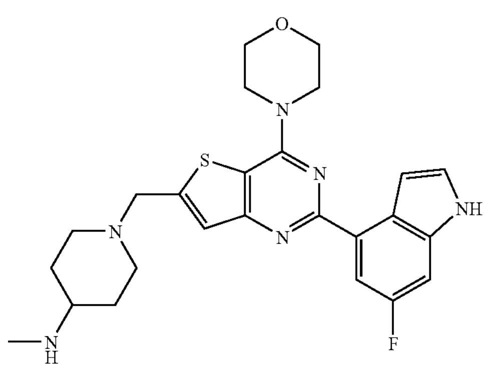 | {1-[2-(6-Fluoro-1H-indol-4-yl)-4-morpholin-4-yl-thieno[3,2-d]pyrimidin-6-ylmethyl]-piperidin-4-yl}-methyl-amine |
| 155 | | 2-(6-Fluoro-1H-indol-4-yl)-6-((R)-3-isopropyl-piperazin-1-ylmethyl)-4-morpholin-4-yl-thieno[3,2-d]pyrimidine | and the pharmaceutically acceptable salts thereof.

The compounds of the invention may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

A suitable synthetic strategy for producing compounds of the invention as defined above employs the precursor carboxaldehyde of formula (IIa) or (IIb):

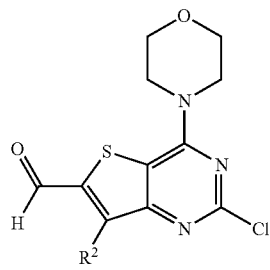
(IIa)

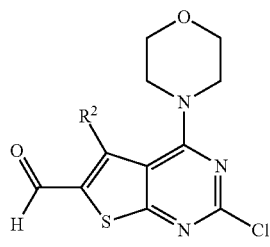
(IIb)

wherein $R^2$ is as defined above. Starting from this precursor the synthesis comprises performing, in either order, a palladium-mediated (Suzuki-type) cross-coupling reaction and a reductive amination. The process comprises (a) treating a compound of formula (IIa) or (IIb):

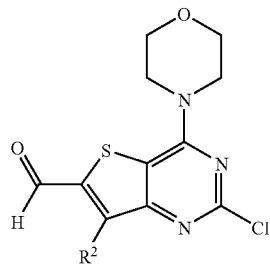
(IIa)

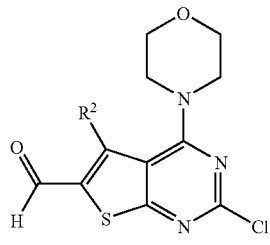
(IIb)

wherein $R^2$ is as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (IIIa) or (IIIb):

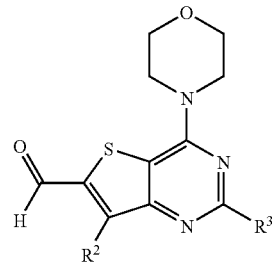
(IIIa)

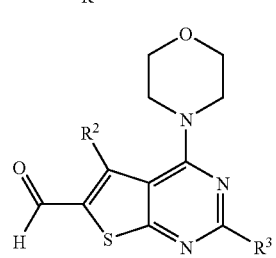
(IIIb)

wherein $R^2$ and $R^3$ are as defined above, with an amine of formula $NHR^4R^5$ in which $R^4$ and $R^5$ are as defined above, in the presence of a suitable reducing agent; or (b) treating a compound of formula (IIa) or (IIb) as defined above with an amine of formula $NHR^4R^5$ wherein $R^4$ and $R^5$ are as defined above, in the presence of a suitable reducing agent; and treating the resulting compound of formula (IVa) or (IVb):

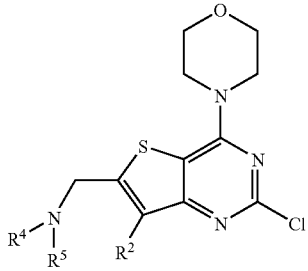
(IVa)

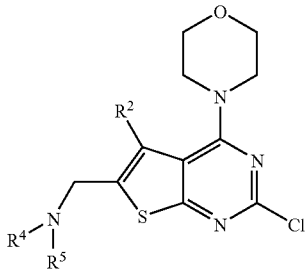
(IVb)

wherein $R^2$, $R^4$ and $R^5$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

Accordingly, the present invention provides a process for producing a compound of the invention as defined above, which process comprises treating a compound of formula (IIIa or (IIIb):

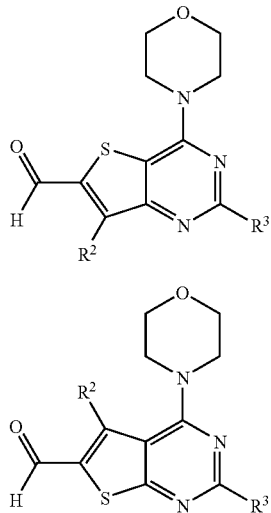

(IIIa)

(IIIb)

wherein $R^2$ and $R^3$ are as defined above, with an amine of formula $NHR^4R^5$ in which $R^4$ and $R^5$ are as defined above, in the presence of a suitable reducing agent.

The process may further comprise producing the compound of formula (IIIa) or (IIIb) by treating a compound of formula (IIa) or (IIb):

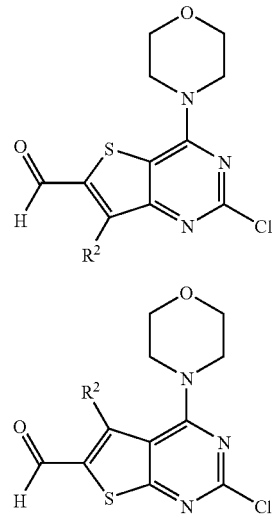

(IIa)

(IIb)

wherein $R^2$ is as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

The invention further provides a process for producing a compound of the invention as defined above, which process comprises treating a compound of formula (IVa) or (IVb):

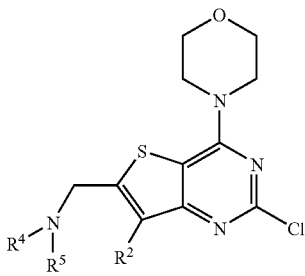

(IVa)

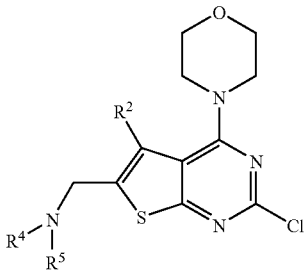

(IVb)

wherein $R^2$, $R^4$ and $R^5$ are as defined above, with a boronic acid or ester thereof of formula $R^3B(OR^{15})_2$ in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

The process may further comprise producing the compound of formula (IVa) or (IVb) by treating a compound of formula (IIa or (IIb):

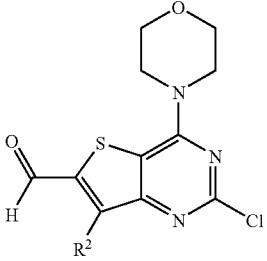

(IIa)

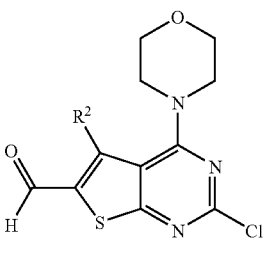

(IIb)

wherein $R^2$ is as defined above, with an amine of formula $NHR^4R^5$ in which $R^4$ and $R^5$ are as defined above, in the presence of a suitable reducing agent.

A pharmaceutically acceptable salt of a thienopyrimidine of the invention may be prepared using conventional techniques. Typically the process comprises treating the thienopyrimidine of formula (I) as defined above with a suitable acid in a suitable solvent. Likewise a salt may be converted into the free compound by conventional methods.

In the process of the invention as defined above, both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_3$, in particular $NaBH(OAc)_3$.

Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulfonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. Typically the salt is a mesylate, a hydrochloride, a phosphate, a benzenesulfonate or a sulfate. Most typically the salt is a mesylate or a hydrochloride.

The salts, for instance salts with any of the inorganic or organic acids mentioned above, may be mono-salts or bis-salts. Thus, for example, the mesylate salt may be the mono-mesylate or the bis-mesylate.

The thienopyrimidines of the invention and their salts may exist as hydrates or solvates.

Compounds of the present invention have been found in biological tests to be inhibitors of PI3 kinase. The compounds are selective for class Ia PI3 kinases over class Ib and typically exhibit at least a 20-fold selectivity for class Ia over class Ib PI3 kinases. In particular, the compounds are selective for the p110δ (delta) isoform. In particular, they are selective for the delta isoform over the alpha and/or the gamma isoform. Certain compound of the invention are selective for the delta isoform over the alpha, beta and gamma isoforms.

A compound of the present invention may thus be used as an inhibitor of PI3 kinase. In particular, it may be used as an inhibitor of a class Ia PI3 kinase, more particularly of the p110δ isoform of PI3 kinase. A compound of the present invention can be used to treat a disease or disorder arising from abnormal cell growth, function or behaviour, in particular abnormal cell growth, function or behaviour associated with PI3 kinase, especially the p110 delta isoform of PI3 kinase. Examples of such diseases and disorders are discussed by Drees et al in Expert Opin. Ther. Patents (2004) 14(5):703-732. These include immune disorders, cardiovascular disease, viral infection, inflammation, metabolism/endocrine disorders and neurological disorders. Examples of metabolism/endocrine disorders include diabetes and obesity.

Specific examples of diseases and conditions treatable according to the methods of this invention include, but are not limited to, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia or Ib and a pharmaceutically acceptable carrier, adjuvant, or vehicle, wherein said compound of Formula Ia or Ib is present in an amount to detectably inhibit PI3 kinase activity.

A human or animal patient suffering from an immune disorder, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Cardiovascular diseases which can be treated according to the methods of this invention include, but are not limited to, restenosis, cardiomegaly, atherosclerosis, myocardial infarction, and congestive heart failure.

Neurological and neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Compounds of the invention may also be useful in treating cancer or in ameliorating the condition of a patient suffering from cancer or harbouring a tumour. Examples of such cancers include leukaemia, brain tumours, renal cancer, gastric cancer and cancer of the skin, bladder, breast, uterus, lung, colon, prostate, ovary and pancreas.

In addition to possessing biochemical potency the compounds of the invention exhibit physicochemical and pharmacokinetic properties which make them particularly well adapted for drug use. In particular the compounds possess good aqueous solubility at physiological pH; many have a solubility of at least 40 µM and a significant number have a solubility of greater than 100 µM. High solubility at physiological pH is desirable since it promotes bioavailability. The compounds also possess high metabolic stability. The compounds of the present invention possess improved physicochemical and pharmacokinetic properties whilst retaining biochemical potency as inhibitors of PI3 kinase, in particular of p110 delta.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

Typically a dose to treat human patients may range from about 10 mg to about 1000 mg of a compound of the invention. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

F) Vaginally, in the form of pessaries, tampons, creams, gels, pastes, foams or spray formulations containing in addition to the active ingredient such carriers as are known in the art to be appropriate.

Sustained-release preparations of a compound of the invention may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

A compound of the invention may be employed alone or in combination with a second therapeutic agent for the treatment of a disease or disorder described herein, such as an immune disorder, an inflammatory condition, a cardiovascular disorder or a neurodegenerative disorder. In certain embodiments, a compound of the invention is combined in a pharmaceutical combination formulation, or dosing regimen as combination therapy, with a second such therapeutic agent. The second compound of the pharmaceutical combination formulation or dosing regimen preferably has complementary activities to the compound of the invention such that they do not adversely affect each other. Such compounds are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The invention will be further described in the Examples which follow:

EXAMPLE 1

General Synthetic Procedures

The following general schemes 1 to 10 are referred to in the Reference Examples and Examples which follow:

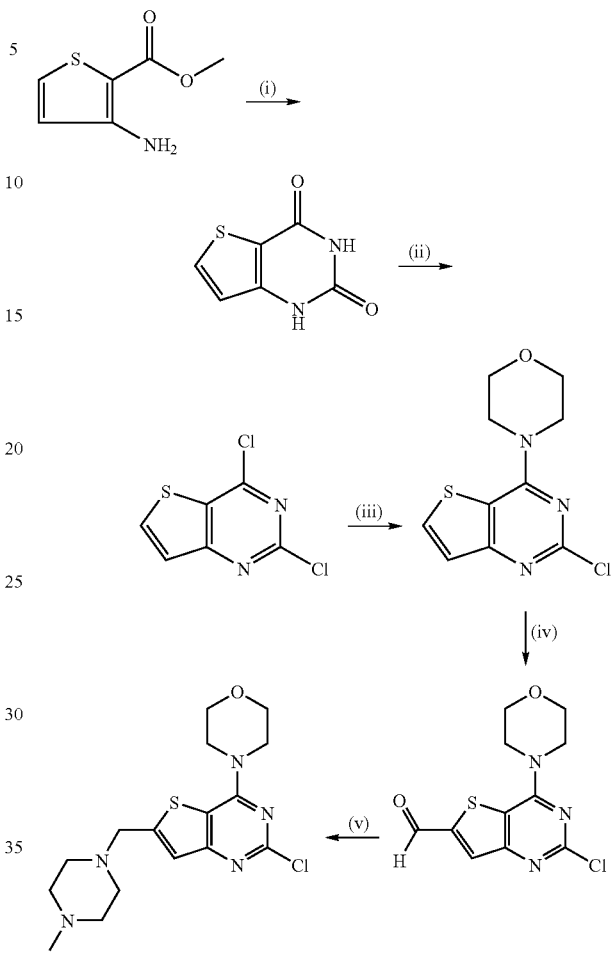

Conditions: (i) urea, 190° C., 2 hours; (ii) POCl₃, 100° C., 24 hours; (iii) morpholine, RT, 1 hour; (iv) n-BuLi, −78° C., 1 hour then DMF −78° C.→room temp; (v) Na(OAc)₃BH, 1,2-dichloroethane, N-methyl piperazine, HOAc, room temp.

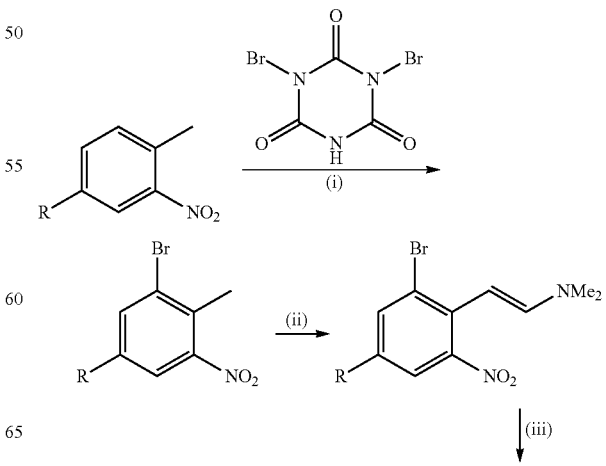

-continued

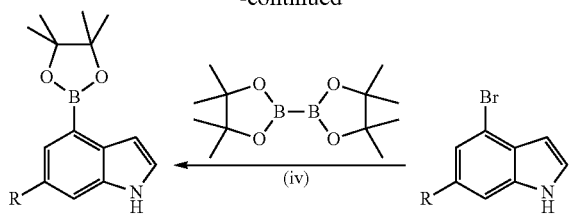

Conditions: (i) H₂SO₄, 21 h. (ii) Dioxane, DMF-DMA, 80° C. 24 h, 90° C. 16 h. (iii) MeOH-THF Raney® Nickel, NH₂NH₂.H₂O, RT, 40 min. (iv) DMSO, KOAc, Pd(dppf)₂Cl₂ 80° C.

Scheme 3

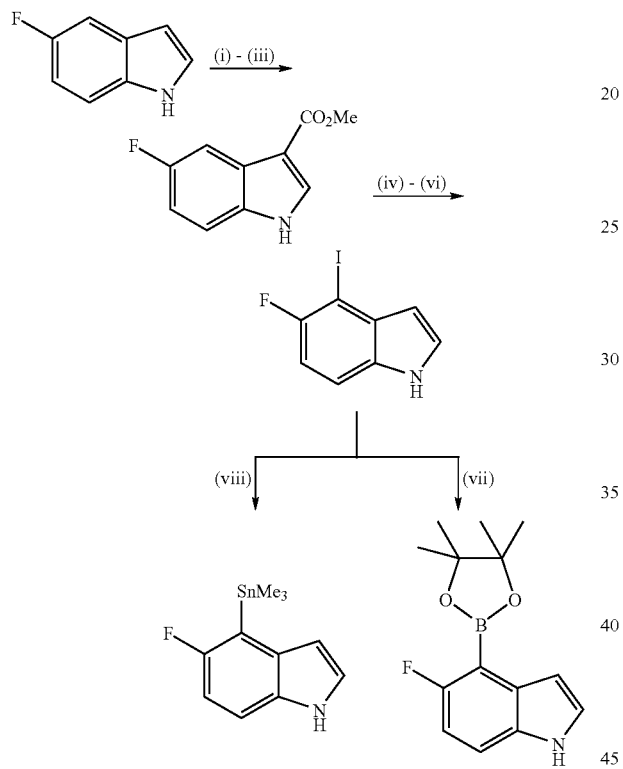

Conditions: (i) DMF, TFAA, 0° C. (ii) 10% aq NaOH, 100° C., 1 h. (iii) MeOH, H₂SO₄, 65° C., 18 h. (iv) Tl(OCOCF₃)₃, TFA, RT, 2 h. (v) H₂O, KI, RT. (vi) MeOH 40% aq NaOH, 65° C., 2 h. (vii) pinacol borane, Et₃N, Dioxane, Pd(OAc)₂, bis(cyclohexyl)phosphino-2-biphenyl, 80° C., 30 min. (viii) (Me₃Sn)₂, PdCl₂(PPh₃)₂, dioxane, 90° C., microwave, 2 h.

Scheme 4

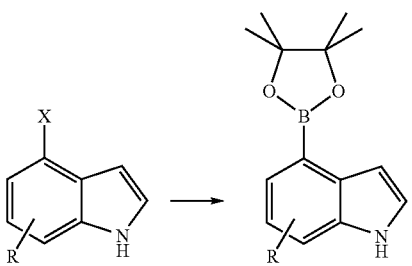

Conditions: (i) (COCl)₂, DCM, 2 h RT. (ii) NH₃—H₂O, 3 d, RT. (iii) POCl₃, Toluene, 111° C., 45 min.

Scheme 5

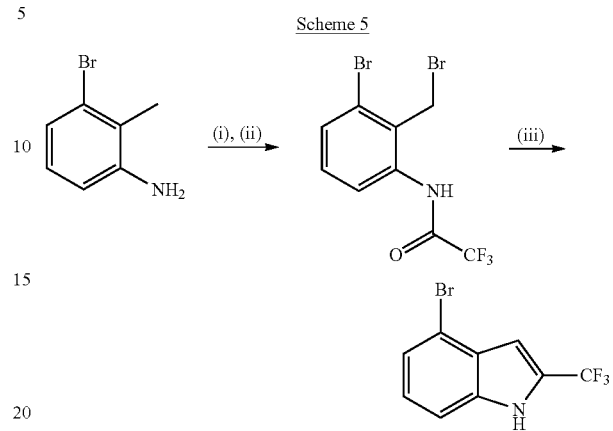

Conditions: (i) DCM-pyridine, 0° C., TFAA, 2 h, RT. (ii) benzoyl peroxide, CCl₄, 80° C., irradiation, Br₂, 16 h. (iii) Toluene, PPh₃, 60° C., 2 h then DMF, 16 h, reflux.

Scheme 6

Scheme 7

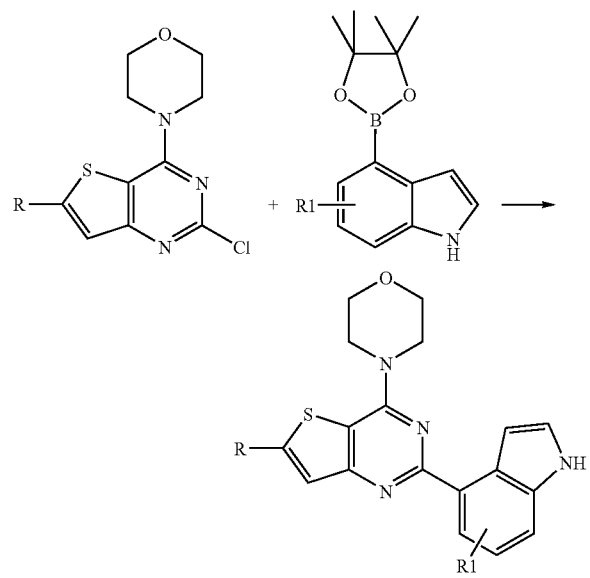

Scheme 8

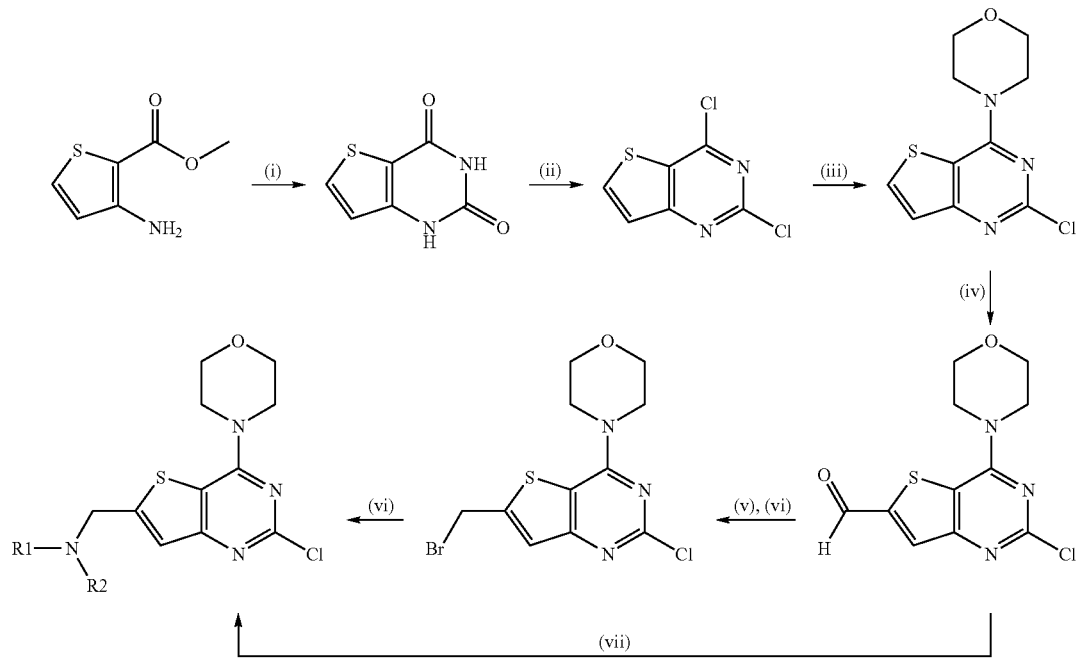

Conditions: (i) urea, 190° C., 2 h; (ii) POCl$_3$, 100° C., 24 h; (iii) morpholine, RT, 1 h; (iv) n-BuLi, −78° C., 1 h then DMF −78° C.→RT; (v) NaBH4, THF-IMS, RT, 2 h. (vi) DCM, PPh$_3$, CBr$_4$, RT, 5 h. (vii) Na(OAc)$_3$BH, 1,2-dichloroethane, R1R2NH, HOAc, RT.

Scheme 9

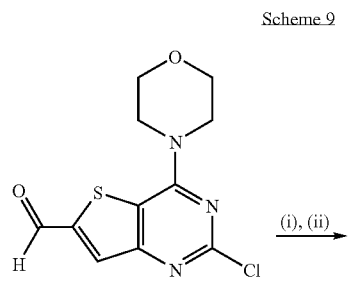

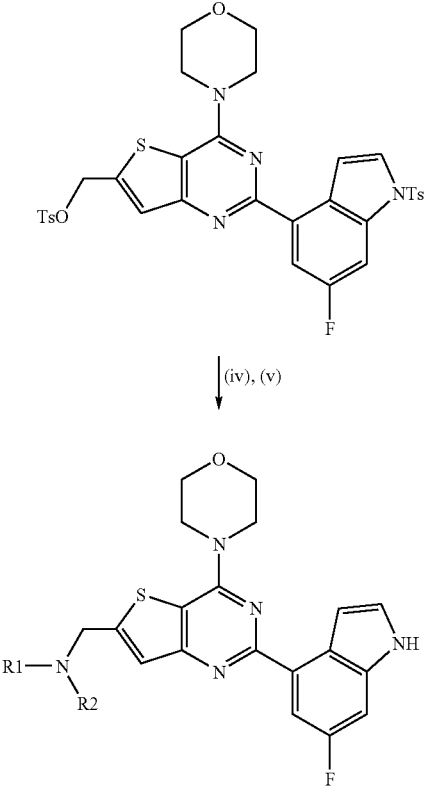

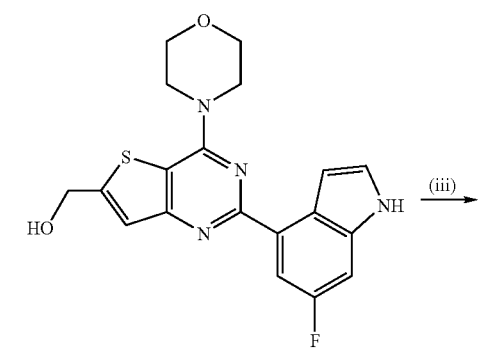

Conditions: (i) NaBH$_4$, THF-IMS, RT, 2 h. (ii) 4-indole boronate ester, CH$_3$CN—H$_2$O, Na$_2$CO$_3$, PdCl$_2$(PPh$_3$)$_2$, 140° C. microwave (iii) THF-DCM, NaH, RT, 10 min then TsCl, 40° C., 3 h. (iv) R2R2NH, DMF, K$_2$CO$_3$, 2 h, RT. (v) Dioxane-IMS, NaOH, H$_2$O RT, 3 h.

General Experimental Details:
All reactions were carried out under an atmosphere of nitrogen unless specified otherwise.
NMR Spectrometry
NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 400 spectrometer with a 5 mm $^1H/^{13}C$ Dual autotune probe operating at 400 MHz for $^1H$ or on a Bruker Avance DPX 300 spectrometer with a standard 5 mm dual frequency probe operating at 300 MHz. Shifts are given in ppm relative to tetramethylsilane @303K.
Purification by Chromatography:
Compounds purified by chromatography were purified by column chromatography on silica gel or Isolute® cartridge or Redisep® cartridge, eluting with gradients from 100-0 to 0-100% of cyclohexane/EtOAc, or from 100-0 to 0-100% pentane/EtOAc or from 100-0 to 70-30% DCM/MeOH (with or without the addition of $NH_3$ 0.1%). 'Silica gel' refers to silica gel for chromatography, 0.035 to 0.070 mm (220 to 440 mesh) (e.g. Fluka silica gel 60), and an applied pressure of nitrogen up to 10 p.s.i accelerated column elution. Where thin layer chromatography (TLC) has been used, it refers to silica gel TLC using plates, typically 3×6 cm silica gel on aluminium foil plates with a fluorescent indicator (254 nm), (e.g. Fluka 60778).
Purification by Preparative HPLC:
Compounds purified by preparative HPLC were purified using either conditions A: Waters XBridge Prep Phenyl column (150×19 mm i.d. column with 5 μm particle size, PDA/MS detection, flow 21.25 ml/min), eluting with gradients from 95-5% to 5-95% water/acetonitrile containing 0.1% dimethylethylamine; or conditions B: C18-reverse-phase column (100×22.5 mm i.d Genesis column with 7 μm particle size, UV detection at 230 or 254 nm, flow 5-15 mL/min), or a Phenyl-Hexyl column (250×21.2 mm i.d. Gemini column with 5 μm particle size, UV detection at 230 or 254 nm, flow 5-20 mL/min), eluting with gradients from 100-0% to 0-100% water/acetonitrile or water/MeOH containing 0.1% TFA or water/acetonitrile containing 0.1% formic acid. The free base was liberated by partitioning between EtOAc and a sat. solution of sodium bicarbonate. The organic layer was dried ($MgSO_4$) and concentrated in vacuo. Alternatively, the free base was liberated by passing through an Isolute® SCX-2 cartridge, eluting with $NH_3$ in methanol.
Abbreviations Used in the Experimental Section:
aq.=aqueous
BOC=t-Butoxycarbonyl
bs=broad singlet (NMR)
$Cs_2CO_3$=cesium carbonate
d=doublet (NMR)
DCM=dichloromethane
DIPEA=diisopropylethylamine
DMA=dimethylacetamide
DMAP=dimethylaminopyridine
DMF=dimethylformamide
DMSO=dimethylsulfoxide
eq.=equivalents
EtOAc=ethyl acetate
EtOH=ethanol
h=hour(s)
HCl=hydrochloric acid
$H_2O$=water
HPLC=high pressure liquid chromatography
IMS=industrial methylated spirit
iPrOH=isopropanol
LCMS=liquid chromatography mass spectrometry
M=molar
m=multiplet (NMR)
MeOH=methanol
mg=milligram
$MgSO_4$=magnesium sulphate
min=minute(s)
mL=millilitre
$Na_2CO_3$=sodium carbonate
NaOH=sodium hydroxide
$Na_2SO_4$=sodium sulfate
NMR=nuclear magnetic resonance
q=quartet (NMR)
Rt=retention time
RT=room temperature
sat=saturated
s=singlet (NMR)
t=triplet (NMR)
TFA=trifluoroacetic acid
THF=tetrahydrofuran
TLC=thin layer chromatography

REFERENCE EXAMPLE 1

General Method Used for the Formation of Boronate Esters

The boronate ester product of scheme 6 above was prepared as follows: To a solution of halide (1 eq.) and bis(pinacolato)diboron (1.3 eq.) in DMSO were added KOAc (3 eq.) and [1,1'-bis(diphenylphosphine)ferrocene]dichloropalladium (0.05 eq.). The mixture was heated at 90° C. until completion of the reaction. The reaction mixture was partioned between EtOAc and $H_2O$. The organic layer was washed successively with $H_2O$ and brine, dried over $Na_2SO_4$ and evaporated to dryness. The resultant residue was then purified by column chromatography.

REFERENCE EXAMPLE 2

Suzuki Coupling

The Suzuki coupling depicted in scheme 7 above was performed using one of the following three synthetic strategies:
Method A
A mixture of 2-chloro-pyrimidine (1 eq.), $Na_2CO_3$ (2 eq.), indole boronate ester (1.5 eq.) and bis(triphenylphosphine)palladium (II) chloride (0.1 eq.) in acetonitrile/water (2:1) was heated at 140° C. for 20-50 min in a microwave reactor (Smith synthetiser or CEM Discover). The resulting mixture was diluted with water then extracted with ethyl acetate. Combined extracts were dried ($Na_2SO_4$), filtered and concentrated then purified by either HPLC or column chromatography to give the desired product.
Method B
A mixture of 2-chloro-pyrimidine (1 eq.), $Cs_2CO_3$ (1.5 eq.), indole boronate ester (1.2 eq.) and tetrakis(triphenylphosphine)palladium (0.05 eq.) in dioxane/water (3:1) was heated at 125° C., for 10-30 min in a microwave reactor (Smith synthetiser). The resulting mixture was diluted with water then extracted with ethyl acetate. The combined organic extracts were dried ($MgSO_4$), filtered and concentrated then purified by either preparative HPLC or column chromatography to give the desired product. Alternatively, the reaction mixture was loaded onto an Isolute® SCX-2 cartridge, washed with MeOH then eluted with 2 M $NH_3$ in MeOH. The resulting residue was then purified by either preparative HPLC or column chromatography to give the desired product.

Method C

A mixture of 2-chloro-pyrimidine (1 eq.), Na₂CO₃ (3 eq.), indole boronate ester (2.0 eq.) and bis(triphenylphosphine) palladium (II) chloride (0.05 eq.) in toluene/ethanol/water (4:2:1) was heated at 130° C. for 1-1.5 h in a microwave reactor (Smith synthetiser or CEM Discover). The resulting mixture was diluted with water then extracted with ethyl acetate. Combined extracts were dried (Na₂SO₄), filtered and concentrated then purified by either HPLC or column chromatography to give the desired product.

REFERENCE EXAMPLE 3

1H-Thieno[3,2-d]pyrimidine-2,4-dione

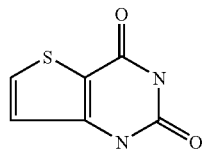

A mixture of methyl 3-amino-2-thiophenecarboxylate (13.48 g, 85.85 mmol) and urea (29.75 g, 5 equivalents) was heated at 190° C. for 2 hours. The hot reaction mixture was then poured onto sodium hydroxide solution (2N, 300 mL) and any insoluble material removed by filtration. The mixture was then acidified to pH 6 by the addition concentrated HCl with cooling. The resultant white precipitate was collected by filtration and air dried (9.49g, 66%).

$\delta$H (400 MHz, d-6 DMSO) 11.60-11.10 (2H, br, s), 8.10 (1H, d, J 5.2), 6.90 (1H, d, J 5.2).

REFERENCE EXAMPLE 4

2,4-Dichloro-thieno[3,2-d]pyrimidine

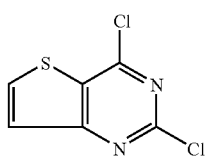

To a suspension of 1H-thieno[3,2-d]pyrimidine-2,4-dione (10.0 g, 59.52 mmol) in acetonitrile (50 mL) was added phosphorous oxychloride (300 mmol, 5 equivalents, 28 mL) and the mixture heated at reflux for 24 hours in a flask fitted with a mechanical stirrer. The reaction mixture was then cooled and poured cautiously onto ice-water (250 mL) maintaining the temperature below 20° C. The mixture was filtered to yield 2,4-dichloro-thieno[3,2-d]pyrimidine as an off-white solid (9.15 g, 75%).

$\delta$H (400 MHz, CDCl₃) 8.13 (1H, d, J 5.5), 7.56 (1H, d, J 5.5).

REFERENCE EXAMPLE 5

2-Chloro-4-morpholin-4-yl-thieno[3,2-d]pyrimidine

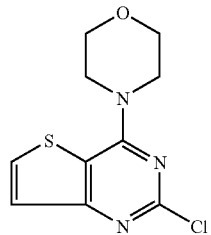

A mixture of 2,4-dichloro-thieno[3,2-d]pyrimidine (8.68 g, 42.34 mmol), morpholine (8.11 mL, 2.2 equivalents) and methanol (150 mL) was stirred at room temperature for 1 hour. The reaction mixture was then filtered, washed with water to yield the title compound as a white solid (11.04 g, 100%).

$\delta$H (400 MHz, d-6 DMSO) 8.30 (1H, d, J 5.6), 7.40 (1H, d, J 5.6), 3.90 (4H, t, J 4.9), 3.74 (4H, t, J 4.9).

REFERENCE EXAMPLE 6

2-Chloro-4-morpholin-4-yl-thieno[3,2-d]pyrimidine-6-carbaldehyde

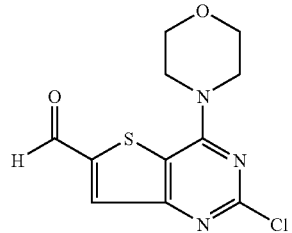

To a suspension of 2-chloro-4-morpholin-4-yl-thieno[3,2-d]pyrimidine (1.75 g, 6.85 mmol) in dry tetrahydrofuran (40 mL) at −78° C. was added nBuLi (3.3 mL, 1.2 equivalents, 2.5 M solution in hexanes). After stirring for 1 hour, dry N,N-dimethylformamide (796 µL, 1.5 equivalents) was added. The reaction mixture was stirred for 1 hour at −78° C. and then warmed slowly to room temperature. After a further 2 hours at room temperature the reaction mixture was poured onto ice-water yielding a yellow precipitate. This was collected by filtration and air-dried to yield the title compound (1.50 g, 77%).

$\delta$H (400 MHz, d-6 DMSO) 10.20 (1H, s), 8.28 (1H, s), 3.95 (4H, t, J 4.9), 3.76 (4H, t, J 4.9).

REFERENCE EXAMPLE 7

2-Chloro-6-(4-methyl-piperazin-1-ylmethyl)-4-morpholin-4-yl-thieno[3,2-d]pyrimidine

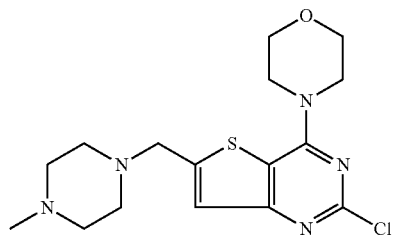

To a mixture of 2-chloro-4-morpholin-4-yl-thieno[3,2-d]pyrimidine-6-carbaldehyde (147 mg, 0.52 mmol), 1-methyl-piperazine (1.5 eq, 87 μL) and acetic acid (1.05 eq, 32 μL) in 1,2-dichloroethane (3 mL) was added sodium triacetoxyborohydride (1.1 eq, 121 mg) and then stirred at room temperature overnight. The reaction mixture was diluted with dichloromethane, washed with saturated solution of sodium hydrogen carbonate, brine, separated and dried (MgSO$_4$). The crude product was evaporated in vacuo and purified by chromatography to give the title compound as an off-white crystalline solid (51 mg, 45%).

REFERENCE EXAMPLE 8

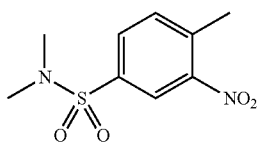

4-N,N-Trimethyl-3-nitro-benzenesulfonamide

To a solution of dimethylamine in H$_2$O (40% w/w, 15.0 mL, 120 mmol) at 0° C. was added a solution of 4-methyl-3-nitro-benzenesulfonyl chloride (9.42 g, 40 mmol) in DCM (60 mL) over 30 min. The resulting mixture was stirred at 0° C. for 30 min before being allowed to warm to RT and stirred overnight. The reaction mixture was diluted with H$_2$O (100 mL) and DCM (40 mL), and the layers were separated. The organic layer was washed in succession with water, HCl (aq., 0.1 M) and brine before being dried over Na$_2$SO$_4$ and evaporated to dryness to give the title compound as a pale yellow solid (9.13 g, 94%).

[M+H]$^+$ 244.9

REFERENCE EXAMPLE 9

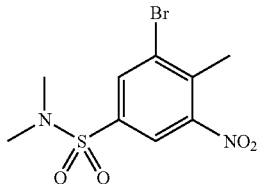

3-Bromo-4,N,N-trimethyl-5-nitro-benzenesulfonamide

To a solution of 4-N,N-trimethyl-3-nitro-benzenesulfonamide (8.57 g, 34.7 mmol) in concentrated sulfuric acid (80 mL) was added 1,3-dibromo-[1,3,5]triazinane-2,4,6-trione (5.97 g, 20.8 mmol) and the orange reaction mixture was stirred at RT for 16 h. A further 2 g of 1,3-dibromo-[1,3,5]triazinane-2,4,6-trione was added and stirring continued for 5 h. The reaction mixture was then poured onto ice and water and stirred for 15 min. The resulting milky/white solid was filtered and washed with H$_2$O, before being dissolved in EtOAc. The organic layer was dried over Na$_2$SO$_4$ and evaporated to dryness to give the title compound as a white solid (10.41 g, 93%).

[M+H]$^+$ 323.1 ($^{79}$Br) 325.0 ($^{81}$Br)

REFERENCE EXAMPLE 10

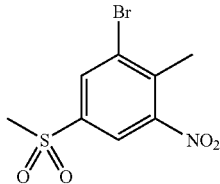

1-Bromo-5-methanesulfonyl-2-methyl-3-nitro-benzene

Prepared according to the method used in the preparation of 3-bromo-4-N,N-trimethyl-5-nitro-benzenesulfonamide using 4-methanesulfonyl-1-methyl-2-nitro-benzene in place of 4-N,N-trimethyl-3-nitro-benzenesulfonamide. The title compound was obtained as a white solid (17.0 g, 85%).

[M+H]$^+$ 294.1 ($^{79}$Br) 296.0 ($^{81}$Br)

REFERENCE EXAMPLE 11

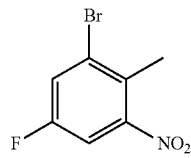

1-Bromo-5-fluoro-2-methyl-3-nitro-benzene

Prepared according to the method used in the preparation of 3-bromo-4-N,N-trimethyl-5-nitro-benzenesulfonamide using 4-fluoro-1-methyl-2-nitro-benzene in place of 4-N,N-trimethyl-3-nitro-benzenesulfonamide. The title compound was obtained as a yellow solid (68.0 g, 79%).

NMR δ$_H$ (300 MHz, CDCl$_3$) 2.59 (s, 3H), 7.50 (dd, J=2.8, 7.6, 1H) and 7.58 (dd, J=2.9, 7.4, 1H).

REFERENCE EXAMPLE 12

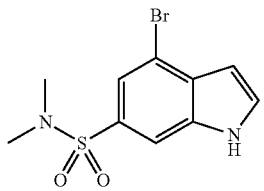

4-Bromo-1H-indole-6-sulfonic acid dimethylamide

To a solution of 3-bromo-4-N,N-trimethyl-5-nitro-benzenesulfonamide (9.15 g, 28.3 mmol) in dioxane (60 mL) was added DMF-DMA (11.3 mL, 84.9 mmol). The deep red reaction mixture was heated at 80° C. for 24 h followed by heating at 90° C. for 16 h. The mixture was cooled to RT and concentrated to 50% of the volume, poured into H$_2$O and extracted into EtOAc. The organic layer was isolated and washed with H₂O, then brine, dried over Na₂SO₄, and evaporated to dryness to give 3-bromo-4-(2-dimethylamino-vinyl)-N,N-dimethyl-5-nitro-benzenesulfonamide as a red solid (10.4 g, 91%). To a suspension of the amide (10.4 g, 25.7 mmol) and Raney®-Nickel (suspension in H₂O, 20 mL) in MeOH:THF (1:1, 200 mL) was added hydrazine monohydrate (1.9 mL, 38.6 mmol) at 0° C. and the mixture stirred at RT for 40 min.

The reaction mixture was then filtered through Celite and the filter cake washed with EtOAc and H₂O. The aqueous layer was isolated and then extracted with EtOAc. The combined organic layers were washed with H₂O, followed by brine, dried over Na₂SO₄ then evaporated to dryness. The resulting pink solid was purified by column chromatography, and subsequently recrystallised from iPrOH and EtOH to give the title compound as a white solid (3.5 g, 41%).

NMR $\delta_H$ (400 MHz, CDCl₃) 2.72 (s, 6H), 6.70 (m, 1H), 7.49 (apparent t, J=2.7, 1H), 7.68 (d, J=1.1, 1H), 7.94 (m, 1H) and 9.04 (bs, 1H).

REFERENCE EXAMPLE 13

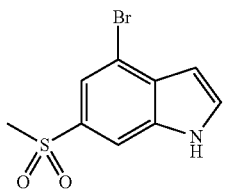

4-Bromo-6-methanesulfonyl-1H-indole

Prepared according to the method used in the preparation of 4-bromo-1H-indole-6-sulfonic acid dimethylamide using 1-bromo-5-methanesulfonyl-2-methyl-3-nitro-benzene in place of 3-bromo-4-N,N-trimethyl-5-nitro-benzenesulfonamide. The title compound was obtained as a white solid (1.8 g, 76%).

NMR $\delta_H$ (300 MHz, CDCl₃) 3.11 (s, 3H), 6.70 (m, 1H), 7.52 (dd, J=2.5, 3.0, 1H), 7.81 (d, J=1.5, 1H), 8.10 (dd, J=1.0, 1.5, 1H) and 9.34 (bs, 1H).

REFERENCE EXAMPLE 14

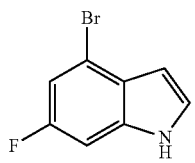

4-Bromo-6-fluoro-1H-indole

Prepared according to the method used in the preparation of 4-bromo-1H-indole-6-sulfonic acid dimethylamide using 1-bromo-5-fluoro-2-methyl-3-nitro-benzene in place of 3-bromo-4-N,N-trimethyl-5-nitro-benzenesulfonamide. The title compound was obtained as a white solid (6.06 g, 33%).

NMR $\delta_H$ (300 MHz, CDCl₃) 6.57 (apparent t, J=2.7, 1H), 7.04 (dd, J=2.1, 9.1, 1H), 7.12 (dd, J=2.1, 9.1, 1H), 7.20-7.25 (m, 1H) and 8.25 (s, 1H).

REFERENCE EXAMPLE 15

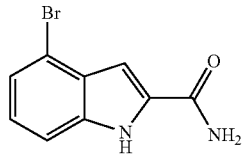

4-Bromo-1H-indole-2-carboxylic acid amide

Oxalyl chloride (0.9 mL, 10 mmol) was added to a suspension of 4-bromo-1H-indole-2-carboxylic acid (2.1 g, 8.8 mmol) in DCM and the mixture was stirred for 2 h. The solution formed was added drop-wise to a stirring mixture of ammonia (37%, 50 mL) and ice (50 mL). The resulting mixture was allowed to stand for 3 days. The mixture was filtered and the filtrate extracted with EtOAc. The solid from the filtration was dissolved in EtOAc and the organic solutions were combined, dried (MgSO₄) and then evaporated to afford the title compound as a brown solid (2.1 g, 100%).

NMR $\delta_H$ (400 MHz, CD₃OD) 7.11 (dd, J=7.5, 8.3, 1H), 7.16 (d, J=0.9, 1H), 7.25 (dd, J=0.78, 7.54, 1H) and 7.43 (d, J=8.3, 1H).

REFERENCE EXAMPLE 16

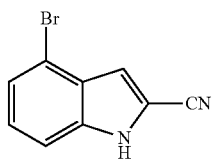

4-Bromo-1H-indole-2-carbonitrile

Phosphorous oxychloride (1.9 mL, 20 mmol) was added to a suspension of 4-bromo-1H-indole-2-carboxylic acid amide (1.32 g, 5.5 mmol.) in toluene (10 mL) and the mixture was stirred at reflux for 45 min. On cooling, the mixture was poured into an aqueous Na₂CO₃ solution (sat., 50 mL) and the mixture stirred until effervescence had subsided. The layers were separated, the aqueous phase extracted with EtOAc and the combined organic layers dried (MgSO₄) and evaporated to dryness. The crude material was purified by column chromatography to afford the title compound as a solid (1.00 g, 82%).

NMR $\delta_H$ (400 MHz, CDCl₃) 7.22-7.28 (m, 2H), 7.35-7.40 (m, 2H) and 8.79 (s, 1H).

REFERENCE EXAMPLE 17

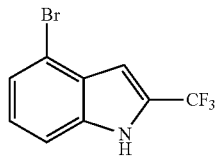

4-Bromo-2-trifluoromethyl-1H-indole

A solution of 2-methyl-3-bromo-aniline (6.05 g, 37 mmol) in pyridine (8 mL) and DCM (150 mL) was cooled to 0° C. and treated drop-wise with trifluoroacetic anhydride (11.5 mL, 81.4 mmol). The reaction mixture was stirred at RT for 2 h, then quenched with an aqueous solution of ammonium chloride. The organic layer was dried over MgSO$_4$, and evaporated to dryness to give N-(3-bromo-2-methyl-phenyl)-2,2,2-trifluoro-acetamide as an off-white solid, which was used without further purification (10 g).

NMR $\delta_H$ (400 MHz, CDCl$_3$) 2.38 (s, 3H), 7.14 (apparent t, J=8.0, 1H), 7.53 (d, J=8.0, 1H), 7.66 (d, J=8.0, 1H) and 7.75 (bs, 1H).

A solution of N-(3-bromo-2-methyl-phenyl)-2,2,2-trifluoro-acetamide (2.1 g, 7.4 mmol) and benzoyl peroxide (100 mg) in carbon tetrachloride (50 mL) was heated to reflux under irradiation (150 W tungsten lamp). A solution of bromine (0.55 mL, 10.4 mmol) in carbon tetrachloride (3 mL) was then added drop-wise to the refluxing solution, and heating was pursued for 16 h. The reaction mixture was left to cool to RT and diluted with DCM. The organic layer was washed with sodium thiosulfate, and evaporated to dryness to give N-(3-bromo-2-bromomethyl-phenyl)-2,2,2-trifluoro-acetamide as a brown residue which was used without further purification (2.9 g).

NMR $\delta_H$ (400 MHz, CDCl$_3$) 4.71 (s, 2H), 7.30 (apparent t, J=8.0, 1H), 7.55 (d, J=8.0, 1H), 7.82 (d, J=8.0, 1H) and 8.79 (bs, 1H).

A solution of N-(3-bromo-2-bromomethyl-phenyl)-2,2,2-trifluoro-acetamide (2.9 g) in toluene (40 mL) was treated with triphenylphosphine (2.3 g, 8.7 mmol). The solution was stirred at 60° C. for 2 h, then cooled to 0° C. The beige solid that precipitated was collected by filtration, washed with diethyl ether, then dissolved in DMF (60 mL), and heated to reflux under nitrogen for 16 h. The reaction mixture was evaporated to dryness, then partitioned between EtOAc and a sat. sodium carbonate solution. The organic layer was isolated, dried (MgSO$_4$), and purified by column chromatography to give the title compound as a yellow solid (1.55 g, 84%).

NMR $\delta_H$ (400 MHz, CDCl$_3$) 7.00 (s, 1H), 7.19 (apparent t, J=7.9, 1H), 7.36-7.41 (m, 2H) and 8.53 (bs, 1H).

REFERENCE EXAMPLE 18

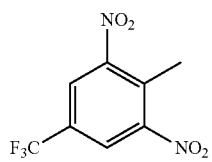

2-Methyl-1,3-dinitro-5-trifluoromethyl-benzene

To a solution of 4-methylbenzo-trifluoride (9.51 g, 59.4 mmol) in concentrated sulphuric acid (120 mL) was added potassium nitrate (15.0 g, 0.149 mol) and the resulting mixture stirred at RT for 16 h. The reaction mixture was poured onto ice and water then extracted into EtOAc. The organic layer was washed successively with H$_2$O and brine, dried over Na$_2$SO$_4$ and evaporated to dryness to give the title compound as a yellow solid (13.84 g, 93%)

NMR $\delta_H$ (400 MHz, CDCl$_3$) 2.67 (s, 3H) and 8.27 (s, 2H).

REFERENCE EXAMPLE 19

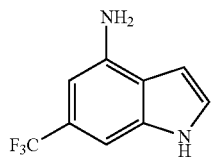

6-Trifluoromethyl-1H-indol-4-ylamine

Prepared according to the method used in the preparation of 4-bromo-1H-indole-6-sulfonic acid dimethylamide using 2-methyl-1,3-dinitro-5-trifluoromethyl-benzene in place of 3-bromo-4,N,N-trimethyl-5-nitro-benzenesulfonamide. The title compound was obtained as a white solid (10.7 g, 99%).

[M+H]$^+$ 201.1

REFERENCE EXAMPLE 20

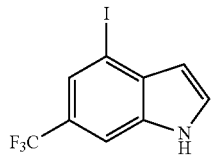

4-Iodo-6-trifluoromethyl-1H-indole

To a suspension of 6-trifluoromethyl-1H-indol-4-ylamine (10.7 g, 53.4 mmol) in HCl (aq., 15%, 240 mL) was added a solution of sodium nitrite (5.52 g, 80.1 mmol) in H$_2$O (10 mL) slowly at 0° C. The reaction mixture was stirred at RT for 1 h before a solution of sodium tetrafluoroborate (23.5 g, 0.214 mol) in H$_2$O (30 mL) was added. After stirring for 15 min, the resulting precipitate was collected by filtration and washed with a sodium tetrafluoroborate solution (aq., sat) before dissolving in acetonitrile (100 mL). This solution was added slowly to a suspension of sodium iodide (24.0 g, 0.160 mol) in acetonitrile (100 mL) and the mixture stirred at RT for 16 h. The reaction mixture was concentrated to 30% of the volume and partioned between EtOAc and H$_2$O. The organic layer was isolated then washed in succession with sodium thiosulfate, H$_2$O and brine, dried over Na$_2$SO$_4$ and evaporated to dryness. The resulting brown oil was purified by column chromatography to give the title compound (9.77 g, 59%).

[M−H]$^-$ 310.1

REFERENCE EXAMPLE 21

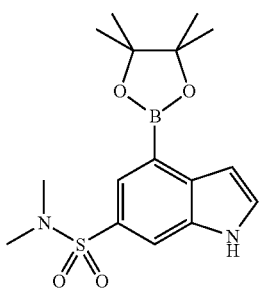

4-(4,4,5,5-Tetramethyl-[1,3,2]dioxaborolan-2-yl)-1H-indole-6-sulfonic acid dimethylamide Prepared according to the general method of Scheme 6. The title compound was obtained as a white solid (1.85 g, 46%).

[M+H]$^+$ 350.2 ($^{10}$B) 351.2 ($^{11}$B)

REFERENCE EXAMPLE 22

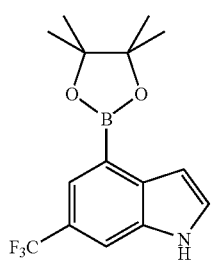

4-(4,4,5,5-Tetramethyl-[1,3,2]dioxaborolan-2-yl)-6-trifluoromethyl-1H-indole

Prepared according to the general method of Scheme 6. The title compound was obtained as a pale yellow solid (1.37 g, 92%).

[M+H]$^+$ 311.2 ($^{10}$B) 312.2 ($^{11}$B)

REFERENCE EXAMPLE 23

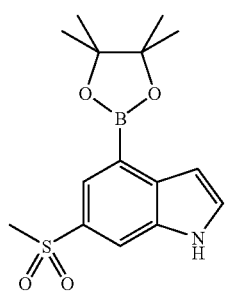

6-Methanesulfonyl-4-(4,4,5,5-tetramethyl-[1,3,2]dioxaborolan-2-yl)-1H-indole

Prepared according to the general method of Scheme 6. The title compound was obtained as a pale yellow solid (2.4 g, 51%).

NMR $\delta_H$ (300 MHz, DMSO-d$_6$) 1.36 (s, 12H), 3.18 (s, 3H), 6.87 (m, 1H), 7.73 (apparent t, J=2.5, 1H), 7.85 (d, J=1.5, 1H), 8.07 (dd, J=1.0, 1.5, 1H) and 11.73 (bs, 1H).

REFERENCE EXAMPLE 24

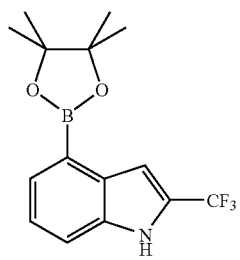

4-(4,4,5,5-Tetramethyl-[1,3,2]dioxaborolan-2-yl)-2-trifluoromethyl-1H-indole

Prepared according to the general method of Scheme 6. The title compound was obtained as a white solid (1.5 g, 55%).

NMR $\delta_H$ (400 MHz, CDCl$_3$) 1.40 (s, 12H), 7.33 (dd, J=7.0, 8.3, 1H), 7.42 (s, 1H), 7.53 (d, J=8.3, 1H), 7.70 (d, J=7.0, 1H) and 8.37 (bs, 1H).

REFERENCE EXAMPLE 25

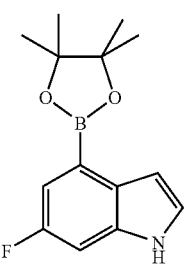

6-Fluoro-4-(4,4,5,5-tetramethyl-[1,3,2]dioxaborolan-2-yl)-1H-indole

Prepared according to the general method of Scheme 2. The title compound was obtained as a white solid (4.6 g, 61%).

NMR $\delta_H$ (300 MHz, CDCl$_3$) 1.39 (s, 12H), 7.02 (m, 1H), 7.14-7.19 (m, 1H), 7.20-7.26 (m, 1H), 7.38 (dd, J=2.4, 9.9, 1H) and 8.16 (s, 1H).

REFERENCE EXAMPLE 26

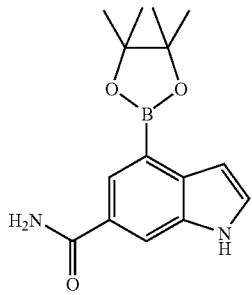

4-(4,4,5,5-Tetramethyl-[1,3,2]dioxaborolan-2-yl)-1H-indole-6-carboxylic acid amide A solution of 4-bromo-1H-indole-6-carbonitrile (1 g, 4.50 mmol) in methanol (10 mL) was treated with 30% aqueous hydrogen peroxide (2.7 mL, 4.95 mmol) and a 1 M aqueous sodium hydroxide solution (5 mL) then heated at 40° C. for 1 h. The reaction mixture was cooled, treated with water and cooled in an ice-bath. The resulting precipitate was collected by filtration, washed with water and dried in vacuo to obtain 4-bromo-1H-indole-6-carboxylic acid amide (1.05 g, 97%), which was transformed into the title boronic ester by the general method (Scheme 1) (0.80 g, 67%).

NMR $\delta_H$ (300 MHz, DMSO-$d_6$) 1.35 (s, 12H), 6.78 (m, 1H), 7.10 (s, 1H), 7.51-7.54 (m, 1H), 7.94-7.97 (m, 2H), 8.06 (s, 1H) and 11.40 (bs, 1H).

REFERENCE EXAMPLE 27

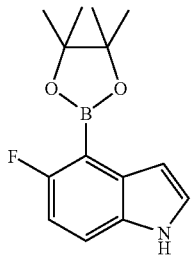

5-Fluoro-4-(4,4,5,5-tetramethyl-[1,3,2]dioxaborolan-2-yl)-1H-indole

A solution of 5-fluoroindole (5 g, 37.0 mmol) in DMF (40 mL) was treated at 0° C. with trifluoroacetic anhydride (6.1 mL, 42.6 mmol). After 30 min, the reaction was poured into water and the resulting precipitate collected by filtration, washed with water, then dried in vacuo. The solid was then dissolved in 10% aqueous NaOH (200 mL) and heated at reflux for 1 h. The reaction mixture was then cooled, washed with dichloromethane and acidified with aqueous HCl. The resulting white precipitate was collected by filtration, washed with water, taken up in dichloromethane, washed with water, dried (MgSO$_4$) and evaporated in vacuo. The resulting material (5 g, 75%) was dissolved in methanol (80 mL) and treated with concentrated sulphuric acid (2 mL) then heated at reflux overnight. The reaction was cooled and the resulting precipitate collected, washed with water and evaporated in vacuo to give 5-fluoro-1H-indole-3-carboxylic acid methyl ester as a peach-coloured solid (4.5 g, 83%).

A solution of thallium tris(trifluoroacetate) (8.45 g, 15.6 mmol) in TFA (35 mL) was added to a solution of 5-fluoro-1H-indole-3-carboxylic acid methyl ester (2 g, 10.4 mmol) in TFA (10 mL) at room temperature and stirred for 2 h. The reaction mixture was evaporated in vacuo and the resulting residue suspended in water (25 mL) before being treated with a solution of potassium iodide (5.2 g, 31.3 mmol) in water (50 mL). The reaction mixture was treated with dichloromethane (100 mL) and methanol (5 mL) and the resulting precipitate removed by filtration through celite.

The organic layer was separated, washed successively with sodium thiosulfate solution and brine, then dried (MgSO$_4$) and evaporated in vacuo. The resultant material was dissolved in methanol (60 mL) and treated with 40% aqueous NaOH solution (60 mL) then refluxed for 2 h. The reaction mixture was cooled and extracted with DCM/MeOH (ratio 95:5), dried (MgSO$_4$), filtered and evaporated in vacuo to give a crude solid. Purification by column chromatography gave 5-fluoro-4-iodo-1H-indole as a pale brown solid (1.05 g, 39%).

NMR $\delta_H$ (300 MHz, CDCl$_3$) 6.49-6.52 (m, 1H), 6.95 (apparent dt, J=0.4, 8.6, 1H), 7.26-7.33 (m, 2H) and 8.35 (s, 1H).

A solution of 5-fluoro-4-iodo-1H-indole (261 mg, 1.0 mmol) in dioxane (1 mL) was treated with triethylamine (0.2 mL, 1.4 mmol), palladium acetate (4.5 mg, 0.02 mmol) and bis(cyclohexyl)phosphino-2-biphenyl (28 mg, 0.08 mmol) then heated to 80° C. A solution of pinacolborane (1 M in THF, 2.66 mL, 2.66 mmol) was added via syringe. After 30 min, the reaction mixture was cooled, then diluted with water (10 mL) and DCM (10 mL). The resulting mixture was passed through a phase separation cartridge, and the dichloromethane layer was evaporated in vacuo to obtain the title compound which was used without further purification.

REFERENCE EXAMPLE 28

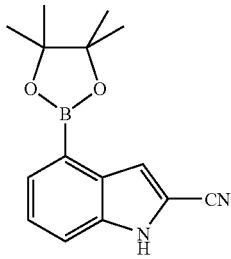

4-(4,4,5,5-Tetramethyl-[1,3,2]dioxaborolan-2-yl)-1H-indole-2-carbonitrile 4,4,5,5-Tetramethyl-[1,3,2]dioxaborolane (2.1 mL, 14.5 mmol) was added drop-wise to a mixture of 4-bromo-1H-indole-2-carbonitrile (1.27 g, 5.8 mmol), palladium acetate (33 mg, 0.145 mmol), triethylamine (1.21 mL, 8.7 mmol) and 2-(dicyclohexylphosphino)biphenyl (203 mg, 0.58 mmol) in dioxane at 80° C. The reaction mixture was stirred at 80° C. for 5 h then allowed to stand at RT overnight. The reaction mixture was diluted with DCM and washed with water, then the organic layer was isolated, dried (MgSO$_4$) then concentrated in vacuo. The resultant crude material was purified by column chromatography to afford the title compound as a brown solid (1.02 g, 66%).

NMR $\delta_H$ (400 MHz, CDCl$_3$) 1.40 (s, 12H), 7.36-7.42 (m, 1H), 7.51 (apparent dt, J=1.0, 8.3, 1H), 7.67-7.74 (m, 2H) and 8.51 (s, 1H).

REFERENCE EXAMPLE 29

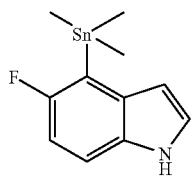

5-Fluoro-4-trimethylstannanyl-1H-indole

A solution of 5-fluoro-4-iodo-1H-indole (1.0 g, 3.83 mmol), hexamethylditin (1.6 mL, 7.66 mmol) and dichlorobis(triphenylphosphine)palladium(II) (280 mg, 0.38 mmol) in dioxane (5 mL) was degassed, then place under a nitrogen atmosphere before being heated at 90° C. in a microwave for 1 h.

A further quantity of hexamethylditin (0.8 mL, 3.83 mmol) and dichlorobis(triphenylphosphine)palladium(II) (280 mg, 0.38 mmol) was added, then the reaction mixture was heated for an additional 1 h at 90° C. in a microwave. The reaction mixture was evaporated in vacuo, and purified by column chromatography on alumina to afford 5-fluoro-4-(trimethylstannyl)-1H-indole (498 mg, 44%) as an oil that was used without further purification.

REFERENCE EXAMPLE 30

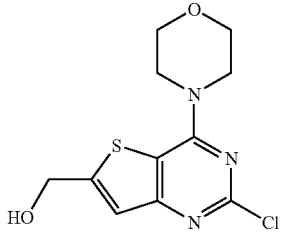

(2-Chloro-4-morpholin-4-yl-thieno[3,2-d]pyrimidin-6-yl)-methanol

To a suspension of 2-chloro-4-morpholin-4-yl-thieno[3,2-d]pyrimidine-6-carbaldehyde (3.2 g, 11.31 mmol) in anhydrous THF (100 mL) and IMS (70 mL) was added sodium borohydride (0.47 g, 12.42 mmol) and the resulting mixture stirred at RT for 2 h. The reaction mixture was partitioned between DCM and a sat. aqueous solution of NaHCO$_3$. The organic layer was isolated, dried (MgSO$_4$) and concentrated in vacuo. The resultant residue was triturated with water gave the title compound as a white solid (2.9 g, 91%).

NMR $\delta_H$ (300 MHz, DMSO-d$_6$) 3.75 (m, 4H), 3.89 (m, 4H), 4.81 (d, J=5, 2H), 5.96 (t, J=5, 1H) and 7.22 (s, 1H).

REFERENCE EXAMPLE 31

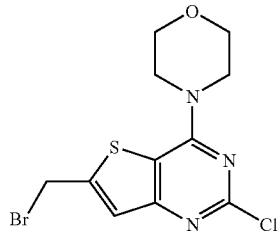

6-Bromomethyl-2-chloro-4-morpholin-4-yl-thieno[3,2-d]pyrimidine

To a solution of (2-chloro-4-morpholin-4-yl-thieno[3,2-d]pyrimidin-6-yl)-methanol (1.46 g, 5.11 mmol) in anhydrous DCM (30 mL) at 0° C. were added triphenylphosphine (1.74 g, 6.64 mmol) and carbon tetrabromide (2.03 g, 6.13 mmol). The resulting brown solution was stirred at RT for 5 h, before additional quantities of triphenylphosphine and carbon tetrabromide were added (0.4 g and 0.34 g, respectively) and stirring was continued at RT for 1 h. The reaction mixture was concentrated in vacuo and DCM and EtOAc were added. The resultant white precipitate was collected by filtration and air dried to give the title compound as a white solid (0.82 g, 46%).

[M+H]$^+$ 348.1 ($^{79}$Br) 350.1 ($^{81}$Br)

REFERENCE EXAMPLE 32

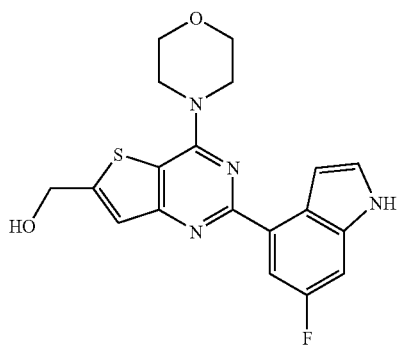

[2-(6-Fluoro-1H-indol-4-yl)-4-morpholin-4-yl-thieno[3,2-d]pyrimidin-6-yl]-methanol Prepared by Suzuki coupling Method A of Reference Example 2. The title compound was obtained as a white solid (1.2 g, 40%).

NMR $\delta_H$ (300 MHz, DMSO-d$_6$) 3.83 (m, 4H), 4.00 (m, 4H), 4.85 (d, J=5.8, 2H), 5.92 (t, J=5.8, 1H), 7.31 (dd, J=2.7, 9.5, 1H), 7.39 (s, 1H), 7.41-7.47 (m, 2H), 7.90 (dd, J=2.7, 11.5, 1H) and 11.30 (bs, 1H).

REFERENCE EXAMPLE 33

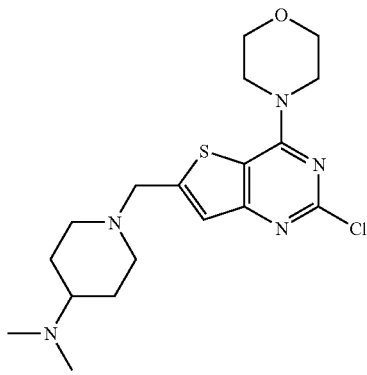

[1-(2-Chloro-4-morpholin-4-yl-thieno[3,2-d]pyrimidin-6-ylmethyl)-piperidin-4-yl]-dimethyl-amine To a suspension of 2-chloro-4-morpholin-4-yl-thieno[3,2-d]pyrimidine-6-carbaldehyde (0.30 g, 1.06 mmol) in anhydrous THF (5 mL) were added dimethyl-piperidin-4-yl-amine (0.27 g, 2.11 mmol), sodium triacetoxyborohydride (0.34 g, 1.60 mmol) and glacial acetic acid (90 μL, 1.59 mmol). The resulting solution was stirred at RT for 17 h, then partitioned between EtOAc and a sat. aqueous solution of NaHCO₃. The organic layer was isolated, dried (MgSO₄) and concentrated in vacuo. The resultant residue was purified by column chromatography to give the title compound as a white solid (0.10 g, 27%).

NMR $\delta_H$ (300 MHz, CDCl₃) 1.62 (m, 2H), 1.86 (d, J=11.8, 2H), 2.12 (dt, J=1.8, 11.8, 2H), 2.24 (m, 1H), 2.34 (s, 6H), 3.00 (d, J=11.8, 2H), 3.78 (s, 2H), 3.84 (m, 4H), 3.99 (m, 4H) and 7.14 (s, 1H).

REFERENCE EXAMPLE 34

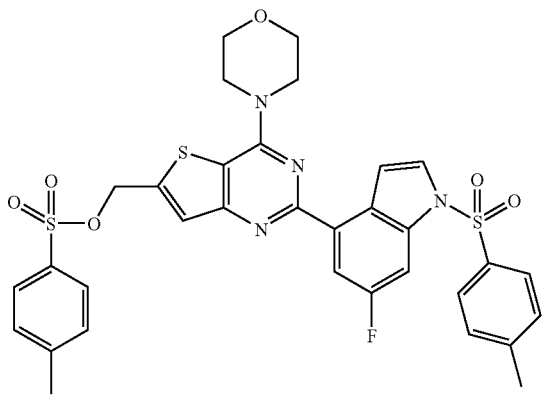

Toluene-4-sulfonic acid 2-[6-fluoro-1-(toluene-4-sulfonyl)-1H-indol-4-yl]-4-morpholin-4-yl-thieno[3,2-d]pyrimidin-6-ylmethyl ester To a suspension of [2-(6-fluoro-1H-indol-4-yl)-4-morpholin-4-yl-thieno[3,2-d]pyrimidin-6-yl]-methanol (0.54 g, 1.41 mmol) in anhydrous THF (20 mL) and DMF (5 mL) was added sodium hydride (60% suspension in mineral oil, 0.34 g, 8.5 mmol). The resulting mixture was stirred at RT for 10 min, then p-toluenesulfonyl chloride (1.08 g, 5.66 mmol) was added and the reaction mixture was heated at 40° C. for 3 h.

The resulting solution was partitioned between EtOAc and a sat. aqueous solution of ammonium chloride. The organic layer was isolated, dried (MgSO₄) and concentrated in vacuo. The resultant residue was purified by column chromatography to give the title compound as a white solid (0.60 g, 62%).

NMR $\delta_H$ (300 MHz, CDCl₃) 2.35 (s, 3H), 2.44 (s, 3H), 3.89 (m, 4H), 4.01 (m, 4H), 5.33 (s, 2H), 7.23 (d, J=8.7, 2H), 7.34 (m, 3H), 7.63 (d, J=3.7, 1H), 7.68 (d, J=3.7, 1H), 7.77 (d, J=8.3, 2H), 7.81-7.86 (m, 3H) and 7.98 (dd, J=2.5, 10.6, 1H).

REFERENCE EXAMPLE 35

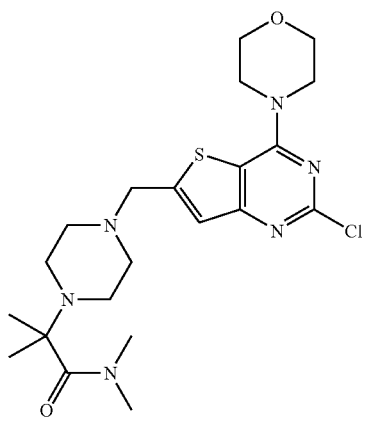

2-[4-(2-Chloro-4-morpholin-4-yl-thieno[3,2-d]pyrimidin-6-ylmethyl)-piperazin-1-yl]-N,N-dimethyl-isobutyramide To a solution of 6-bromomethyl-2-chloro-4-morpholin-4-yl-thieno[3,2-d]pyrimidine (146 mg, 0.42 mmol) in DMF (5 mL) were added N,N-dimethyl-2-piperazin-1-yl-isobutyramide (100 mg, 0.50 mmol), cesium carbonate (273 mg, 0.837 mmol) and water (23 μL, 1.26 mmol). The resulting mixture was stirred at RT for 17 h. The reaction mixture was loaded directly onto an Isolute® SCX-2 cartridge, washed with MeOH, then eluted with 2 M NH₃ in MeOH. The resulting residue was purified by column chromatography to give the title compound as an off-white solid (131mg, 67%).

[M+H]⁺ 467.3

REFERENCE EXAMPLE 36

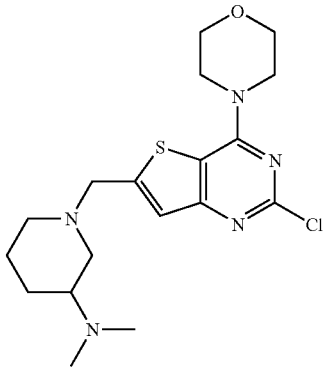

[1-(2-Chloro-4-morpholin-4-yl-thieno[3,2-d]pyrimidin-6-ylmethyl)-piperidin-3-yl]-dimethyl-amine Prepared using the method used in the preparation of 2-[4-(2-chloro-4-morpholin-4-yl-thieno[3,2-d]pyrimidin-6-ylmethyl)-piperazin-1-yl]-N,N-dimethyl-isobutyramide using dimethyl-piperidin-3-yl-amine in place of N,N-dimethyl-2-piperazin-1-yl-isobutyramide. The title compound was obtained as an off-white solid (180 mg, 76%).
[M+H]+ 396.3

REFERENCE EXAMPLE 37

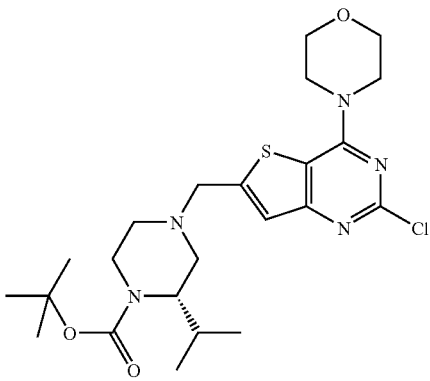

(S)-4-(2-Chloro-4-morpholin-4-yl-thieno[3,2-d]pyrimidin-6-ylmethyl)-2-isopropyl-piperazine-1-carboxylic acid tert-butyl ester Prepared using the method used in the preparation of 2-[4-(2-chloro-4-morpholin-4-yl-thieno[3,2-d]pyrimidin-6-ylmethyl)-piperazin-1-yl]-N,N-dimethyl-isobutyramide using (S)-2-isopropyl-piperazine-1-carboxylic acid tert-butyl ester in place of N,N-dimethyl-2-piperazin-1-yl-isobutyramide. The title compound was obtained as an off-white solid (182 mg, 80%).
[M+H]+ 496.3

REFERENCE EXAMPLE 38

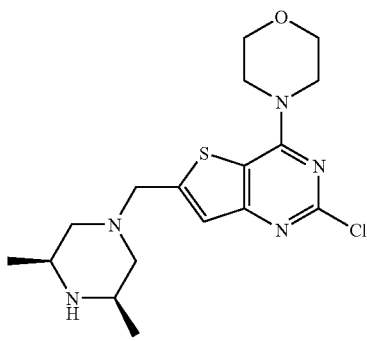

2-Chloro-6-(cis-3,5-dimethyl-piperazin-1-ylmethyl)-4-morpholin-4-yl-thieno[3,2-d]pyrimidine To a solution of 6-bromomethyl-2-chloro-4-morpholin-4-yl-thieno[3,2-d]pyrimidine (150 mg, 0.43 mmol) in DMF (4 mL) were added (cis)-2,6-dimethyl-piperazine (74 mg, 0.648 mmol) and potassium carbonate (117 mg, 0.847 mmol). The resulting mixture was stirred at RT for 17 h, then concentrated in vacuo. The resulting residue was triturated with water to give the title compound as an off-white solid (127 mg, 77%).
[M+H]+ 382.3

REFERENCE EXAMPLE 39

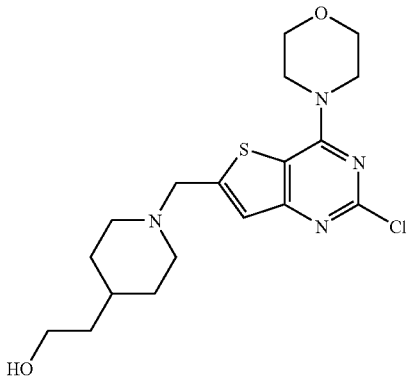

2-Chloro-6-[4-(2-methoxy-ethyl)-piperidin-1-ylmethyl]-4-morpholin-4-yl-thieno[3,2-d]pyrimidine To a solution of 4-piperidine ethanol (1.95 g) in acetonitrile (25 mL) was added triethylamine (2.53 mL) followed by tert-butyl dicarbonate (3.63 g). The mixture was stirred at room temperature for 22 hours and partitioned between 0.5 M hydrochloric acid and ethyl acetate. The organic layer was washed with brine, dried (MgSO$_4$) and the solvent evaporated to give 4-(2-hydroxy-ethyl)-piperidine-1-carboxylic acid tert-butyl ester (3.46 g).

This was dissolved in tetrahydrofuran (50 mL) and sodium hydride added (664 mg; 60% dispersion in mineral oil) at 0° C. After 30 minutes iodomethane (3.76 mL) was added and the mixture stirred for 22 hours. The mixture was diluted with ethyl acetate and washed with water, brine and dried (MgSO$_4$). The solvent was evaporated and the residue purified by flash chromatography to give 4-(2-methoxy-ethyl)-piperidine-1-carboxylic acid tert-butyl ester (3.12 g).

To a solution of 4-(2-methoxy-ethyl)-piperidine-1-carboxylic acid tert-butyl ester (3.12 g) in dichloromethane (40 mL) was added 4 M hydrogen chloride in dioxane (16 mL) and the mixture stirred for 21 hours. The solvent was evaporated to give 4-(2-methoxy-ethyl)-piperidine hydrochloride salt as a white solid Reductive amination with 2-chloro-4-morpholin-4-yl-thieno[3,2-d]pyrimidine-6-carbaldehyde using the method described in the presence of triethylamine gave the title compound as a white solid (1.73 g).

$\delta_H$ (400 MHz, CDCl$_3$) 1.31 (m, 2H), 1.37 (m, 1H), 1.56 (m, 2H), 1.71 (m, 2H), 2.10 (m, 2H), 2.94 (m, 2H), 3.35 (s, 3H), 3.44 (t, J=6.5, 2H), 3.78 (s, 2H), 3.86 (t, J=4.9, 4H), 4.01 (t, J=4.9, 4H), 7.16 (s, 1H).

REFERENCE EXAMPLE 40

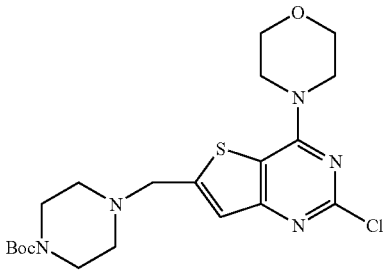

4-(2-Chloro-4-morpholin-4-yl-thieno[3,2-d]pyrimidin-6-ylmethyl)-piperazine-1-carboxylic acid tert-butyl ester Prepared using the standard reductive amination conditions with 2-chloro-4-morpholin-4-yl-thieno[3,2-d]pyrimidine-6-carbaldehyde and tert-butyl-1-piperazinecarboxylate.

$\delta_H$(400MHz, CDCl$_3$) 1.48 (s, 9H), 2.51 (t, J=4.8, 4H), 3.49 (t, J=4.8, 4H), 3.82 (s, 2H), 3.86 (t, J=4.8, 4H), 4.01 (t, J=4.8, 4H), 7.19 (s, 1H).

REFERENCE EXAMPLE 41

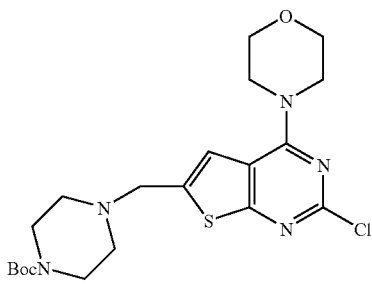

4-(2-Chloro-4-morpholin-4-yl-thieno[2,3-d]pyrimidin-6-ylmethyl)-piperazine-1-carboxylic acid tert-butyl ester Prepared using the standard reductive amination conditions with 2-chloro-4-morpholin-4-yl-thieno[2,3-d]pyrimidine-6-carbaldehyde.

$\delta_H$(400 MHz, CDCl$_3$) 1.46 (s, 9H), 2.45 (m, 4H), 3.44 (m, 4H), 3.72 (s, 2H), 3.83 (m, 4H), 3.93 (m, 4H), 7.09 (s, 1H).

REFERENCE EXAMPLE 42

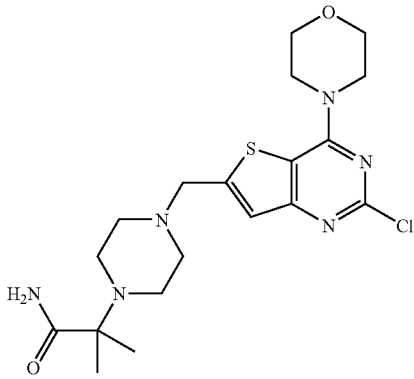

2-[4-(2-Chloro-4-morpholin-4-yl-thieno[3,2-d]pyrimidin-6-ylmethyl)-piperazin-1-yl]-isobutyramide To a solution of tert-butyl-1-piperazinecarboxylate (15.0 g) in dichloromethane (150 mL) and methanol (150 ml) at 0° C. was added hydrogen chloride (40 mL; 2M solution in diethyl ether). The mixture was stirred at room temperature for 1.5 hours and reduced in vacuo to yield tert-butyl-1-piperazinecarboxylate hydrochloride (17.9 g).

To a solution of tert-butyl-1-piperazinecarboxylate hydrochloride (17.9 g) in water (200 mL) at room temperature was added sodium cyanide (3.94 g). A solution of acetone (5.9 mL) in water (20 mL) was then added dropwise and stirred at room temperature for 48 hours. The mixture was partitioned between ethyl acetate and water. The combined organic layers were washed with brine, separated, dried (MgSO$_4$) and reduced in vacuo to yield 4-(cyano-dimethyl-methyl)-piperazine-1-carboxylic acid tert-butyl ester (17.5 g).

To a solution of 4-(cyano-dimethyl-methyl)-piperazine-1-carboxylic acid tert-butyl ester (960 mg) in methyl sulfoxide (20 mL) at 0° C. was added potassium carbonate (104 mg). Hydrogen peroxide (2.0 mL; 27.5 wt % solution in water) was then added dropwise. The resulting mixture was heated to 40° C. overnight. To the cooled mixture was added water and the precipitated solid filtered and dried yielding 4-(1-carbamoyl-2-methyl-ethyl)-piperazine-1-carboxylic acid tert-butyl ester (677 mg). The BOC-group was removed using HCl in ether under standard conditions to give 2-piperazine-1-yl-isobutyramide di-hydrochloride (600 mg) which was reacted with 2-chloro-4-morpholin-4-yl-thieno[3,2-d]pyrimidine-6-carbaldehyde under the standard reductive amination conditions to give the title compound (143 mg).

$\delta_H$ (400 MHz, CDCl$_3$) 1.25 (s, 6H), 2.60 (m, 8H), 3.82 (s, 2H), 3.86 (t, J=4.8, 4H), 4.01 (t, J=4.8, 4H), 5.20 (br s, 1H), 7.07 (br s, 1H), 7.18 (s, 1H).

REFERENCE EXAMPLE 43

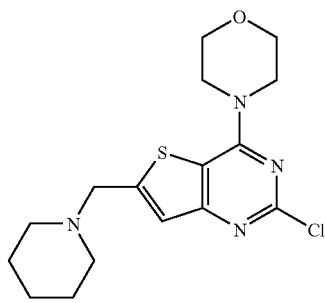

2-Chloro-4-morpholin-4-yl-6-piperidin-1-ylmethyl-thieno[3,2-d]pyrimidine

Prepared by reductive amination of 2-chloro-4-morpholin-4-yl-thieno[3,2-d]pyrimidine-6-carbaldehyde with piperidine under the standard conditions.

$\delta_H$(400 MHz, CDCl$_3$) 1.50 (m, 2H), 1.64 (m, 4H), 2.49 (m, 4H), 3.76 (s, 2H), 3.86 (t, J=4.8, 4H), 4.01 (t, J=4.8, 4H), 7.16 (s, 1H).

REFERENCE EXAMPLE 44

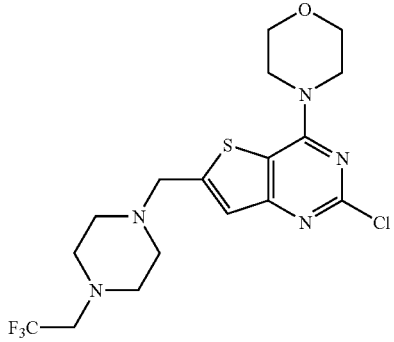

2-Chloro-4-morpholin-4-yl-6-[4-(2,2,2-trifluoro-ethyl)-piperazin-1-ylmethyl]-thieno[3,2-d]pyrimidine 4-(2,2,2-Trifluroroethyl)piperazine was prepared as described in *J. Org. Chem.*, 1966, 31, 3867-3868. Reductive amination with 2-chloro-4-morpholin-4-yl-thieno[3,2-d]pyrimidine-6-carbaldehyde under the standard reductive amination conditions yielded the title compound.

$\delta_H$ (400 MHz, CDCl$_3$) 2.60-2.62 (m, 4H), 2.75-2.77 (m, 4H), 3.01 (q, J=9.6, 2H), 3.82 (s, 2H), 3.85-3.87 (m, 4H), 4.00-4.02 (m, 4H), 7.19 (s, 1H).

REFERENCE EXAMPLE 45

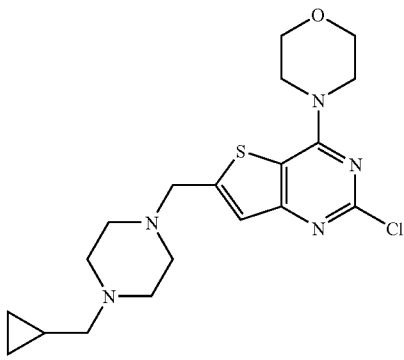

2-Chloro-6-(4-cyclopropylmethyl-piperazin-1-ylmethyl)-4-morpholin-4-yl-thieno[3,2-d]pyrimidine 4-Cyclopropylmethylpiperazine was prepared as described in *J. Med. Chem.*, 2004, 47, 2833-2838. Reductive amination with 2-chloro-4-morpholin-4-yl-thieno[3,2-d]pyrimidine-6-carbaldehyde under the standard reductive amination conditions yielded the title compound.

$\delta_H$ (400 MHz, CDCl$_3$) −0.02-0.02 (m, 2H), 0.42-0.48 (m, 2H), 0.75-0.80 (m, 1H), 2.18 (d, J=6.4, 2H), 2.51 (br s, 8H), 3.71 (s, 2H), 3.73-3.75 (m, 4H), 3.88-3.90 (m, 4H), 7.07 (s, 1H).

REFERENCE EXAMPLE 46

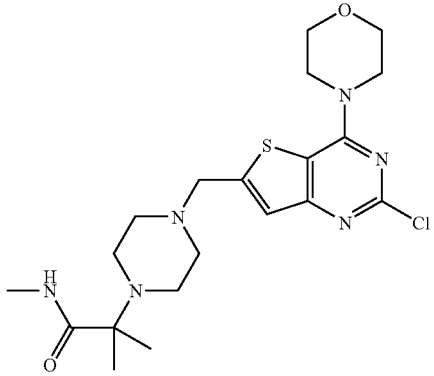

2-[4-(2-Chloro-4-morpholin-4-yl-thieno[3,2-d]pyrimidin-6-ylmethyl)-piperazin-1-yl]-N-methyl-isobutyramide To a mixture of dichloromethane (20 mL), saturated sodium bicarbonate (20 mL), sodium carbonate (1.84 g) and water (20 mL) at 0° C. was added methylamine hydrochloride (640 mg) followed by 2-bromoisobutyryl bromide (2.0 g) and the mixture stirred vigorously. The mixture was stirred at 0° C. for 2 hours and then extracted into dichloromethane. The combined organic layers were washed with brine, separated, dried (MgSO$_4$) and reduced in vacuo to yield 2-bromo-2-N-dimethyl-propionamide (1.74 g).

A mixture of 2-bromo-2-N-dimethyl-propionamide (1.74 g), tert-butyl-1-piperazinecarboxylate (1.79 g) and silver(I) oxide (2.67 g) in toluene (20 mL) was heated at reflux in the dark overnight. The mixture was filtered through celite. The filtrate was partitioned between dichloromethane and saturated sodium bicarbonate. The combined organic layers were washed with brine, separated, dried (MgSO$_4$) and reduced in vacuo to yield 4-(1-methyl-1-methylcarbamoyl-ethyl)-piperazine-1-carboxylic acid tert-butyl ester (3.08g). The BOC-group was removed using HCl in ether under standard conditions to give N-methyl-2-piperazin-2-yl-1-piperazine-1-yl-isobuytramide di-hydrochloride (1.96 g) which was reacted with 2-chloro-4-morpholin-4-yl-thieno[3,2-d]pyrimidine-6-carbaldehyde under the standard reductive amination conditions to give the title compound (138 mg).

$\delta_H$ (400 MHz, CDCl$_3$) 1.13 (s, 6H), 2.48 (m, 8H), 2.72 (d, J=5.0, 3H), 3.72 (s, 2H), 3.76 (t, J=4.8, 4H), 3.91 (t, J=4.8, 4H), 7.10 (br m, 2H).

REFERENCE EXAMPLE 47

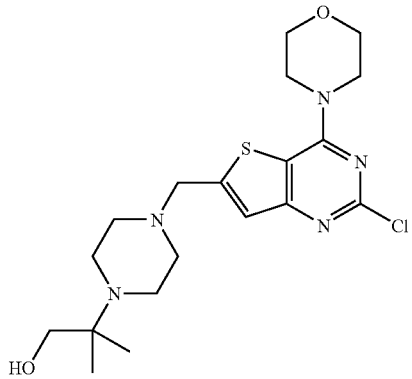

2-[4-(2-Chloro-4-morpholin-4-yl-thieno[3,2-d]pyrimidin-6-ylmethyl)-piperazin-1-yl]-2-methyl-propan-1-ol To a stirring solution of ethyl-2-bromoisobutyrate (2.65 g, 13.6 mmol) in anhydrous acetonitrile (25 mL) at room temperature was added tert-butyl-1-piperazinecarboxylate (2.48 g, 13.3 mmol) followed by potassium carbonate (1.88 g, 13.6 mmol). The mixture was heated to 85° C. overnight. The cooled reaction mixture was partitioned between ethyl acetate and water. The combined organic layers were washed with brine, separated and dried (MgSO$_4$). The crude product was purified by column chromatography to yield 4-(1-ethoxycarbonyl-1-methyl-ethyl)-piperazine-1-carboxylic acid tert-butyl ester as a colourless oil (1.28 g).

To a suspension of lithium aluminium hydride powder (0.324 g) in anhydrous tetrahydrofuran (30 mL) at 0° C. under argon was added 4-(1-ethoxycarbonyl-1-methyl-ethyl)-piperazin-1-carboxylic acid tert-butyl ester (1.28 g). The reaction mixture was allowed to warm to room temperature and stirred for 2 hours, then quenched with saturated aqueous ammonium chloride (10 mL). The reaction mixture was partitioned between water and dichloromethane and the combined organic layers washed with brine and dried (MgSO$_4$). The solution was evaporated to give 4-(2-hydroxy-1,1-dimethyl-ethyl)-piperazin-1-carboxylic acid tert-butyl ester (0.43 g).

To a solution of 4-(2-hydroxy-1,1-dimethyl-ethyl)-piperazin-1-carboxylic acid tert-butyl ester (0.42 g) in anhydrous dichloromethane (10 mL) was added 2M hydrogen chloride (8.4 ml) and the mixture stirred for 12 hours. The solvent was evaporated to give 2-methyl-2-piperazin-1-yl-propan-1-ol hydrochloride salt as a white solid.

Reductive amination with 2-chloro-4-morpholin-4-yl-thieno[3,2-d]pyrimidine-6-carbaldehyde under the standard conditions in the presence of triethylamine gave the title compound as a white solid (0.169 g).

δ$_H$ (400 MHz, CDCl$_3$) 2.25 (br s, 8H), 3.34 (s, 2H), 3.72 (s, 2H), 3.77 (m, 4H), 3.92 (m, 4H), 7.10 (s, 1H).

REFERENCE EXAMPLE 48

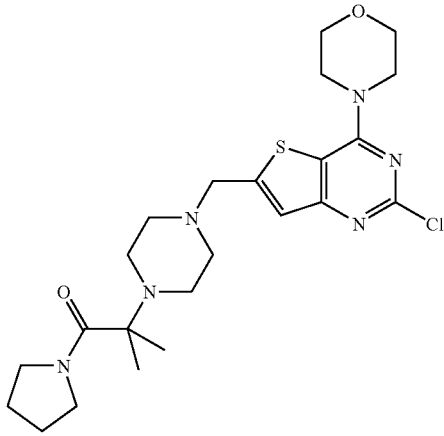

2-[4-(2-Chloro-4-morpholin-4-yl-thieno[3,2-d]pyrimidin-6-ylmethyl)-piperazin-1-yl]-2-methyl-1-pyrrolidin-1-yl-propan-1-one To a solution of tert-butyl-1-piperazinecarboxylate (1.20 g) in acetonitrile (15 mL) was added ethyl 2-bromoisobutyrate (5.00 g) followed by potassium carbonate (0.975 g). The reaction mixture was heated at 80° C. for 12 hours, then cooled and partitioned between water and dichloromethane. The organic layer was washed with brine, dried (MgSO$_4$). The solvent was evaporated and the residue purified by flash chromatography to give 4-(1-ethoxycarbonyl-1-methyl-ethyl)-piperazine-1-carboxylic acid tert-butyl ester (2.19 g).

To a solution of pyrrolidine (0.331 g) in anhydrous tetrahydrofuran (10 mL) at 0° C. under an argon atmosphere was added n-butyl lithium (1.86 mL; 2.5 M in hexane) and stirred for 30 minutes at 0° C. then at room temperature for 12 hours. The reaction mixture was quenched with saturated aqueous ammonium chloride solution and partitioned between water and dichloromethane. The combined organic solvents were dried and purified by flash chromatography to give 4-(1,1-dimethyl-2-oxo-2-pyrrolidin-1-yl-ethyl)-piperazine-1-carboxylic acid tert-butyl ester (0.745 g).

To a solution of 4-(1,1,1-dimethyl-2-oxo-2-pyrrolidin-1-yl-ethyl)-piperazine-1-carboxylic acid tert-butyl ester (0.745 g) in dichloromethane (10 mL) was added 2M hydrogen chloride in diethyl ether (4 mL) and the mixture stirred at room temperature for 12 hours. The solvent was evaporated to give 2-methyl-2-piperazin-1-yl-1-pyrrolidin-1-yl-propan-1-one hydrochloride salt as a beige solid. Reductive amination with 2-chloro-4-morpholin-4-yl-thieno[3,2-d]pyrimidine-6-carbaldehyde using the standard method in the presence of triethylamine gave the title compound as a white solid (0.355 g).

REFERENCE EXAMPLE 49

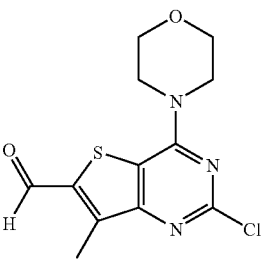

2-Chloro-7-methyl-4-morpholin-4-yl-thieno[3,2-d]pyrimidine-6-carbaldehyde

A solution of methyl 3-amino-4-methylthiophene-2-carboxylate (10.0 g, 58.4 mmol), in dichloromethane (120 mL) was cooled down to −78° C. Chlorosulfonyl isocyanate (6.6 mL, 75.8 mmol) was added dropwise over 2 minutes. The reaction mixture was stirred at −78° C. for 20 minutes and then the cooling bath was removed and the mixture allowed to warm to room temperature. The reaction mixture thickened and was diluted with dichloromethane and evaporated down to give an off-white solid. This was treated with 6 M hydrochloric acid (150 mL) and heated to reflux for 2 hours.

To the cooled reaction mixture was added water and the precipitated solid filtered and dried to give a white solid as 4-methyl-3-ureido-thiophene-2-carboxylic acid methyl ester (9.46 g). This intermediate was heated to reflux in methanol (150 mL) and 2M sodium hydroxide solution (100 mL) for 2 hours. The cooled reaction mixture was acidified with concentrated hydrochloric acid and the precipitated solid filtered, washed with water and dried to give a white solid as 7-methyl- 1H-thieno[3,2-d]pyrimidine-2,4-dione (6.96 g). This was converted to the title compound using the methods described above.

$\delta_H$ (400 MHz, CDCl$_3$) 2.78 (s, 3H), 3.87 (t, J=4.8, 4H), 4.07 (t, J=4.8, 4H), 10.41 (s,1H).

REFERENCE EXAMPLE 50

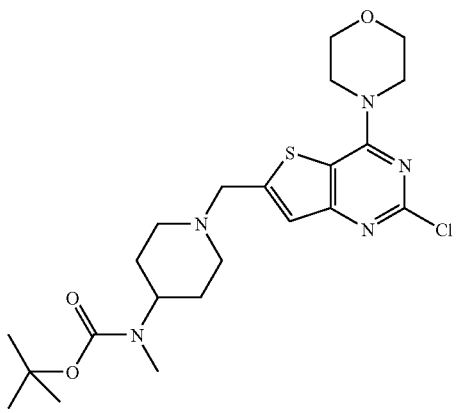

[1-(2-Chloro-4-morpholin-4-yl-thieno[3,2-d]pyrimidin-6-ylmethyl)-piperidin-4-yl]-methyl-carbamic acid tert-butyl ester To a solution of 6-bromomethyl-2-chloro-4-morpholin-4-yl-thieno[3,2-d]pyrimidine (85 mg, 0.244 mmol) in DMF (2 mL) were added water (13 µL), methyl-piperidin-4-yl-carbamic acid tert-butyl ester (105 mg, 0.489 mmol) and cesium carbonate (159 mg, 0.489 mmol). The resulting mixture was stirred at RT for 18 h. The reaction mixture was loaded onto an Isolute® SCX-2 cartridge, washed with MeOH then eluted with 2 M NH$_3$ in MeOH. The resultant residue was purified by column chromatography to give the title compound as a pale brown solid (73 mg, 62%).

[M+H]$^+$ 482.2

REFERENCE EXAMPLE 51

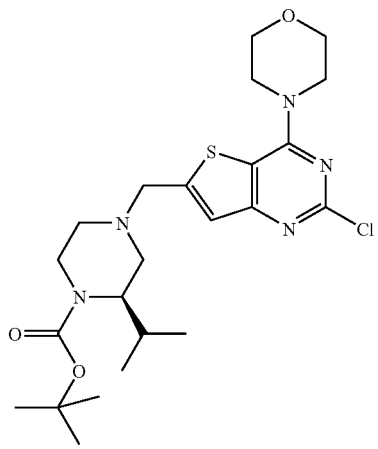

(R)-4-(2-Chloro-4-morpholin-4-yl-thieno[3,2-d]pyrimidin-6-ylmethyl)-2-isopropyl-piperazine-1-carboxylic acid tert-butyl ester To a solution of 6-bromomethyl-2-chloro-4-morpholin-4-yl-thieno[3,2-d]pyrimidine (100 mg, 0.29 mmol) in DMF (3 mL) were added (R)-2-isopropyl-piperazine-1-carboxylic acid tert-butyl ester hydrochloride (87 mg, 0.33 mmol) and potassium carbonate (124 mg, 0.90 mmol). The resulting mixture was stirred at RT for 18 h, then diluted with water and DCM. The organic layer was separated, dried (Na$_2$SO$_4$) and concentrated in vacuo. The resultant residue was purified by column chromatography to give the title compound as a white solid (139 mg, 97%).

[M]$^+$ 496.3

EXAMPLE 2

2-(1H-Indol-4-yl)-4-morpholin-4-yl-6-[4-(3-morpholin-4-yl-propane-1-sulfonyl)-piperazin-1-ylmethyl]-thieno[3,2-d]pyrimidine 4-(3-Chloro-propane-1-sulfonyl)-piperazine-1-carboxylic acid tert-butyl ester To a solution of 1-BOC-piperazine (3.26 g) and triethylamine (2.68 mL) in dry chloroform (25 mL) was added 3-chloropropanesulfonyl chloride (2.62 g) at 0° C. After 2 h wash with water, dry (Na$_2$SO$_4$), filter and concentrate to give crude material. Product was isolated by flash chromatography (95%).

4-[3-(Piperazine-1-sulfonyl)-propyl]-morpholine dihydrochloride 4-(3-Chloro-propane-1-sulfonyl)-piperazine-1-carboxylic acid tert-butyl ester (4.64 g), morpholine (1.6 mL, 1.3 eq.), potassium carbonate (2.17 g, 1.1 eq.), potassium iodide (1.11 g, 0.47 eq.) were refluxed together in dry MeCN (100 mL) overnight. Concentration in vacuo, then aqueous work-up followed by flash chromatography gave 4-(3-morpholin-4-yl-propane-1-sulfonyl)-piperazine-1-carboxylic acid tert-butyl ester (89%). Treatment with 2M HCl in ether gave product (4.46 g).

2-Chloro-4-morpholin-4-yl-6-[4-(3-morpholin-4-yl-propane-1-sulfonyl)-piperazin-1-ylmethyl]-thieno[3,2-d]pyrimidine 2-Chloro-4-morpholin-4-yl-6-[4-(3-morpholin-4-yl-propane-1-sulfonyl)-piperazin-1-ylmethyl]-thieno[3,2-d]pyrimidine was prepared following the standard procedure using 4-[3-(piperazine-1-sulfonyl)-propyl]-morpholine dihydrochloride (650 mg). Aqueous work-up followed by flash chromatography gave product (31%).

Reaction of 2-chloro-4-morpholin-4-yl-6-[4-(3-morpholin-4-yl-propane-1-sulfonyl)-piperazin-1-ylmethyl]-thieno[3,2-d]pyrimidine (66 mg) with indole boronic acid under standard conditions (as described for 2-(1H-indol-4-yl)-6-(4-methyl-piperazin-1-ylmethyl)-4-morpholin-4-yl-thieno[2,3-d]pyrimidine) followed by aqueous work-up and flash chromatography gave product (8.8%).

NMR: (DMSO):1.81 (m, 2H, CH2), 2.33-2.36 (m, 6H, 3×CH2), 2.58 (m, 4H, 2×CH2), 3.06-3.10 (m, 2H, CH2), 3.21 (m, 4H, 2×CH2), 3.55-3.57 (m, 4H, 2×CH2), 3.81-3.82 (m, 4H, 2×CH2), 3.93 (s, 2H, CH2), 3.96-3.98 (m, 4H, 2×CH2), 7.17 (t, H, ArH, J=7.76 Hz), 7.41-7.43 (m, 2H, 2×ArH), 7.50 (d, H, ArH, J=8.02 Hz), 8.10 (d, H, ArH, J=7.37 Hz), 11.32 (bs, H, NH).

MS: (ESI+): MH+=626.15

EXAMPLE 3

(3-{4-[2-(1H-Indol-4-yl)-4-morpholin-4-yl-thieno[3,2-d]pyrimidin-6-ylmethyl]-piperazine-1-sulfonyl}-propyl)-dimethyl-amine Preparation of dimethyl-[3-(piperazine-1-sulfonyl)-propyl]-amine dihydrochloride To 1-BOC-piperazine (6.00 g) in dry dichloromethane (60 ml) and triethylamine (5.85 ml) at 0° C. was added 3-chloropropanesulfonyl chloride (4.5 ml). The reaction mixture was stirred for 2 hours, diluted with dichloromethane, washed with brine, dried ($MgSO_4$), filtered and volatiles removed in vacuo. Purification on silica gave 4-(3-chloro-propane-1-sulfonyl)-piperazine-1-carboxylic acid tert-butyl ester (9.85 g). This was reacted with dimethylamine hydrochloride in acetonitrile and potassium carbonate to give 4-(3-dimethylamino-propane-1-sulfonyl)-piperazine 1-carboxylic acid tert-butyl ester. BOC-group was removed using HCl in ether under standard procedures to give the title compound.

{3-[4-(2-Chloro-4-yl-thieno[3.2-d]pyrimidin-6-ylmethyl)-piperazine-1-sulfonyl]-propyl}-dimethyl-amine was prepared from 6-bromomethyl-2-chloro-4-morpholin-4-yl-thieno[3.2-d]pyrimidine and dimethyl-[3-(piperazine-1-sulfonyl)-propyl]-amine dihydrochloride in DMF and potassium carbonate.

{3-[4-(2-Chloro-4-yl-thieno[3.2-d]pyrimidin-6-ylmethyl)-piperazine-1-sulfonyl]-propyl}-dimethyl-amine (80 mg), 4-indole-boronic acid (51 mg), sodium hydrogen carbonate (40 mg) and $PdCl_2(PPh_3)_2$ (10 mg) in toluene (2 ml), ethanol (1 ml) and water (0.5 ml) were heated in a microwave at 130° C. for 120 min. Dichloromethane/water extraction and purification on silica gave the title compound (27 mg).

NMR: ($CDCl_3$): 2.00-2.08 (2H, m), 2.26 (6H, s), 2.42 (2H, t, J=6.7), 2.68-2.72 (4H, m), 3.00-3.05 (2H, m), 3.37-3.41 (4H, m), 3.90 (2H, S), 3.92-3.96 (4H, m), 4.08-4.12 (4H, m), 7.28-7.33 (2H, m), 7.38 (1H, s), 7.50 (1H, d, J=8.0), 7.56 (1H, s), 8.20 (1H, d, J=7.3), 8.30 (1H, br)

MS: (ESI+) MH+ 584 (4%)

EXAMPLE 4

2-(1H-Indol-4-yl)-6-(4-methyl-piperazin-1-ylmethyl)-4-morpholin-4-yl-thieno[2,3-d]pyrimidine 2-Chloro-6-(4-methyl-piperazin-1-ylmethyl)-4-morpholin-4-yl-thieno[2,3-d]pyrimidine 2-Chloro-4-morpholin-4-yl-thieno[2,3-d]pyrimidine-6-carbaldehyde (400 mg) and N-methylpiperazine (1.3 eq.) were stirred together in dry 1,2-dichloroethane (20 mL). After 4 h sodium triacetoxyborohydride (2.3 eq.) was added and the mixture stirred overnight. The mixture was diluted with $Na_2CO_3$ solution then extracted with ethyl acetate. Combined extracts were dried ($Na_2SO_4$), filtered, concentrated and then purified by flash chromatography to give product (57%).

A mixture of 2-chloro-6-(4-methyl-piperazin-1-ylmethyl)-4-morpholin-4-yl-thieno[2,3-d]pyrimidine (100 mg), $Na_2CO_3$ (3 eq.), indazole boronate ester (1.5 eq.) and bis(triphenylphosphine)palladium (II) chloride (0.05 eq.) in toluene/ethanol/water (4:2:1) was heated at 136° C., with cooling, for 1.5 h in a microwave reactor. The resulting mixture was diluted with water then extracted with ethyl acetate. Combined extracts were dried ($Na_2SO_4$), filtered and concentrated then triturated to give product (87%).

400 MHz (1H NMR $CDCl_3$) 2.31 (s, 3H, CH3), 2.49 (m, 4H, 2×CH2), 2.59 (m, 4H, 2×CH2), 3.77 (s, 2H, CH2), 3.90-3.93 (m, 4H, 2×CH2), 3.97-3.99 (m, 4H, 2×CH2), 7.14 (s, H, ArH), 7.28-7.33 (m, 2H, 2×ArH), 7.49 (d, H, ArH, J=8.13 Hz), 7.59 (m, H, ArH), 8.23 (s, H, ArH), 8.24 (bs, H, NH).

MH+=449.20

EXAMPLE 5

2-(1H-Indol-4-yl)-6-(4-methanesulfonyl-piperazin-1-ylmethyl)-4-morpholin-4-yl-thieno[2,3-d]pyrimidine 2-Chloro-6-(4-methyl-piperazin-1-ylmethyl)-4-morpholin-4-yl-thieno[2,3-d]pyrimidine 2-Chloro-4-morpholin-4-yl-thieno[2,3-d]pyrimidine-6-carbaldehyde (400 mg) and 1-methanesulfonyl-piperazine hydrochloride (1.3 eq.) were stirred together in dry 1,2-dichloroethane (20 mL). After 4 h sodium triacetoxyborohydride (2.3 eq.) was added and the mixture stirred overnight. The mixture was diluted with $Na_2CO_3$ solution then extracted with ethyl acetate. Combined extracts were dried ($Na_2SO_4$), filtered and concentrated. Trituration gave product (60%).

Suzuki coupling under standard conditions with 4-indole boronate ester gave the title compound which was purified by trituration (61%).

400 MHz (1H NMR $CDCl_3$) 2.66-2.68 (m, 4H, 2×CH2), 2.80 (s, 3H, CH3), 3.29 (m, 4H, 2×CH2), 3.82 (s, 2H, CH2), 3.91-3.93 (m, 4H, 2×CH2), 3.97-4.00 (m, 4H, 2×CH2), 7.15 (s, H, ArH), 7.28-7.33 (m, 2H, 2×ArH), 7.50 (d, H, ArH, J=8.08 Hz), 7.57 (s, H, ArH), 8.23 (m, 2H ArH+NH).

MH+=513.13

EXAMPLE 6

2-(7-Methyl-1H-indol-4-yl)-6-(4-methyl-piperazin-1-ylmethyl)-4-morpholin-4-yl-thieno[3,2-d]pyrimidine To a solution of 4-bromo-2-nitrotoluene (3.0 g, 13.9 mmol) in THF (40 mL) at −40° C. was added vinyl magnesium bromide (48.6 mmol, 48.6 mL; 1.0 M in THF) dropwise over 15 minutes and the mixture stirred at −40° C. for 1.5 hours. The reaction was quenched by the addition of saturated aqueous ammonium chloride and extracted with ethyl acetate. The combined organic layers were washed with brine, separated and dried ($MgSO_4$). The residue was evaporated and purified by column chromatography to yield 4-bromo-7-methylindole (1.03 g).

To a suspension of 4-bromo-7-methylindole (349 mg, 1.66 mmol), bispinacolatodiboron (2.66 mmol, 674 mg) and potassium acetate (4.98 mmol, 489 mg) in DMSO (12 mL) was added $Pd(dppf)_2Cl_2$ (0.05 mmol, 41 mg). The mixture was degassed with argon and heated at 80° C. for 8 hours. The mixture was allowed to cool and partitioned between ether and water and the aqueous later extracted with ether. The combined organic layers were washed with brine, separated and dried. The crude product was purified by chromatography to yield 7-methyl-4-(4,4,5,5-tetramethyl-[1,3,2]dioxaborolan-2-yl)-1H-indole as a solid which was triturated in petrol giving a white crystalline solid (117 mg).

To a mixture of 2-Chloro-6-(4-methyl-piperazin-1-ylmethyl)-4-morpholin-4-yl-thieno[3,2-d]pyrimidine (0.23 mmol, 84 mg) and 7-Methyl-4-(4,4,5,5-tetramethyl-[1,3,2]dioxaborolan-2-yl)-1H-indole (0,46 mmol, 117 mg) in toluene (2 mL), ethanol (1 mL) and water (0.5 mL) was added sodium carbonate (0.69 mmol, 73 mg). Pd (PPh$_3$)$_2$Cl$_2$ (0.012 mmol, 8 mg) was added and the mixture heated in a microwave reactor at 130° C. for 1.5 hours. The mixture was allowed to cool and partitioned between water and dichloromethane. The combined organic layers were washed with brine, separated and dried (MgSO$_4$). The solvent was evaporated and the crude product purified by column chromatography to yield 2-(7-methyl-1H-indol-4-yl)-6-(4-methyl-piperazin-1-ylmethyl)-4-morpholin-4-yl-thieno[3,2-d]pyrimidine as a pale cream solid (75 mg).

δH (400 MHz, CDCl$_3$) 2.34 (s, 3H), 2.56 (s, 7H), 2.64 (s, 4H), 3.85 (s, 2H), 3.98 (t, J=4.8, 4H), 4.07 (t, J=4.8, 4H), 7.11 (d, J=7.6, 1H), 7.33 (m 1H), 7.36 (s, 1H), 7.58 (m, 1H), 8.13 (d, J=7.6, 1H), 8.17 (br s, 1H).

[M+H]+ 463.

EXAMPLE 7

2-(1H-Indol-4-yl)-7-methyl-6-(4-methyl-piperazin-1-ylmethyl)-4-morpholin-4-yl-thieno[3,2-d]pyrimidine 4-(4,4,5,5-Tetramethyl-[1,3,2]dioxaborolan-2-yl)-1H-indole was prepared by the general method described. 2-Chloro-7-methyl-6-(4-methyl-piperazin-1-ylmethyl)-4-morpholin-4-yl-thieno[3,2-d]pyrimidine was prepared from 3-amino-4-methyl-thiophene-2-carboxylic acid methyl ester using the method described above. Suzuki coupling was carried out using the general method described yielded the title compound (32 mg) as an off-white solid.

δH (400 MHz, CDCl$_3$) 2.32 (s, 3H), 2.50 (br s, 4H), 2.53 (s, 3H), 2.63 (br s, 4H), 3.83 (s, 2H), 3.91 (t, J=4.8, 4H), 4.08 (t, J=4.8, 4H), 5.49 (t, J=7.8, 1H), 7.33 (m, 1H), 7.49 (d, J=8.0, 1H), 7.72 (m, 1H), 8.24 (br s, 1H), 8.30 (d, J=7.1, 1H)

[M+H]+ 463.

EXAMPLE 8

Benzyl-{1-[2-(1H-indol-4-yl)-4-morpholin-4-yl-thieno[3,2-d]pyrimidine-6-ylmethyl]-piperidin-4-yl}-(2-methoxy-ethyl)-amine 1-BOC-4-piperidone (2.00 g) and 2-methoxyethylamine (872 μl) were stirred together in methanol (20 ml) at room temperature for 12 hours. Sodium borohydride (760 mg) was added in several aliquots over 30 minutes and the reaction mixture stirred for a further 12 hours at ambient temperature. The solvents were removed in vacuo and the residue diluted with dichloromethane (50 ml) and washed with brine, dried (MgSO$_4$). The solvents were removed in vacuo to give a residue which was purified by flash silica chromatography to give 4-(2-methoxy-ethylamino)-piperidine-1-carboxylic acid tert-butyl ester (1.69 g) as a colourless oil. To a solution of 4-(2-methoxy-ethylamino)-piperidine-1-carboxylic acid tert-butyl ester (425 mg) stirring in anhydrous acetonitrile (10 ml) was added benzyl bromide (215 μl), followed by potassium carbonate (340 mg) and the reaction mixture heated to reflux for 12 hours.

The reaction mixture was cooled and diluted with dichloromethane (30 ml), washed with water, brine and dried (MgSO$_4$). The solvents were removed in vacuo to give a residue which was purified by silica flash chromatography to give 4-[benzyl-(2-methoxy-ethyl)-amino]-piperidine-1-carboxylic acid tert-butyl ester as a white solid (484 mg). 4-[Benzyl-(2-methoxy-ethyl)-amino]-piperidine-1-carboxylic acid tert-butyl ester (442 mg), and 2-chloro-4-morpholin-4-yl-thieno[3,2-d]pyrimidine-6-carbaldehyde (300 mg) were treated under standard reductive amination conditions to give benzyl-[1-(2-chloro-4-morpholin-4-yl-thieno[3,2-d]pyrimidine-6-ylmethyl)-piperidin-4-yl]-(2-methoxy-ethyl)-amine (379 mg), as an oil which crystallized on standing.

Benzyl-[1-(2-chloro-4-morpholin-4-yl-thieno[3,2-d]pyrimidine-6-ylmethyl)-piperidin-4-yl]-(2-methoxy-ethyl)-amine (150 mg), was used in a Suzuki coupling with 4-(4,4,5,5-tetramethyl-[1,3,2]dioxaborolan-2-yl)-1H-indole (141 mg), to give after flash silica purification the title compound (105 mg) as a white solid.

1H NMR (400 MHz CDCl$_3$) 8.24 (bs, 1H); 8.18 (d, 1H, J=7.2 Hz); 7.49 (m, 3H); 7.34-7.22 (m, 7H); 4.09 (m, 4H); 3.92 (m, 4H); 3.80 (s, CH2); 3.72 (s, CH2); 3.34 (t, 2H, J=6.6 Hz); 3.26 (s, 3H); 3.04 (m, 2H); 2.75 (t, 2H, J=6.7 Hz); 2.56 (m, 1H); 2.06 (m, 2H); 1.72 (m, 4H)

LC/MS (m+1)=597.3 Purity>95%

EXAMPLE 9

2-(6-Methoxy-1H-indol-4-yl)-6-(4-methyl-piperazin-1-ylmethyl)-4-morpholin-4-yl-thieno[3,2-d]pyrimidine 6-Methoxy-4-(4,4,5,5-tetramethyl-[1,3,2]dioxaborolan-2-yl)-1H-indole was prepared by the general method described and coupled with 2-chloro-6-(4-methyl-piperazin-1-ylmethyl)-4-morpholin-4-yl-thieno[3,2-d]pyrimidine using the standard Suzuki coupling to yield the title compound as a pale yellow solid.

δH (400 MHz, CDCl$_3$) 2.18 (s, 3H), 2.51 (br s, 4H), 2.63 (br s, 4H), 3.84 (s, 2H), 3.90 (t, J=4.8, 4H), 4.07 (t, J=4.8, 4H), 7.01 (d, J=1.7, 1H), 7.21 (m, 1H), 7.37 (s, 1H), 7.46 (m, 1H), 7.89 (d, J=2.3, 1H), 8.12 (br s, 1H).

[M+H]+ 479.

EXAMPLE 10

1-(2-hydroxy-ethyl)-4-[2-(1H-indol-4-yl)-4-morpholin-4-yl-thieno[3,2-d]pyrimidine-6-ylmethyl]-piperazin-2-one To 4-Cbz-piperazin-2-one (1.95 g) in N,N-dimethylformamide (5 mL) at 0° C. was added sodium hydride (60% dispersion in mineral oil, 660 mg) in several aliquots. After stirring for 1 hour, 2-bromoethylacetate (1.38 ml) was added. After stirring overnight at room temperature, the mixture was diluted with ethyl acetate, washed with brine, dried (MgSO$_4$) and the solvent removed in vacuo. The residue was purified using flash chromatography to yield 4-(2-acetoxy-ethyl)-3-oxo-piperazine-1-carboxylic acid benzyl ester (925 mg).

To 4-(2-acetoxy-ethyl)-3-oxo-piperazine-1-carboxylic acid benzyl ester (925 mg) in methanol (10 ml) was added potassium carbonate (800 mg) in water (4 mL). After 2 hours at room temperature the mixture was diluted with chloroform, washed with brine, dried (MgSO$_4$) and the solvent removed in vacuo to yield 4-(2-hydroxy-ethyl)-3-oxo-piperazine-1-carboxylic acid benzyl ester (780 mg). This material was dissolved in ethanol and stirred over 10% Pd/C under an atmosphere of hydrogen for 24 hours. The reaction mixture was then filtered through celite and the solvent removed in vacuo to give 1-(2-hydroxy-ethyl)-piperazin-2-one (413 mg), which was used in a standard reductive amination procedure with 2-chloro-4-morpholin-4-yl-thieno[3,2-d]pyrimidine-6-carbaldehyde to give 4-(2-chloro-4-morpholin-4-yl-thieno[3,2-d]pyrimidin-6-ylmethyl)-1-(2-hydroxy-ethyl)-piperazin-2-one. This compound (150 mg) was used in a Suzuki coupling with 4-(4,4,5,5-tetramethyl-[1,3,2]dioxaborolan-2-yl)-1H-indole (96 mg) to give after flash silica purification the title compound (39 mg) as a white solid.

1H NMR (400 MHz CDCl$_3$) 8.28 (bs, 1H); 8.19 (d, 1H, J=7.3 Hz); 7.52 (m, 2H); 7.40 (s, 1H); 7.29 (m, 2H); 4.09 (m, 4H); 3.91 (m, 4H); 3.83 (m, CH2); 3.59 (m, CH2); 3.47 (m, CH2); 3.37 (s, CH2); 2.91 (bs, 1H); 2.82 (m, CH2)

LC/MS (m+1)=493.2; Purity>95%

EXAMPLE 11

2-(1H-Indol-4-yl)-4-morpholin-4-yl-6-(4-thiazol-4-ylmethyl-piperazin-1-ylmethyl)-thieno[3,2-d]pyrimidine To a suspension of 4-thiazolecarboxylic acid (500 mg) in tetrahydrofuran (10 mL) was added borane-dimethylsulfide complex (0.73 mL). After 24 hours the mixture was cooled to 0° C. and quenched by the addition of 2M hydrochloric acid and extracted into ethyl acetate. The organic layers were washed with brine and dried (MgSO$_4$). The solvent was evaporated and the residue stirred in dichloromethane-methanol overnight. The mixture was concentrated and the residue purified by flash chromatography to give thiazol-4-yl-methanol (173 mg).

To a solution of thiazol-4-yl-methanol (168 mg) in dichloromethane (5 mL) was added triethylamine (0.33 mL) followed by methanesulfonyl chloride (0.17 mL) at 0° C. The mixture was stirred at room temperature for 10 minutes and diluted with dichloromethane, washed with brine and dried (MgSO$_4$). The crude product was purified by flash chromatography to give methanesulfonic acid thiazol-4-yl methyl ester (263 mg).

To a solution of 2-chloro-4-morpholin-4-yl-6-piperazin-1-ylmethyl-thieno[3,2-d]pyrimidine (300 mg) and methanesulfonic acid thiazol-4-yl methyl ester (213 mg) in acetonitrile (10 mL) was added potassium carbonate (164 mg) and the mixture heated at 80° C. for 8 hours. The cooled mixture was filtered, the solvent evaporated and the residue partitioned between dichloromethane and water. The organic layer was washed with brine, dried (MgSO$_4$) and the solvent evaporated. The residue was purified by flash chromatography to give 2-chloro-4-morpholin-4-yl-6-(4-thiazol-4-ylmethyl-piperazin-1-ylmethyl)-thieno[3,2-d]pyrimidine (249 mg). Suzuki coupling between this compound (83 mg) and 4-(4,4,5,5-tetramethyl-[1,3,2]dioxaborolan-2-yl)-1H-indole (87 mg) using the general method described gave the title compound as an off-white solid (54 mg).

δH (400 MHz, CDCl$_3$) 2.63 (br s, 8H), 3.78 (s, 2H), 3.85 (s, 2H), 3.91 (t, =4.8, 4H), 3.99 (t, J=4.8, 4H), 7.20 (d, J=1.7,1H), 7.30-7.33 (m, 2H), 7.36 (s, 1H), 7.48 (d, J=8.1, 1H), 7.54 (m, 1H), 8.18 (d, J=7.4, 1H), 8.28 (br s, 1H), 8.78 (d, J=2.0, 1H). [M+H]+ 532.

EXAMPLE 12

6-[4-(1H-Imidazol-2-ylmethyl)-piperazin-1-ylmethyl]-2-(1H-indol-4-yl)-4-morpholin-4-yl-thieno[3,2-d]pyrimidine 2-Chloro-4-morpholin-4-yl-6-piperazin-1-ylmethyl-thieno[3,2-d]pyrimidine was prepared using standard reductive amination conditions with 1-BOC-piperazine followed by treatment with HCl. Reaction of this compound with imidazole-2-carboxaldehyde using standard reductive amination conditions yielded 2-chloro-6-[4-(1H-imidazol-2-ylmethyl)-piperazin-1-ylmethyl]-4-morpholin-4-yl-thieno[3,2-d]pyrimidine (75 mg) which was used in a Suzuki coupling with 4-(4,4,5,5-tetramethyl-[1,3,2]dioxaborolan-2-yl)-1H-indole (84 mg) to give, after flash silica purification, the title compound (36 mg) as a white solid.

1H NMR (400 MHz CDCl$_3$) 8.29 (bs, 1H); 8.18 (d, 1H, J=8.1 Hz); 7.51 (m, 2H); 7.31 (m, 3H); 7.00 (s, 2H); 4.08 (m, 4H); 3.91 (m, 4H); 3.86 (s, 2H); 3.69 (s, 2H); 2.60 (bs, 8H).

LC/MS (m=1)=515.2; Purity=95%

EXAMPLE 13

2-(1H-Indol-4-yl)-4-morpholin-4-yl-6-(4-pyridin-2-ylmethyl-piperidin-1-ylmethyl)-thieno[3,2-d]pyrimidine 4-Pyridin-2-ylmethyl-piperidine-1-carboxylic acid tert-butyl ester was synthesized according to the procedure mentioned in *J. Org. Chem*, 2001, 66, pp 2487-2492. It was treated further with HCl in dichloromethane/methanol to yield 2-piperidin-4-ylmethyl-pyridine dihydrochloride salt.

2-Chloro-4-morpholin-4-yl-6-(4-pyridin-2-ylmethyl-piperidin-1-ylmethyl)-thieno[3,2d]pyrimidine was prepared using the procedure for 2-chloro-4-morpholin-4-yl-6-(4-pyrimidin-2-yl-piperazin-1-ylmethyl)-thieno[3,2-d]pyrimidine. 2-(1H-Indol-4-yl)-4-morpholin-4-yl-6-(4-pyridin-2-ylmethyl-piperidin-1-ylmethyl)-thieno[3,2-d]pyrimidine was prepared by the standard Suzuki coupling.

δH (400 MHz; CDCl$_3$) 1.43(2H, m); 1.66(2H, m); 1.84 (1H, m); 2.10 (2H, t, J=10.6 Hz); 2.75 (2H, d, J=7.1 Hz); 2.98 (2H, d, J=11.4 Hz); 3.82 (2H, s); 3.98 (4H, t, J=4.8 Hz); 4.08 (4H, t, J=4.8 Hz); 7.10 (2H, m); 7.30 (3H, m); 7.49 (1H, d, J=8.1 Hz); 7.55 (2H, m); 8.19 (1H, d, J=7.2 Hz); 8.27 (1H, br s); 8.57 (1H,m).

M+H(525)

EXAMPLE 14

2-(1H-Indol-4-yl)-4-morpholin-4-yl-6-(4-pyrimidin-2-yl-piperazin-1-ylmethyl)-thieno[3,2-d]pyrimidine A mixture of 1-(2-pyrimidyl)piperazine dihydrochloride (0.218 g), 2-chloro-4-morpholin-4-yl-thieno[3,2-d]pyrimidine-6-carbaldehyde (0.20 g) and triethylamine (0.28 ml) in 1,2-dichloroethane (3 ml) was stirred for 1 hour. Acetic acid (0.040 ml) and sodium triacetoxyborohydride (0.195 g) were then added. After stirring for 24 hours the reaction mixture was diluted with dichloromethane, washed with sodium bicarbonate solution, dried (MgSO$_4$) and the solvent removed in vacuo. The residue was purified by flash chromatography to 2-chloro-4-morpholin-4-yl-6-(4-pyrimidin-2-yl-piperazin-1-ylmethyl)-thieno[3,2-d]pyrimidine (0.115 g). 2-(1H-Indol-4-yl)-4-morpholin-4-yl-6-(4-pyrimidin-2-yl-piperazin-1-ylmethyl)-thieno[3,2-d]pyrimidine was prepared using the standard Suzuki coupling.

δH (400 MHz; CDCl$_3$) 2.64 (4H, t, J=5.0 Hz); 3.90 (10H, m); 4.10 (4H, t, J=4.8 Hz); 6.49 (1H, t, J=4.8 Hz); 7.32 (2H, m); 7.40 (1H, s); 7.50 (1H, d, J=8.0 Hz); 7.56 (1H, s); 8.20 (1H, d, J=7.3 Hz); 8.25 1H, br s); 8.30 (2H, d, J=4.7 Hz).

M+H (513)

EXAMPLE 15

1'-[2-(1H-Indol-4-yl)-4-morpholin-4-yl-thieno[3,2-d]pyrimidin-6-ylmethyl]-[1,4']bipiperidinyl)

This compound was prepared using the general methods described above.

δH (400 MHz, CDCl$_3$) 1.37 (m, 2H), 1.51-1.62 (m, 6H), 1.69 (m, 2H), 2.03 (m, 2H), 2.21 (m, 2H), 2.46 (m, 4H), 2.98 (m, 2H), 3.74 (s, 2H), 3.83 (t, J=4.8, 4H), 4.00 (t, J=4.8, 4H), 7.19 (s, 1H), 7.20-7.24 (m, 3H), 7.40 (d, J=8.2, 1H), 7.47 (m, 1H), 8.11 (dd, J=7.4, 0.7, 1H), 8.25 (br s, 1H).

[M+H]+ 517.

EXAMPLE 16

2-(1H-indol-4-yl)-6-[4-(1-methyl-1H-imidazol-2-ylmethyl)-piperazin-1-ylmethyl]-4-morpholin-4-yl-thieno[3,2-d]pyrimidine Prepared in a similar manner to 6-[4-(1H-imidazol-2-ylmethyl)-piperazin-1-ylmethyl]-2-(1H-indol-4-yl)-4-morpholin-4-yl-thieno[3,2-d]pyrimidine 1H NMR (400 MHz CDCl$_3$) 8.28 (bs, 1H); 8.18 (d, 1H, J=7.1 Hz); 7.51 (m, 2H); 7.38 (m, 3H); 6.93 (s, 1H); 6.84 (s, 1H); 4.08 (m, 4H); 3.91 (m, 4H); 3.83 (s, 2H); 3.70 (s, 3H); 3.63 (s, 2H); 2.54 (bs, 8H)

LC-MS (m+1) 529.3 Purity>95%

EXAMPLE 17

[2-(1H-indol-4-yl)-4-morpholin-4-yl-thieno[3,2-d]pyrimidin-6-ylmethyl]-(1-methanesulphonyl-piperidin-4-yl)-methyl-amine To a solution of 1-methanesulfonyl-piperidine-4-one (173 mg; prepared from N-BOC-piperidone by reaction of piperidone-4-one TFA salt with methane sulfonyl chloride) stirring in anhydrous 1,2-dichloroethane (10 ml), was added 2-chloro-4-morpholin-4-yl-thienopyrimidine-6-ylmethyl methylamine (291 mg; as prepared from 2-chloro-4-morpholin-4-yl-thienopyrimidine-6-carbaldehyde and methylamine under reductive amination conditions), followed by glacial acetic acid (59 µl). Sodium triacetoxyborohydride (269 mg) was added in several aliquots and then stirred for 12 hours at room temperature. The reaction mixture was diluted with dichloromethane (30 ml) and washed with 50% sodium hydrogen carbonate solution, brine, and dried (MgSO$_4$). The solvents were removed in vacuo to give a residue which after purification by flash silica chromatography gave (2-chloro-4-morpholin-4-yl-thieno[3,2-d]pyrimidine-6-ylmethyl)-(1-methanesulphonyl-piperidin-4-yl)-methyl-amine (408 mg), which was used in a Suzuki coupling with 4-(4,4,5,5-tetramethyl-[1,3,2]dioxaborolan-2-yl)-1H-indole, to give, after flash silica purification the title compound (55 mg) as a white solid.

1H NMR (400 MHz CDCl$_3$) 8.25 (bs, 1H); 8.19 (d, 1H, J=7.4 Hz); 7.52 (m, 2H); 7.31 (m, 3H); 4.08 (m, 4H); 3.95 (s, 2H); 3.89 (m, 4H+CH2); 2.78 (s, 3H); 2.68 (m, CH2+CH); 2.39 (s, 3H); 1.95 (m, 2H); 1.76 (m, 2H).

LC-MS (m+1)=541.3 Purity>95%

EXAMPLE 18

N-{1-[2-(1H-Indol-4-yl)-4-morpholin-4-yl-thieno[3,2-d]pyrimidin-6-ylmethyl]-pyrrolidin-3-yl}-N-methyl-methanesulfonamide 3-Methylamino-pyrrolidine-1-carboxylic acid tert-butyl ester was prepared as described below for [2-(1H-Indol-4-yl)-4-morpholin-4-yl-thieno[3,2-d]pyrimidin-6-ylmethyl]-(1-methanesulfonyl-pyrrolidin-3-yl)-methyl-amine.

To a solution of 3-methylamino-pyrrolidine-1-carboxylic acid tert-butyl ester (0.50 g) in dichloromethane (10 ml) was added triethylamine (0.38 ml) followed by methanesulfonyl chloride (0.21 ml). After stirring for 24 hours the reaction mixture was diluted with dichloromethane, washed with sodium bicarbonate solution, dried (Mg$_2$SO$_4$) and the solvent removed in vacuo. The residue was purified by flash chromatography to yield 3-(methanesulfonyl-methyl-amino)-pyrrolidine-1-carboxylic acid tert-butyl ester (0.52 g). Treatment of this compound with HCl in dichloromethane/methanol yielded N-Methyl-N-pyrrolidin-3-yl-methanesulfonamide hydrochloride salt (0.41 g).

N-[1-(2-Chloro-4-morpholin-4-yl-thieno[3,2-d]pyrimidin-6-ylmethyl)-pyrrolidin-3-yl]-N-methyl-methanesulfonamide was prepared by the method described for N-[1-(2-chloro-4-morpholin-4-yl-thieno[3,2-d]pyrimidin-6-ylmethyl)-pyrrolidin-2-ylmethyl]-N-methyl-methanesulfonamide.

N-{1-[2-(1H-Indol-4-yl)-4-morpholin-4-yl-thieno[3,2-d]pyrimidin-6-ylmethyl]-pyrrolidin-3-yl}-N-methyl-methanesulfonamide was prepared by standard Suzuki coupling.

δH (400 MHz; CDCl$_3$) 1.93 (1H, m); 2.22 (1H, m); 2.47 (1H, q, J=8.3 Hz); 2.68 (1H, t, J=9.2 Hz); 2.80 (3H, s); 2.87 (1H, dd, J=3.9 Hz); 2.94 (3H, s); 3.00 (1H, m); 3.90 6H, m); 4.10 (4H, t, J=4.8 Hz); 4.62 (1H, m); 7.32 (3H, m); 7.50 (1H, d, J=8.0 Hz); 7.55 1H, s); 8.20 (1H, d, J=7.4 Hz); 8.27(1H, br s).

M+H (527)

EXAMPLE 19

{1-[2-(1H-Indol-4-yl)-4-morpholin-4-yl-thieno[3,2-d]pyrimidin-6-ylmethyl]piperidin-4-yl}-(2-methoxy-ethyl)-thiazol-2-ylmethyl-amine 1-BOC-4-piperidone (2.00 g) and 2-methoxyethylamine (872 µl) were stirred together in methanol (20 ml) at room temperature for 12 hours. Sodium borohydride (760 mg) was added in several aliquots over 30 minutes and the reaction mixture stirred for a further 12 hours at ambient. The solvents were removed in vacuo and the residue diluted with dichloromethane (50 ml) and washed with brine and dried (MgSO$_4$). The solvents were removed in vacuo to give a residue which was purified by flash silica chromatography to give 4-(2-methoxy-ethylamino)-piperidine-1-carboxylic acid tert-butyl ester (1.69 g) as a colourless oil.

To a mixture of 4-(2-methoxy-ethylamino)-piperidine-1-carboxylic acid tert-butyl ester (465 mg), and 2-thiazolecarboxaldehyde (190 µl) stirring in anhydrous 1,2-dichloroethane (5 ml) was added glacial acetic acid (1 equiv.) and sodium triacetoxyborohydride (458 mg). The reaction mixture was stirred for 12 hours at room temperature, then diluted with dichloromethane (40 ml), washed with brine, dried (MgSO$_4$) and the solvents removed in vacuo. The residue was purified using flash silica chromatography to give 4[(2-methoxy-ethyl)-thiazol-2-ylmethyl-amino]-piperidine-1-carboxylic acid tert-butyl ester (574 mg). Treatment of this compound with HCl in dichloromethane/methanol and a basic wash with sodium hydrogen carbonate yielded (2-methoxyethyl)-piperidin-4-yl-thiazol-2-ylmethyl-amine.

Treatment of this compound with 2-chloro-4-morpholin-4-yl-thieno[3,2-d]pyrimidine-6-carbaldehyde under standard reductive amination conditions gave [1-(2-chloro-4-morpholin-4-yl-thieno[3,2-d]pyrimidin-6-ylmethyl)-piperidin-4-yl]-(2-methoxy-ethyl)-thiazol-2-ylmethylamine as a white solid, which was used in a Suzuki coupling with 4-(4,4,5,5-tetramethyl-[1,3,2]dioxaborolan-2-yl)-1H-indole, to give after flash silica purification the title compound (145 mg) as a white solid.

1H NMR (400 MHz CDCl$_3$) 8.25 (bs, 1H); 8.18 (d, 1H, J=7.3 Hz); 7.69 (d, 1H, J=3.3 Hz); 7.54 (s, 1H); 7.49 (d, 1H, J=7.9 Hz); 7.28 (m, 4H); 4.09 (m, 4H+CH2); 3.92 (m, 4H); 3.80 (s, 2H); 3.47 (t, 2H, J=6.2 Hz); 3.30 (s, 3H); 3.04 (m, 2H); 2.86 (t, 2H, J=6.2 Hz); 2.62 (m, 2H); 2.08 (m, 2H)1.82 (m, 2H); 1.67 (m, 2H).

LC-MS (m+1)=604.3 Purity>95%

EXAMPLE 20

N-{1-[2-(1H-Indol-4-yl)-4-morpholin-4-yl-thieno[3,2-d]pyrimidin-6-ylmethyl]-pyrrolidin-2-ylmethyl}-N-methyl-methanesulfonamide Hydrogen chloride gas (4 g) was bubbled through methanol (120 mL) at 0° C. Proline (3.80 g) was then added and stirred for 4.5 hours, reduced in vacuo to give pyrrolidine-2-carboxylic acid methyl ester hydrochloride salt (5.5 g). To a suspension of pyrrolidine-2-carboxylic acid methyl ester hydrochloride salt (5.5 g) in acetonitrile (90 mL) was added triethylamine (10.2 mL) and di-tert-butyldicarbonate (8.0 g). After stirring for 16 hours the reaction mixture was reduced in vacuo. The residue was redissolved in dichloromethane (40 mL), washed with brine (40 mL), dried (MgSO4), reduced in vacuo and purified by column chromatography to give pyrrolidine-1,2-dicarboxylic acid 1-tert-butyl ester 2-methyl ester (6.33 g).

To a solution of pyrrolidine-1,2-dicarboxylic acid 1-tert-butyl ester 2-methyl ester (3.5 g) in toluene (40 mL) at −78° C. was added dropwise diisobutylaluminium hydride (20 mL of a 1.5 M solution in toluene) maintaining the temperature below −65° C. The reaction mixture was stirred at −78° C. for 2 hours and then quenched with methanol (10 mL). The mixture was then diluted with diethyl ether (50 mL), potassium sodium tartrate tetrahydrate was added and the mixture stirred vigorously for 20 min at room temperature. The two phases were then separated and the aqueous layer extracted with dichloromethane (2×50 mL). The combined organics were then washed with brine (100 mL), dried (MgSO$_4$), reduced in vacuo and purified by column chromatography to give 2-formyl-pyrrolidine-1-carboxylic acid tert-butyl ester (2.68 g).

To a suspension of 2-formyl-pyrrolidine-1-carboxylic acid tert-butyl ester (2.68 g) in methanol (30 mL) was added a solution of methylamine (0.83 g) in methanol (3 mL). The reaction mixture was stirred for 72 hours and then sodium borohydride (0.76 g) and molecular sieves were added. After stirring for 2 hours, the reaction mixture was filtered and the filtrate reduced in vacuo. The residue was re-dissolved in dichloromethane (30 mL), washed with saturated sodium bicarbonate solution (30 mL), brine (30 mL), dried (MgSO$_4$) and reduced in vacuo to give 2-methylaminomethyl-pyrrolidine-1-carboxylic acid tert-butyl ester (2.56 g). To a solution of 2-methylaminomethyl-pyrrolidine-1-carboxylic acid tert-butyl ester (0.50 g) in dichloromethane (10 mL) was added triethylamine (0.36 mL) followed by methanesulfonyl chloride (0.20 mL). After stirring for 3 hours the reaction mixture was diluted with dichloromethane, washed with sodium bicarbonate solution, dried (MgSO$_4$) and the solvent removed in vacuo. The residue was purified by flash chromatography to yield 2-[(methanesulfonyl-methyl-amino)-methyl]-pyrrolidine-1-carboxylic acid tert-butyl ester as a white solid (0.63 g). Treatment of this compound with HCl in dichloromethane/methanol yielded N-methyl-N-pyrrolidin-2-ylmethyl-methanesulfonamide hydrochloride (0.49 g).

N-[1-(2-chloro-4-morpholin-4-yl-thieno[3,2-d]pyrimidin-6-ylmethyl)-pyrrolidin-2-ylmethyl]-N-methyl-methanesulfonamide was prepared by the standard Suzuki coupling method δH (400 MHz; CDCl$_3$) 1.82 (3H, m); 2.03 (1H, m); 2.41 (1H, m); 2.80 (3H, s); 2.97 (4H, m); 3.17 (2H, d, J=5.9 Hz); 3.88 (1H, d, J=14.8 Hz); 4.00(4H, t, J=4.8 Hz); 4.08 (4H, t, J=4.8 Hz); 4.28 (1H, d, J=14.6 Hz); 7.30 (2H, m); 7.38 (1H, s); 7.50 (1H, d, J=8.0 Hz); 7.55 (1H, m); 8.18 (1H, d, J=7.2 Hz); 8.27(1H, br s).

M+H (541)

EXAMPLE 21

2-(2-Methyl-1H-indol-4-yl)-6-(4-methyl-piperazin-1-ylmethyl-4-morpholin-4-yl-thieno[3,2-d]pyrimidine 4-Bromo-2-methyl-1H-indole was prepared as described in *J. Am Chem. Soc.*, 2006, 128, 1058-1059.

2-Methyl-4-(4,4,5,5-tetramethyl-[1,3,2]dioxaborolan-2-yl)-1H-indole was prepared using the standard method and coupled in the standard Suzuki reaction to give the title compound.

δH (400 MHz; CDCl$_3$) 2.33 (3H, s); 2.58 (8H+3H, m); 3.86 (2H, s); 3.92 (4H, t, J=4.7 Hz); 4.08 (4H, t, J=4.7 Hz); 7.22 (2H, m); 7.38 (2H, m); 7.96 (1H, br s); 8.14 (1H, d, J=7.4 Hz).

M+H (463)

EXAMPLE 22

2-(6-Fluoro-1H-indol-4-yl)-6-(4-methyl-piperazin-1-ylmethyl)-4-morpholin-4-yl-thieno[3,2-d]pyrimidine To a solution of 4-fluoro-2-nitrotoluene (2.0 g) in trifluroacetic acid (8 ml) was added concentrated sulfuric acid (2.5 ml) followed by N-bromosuccinimide (3.4 g). After stirring for 24 hours the reaction mixture was then diluted with ethyl acetate, washed with water, brine, dried (MgSO$_4$) and the solvent removed in vacuo. The residue was purified by flash chromatography to give 1-bromo-5-fluoro-2-methyl-3-nitro-benzene (2.48 g).

Preparation of 4-bromo-6-fluoro-1H-indole

To a solution of 1-bromo-5-fluoro-2-methyl-3-nitro-benzene (1.78 g) in dimethylfornamide (15 ml) was added dimethylformamide dimethyl acetal (3.0 ml) followed by pyrrolidine (0.63 ml) and heated to 110° C. After 24 hours the cooled reaction mixture was diluted with ethyl acetate, washed with water, brine, dried (MgSO$_4$) and the solvent removed in vacuo to yield crude 1-[2-(2-bromo-4-fluoro-6-nitro-phenyl)-vinyl]-pyrrolidine.

To a solution of crude 1-[2-(2-bromo-4-fluoro-6-nitro-phenyl)-vinyl]-pyrrolidine (2.74 g) in tetrahydrofuran (25 ml) and methanol (25 ml) was added Raney nickel, 50% slurry in water, active catalyst (5.0 ml) followed by careful addition of hydrazine monohydrate (0.63 ml). After stirring for 24 hours the reaction mixture was filtered through celite and the filtrate reduced in vacuo. The residue was purified by flash chromatography to give 4-bromo-6-fluoro-1H-indole (0.80 g).

6-Fluoro-4-(4,4,5,5-tetramethyl-[1,3,2]dioxaborolan-2-yl)-1H-indole was prepared from 4-bromo-6-fluoro-1H-indole using the general method described 2-Chloro-6-(4-methyl-piperazin-1-ylmethyl)-4-morpholin-4-yl-thieno[3,2-d]pyrimidine (0.125 g) and 6-fluoro-4-(4,4,5,5-tetramethyl-[1,3,2]dioxaborolan-2-yl)-1H-indole (0.17 g) were subjected to the standard Suzuki coupling conditions to give the title compound (0.033 g).

δH (400 MHz; CDCl$_3$) 2.24 (3H, s); 2.58 (8H, m); 3.84 (2H, s); 3.92 (4H, t, J=4.8 Hz); 4.08 (4H, t, J=4.8 Hz); 7.17 (1H, dd, J=1.7, 7.1 Hz); 7.30(1H, m); 7.37(1H, s); 7.56 (1H, m); 7.98 (1H, dd, J=2.3, 8.9 Hz); 8.25 (1H, br s).

M+H (467).

EXAMPLE 23

4-[6-(4-Methyl-piperazin-1-ylmethyl)-4-morpholin-4-yl-thieno[3,2-d]pyrimidin-2-yl]-1H-indole-6-carbonitrile 4-(4,4,5,5-Tetramethyl-[1,3,2]dioxaborolan-2-yl)-1H-indole-6-carbonitrile was prepared using the general method described and coupled with 2-chloro-6-(4-methyl-piperazin-1-ylmethyl)-4-morpholin-4-yl-thieno[3,2-d]pyrimidine using the standard method to yield the title compound as a white waxy solid.

δH (400 MHz, CDCl$_3$) 2.32 (s, 3H), 2.51 (br s, 4H), 2.63 (s, 4H), 3.85 (s, 2H), 3.92 (t, J=4.9, 4H), 4.08 (t, J=4.09, 4H), 7.37 (s, 1H), 7.51 (m, 1H), 7.67 (m, 1H), 7.77 (s, 1H), 8.45 (d, J=1.3, 1H), 8.74 (br s, 1H).

EXAMPLE 24

[2-(1H-Indol-4-yl)-4-morpholin-4-yl-thieno[3,2-d]pyrimidin-6-ylmethyl]-(1-methanesulfonyl-pyrrolidin-3-yl)-methyl-amine To a solution of 1-N-BOC-3-pyrrolidinone (3.0 g) in methanol (30 ml) was added a solution of freshly prepared methylamine (0.75 g) in methanol (3.1 ml). The reaction mixture was stirred for 1 hour and then sodium borohydride (0.61 g) was added. After stirring for 4 hours the reaction mixture was then diluted with dichloromethane, washed with sodium bicarbonate solution, dried (MgSO$_4$) and the solvent removed in vacuo to give 3-methylamino-pyrrolidine-1-carboxylic acid tert-butyl ester (3.18 g).

To a mixture of 6-Bromomethyl-2-chloro-4-morpholino-4-yl-thieno[3,2,-d]pyrimidine (0.50 g) and 3-methylamino-pyrrolidine-1-carboxylic acid tert-butyl ester (0.34 g) in acetonitrile (10 ml) was added potassium carbonate (0.30 g) and heated to 80° C. for 3 hours. The reaction mixture was then diluted with dichloromethane, washed with sodium bicarbonate solution, dried (MgSO$_4$) and the solvent removed in vacuo. The residue was purified by flash chromatography to yield 3-[(2-chloro-4-morpholin-4-yl-thieno[3,2,-d]pyrimidin-6-ylmethyl)-amino]-pyrrolidine-1-carboxylic acid tert-butyl ester (0.65 g). Treatment of this compound with HCl in dichloromethane/methanol yielded (2-chloro-4-morpholin-4-yl-thieno[3,2,-d]pyrimidin-6-ylmethyl)-amino-pyrrolidin-3-amine_hydrochloride salt (0.56 g).

To a suspension of (2-chloro-4-morpholin-4-yl-thieno[3,2,-d]pyrimidin-6-ylmethyl)-amino-pyrrolidin-3-amine hydrochloride salt (0.56 g) in dichloromethane (10 ml) was added triethylamine (0.42 ml) followed by methanesulfonyl chloride (0.12 ml). After stirring for 3 hours the reaction mixture was diluted with dichloromethane, washed with sodium bicarbonate solution, dried (MgSO$_4$) and the solvent removed in vacuo. The residue was purified by flash chromatography to yield (2-chloro-4-morpholin-4-yl-thieno[3,2,-d]pyrimidin-6-ylmethyl)-(1-methanesulfonyl-pyrrolidin-3-yl)-methyl-amine (0.25 g).

A mixture of (2-chloro-4-morpholin-4-yl-thieno[3,2,-d]pyrimidin-6-ylmethyl)-(1-methanesulfonyl-pyrrolidin-3-yl)-methyl-amine (0.090 g) and 4-(4,4,5,5-tetramethyl-[1,3,2]dioxaborolan-2-yl)-1H-indole (0.098 g) were reacted under the standard Suzuki conditions to give the title compound (0.052 g).

δH (400 MHz; CDCl$_3$); 2.03 (1H, m); 2.22 (1H, m); 2.36 (3H, s); 2.87 (3H, s); 3.22-3.70 (5H, m); 3.92 (4H+2H, m); 4.10 (4H, t, J=4.5 Hz); 7.32 (3H, m); 7.50 (1H, d, J=8.0 Hz); 7.50(1H, m); 8.20(1H, d, J=7.4 Hz); 8.30(1H, br s).

M+H (527)

EXAMPLE 25

4-(4-Morpholin-4-yl-6-piperazin-1-ylmethyl-thieno[3,2-d]pyrimidin-2-yl)-1H-indole-6-sulfonic acid dimethylamide Prepared using Suzuki coupling method A of Reference Example 2, followed by BOC-deprotection using TFA:DCM (1:1). The title compound was obtained as a white solid (43.9 mg, 37%).

[M+H]$^+$ 542.1

NMR δ$_H$ (400 MHz, DMSO-d$_6$) 2.62 (s, 6H), 2.71 (bs, 4H), 3.11 (bs, 4H), 3.78 (m, 4H), 3.94 (m, 6H), 7.49 (s, 1H), 7.51 (m, 1H), 7.75 (apparent t, J=2.8, 1H), 7.90 (s, 1H), 8.41 (d, J=1.4, 1H), 8.60 (bs, 1H) and 11.74 (bs, 1H).

EXAMPLE 26

4-[6-(4-Cyclopropylmethyl-piperazin-1-ylmethyl)-4-morpholin-4-yl-thieno[3,2-d]pyrimidin-2-yl]-1H-indole-6-sulfonic acid dimethylamide Prepared using Suzuki coupling method A of Reference Example 2. The title compound was obtained as a white solid (100 mg, 76%).

[M+H]$^+$ 596.3

NMR δ$_H$ (400 MHz, CDCl$_3$) 0.08 (m, 2H), 0.49 (m, 2H), 0.85 (m, 1H), 2.26 (d, J=6.7, 2H), 2.61 (m, 8H), 2.69 (s, 6H), 3.83 (s, 2H), 3.87 (dd, J=4.4, 5.1, 4H), 4.04 (dd, J=4.4, 5.1, 4H), 7.34 (s, 1H), 7.50 (apparent t, J=2.8, 1H), 7.61 (m, 1H), 7.96 (m, 1H), 8.53 (d, J=1.6, 1H) and 8.96 (bs, 1H).

EXAMPLE 27

2-{4-[2-(6-Dimethylsulfamoyl-1H-indol-4-yl)-4-morpholin-4-yl-thieno[3,2-d]pyri-midin-6-ylmethyl]-piperazin-1-yl}-isobutyramide Prepared by using Suzuki coupling method A of Reference Example 2. The title compound was obtained as a white solid (32 mg, 23%).

[M+H]$^+$ 627.4

NMR δ$_H$ (400 MHz, DMSO-d$_6$) 1.08 (s, 6H), 2.47 (bs, 4H), 2.56 (bs, 4H), 2.63 (s, 6H), 3.83 (m, 4H), 3.87 (s, 2H), 4.00 (m, 4H), 6.95 (d, J=3.2, 1H), 7.07 (d, J=3.2, 1H), 7.50 (s, 1H), 7.52 (m, 1H), 7.78 (apparent t, J=2.7, 1H), 7.92 (m, 1H), 8.42 (d, J=1.2, 1H) and 11.75 (bs, 1H).

EXAMPLE 28

4-{4-Morpholin-4-yl-6-[4-(2,2,2-trifluoro-ethyl)-piperazin-1-ylmethyl]-thieno[3,2-d]pyrimidin-2-yl}-1H-indole-6-sulfonic acid dimethylamide Prepared using Suzuki coupling method A of Reference Example 2. The title compound was obtained as a white solid (74.9 mg, 55%).

[M+H]$^+$ 624.3

NMR $\delta_H$ (400 MHz, CDCl$_3$) 2.62 (m, 4H), 2.72 (s, 6H), 2.76 (m, 4H), 2.95 (d, J=9.6, 1H), 3.03 (d, J=9.6, 1H), 3.84 (s, 2H), 3.91 (m, 4H), 4.07 (m, 4H), 7.37 (m, 1H), 7.53 (dd, J=2.7, 2.9, 1H), 7.63 (m, 1H), 7.99 (m, 1H), 8.55 (m, 1H) and 8.94 (bs, 1H).

EXAMPLE 29

4-Morpholin-4-yl-6-piperazin-1-ylmethyl-2-(6-trifluoromethyl-1H-indol-4-yl)-thieno[3,2-d]pyrimidine Prepared using Suzuki coupling method A of Reference Example 2 followed by BOC-deprotection using TFA:DCM (1:1). The title compound was obtained as a white solid (48.3 mg, 57%).

[M+H]$^+$ 503.4

NMR $\delta_H$ (400 MHz, DMSO-d$_6$) 2.42 (bs, 4H), 2.72 (t, J=4.1, 4H), 3.84 (m, 6H), 4.00 (m, 4H), 7.47 (s, 1H), 7.52 (bs, 1H), 7.72 (m, 1H), 7.85 (bs, 1H), 8.37 (bs, 1H) and 11.70 (bs, 1H).

EXAMPLE 30

6-(4-Cyclopropylmethyl-piperazin-1-ylmethyl)-4-morpholin-4-yl-2-(6-trifluoro-methyl-1H-indol-4-yl)-thieno[3,2-d]pyrimidine Prepared by using Suzuki coupling method A of Reference Example 2. The title compound was obtained as a white solid (76 mg, 62%).

[M+H]$^+$ 557.5

NMR $\delta_H$ (400 MHz, CDCl$_3$) 0.11 (m, 2H), 0.52 (m, 2H), 0.88 (m, 1H), 2.29 (d, J=6.6, 2H), 2.64 (bs, 8H), 3.85 (m, 2H), 3.91 (m, 4H), 4.08 (m, 4H), 7.38 (s, 1H), 7.44 (apparent t, J=3.2, 1H), 7.60 (m, 1H), 7.73 (bs, 1H), 8.44 (m, 1H) and 8.66 (bs, 1H),

EXAMPLE 31

2-{4-[4-Morpholin-4-yl-2-(6-trifluoromethyl-1H-indol-4-yl)-thieno[3,2-d]pyri-midin-6-ylmethyl]-piperazin-1-yl}-isobutyramide Prepared by using Suzuki coupling method A of Reference Example 2. The title compound was obtained as a white solid (107 mg, 83%).

[M+H]$^+$ 588.5

NMR $\delta_H$ (400 MHz, DMSO-d$_6$) 1.08 (s, 6H), 2.47 (bs, 4H), 2.56 (bs, 4H), 3.84 (m, 6H), 4.00 (m, 4H), 6.95 (d, J=3.5, 1H), 7.07 (d, J=3.5, 1H), 7.48 (s, 1H), 7.52 (bs, 1H), 7.72 (apparent t, J=2.8, 1H), 7.85 (bs, 1H), 8.36 (bs, 1H) and 11.68 (bs, 1H).

EXAMPLE 32

4-Morpholin-4-yl-6-[4-(2,2,2-trifluoro-ethyl)-piperazin-1-ylmethyl]-2-(6-tri-fluoromethyl-1H-indol-4-yl)-thieno[3,2-d]pyrimidine Prepared by using Suzuki coupling method A of Reference Example 2. The title compound was obtained as a white solid (48.3 mg, 38%).

[M+H]$^+$ 585.3

NMR $\delta_H$ (400 MHz, CDCl$_3$) 2.61 (m, 4H), 2.76 (m, 4H), 2.97 (d, J=9.8, 1H), 3.02 (d, J=9.8, 1H), 3.84 (s, 2H), 3.92 (m, 4H), 4.08 (m, 4H), 7.37 (m, 1H), 7.44 (apparent t, J=2.9, 1H), 7.59 (m, 1H), 7.72 (m, 1H), 8.43 (s, 1H) and 8.63 (bs, 1H).

EXAMPLE 33

4-Morpholin-4-yl-6-piperazin-1-ylmethyl-2-(2-trifluoromethyl-1H-indol-4-yl)-thieno[3,2-d]pyrimidine Prepared by using Suzuki coupling method B of Reference Example 2 followed by BOC-deprotection using TFA:DCM (1:4). The title compound was obtained as a yellow solid (75 mg, 90%).

[M+H]$^+$ 502.6

NMR $\delta_H$ (400 MHz, DMSO-d$_6$) 2.71 (s, 4H), 3.15 (s, 4H), 3.84 (m, 4H), 4.01 (m, 6H), 7.41 (apparent t, J=7.9, 1H), 7.56 (s, 1H), 7.63 (d, J=8.1, 1H), 7.96 (s, 1H), 8.25 (d, J=7.5, 1H), 8.63 (bs, 1H) and 12.44 (s, 1H).

EXAMPLE 34

2-{4-[4-Morpholin-4-yl-2-(2-trifluoromethyl-1H-indol-4-yl)-thieno[3,2-d]pyrimidin-6-ylmethyl]-piperazin-1-yl}-isobutyramide Prepared by using Suzuki coupling method B of Reference Example 2. The title compound was obtained as a white solid (65 mg, 55%).

[M+H]$^+$ 587.7

NMR $\delta_H$ (400 MHz, DMSO-d$_6$) 1.02 (s, 6H), 2.42 (s, 4H), 2.52 (s, 4H), 3.78 (t, J=5.0, 4H), 3.81 (s, 2H), 3.95 (t, J=4.7, 4H), 6.9 (d, J=3.5, 1H), 7.03 (d, J=3.5, 1H), 7.38 (apparent t, J=7.9, 1H), 7.48 (s, 1H), 7.61 (d, J=8.1, 1H), 7.96 (s, 1H), 8.23 (d, J=7.5, 1H) and 12.36 (s, 1H).

EXAMPLE 35

6-(4-Cyclopropylmethyl-piperazin-1-ylmethyl)-4-morpholin-4-yl-2-(2-trifluoro-methyl-1H-indol-4-yl)-thieno[3,2-d]pyrimidine Prepared using Suzuki coupling method B of Reference Example 2. The title compound was obtained as a beige solid (80 mg, 72%).

[M+H]$^+$ 556.7

NMR $\delta_H$ (400 MHz, DMSO-d$_6$) 0.05 (m, 2H), 0.44 (m, 2H), 0.75-0.86 (m, 1H), 2.17 (d, J=6.8, 2H), 2.50 (m, 8H), 3.82 (t, J=4.8, 4H), 3.85 (s, 2H), 3.99 (t, J=4.8, 4H), 7.42 (apparent t, J=7.8, 1H), 7.48 (s, 1H), 7.6 (d, J=8.1, 1H), 7.96 (s, 1H), 8.26 (d, J=7.5, 1H) and 12.39 (s, 1H).

EXAMPLE 36

4-Morpholin-4-yl-6-[4-(2,2,2-trifluoro-ethyl)-piperazin-1-ylmethyl]-2-(2-tri-fluoromethyl-1H-indol-4-yl)-thieno[3,2-d]pyrimidine Prepared using Suzuki coupling method B of Reference Example 2. The title compound was obtained as a white solid (80 mg, 69%).

[M+H]$^+$ 584.6

NMR $\delta_H$ (400 MHz, DMSO-d$_6$) 2.46-2.54 (m, 4H), 2.66 (m, 4H), 3.16 (q, J=10.6, 2H), 3.81 (t, J=4.6, 4H), 3.86 (s, 2H), 3.98 (t, J=4.6, 4H), 7.40 (apparent t, J=7.9, 1H), 7.47 (s, 1H), 7.59 (d, J=8.1, 1H), 7.95 (s, 1H), 8.23 (d, J=7.5, 1H) and 12.39 (bs, 1H).

EXAMPLE 37

2-(6-Methanesulfonyl-1H-indol-4-yl)-4-morpholin-4-yl-6-piperazin-1-ylmethyl-thieno[3,2-d]pyrimidine Prepared by using Suzuki coupling method A of Reference Example 2. followed by BOC-deprotection using TFA:DCM (1:1). The title compound was obtained as a white solid (52 mg, 39%).

[M+H]$^+$ 512.7

NMR $\delta_H$ (400 MHz, DMSO-d$_6$) 2.49 (m, 4H), 2.75 (t, J=4.6, 4H), 3.21 (s, 3H), 3.83 (m, 6H), 4.00 (m, 4H), 7.45 (s, 1H), 7.52 (m, 1H), 7.78 (apparent t, J=2.6, 1H), 8.06 (m, 1H), 8.56 (d, J=1.7, 1H) and 11.84 (bs, 1H).

EXAMPLE 38

6-(4-Cyclopropylmethyl-piperazin-1-ylmethyl)-2-(6-methanesulfonyl-1H-indol-4-yl)-4-morpholin-4-yl-thieno[3,2-d]pyrimidine Prepared using Suzuki coupling method A of Reference Example 2. The title compound was obtained as a white solid (82.4 mg, 66%).

[M+H]$^+$ 566.8

NMR $\delta_H$ (400 MHz, DMSO-d$_6$) 0.02-0.07 (m, 2H), 0.40-0.46 (m, 2H), 0.76-0.88 (m, 1H), 2.16 (d, J=6.7, 2H), 2.48-2.56 (m, 8H), 3.21 (s, 3H), 3.84 (m, 4H), 3.85 (s, 2H), 4.01 (m, 4H), 7.49 (s, 1H), 7.51 (m, 1H), 7.78 (apparent t, J=2.7, 1H), 8.07 (m, 1H), 8.57 (d, J=1.8, 1H) and 11.84 (bs, 1H).

EXAMPLE 39

2-{4-[2-(6-Methanesulfonyl-1H-indol-4-yl)-4-morpholin-4-yl-thieno[3,2-d]pyrimidin-6-ylmethyl]-piperazin-1-yl}-isobutyramide Prepared by Suzuki coupling method A of Reference Example 2. The title compound was obtained as a white solid (41.5 mg, 34%).

[M+H]$^+$ 597.8

NMR $\delta_H$ (400 MHz, CD$_3$OD) 1.2 (s, 6H), 2.58-2.72 (m, 8H), 3.2 (s, 3H), 3.91 (m, 6H), 4.10 (m, 4H), 7.38 (s, 1H), 7.46 (dd, J=0.8, 3.0, 1H), 7.67 (d, J=3.1, 1H), 8.12 (dd, J=0.9, 1.8, 1H) and 8.49 (d, J=1.8, 1H).

EXAMPLE 40

2-(6-Methanesulfonyl-1H-indol-4-yl)-4-morpholin-4-yl-6-[4-(2,2,2-trifluoro-ethyl)piperazin-1-ylmethyl]-thieno[3,2-d]pyrimidine Prepared by Suzuki coupling method A of Reference Example 2. The title compound was obtained as a white solid (66.7 mg, 50%).

[M+H]$^+$ 594.7

NMR $\delta_H$ (400 MHz, DMSO-d$_6$) 2.48-2.56 (m, 4H), 2.64-2.72 (m, 4H), 3.18 (q, J=10.3, 2H), 3.23 (s, 3H), 3.81-3.87 (m, 4H), 3.88 (s, 2H), 3.98-4.04 (m, 4H), 7.49 (s, 1H), 7.53 (d, J=2.8, 1H), 7.80 (m, 1H), 8.07 (m, 1H), 8.57 (d, J=1.6, 1H) and 11.85 (s, 1H).

EXAMPLE 41

2-{4-[2-(5-Fluoro-1H-indol-4-yl)-4-morpholin-4-yl-thieno[3,2-d]pyrimidin-6-ylmethyl]-piperazin-1-yl}-isobutyramide Prepared using Suzuki coupling method A of Reference Example 2. The title compound was obtained as a white solid (77 mg, 78%).

[M+H]$^+$ 538.4

NMR $\delta_H$ (400 MHz, CD$_3$OD) 1.90 (s, 6H), 2.56-2.64 (m, 8H), 3.82 (m, 4H), 3.87 (m, 2H), 4.02 (m, 4H), 6.58 (dd, J=0.8, 3.7, 1H), 6.95 (dd, J=8.8, 11.0, 1H), 7.28 (s, 1H), 7.30 (s, 1H) and 7.41 (ddd, J=0.8, 4.0, 8.8, 1H).

EXAMPLE 42

2-(5-Fluoro-1H-indol-4-yl)-4-morpholin-4-yl-6-[4-(2,2,2-trifluoro-ethyl)-piperazin-1-ylmethyl]-thieno[3,2-d]pyrimidine Prepared using Suzuki coupling method A of Reference Example 2. The title compound was obtained as a white solid (41.9 mg, 42%).

[M+H]$^+$ 535.1

NMR $\delta_H$ (400 MHz, CD$_3$OD) 2.59 (m, 4H), 2.71 (m, 4H), 3.04 (q, J=9.9, 2H), 3.81 (m, 4H), 3.85 (s, 2H), 4.01 (m, 4H), 6.58 (d, J=3.0, 1H), 6.95 (dd, J=8.9, 10.7, 1H), 7.28 (m, 2H) and 7.40 (dd, J=4.0, 8.7, 1H).

EXAMPLE 43

6-(4-Cyclopropylmethyl-piperazin-1-ylmethyl)-2-(5-fluoro-1H-indol-4-yl)-4-morpholin-4-yl-thieno[3,2-d]pyrimidine Prepared using Suzuki coupling method A of Reference Example 2. The title compound was obtained as a white solid (67.8 mg, 77%).

[M+H]$^+$ 507.1

NMR $\delta_H$ (400 MHz, CD$_3$OD) 0.10-0.14 (m, 2H), 0.49-0.54 (m, 2H), 0.81-0.91 (m, 1H), 2.28 (d, J=6.8, 2H), 3.81 (m, 8H), 3.89 (s, 2H), 4.00-4.04 (m, 8H), 6.30 (dd, J=8.8, 11.0, 1H), 6.58 (dd, J=0.9, 3.4, 1H), 7.29 (m, 2H) and 7.41 (ddd, J=0.9, 3.8, 8.8, 1H).

EXAMPLE 44

4-(4-Morpholin-4-yl-6-piperazin-1-ylmethyl-thieno[3,2-d]pyrimidin-2-yl)-1H-indole-6-carboxylic acid amide Prepared using Suzuki coupling method A of Reference Example 2 followed by BOC-deprotection using TFA:DCM (1:1). The title compound was obtained as a white solid (44 mg, 42%).

[M+H]$^+$ 478.3

NMR $\delta_H$ (400 MHz, DMSO-d$_6$) 2.46 (m, 4H), 2.80 (m, 4H), 3.79 (m, 4H), 3.81 (s, 2H), 3.96 (m, 4H), 7.12 (bs, 1H), 7.37 (m, 1H), 7.41 (s, 1H), 7.54 (apparent t, J=3.0, 1H), 7.93 (bs, 1H), 8.00 (m, 1H), 8.55 (m, 1H) and 11.47 (s, 1H).

EXAMPLE 45

4-{6-[4-(1-Carbamoyl-1-methyl-ethyl)-piperazin-1-ylmethyl]-4-morpholin-4-yl-thieno[3,2-d]pyrimidin-2-yl}-1H-indole-6-carboxylic acid amide Prepared using Suzuki coupling method A of Reference Example 2. The title compound was obtained as a white solid (40 mg, 31%).

[M+H]$^+$ 563.1

NMR $\delta_H$ (400 MHz, DMSO-d$_6$) 1.03 (s, 6H), 2.40-2.50 (m, 8H), 3.77-3.82 (m, 6H), 3.96 (m, 4H), 6.90 (d, J=3.6, 1H), 7.03 (d, J=3.6, 1H), 7.13 (bs, 1H), 7.38 (m, 1H), 7.40 (s, 1H), 7.55 (apparent t, J=3.0, 1H), 7.95 (bs, 1H), 8.01 (s, 1H), 8.56 (d, J=1.6, 1H) and 11.47 (s, 1H).

EXAMPLE 46

4-{4-Morpholin-4-yl-6-[4-(2,2,2-trifluoro-ethyl)-piperazin-1-ylmethyl]-thieno[3,2-d]pyrimidin-2-yl}-1H-indole-6-carboxylic acid amide Prepared using Suzuki coupling method A of Reference Example 2. The title compound was obtained as a white solid (71 mg, 61%).

[M+H]$^+$ 560.1

NMR $\delta_H$ (400 MHz, CD$_3$OD) 2.57-2.61 (m, 4H), 2.71 (m, 4H), 3.04 (q, J=9.7, 2H), 3.85 (m, 6H), 4.07 (m, 4H), 7.29 (dd, J=1.4, 3.2, 1H), 7.33 (s, 1H), 7.49 (d, J=3.0, 1H), 8.06 (m, 1H) and 8.44 (d, J=1.4, 1H).

EXAMPLE 47

4-[6-(4-Cyclopropylmethyl-piperazin-1-ylmethyl)-4-morpholin-4-yl-thieno[3,2-d]pyrimidin-2-yl]-1H-indole-6-carboxylic acid amide Prepared using Suzuki coupling method A of Reference Example 2. The title compound was obtained as a white solid (60 mg, 46%).

[M+H]$^+$ 532.2

NMR $\delta_H$ (400 MHz, DMSO-d$_6$) 0.07 (m, 2H), 0.43-0.48 (m, 2H), 0.77-0.87 (m, 1H), 2.20 (s, 2H), 2.40-2.60 (m, 8H), 3.83 (m, 4H), 3.87 (s, 2H), 3.99-4.03 (m, 4H), 7.18 (bs, 1H), 7.42 (m, 1H), 7.45 (s, 1H), 7.59 (apparent t, J=2.7, 1H), 7.99 (bs, 1H), 8.05 (m, 1H), 8.60 (d, J=1.6, 1H) and 11.52 (s, 1H).

EXAMPLE 48

4-{4-Morpholin-4-yl-6-[4-(2,2,2-trifluoro-ethyl)-piperazin-1-ylmethyl]-thieno[3,2-d]pyrimidin-2-yl}-1H-indole-2-carbonitrile Prepared using Suzuki coupling method B of Reference Example 2. The title compound was obtained as a beige solid (21 mg, 13%).

[M+H]$^+$ 542.1

NMR $\delta_H$ (400 MHz, DMSO-d$_6$) 2.52 (m, 4H), 2.67 (m, 4H), 3.18 (q, J=10.4, 2H), 3.82 (m, 4H), 3.87 (s, 2H), 3.99 (m, 4H), 7.46 (apparent t, J=7.7, 1H), 7.51 (s, 1H), 7.59 (d, J=8.2, 1H), 8.26 (m, 1H), 8.27 (d, J=0.7, 1H) and 12.53 (bs, 1H).

EXAMPLE 49

2-{4-[2-(2-Cyano-1H-indol-4-yl)-4-morpholin-4-yl-thieno[3,2-d]pyrimidin-6-ylmethyl]-piperazin-1-yl}-isobutyramide Prepared using Suzuki coupling method B of Reference Example 2. The title compound was obtained as a buff solid (52.9 mg, 32%).

[M+H]$^+$ 545.1

NMR $\delta_H$ (400 MHz, DMSO-d$_6$) 1.08 (s, 6H), 2.47 (m, 4H), 2.56 (m, 4H), 3.82 (t, J=4.6, 4H), 3.87 (s, 2H), 3.98 (t, J=4.6, 4H), 6.94 (d, J=3.2, 1H), 7.07 (d, J=3.2, 1H), 7.47 (apparent t, J=7.6, 1H), 7.51 (s, 1H), 7.59 (d, J=8.2, 1H), 8.26 (m, 2H) and 12.50 (bs, 1H).

EXAMPLE 50

4-[6-(4-Cyclopropylmethyl-piperazin-1-ylmethyl)-4-morpholin-4-yl-thieno[3,2-d]pyrimidin-2-yl]-1H-indole-2-carbonitrile Prepared using Suzuki Method B of Reference Example 2. The title compound was obtained as a beige solid (21 mg, 14%).

[M+H]$^+$ 514.1

NMR $\delta_H$ (400 MHz, CDCl$_3$) 0.12 (m, 2H), 0.53 (m, 2H), 0.89 (m, 1H), 2.31 (d, J=6.6, 2H), 2.66 (m, 8H), 3.87 (s, 2H), 3.92 (t, J=4.8, 4H), 4.08 (t, J=4.7, 4H), 7.38 (s, 1H), 7.49 (d, J=4.4, 2H), 8.27 (m, 2H) and 9.02 (bs, 1H).

EXAMPLE 51

4-{4-Morpholin-4-yl-6-[4-(2,2,2-trifluoro-ethyl)-piperazin-1-ylmethyl]-thieno[3,2-d]pyrimidin-2-yl}-1H-indole-6-carbonitrile Prepared by using Suzuki coupling method B of Reference Example 2. The title compound was obtained as a white solid (65 mg, 60%).

[M+H]$^+$ 542.3

NMR $\delta_H$ (400 MHz, DMSO-d$_6$) 2.53 (m, 4H), 2.67 (t, J=4.0, 4H), 3.18 (m, 2H), 3.83 (t, J=4.5, 4H), 3.87 (s, 2H), 3.99 (t, J=4.5, 4H), 7.46 (s, 1H), 7.56 (d, J=2.4, 1H), 7.77 (d, J=2.7, 1H), 8.00 (m, 1H), 8.34 (d, J=1.4, 1H) and 11.8 (s, 1H).

EXAMPLE 52

4-[6-(4-Cyclopropylmethyl-piperazin-1-ylmethyl)-4-morpholin-4-yl-thieno[3,2-d]pyrimidin-2-yl]-1H-indole-6-carbonitrile Prepared using Suzuki coupling method B of Reference Example 2. The title compound was obtained as a pale yellow solid (75 mg, 49%).

[M+H]$^+$ 514.4

NMR $\delta_H$ (400 MHz, DMSO-d$_6$) 0.06 (m, 2H), 0.44 (m, 2H), 0.81 (m, 1H), 2.18 (d, J=6.7, 2H), 2.51 (m, 8H), 3.83 (t, J=4.5, 4H), 3.86 (s, 2H), 4.0 (t, J=4.5, 4H), 7.46 (s, 1H), 7.57 (m, 1H), 7.77 (apparent t, J=2.7, 1H), 8.00 (m, 1H), 8.34 (d, J=1.5, 1H) and 11.81 (bs, 1H).

EXAMPLE 53

6-(4-Cyclopropylmethyl-piperazin-1-ylmethyl)-2-(6-fluoro-1H-indol-4-yl)-4-morpholin-4-yl-thieno[3,2-d]pyrimidine Prepared using Suzuki coupling method B of Reference Example 2. The title compound was obtained as a pale yellow solid (65 mg, 64%).

[M+H]$^+$ 507.3

NMR $\delta_H$ (400 MHz, DMSO-d$_6$) 0.06 (m, 2H), 0.44 (m, 2H), 0.81 (m, 1H), 2.18 (d, J=6.5, 2H), 2.51 (m, 8H), 3.82 (t, J=4.6, 4H), 3.86 (s, 2H), 3.98 (t, J=4.6, 4H), 7.30 (dd, J=2.5, 9.3, 1H), 7.44 (m, 3H), 7.89 (dd, J=2.5, 11.5, 1H) and 11.28 (bs, 1H).

EXAMPLE 54

2-(6-Fluoro-1H-indol-4-yl)-4-morpholin-4-yl-6-[4-(2,2,2-trifluoro-ethyl)-piperazin-1-ylmethyl]-thieno[3,2-d]pyrimidine Prepared using method B of Reference Example 2. The title compound was obtained as a pale yellow solid (65 mg, 61%).

[M+H]$^+$ 535.0

NMR $\delta_H$ (400 MHz, DMSO-d$_6$) 2.47 (m, 4H), 2.57 (bs, 4H), 3.12 (q, J=10.2, 2H), 3.77 (t, J=4.4, 4H), 3.81 (s, 2H), 3.93 (t, J=4.4, 4H), 7.24 (dd, J=2.5, 9.2, 1H), 7.39 (m, 3H), 7.84 (dd, J=2.5, 11.4, 1H) and 11.2 (bs, 1H).

EXAMPLE 55

2-(6-Fluoro-1H-indol-4-yl)-4-morpholin-4-yl-6-piperazin-1-ylmethyl-thieno[3,2-d]pyrimidine Prepared using Suzuki coupling method A of Reference Example 2 followed by BOC-deprotection using TFA:DCM (1:1). The title compound was obtained as a white solid (40.9 mg, 41%).

[M+H]$^+$ 453.3

NMR $\delta_H$ (400 MHz, DMSO-d$_6$) 2.41 (m, 4H), 2.72 (t, J=4.5, 4H), 3.78 (m, 6H), 3.98 (t, J=5.2, 4H), 7.30 (dd, J=2.5, 9.2, 1H), 7.44 (m, 3H), 7.89 (dd, J=2.5, 11.5, 1H) and 11.3 (bs, 1H).

EXAMPLE 56

2-(5-Fluoro-1H-indol-4-yl)-4-morpholin-4-yl-6-piperazin-1-ylmethyl-thieno[3,2-d]pyrimidine A solution of 4-(2-chloro-4-morpholin-4-yl-thieno[3,2-d]pyrimidin-6-ylmethyl)-piperazine-1-carboxylic acid tert-butyl ester (100 mg, 0.22 mmol) and sodium thiomethoxide (30 mg, 0.44 mmol) in DMF was heated at 100° C. in a sealed tube under nitrogen for 1 h. More sodium thiomethoxide (15 mg, 0.22 mmol) was added, and the heating pursued for 1 h. The mixture was left to cool to RT and was then partitioned between a sat. sodium carbonate solution and EtOAc. The organic layer was isolated, dried (MgSO$_4$) and evaporated to dryness to afford 4-(2-methylsulfanyl-4-morpholin-4-yl-thieno[3,2-d]pyrimidin-6-ylmethyl)-piperazine-1-carboxylic acid tert-butyl ester as a yellow solid (100 mg, 98%).

NMR $\delta_H$ (400 MHz, CDCl$_3$) 1.46. (s, 9H), 2.48 (s, 4H), 2.56 (s, 3H), 3.46 (s, 4H), 3.78 (s, 2H), 3.80-3.85 (m, 4H), 3.92-3.99 (m, 4H) and 7.12 (s, 1H).

A solution of 5-fluoro-4-(trimethylstannyl)-1H-indole (100 mg, 0.33 mmol), 4-(2-methylsulfanyl-4-morpholin-4-yl-thieno[3,2-d]pyrimidin-6-ylmethyl)-piperazine-1-carboxylic acid tert-butyl ester (71 mg, 0.15 mmol) and copper (I) bromide-dimethyl sulfide complex (70 mg, 0.33 mmol) in THF (3 mL) was degassed with argon, treated with tetrakis (triphenylphosphine)palladium(0) (10 mg, 0.008 mmol) and heated at 90° C. overnight. The reaction mixture was purified by column chromatography. The foregoing compound was treated with TFA-DCM (1:1, 2 mL), evaporated in vacuo and purified by ion-exchange chromatography (Isolute® SCX-2 cartridge, eluting with NH$_3$ in methanol) and preparative TLC to give the title compound (6.5 mg, 10%).

[M+H]$^+$ 453.1

NMR $\delta_H$ (400 MHz, DMSO-d$_6$) 2.45-2.41 (m, 4H), 2.74 (m, 4H), 3.50 (s, 1H), 3.77 (m, 4H), 3.82 (s, 2H), 3.93 (m, 4H), 6.67 (t, J=2.2, 1H), 6.99 (dd, J=8.8, 11.1, 1H), 7.38 (s, 1H), 7.42 (apparent t, J=2.7, 1H), 7.45 (dd, J=4.0, 8.8, 1H) and 11.29 (s, 1H).

EXAMPLE 57

4-(4-Morpholin-4-yl-6-piperazin-1-ylmethyl-thieno[3,2-d]pyrimidin-2-yl)-1H-indole-6-carbonitrile Prepared using Suzuki coupling method A of Reference Example 2 followed by standard BOC deprotection and generation of free base by aqueous extraction to give a pale brown solid (26 mg).

$\delta_H$ (400 MHz, CDCl$_3$) 2.48 (br s, 4H), 2.88 (br s, 4H), 3.76 (s, 2H), 3.85 (t, J=4.8, 4H), 4.02 (t, J=4,8, 4H), 7.30 (s, 1H), 7.45 (t, J=2.8, 1H), 7.61 (t, J=2.1, 1H), 7.72 (d, J=1.0, 1H), 8.38 (d, J=1.3, 1H), 8.54 (br s, 1H).

[M+H]$^+$ 460.25.

EXAMPLE 58

4-[6-(4-Isopropyl-piperazin-1-ylmethyl)-4-morpholin-4-yl-thieno[3,2-d]pyrimidin-2-yl]-1H-indole-6-carbonitrile Prepared using Suzuki coupling method A of Reference Example 2 to give a white solid (67 mg).

δ$_H$(400 MHz, CDCl$_3$) 1.00 (d, 6H), 2.55 (br s, 9H), 3.78 (s, 2H), 3.85 (t, J=4.8, 4H), 4.01 (t, J=4.83, 4H), 7.30 (s, 1H), 7.45 (t, J=2.9, 1H), 7.62 (t, J=2.3, 1H), 7.72 (t, J=1.1, 1H), 8.38 (d, J=1.4, 1H), 8.48 (br s, 1H).
[M+H]$^+$ 502.36.

EXAMPLE 59

2-(6-Methanesulfonyl-1H-indol-4-yl)-4-morpholin-4-yl-6-piperidin-1-ylmethyl-thieno[3,2-d]pyrimidine Prepared using Suzuki coupling method A of Reference Example 2 to give an off-white solid (139 mg).
δ$_H$(400 MHz, CDCl$_3$) 1.51 (m, 2H), 1.66 (m, 4H), 2.54 (s, 4H), 3.17 (s, 3H), 3.83 (s, 2H), 3.94 (t, J=4.8, 4H), 4.11 (t, J=4.8, 4H), 7.37 (s, 1H), 7.58 (t, J=2.84, 1H), 7.70 (t, J=2.3, 1H), 8.14 (t, J=1.2, 1H), 8.73 (br s, 1H), 8.74 (d, J=1.6, 1H).
[M+H]$^+$ 512.27.

EXAMPLE 60

2-(6-Methanesulfonyl-1H-indol-4-yl)-6-[4-(2-methoxy-ethyl)-piperidin-1-ylmethyl]-4-morpholin-4-yl-thieno[3,2-d]pyrimidine Prepared using Suzuki coupling method A of Reference Example 2 to give an off-white solid (122 mg).
δ$_H$(400 MHz, CDCl$_3$) 1.28 (dt, J=12.2, 3.3, 2H), 1.47 (q, J=6.5, 2H+m, 1H), 1.64 (m, 2H), 2.03 (t, J=10.6, 2H), 2.90 (m, 2H), 3.07 (s, 3H), 3.26 (s, 3H), 3.35 (t, J=6.5, 4H), 3.84 (t, J=4.8, 4H), 4.01 (t, J=4.8, 4H), 7.27 (s, 1H), 7.48 (t, J=2.8, 1H), 7.60 (t, J=2.2, 1H), 8.05 (s, 1H), 8.65 (d, J=1.6, 1H), 8.74 (br s, 1H).
[M+H]$^+$ 570.38.

EXAMPLE 61

4-{6-[4-(2-Methoxy-ethyl)-piperidin-1-ylmethyl]-4-morpholin-4-yl-thieno[3,2-d]pyrimidin-2-yl}-1H-indole-6-carbonitrile Prepared using Suzuki coupling method A of Reference Example 2 to give a waxy white solid (54 mg).
δ$_H$ (400 MHz, CDCl$_3$) 1.33 (m, 1H), 1.47 (q, J=6.5, 2H), 1.63 (m, 2H), 2.02 (m, 2H), 2.90 (m, 2H), 3.26 (s, 3H), 3.45 (t, J=4.5, 2H), 3.74 (d, J=0.4, 2H), 3.84 (t, J=4.8, 4H), 4.00 (t, J=4.8, 4H), 7.19 (s, 1H), 7.41 (t, J=2.7, 1H), 7.57 (m, 1H), 7.66 (t, J=1.1, 1H), 8.35 (d, J=1.3, 1H), 8.92 (br s, 1H).
[M+H]$^+$ 517.34.

EXAMPLE 62

4-{6-[4-(2-Methoxy-ethyl)-piperidin-1-ylmethyl]-4-morpholin-4-yl-thieno[3,2-d]pyrimidin-2-yl}-1H-indole-6-sulfonic acid dimethylamide Prepared using Suzuki coupling method A of Reference Example 2 to give a white solid (92 mg).
δ$_H$(400 MHz, CDCl$_3$) 1.25 (m, 1H), 1.46 (m, 3H), 1.64 (m, 2H), 2.00 (t, J=12.1, 2H), 2.67 (s, 6H), 2.90 (m, 2H), 3.26 (s, 3H), 3.35 (t, J=6.5, 2H), 3.75 (s, 2H), 3.83 (t, J=4.8, 4H), 4.00 (t, J=4.8, 4H), 7.28 (s, 1H), 7.46 (t, J=2.9, 1H), 7.90 (t, J=2.2, 1H), 8.50 (d, J=1.7, 1H), 8.53 (br s, 1H).
[M+H]$^+$ 599.36.

EXAMPLE 63

2-(6-Methanesulfonyl-1H-indol-4-yl)-4-morpholin-4-yl-6-piperazin-1-ylmethyl-thieno[2,3-d]pyrimidine Prepared using Suzuki coupling method A of Reference Example 2 followed by standard BOC deprotection and basic aqueous washing to give a white solid (38 mg).
δ$_H$(400 MHz, CDCl$_3$) 2.47 (br s, 4H), 2.87 (t, J=4.8, 4H), 3.08 (s, 3H), 3.70 (s, 2H), 3.86 (t, J=4.5, 4H), 3.92 (t, J=4.6, 4H), 6.93 (s, 1H), 7.50 (t, J=2.8, 1H), 7.65 (m, 1H), 8.05 (s, 1H), 8.56 (br s, 1H), 8.70 (d, J=1.6, 1H).
[M+H]$^+$ 513.45.

EXAMPLE 64

2-(5-Fluoro-1H-indol-4-yl)-6-[4-(2-methoxy-ethyl)-piperidin-1-ylmethyl]-4-morpholin-4-yl-thieno[3,2-d]pyrimidine Prepared using Suzuki coupling method A of Reference Example 2 to give a white solid (70 mg).
δ$_H$(400 MHz, CDCl$_3$) 1.19 (m, 2H), 1.29 (m, 1H), 1.47 (q, J=6.5, 2H), 1.64 (m, 2H), 2.02 (m, 2H), 2.91 (m, 2H), 3.26 (s, 3H), 3.35 (t, J=6.6, 2H), 3.74 (s, 2H), 3.79 (t, J=4.8, 4H), 3.98 (t, J=4.8, 4H), 6.83 (m, 1H), 6.98 (dd, J=10.9, 8.7, 1H), 7.21 (t, J=2.8, 1H), 7.27 (s, 1H), 7.29 (m, 1H), 8.21 (br s, 1H).
[M+H]$^+$ 510.25.

EXAMPLE 65

4-{6-[4-(2-Methoxy-ethyl)-piperidin-1-ylmethyl]-4-morpholin-4-yl-thieno[3,2-d]pyrimidin-2-yl}-1H-indole-2-carbonitrile Prepared using Suzuki coupling method B of Reference Example 2 to give an off-white solid (65 mg).
δ$_H$ (400 MHz, CDCl$_3$) 1.35-1.41 (m, 3H), 1.57 (m, 2H), 1.73 (m, 2H), 2.13 (m, 2H), 3.00 (m, 2H), 3.36 (s, 3H), 3.45 (t, J=6.5, 2H), 3.85 (s, 2H), 3.94 (t, J=4.8, 4H), 4.10 (t, J=4.8, 4H), 7.38 (s, 1H), 7.52 (d, J=4.7, 2H), 8.30 (m, 2H), 8.62 (br s, 1H).
[M+H]$^+$ 517.35.

EXAMPLE 66

4-[6-(4-Methyl-piperazin-1-ylmethyl)-4-morpholin-4-yl-thieno[3,2-d]pyrimidin-2-yl]-1H-indole-6-carboxylic acid dimethylamide Prepared using Suzuki coupling method A of Reference Example 2 to give an off-white solid (2 mg).
δ$_H$ (400 MHz, CDCl$_3$) 2.38 (s, 3H), 2.60 (m, 8H), 3.10 (s, 6H), 3.86 (s, 2H), 3.90 (t, J=4.7, 4H), 4.07 (t, J=4.7, 4H), 7.38 (s, 1H); 7.40 (m, 1H), 7.60 (m, 1H), 7.64 (s, 1H), 8.29 (s, 1H), 8.43 (br s, 1H).
[M+H]$^+$ 520.45.

EXAMPLE 67

2-{4-[2-(6-Cyano-1H-indol-4-yl)-4-morpholin-4-yl-thieno[3,2-d]pyrimidin-6-ylmethyl]-piperazin-1-yl}-isobutyramide Prepared using Suzuki coupling method A of Reference Example 2 to give a cream solid (41 mg).

δ$_H$ (400 MHz, CDCl$_3$) 1.27 (s, 6H), 2.63 (m, 8H), 3.88 (s, 2H), 3.94 (t, J=4.7, 4H), 4.11 (t, J=4.7, 4H), 5.21 (br s, 1H), 7.12 (br s, 1H), 7.39 (s, 1H), 7.55 (t, J=5.6, 1H), 7.69 (s, 1H), 7.82 (s, 1H), 8.47 (s, 1H), 8.60 (br s, 1H).
[M+H]$^+$ 545.35.

EXAMPLE 68

2-{4-[2-(6-Fluoro-1H-indol-4-yl)-4-morpholin-4-yl-thieno[3,2-d]pyrimidin-6-ylmethyl]-piperazin-1-yl}-isobutyramide Prepared using Suzuki coupling method A of Reference Example 2 to give an off-white solid (95 mg).
δ$_H$ (400 MHz, CDCl$_3$) 1.26 (s, 6H), 2.63 (m, 8H), 3.87 (s, 2H), 3.93 (t, J=4.8, 4H), 4.10 (t, J=4.8, 4H), 5.18 (br s, 1H), 7.10 (br s, 1H), 7.20 (dd, J=1.1, 6.5, 1H), 7.32 (m, 1H), 7.38 (s, 1H), 7.56 (s, 1H), 8.99 (dd, J=2.3, 8.8, 1H), 8.26 (br s, 1H).
[M+H]$^+$ 538.38.

EXAMPLE 69

2-(6-Fluoro-1H-indol-4-yl)-4-morpholin-4-yl-6-piperidin-1-ylmethyl-thieno[3,2-d]pyrimidine Prepared using Suzuki coupling method A of Reference Example 2 to give a white solid (68 mg).
δ$_H$ (400 MHz, CDCl$_3$) 1.50 (m, 2H), 1.65 (m, 4H), 2.53 (m, 4H), 3.82 (s, 2H), 3.93 (t, J=4.8, 4H), 4.10 (t, J=4.8, 4H), 7.19 (dd, J=1.1, 6.5, 1H), 7.31 (m, 1H), 7.36 (s, 1H), 7.56 (m, 1H), 7.99 (dd, J=2.3, 8.9, 1H), 8.23 (br s, 1H).
[M+H]$^+$ 452.25.

EXAMPLE 70

2-(6-Fluoro-1H-indol-4-yl)-6-[4-(2-methoxy-ethyl)-piperidin-1-ylmethyl]-4-morpholin-4-yl-thieno[3,2-d]pyrimidine Prepared using Suzuki coupling method A of Reference Example 2 to give a white solid (91 mg).
δ$_H$ (400 MHz, CDCl$_3$) 1.26-1.62 (m, 5H), 1.73 (m, 2H), 2.12 (t, J=10.7, 2H), 3.00 (d, J=11.3, 2H), 3.35 (s, 3H), 3.44 (t, J=6.5, 2H), 3.83 (s, 2H), 3.93 (t, J=4.7, 4H), 4.10 (t, J=4.7, 4H), 7.19 (dd, J=1.9, 6.7, 1H), 7.31 (m, 1H), 7.36 (s, 1H), 7.56 (m, 1H), 7.99 (dd, J=2.3, 8.9, 1H), 8.24 (br s, 1H).
[M+H]$^+$ 510.30.

EXAMPLE 71

4-(4-Morpholin-4-yl-6-piperidin-1-ylmethyl-thieno[3,2-d]pyrimidin-2-yl)-1H-indole-6-carbonitrile Prepared using Suzuki coupling method A of Reference Example 2 to give a white solid (48 mg).
δ$_H$ (400 MHz, CDCl$_3$) 1.51 (m, 2H), 1.65 (m, 4H), 2.53 (m, 4H), 3.83 (s, 2H), 3.94 (t, J=4.8, 4H), 4.11 (t, J=4.8, 4H), 7.36 (s, 1H), 7.54 (m, 1H), 7.71 (m, 1H), 7.81 (s, 1H), 8.47 (s, 1H), 8.55 (br s, 1H).
[M+H]$^+$ 459.26.

EXAMPLE 72

2-(6-Fluoro-1H-indol-4-yl)-4-morpholin-4-yl-6-piperazin-1-ylmethyl-thieno[2,3-d]pyrimidine Prepared using Suzuki coupling method A of Reference Example 2 to give 2-(6-fluoro-1H-indol-4-yl)-morpholin-4-yl-thieno[2,3-d]pyrimidin-6-ylmethyl]-piperazine-1-carboxylic acid tert-butyl ester as a white solid (91 mg). Removal of the BOC-group using HCl in ether under standard conditions gave a yellow solid (40 mg).
δ$_H$ (400 MHz, CDCl$_3$) 2.63 (m, 4H), 3.04 (m, 4H), 3.81 (s, 2H), 3.95 (m, 4H), 4.00 (m, 4H), 7.18 (m, 2H) 7.32 (m, 2H), 7.60 (m, 1H), 8.03 (dd, 1H), 8.25 (br s, 1H).
[M+H]$^+$ 453.27.

EXAMPLE 73

2-{4-[2-(6-Fluoro-1H-indol-4-yl)-4-morpholin-4-yl-thieno[3,2-d]pyrimidin-6-ylmethyl]-piperazin-1-yl}-N-methyl-isobutyramide Prepared using Suzuki coupling method A of Reference Example 2 to give a yellow solid (80 mg).
δ$_H$ (400 MHz, CDCl$_3$) 2.23 (s, 6H), 2.58 (br m, 8H), 2.83 (d, J=4.9, 3H), 3.88 (s, 2H), 3.93 (t, J=4.7, 4H), 4.10 (t, J=4.7, 4H), 7.20 (dd, J=1.5, 7.2, 1H), 7.26 (m, 1H) 7.33 (m, 1H), 7.38 (s, 1H), 7.53 (m, 1H), 7.98 (dd, J=2.3, 8.8, 1H), 8.32 (br s, 1H).
[M+H]$^+$ 552.32.

EXAMPLE 74

2-(6-Fluoro-1H-indol-4-yl)-6-[4-(2-methoxy-ethyl)-piperidin-1-ylmethyl]-7-methyl-4-morpholin-4-yl-thieno[3,2-d]pyrimidine Prepared using Suzuki coupling method A of Reference Example 2 to give an off-white solid (53 mg).
δ$_H$ (400 MHz, CDCl$_3$) 1.17-1.50 (m, 5H), 1.63 (m, 2H), 2.04 (t, J=1.5, 2H), 2.43 (s, 3H), 2.92 (m, 2H), 3.26 (s, 3H), 3.35 (t, J=6.9, 2H), 3.72 (s, 2H), 3.83 (t, J=4.8, 4H), 4.00 (t, J=4.8, 4H), 7.10 (dd, 1H), 7.23 (t, 1H), 7.62 (m, 1H), 8.01 (dd, 1H), 8.14 (br s, 1H).
[M+H]$^+$ 524.32.

EXAMPLE 75

4-{6-[4-(2-Methoxy-ethyl)-piperidin-1-ylmethyl]-7-methyl-4-morpholin-4-yl-thieno[3,2-d]pyrimidin-2-yl}-1H-indole-6-carbonitrile Prepared using Suzuki coupling method A of Reference Example 2 to give an off-white solid (45 mg).
δ$_H$ (400 MHz, CDCl$_3$) 1.27-1.62 (m, 5H), 1.73 (m, 2H), 2.13 (br t, J=10.5, 2H), 2.53 (s, 3H), 3.02 (m, 2H), 3.35 (s, 3H), 3.44 (t, J=6.5, 2H), 3.82 (s, 2H), 3.94 (t, J=4.7, 4H), 4.10 (t, J=4.7, 4H), 7.55 (t, J=2.8, 1H), 7.82 (s, 1H), 7.85 (m, 1H), 8.54 (br s, 1H), 8.57 (s, 1H).
[M+H]$^+$ 531.33.

EXAMPLE 76

2-{4-[2-(6-Fluoro-1H-indol-4-yl)-7-methyl-4-morpholin-4-yl-thieno[3,2-d]pyrimidin-6-ylmethyl]-piperazin-1-yl}-isobutyramide Prepared using Suzuki coupling method A of Reference Example 2 to give a white solid (61 mg).
δ$_H$ (400 MHz, CDCl$_3$) 1.26 (s, 6H), 2.55 (s, 3H), 2.63 (m, 8H), 3.85 (s, 2H), 3.93 (t, J=4.7, 4H), 4.10 (t, J=4.7, 4H), 5.22 (br s, 1H), 7.14 (br s, 1H), 7.20 (dd, J=1.6, 7.2, 1H), 7.34 (t, J=2.8, 1H), 7.71 (t, J=2.2, 1H), 8.09 (dd, J=2.3, 9.0, 1H), 8.28 (br s, 1H).
[M+H]$^+$ 552.36.

EXAMPLE 77

2-(6-Methanesulfonyl-1H-indol-4-yl)-6-[4-(2-methoxy-ethyl)-piperidin-1-ylmethyl]-7-methyl-4-morpholin-4-yl-thieno[3,2-d]pyrimidine Prepared using Suzuki coupling method A of Reference Example 2 to give a white solid (46 mg).

$\delta_H$ (400 MHz, CDCl$_3$) 1.26-1.60 (m, 5H), 1.73 (m, 2H), 2.13 (br t, J=10.5, 2H), 2.53 (s, 3H), 3.02 (m, 2H), 3.16 (s, 3H), 3.35 (s, 3H), 3.45 (t, J=6.4, 2H), 3.83 (s, 3H), 3.93 (t, J=4.7, 4H), 4.10 (t, J=4.7, 4H), 7.59 (t, J=2.7, 1H), 7.84 (s, 1H), 8.14 (s, 1H), 8.68 (br s, 1H), 8.81 (s, 1H).

[M+H]$^+$ 584.39.

EXAMPLE 78

2-{4-[2-(6-Cyano-1H-indol-4-yl)-7-methyl-4-morpholin-4-yl-thieno[3,2-d]pyrimidin-6-ylmethyl]-piperazin-1-yl}-isobutyramide Prepared using Suzuki coupling method A of Reference Example 2 to give a white solid (61 mg).

$\delta_H$ (400 MHz, CDCl$_3$) 1.27 (s, 6H), 2.55 (s, 3H), 2.64 (m, 8H), 3.86 (s, 2H), 3.94 (t, J=4.8, 4H), 4.10 (t, J=4.8, 4H), 5.20 (br s, 1H), 7.12 (br s, 1H), 7.55 (t, J=2.8, 1H), 7.82 (s, 1H), 7.84 (t, J=2.5, 1H), 8.57 (s, 2H).

[M+H]$^+$ 559.28.

EXAMPLE 79

2-{4-[2-(6-Methanesulfonyl-1H-indol-4-yl)-7-methyl-4-morpholin-4-yl-thieno[3,2-d]pyrimidin-6-ylmethyl]-piperazin-1-yl}-isobutyramide Prepared using Suzuki coupling method A of Reference Example 2 to give a white solid (85 mg).

$\delta_H$ (400 MHz, CDCl$_3$) 1.27 (s, 6H), 2.55 (s, 3H), 2.63 (m, 8H), 3.16 (s, 3H), 3.86 (s, 2H), 3.93 (t, J=4.8, 4H), 4.10 (t, J=4.8, 4H), 5.2 (br s, 1H), 7.12 (br s, 1H), 7.59 (t, J=2.8, 1H), 7.83 (t, J=2.2, 1H), 8.15 (s, 1H), 8.78 (br s, 1H), 8.81 (s, 1H).

[M+H]$^+$ 612.27.

EXAMPLE 80

2-{4-[2-(1H-Indol-4-yl)-4-morpholin-4-yl-thieno[3,2-d]pyrimidin-6-ylmethyl]-piperazin-1-yl}-2-methyl-1-pyrrolidin-1-yl-propan-1-one Prepared using Suzuki coupling method B of Reference Example 2 to give a white solid (102 mg)

$\delta_H$ (400 MHz, CDCl$_3$) 1.28 (s, 6H), 1.82 (m, 4H), 2.57 (s, 8H), 3.48 (m, 4H), 3.83 (s, 2H), 3.91 (m, 4H), 4.11 (m, 4H), 7.32 (m, 3H), 7.49 (d, J=7.9, 1H), 7.54 (s, 1H), 8.18 (d, J=7.4, 1H) 8.29 (br s, 1H).

[M+H]$^+$ 574.4.

EXAMPLE 81

Cyclopropylmethyl-{1-[2-(1H-indol-4-yl)-4-morpholin-4-yl-thieno[3,2-d]pyrimidin-6-ylmethyl]-piperidin-4-yl}-(2-methoxy-ethyl)-amine Prepared using Suzuki coupling method B of Reference Example 2 to give an off-white solid (83 mg)

$\delta_H$ (400 MHz, CDCl$_3$) 0.10 (m, 2H), 0.40 (m, 2H), 0.73 (m,1H), 1.62 (m, 4H), 1.99 (m, 2H), 2.35 (m, 2H), 2.56 (m, 2H), 2.65 (m, 2H), 2.93 (m, 2H), 3.25 (s, 3H), 3.37 (m, 2H), 3.71 (s, 2H), 3.81 (m, 4H), 3.98 (m, 4H), 7.20 (m, 3H), 7.38 (d, J=7.9, 1H), 7.43 (s, 1H), 8.07 (d, J=7.2, 1H), 8.16 (br s, 1H).

[M+H]$^+$ 561.3.

EXAMPLE 82

2-(1H-Indol-4-yl)-6-(4-isopropyl-piperazin-1-ylmethyl)-4-morpholin4yl-thieno[3,2-d]pyrimidine Prepared using Suzuki coupling method A of Reference Example 2 to give an off-white solid (172 mg).

$\delta_H$ (400 MHz, CDCl$_3$) 1.07 (d, J=5.5, 6H), 1.57 (br s, 1H), 2.62 (br s, 8H), 3.84 (s, 2H), 3.91 (t, J=4.8, 4H), 4.08 (t, J=4.8, 4H), 7.29 (t, J=7.7, 1H), 7.32 (m, 1H), 9.82 (s, 1H), 7.49 (d, J=8.2, 1H), 7.55 (m, 1H), 8.31 (d, J=7.2, 1H), 8.27 (br s, 1H).

[M+H]$^+$ 477.2.

EXAMPLE 83

2-(1H-Indol-4-yl)-6-(4-isopropyl-piperazin-1-ylmethyl)-4-morpholin-4-yl-thieno[2,3-d]pyrimidine Prepared using Suzuki coupling method B of Reference Example 2 to give a white solid (160 mg)

$\delta_H$ (400 MHz, CDCl$_3$) 1.06 (d, 6H), 1.61 (br s, 1H), 2.59 (br s, 8H), 3.77 (s, 2H), 3.92 (m, 4H), 3.99 (m, 4H), 7.14 (s, 1H), 7.32 (m, 2H), 7.49 (d, J=7.9, 1H), 7.59 (s, 1H), 8.25 (br s, 1H).

[M+H]$^+$ 477.3.

EXAMPLE 84

6-[4-(2-Methoxy-ethyl)-piperidin-1-ylmethyl]-4-morpholin-4-yl-2-(6-trifluoromethyl-1H-indol-4-yl)-thieno[3,2-d]pyrimidine Prepared using Suzuki coupling Method B.

$\delta_H$ (400 MHz, CDCl$_3$) 1.27-1.52 (m, 3H), 1.73 (m, 2H), 2.12 (t, J=10.7, 2H), 3.99 (m, 2H), 3.35 (s, 3H), 3.44 (t, J=6.5, 2H), 3.84 (s, 3H), 3.94 (t, J=4.7, 4H), 4.10 (t, J=4.7, 4H), 7.38 (s, 1H), 7.48 (m, 1H), 7.64 (m, 4H), 7.11 (s, 1H), 8.47 (br s, 2H).

[M+H]$^+$ 560.21.

EXAMPLE 85

2-(1H-Indol-4-yl)-4-morpholin-4-yl-6-piperazin-1-ylmethyl-thieno[2,3-d]pyrimidine Prepared using Suzuki coupling method A of Reference Example 2 and then by standard BOC deprotection methods to give an off-white solid (34 mg).

$\delta_H$ (400 MHz, CDCl$_3$) 2.38 (m, 4H), 2.70 (m, 4H), 3.73 (s, 2H), 3.81 (m, 4H), 3.92 (m, 4H), 7.18 (m, 1H), 7.38 (s, 1H), 7.41 (m, 1H), 7.51 (m, 2H), 8.11 (d, J=7.3, 1H), 11.25 (br s, 1H).

[M+H]$^+$ 435.2.

EXAMPLE 86

4-Morpholin-4-yl-6-piperazin-1-ylmethyl-2-(6-trifluoromethyl-1H-indol-4-yl)-thieno[2,3-d]pyrimidine Prepared using Suzuki coupling method B of Reference Example 2 and then by standard BOC deprotection methods to give an off-white solid (33 mg).

$\delta_H$ (400 MHz, CDCl$_3$) 2.56 (br s, 4H), 2.96 (t, J=4.7, 4H), 3.79 (s, 2H), 3.95 (t, J=4.6, 4H), 4.01 (t, J=4.6, 4H), 7.19 (s, 1H), 7.50 (t, J=3.0, 1H), 7.69 (s, 1H), 7.79 (s, 1H), 8.52 (br s, 8.52).

[M+H]$^+$ 503.18.

EXAMPLE 87

2-{4-[2-(1H-Indol-4-yl)-4-morpholin-4-yl-thieno[2,3-d]pyrimidin-6-ylmethyl]-piperazin-1-yl}-ethanol Prepared using Suzuki coupling method B of Reference Example 2 to give a white solid (22 mg).

$\delta_H$ (400 MHz, CDCl$_3$) 2.63 (br s, 10H), 3.65 (m, 2H), 3.79 (s, 2H), 3.92 (m, 4H), 3.98 (m, 4H), 7.15 (s, 1H), 7.29 (m, 2H), 7.50 (d, J=7.9, 1H), 7.58 (s, 1H), 8.23 (d, J=7.4, 1H), 8.25 (br s, 1H).

[M+H]$^+$ 479.3.

EXAMPLE 88

4-[6-(4-Isopropyl-piperazin-1-ylmethyl)-4-morpholin-4-yl-thieno[2,3-d]pyrimidin-2-yl]-1H-indole-6-carbonitrile Prepared using Suzuki coupling method A of Reference Example 2 to give a white solid (124 mg).

$\delta_H$ (400 MHz, CDCl$_3$) 0.99 (br s, 6H), 2.52 (br s, 8H), 2.67 (br s, 2H), 3.84 (m, 6H), 3.94 (m, 4H), 7.52 (s, 1H), 7.58 (s, 1H), 7.79 (d, J=5.5, 1H), 8.01 (s, 1H), 8.35 (s, 1H), 11.9 (br s, 1H).

[M+H]$^+$ 502.4

EXAMPLE 89

4-(4-Morpholin-4-yl-6-piperazin-1-ylmethyl-thieno[2,3-d]pyrimidin-2-yl)-1H-indole-6-carbonitrile Prepared using Suzuki coupling method A of Reference Example 2 and then by standard BOC deprotection methods to give an off-white solid (70 mg).

$\delta_H$ (400 MHz, d6-DMSO) 2.49 (m, 4H), 2.72 (m, 4H), 3.76 (s, 2H), 3.83 (m, 4H), 3.94 (m, 4H), 7.52 (d, 1H), 7.55 (s, 1H), 7.80 (d, 1H), 8.02 (s, 1H), 8.35 (s, 1H).

[M+H]$^+$ 501.3.

EXAMPLE 90

4-(4-Morpholin-4-yl-6-piperidin-1-ylmethyl-thieno[3,2-d]pyrimidin-2-yl)-1H-indole-6-carboxylic acid amide Prepared using Suzuki coupling method A of Reference Example 2 to give a white solid (24 mg).

$\delta_H$ (400 MHz, CDCl$_3$) 1.49 (m, 2H), 1.65 (m, 4H), 2.54 (m, 4H), 3.50 (m, 2H), 3.83 (s, 2H), 3.94 (m, 4H), 4.12 (m, 4H), 7.37 (s, 1H), 7.49 (t, J=5.6, 1H), 7.58 (s, 1H), 8.20 (s, 1H), 8.51 (s, 1H), 8.56 (br s, 1H).

[M+H]$^+$ 477.3

EXAMPLE 91

4-(4-Morpholin-4-yl-6-piperidin-1-ylmethyl-thieno[3,2-d]pyrimidin-2-yl)-1H-indole-6-sulfonic acid dimethylamide Prepared using Suzuki coupling method A of Reference Example 2 to give a white solid (103 mg).

$\delta_H$ (400 MHz, CDCl$_3$) 1.50 (m, 2H), 1.64 (m, 4H), 2.54 (m, 4H), 2.76 (s, 6H), 3.83 (s, 2H), 3.93 (m, 4H), 4.09 (m, 4H), 7.37 (s, 1H), 7.55 (m, 1H), 7.68 (m, 1H), 7.99 (s, 1H), 8.59 (s, 1H), 8.66 (br s, 1H).

[M+H]$^+$ 541.3.

EXAMPLE 92

4-{6-[4-(2-Methoxy-ethyl)-piperidin-1-ylmethyl]-4-morpholin-4-yl-thieno[3,2-d]pyrimidin-2-yl}-1H-indole-6-carboxylic acid amide Prepared using Suzuki coupling method A of Reference Example 2 to give a white solid (51 mg).

$\delta_H$ (400 MHz, CDCl$_3$) 1.39 (m, 1H), 1.58-1.54 (m, 8H), 1.73 (d, J=11.5, 2H), 2.10 (t, J=9.7, 2H), 2.99 (d, 2H), 3.35 (s, 3H), 3.84 (s, 2H), 3.94 (m, 4H), 4.14 (m, 4H), 7.37 (s, 1H), 7.49 (t, J=5.6, 1H), 7.57 (s, 1H), 8.19 (s, 1H), 8.56 (s, 1H), 8.62 (br s, 1H).

[M+H]$^+$ 535.4.

EXAMPLE 93

4-(4-Morpholin-4-yl-6-piperazin-1-ylmethyl-thieno[2,3-d]pyrimidin-2-yl)-1H-indole-6-sulfonic acid dimethylamide Prepared using Suzuki coupling method A of Reference Example 2 and then by standard BOC deprotection methods to give a white solid (140 mg).

$\delta_H$ (400 MHz, d6-DMSO) 2.41 (m, 4H), 2.64 (s, 6H), 2.73 (m, 4H), 3.76 (s, 2H), 3.83 (m, 4H), 3.94 (m, 4H), 7.50 (s, 1H), 7.57 (s, 1H), 7.79 (s, 1H), 7.92 (s, 1H), 8.43 (s, 1H).

[M+H]$^+$ 542.6.

EXAMPLE 94

4-(4-Morpholin-4-yl-6-piperazin-1-ylmethyl-thieno[2,3-d]pyrimidin-2-yl)-1H-indole-6-carboxylic acid amide Prepared using Suzuki coupling method A of Reference Example 2 and then by standard BOC deprotection methods to give a white solid (58 mg).

$\delta_H$ (400 MHz, DMSO) 2.39 (m, 4H), 2.71 (m, 4H), 3.75 (s, 2H), 3.83 (m, 4H), 3.95 (m, 4H), 7.20 (br s, 1H), 7.40 (s, 1H), 7.54 (s, 1H), 7.62 (s, 1H), 8.02 (br s, 1H), 8.06 (s, 1H), 8.61 (s, 1H).

[M+H]$^+$ 478.3.

EXAMPLE 95

2-{4-[2-(6-Methanesulfonyl-1H-indol-4-yl)-4-morpholin-4-yl-thieno[3,2-d]pyrimidin-6-ylmethyl]-piperazin-1-yl}-N-methyl-isobutyramide Prepared using Suzuki coupling method A of Reference Example 2 to give a white solid (86 mg).

$\delta_H$ (400 MHz, CDCl$_3$) 1.21 (s, 6H), 2.60 (m, 8H), 2.83 (d, J=4.8, 1H), 3.17 (s, 3H), 3.89 (s, 2H), 3.94 (m, 4H), 4.11 (m, 4H), 7.21 (d, J=4.4, 1H), 7.39 (s, 1H), 7.58 (t, J=6.0, 1H), 7.69 (t, J=4.4, 1H), 8.15 (t, J=2.4, 1H), 8.73 (br s, 1H), 8.76 (s, 1H).

[M+H]$^+$ 612.3.

EXAMPLE 96

2-(5-Fluoro-1H-indol-4-yl)-4-morpholin-4-yl-6-piperidin-1-ylmethyl-thieno[3,2-d]pyrimidine Prepared using Suzuki coupling method A of Reference Example 2 to give a white solid (69 mg).
$\delta_H$ (400 MHz, CDCl$_3$) 1.68-1.49 (m, 6H), 2.53 (br s, 4H), 3.83 (s, 2H), 3.89 (m, 4H), 4.08 (m, 4H), 6.92 (m, 1H), 7.06 (m, 1H), 7.39-7.30 (m, 3H), 8.28 (br s, 1H).
[M+H]$^+$ 452.3

EXAMPLE 97

4-(4-Morpholin-4-yl-6-piperidin-1-ylmethyl-thieno[3,2-d]pyrimidin-2-yl)-1H-indole-2-carbonitrile Prepared using Suzuki coupling method A of Reference Example 2 to give a white solid (98 mg).
$\delta_H$ (400 MHz, CDCl$_3$) 1.42 (m, 2H), 1.57 (m, 4H), 2.45 (m, 4H), 3.74 (s, 2H), 3.84 (m, 4H), 4.0 (m, 4H), 7.28 (s, 1H), 7.42 (m, 2H), 8.22 (m, 2H), 8.52 (br s, 1H).
[M+H]$^+$ 459.2.

EXAMPLE 98

4-{6-[4-(2-Hydroxy-ethyl)-piperazin-1-ylmethyl]-4-morpholin-4-yl-thieno[3,2-d]pyrimidin-2-yl}-1H-indole-6-carbonitrile Prepared using Suzuki coupling method A of Reference Example 2 to give a white solid (20 mg).
$\delta_H$ (400 MHz, CDCl$_3$) 2.52 (m, 2H), 2.62 (m, 8H), 3.66 (m, 2H), 3.82 (s, 2H), 3.93 (m, 4H), 4.06 (m, 4H), 7.39 (s, 1H), 7.53 (t, J5.6, 1H), 7.69 (t, J=4.3, 1H), 7.79 (s, 1H), 8.46 (s, 1H), 8.76 (br s, 1H).
[M+H]$^+$ 504.2

EXAMPLE 99

2-{4-[2-(6-Methanesulfonyl-1H-indol-4-yl)-4-morpholin-4-yl-thieno[3,2-d]pyrimidin-6-ylmethyl]-piperazin-1-yl}-ethanol Prepared using Suzuki coupling method A of Reference Example 2 to give a white solid (23 mg).
$\delta_H$ (400 MHz, DMSO) 2.70 (m, 2H), 3.31 (s, 3H), 3.35 (m, 8H), 3.88 (m, 4H), 3.95 (m, 2H), 4.04 (m, 4H), 7.55 (s, 2H), 7.82(s, 1H), 8.12 (s, 1H), 8.60 (s, 1H), 11.85 (br s, 1H).
[M+H]$^+$ 557.3.

EXAMPLE 100

4-{6-[4-(2-Hydroxy-1,1-dimethyl-ethyl)-piperazin-1-ylmethyl]-4-morpholin-4-yl-thieno[3,2-d]pyrimidin-2-yl}-1H-indole-6-carbonitrile Prepared using Suzuki coupling method A of Reference Example 2 to give a white solid (23 mg).
$\delta_H$ (400 MHz, CDCl$_3$) 1.01 (br s, 6H), 2.59 (br s, 8H), 3.39 (br s, 2H), 3.78 (s, 2H), 3.86 (m, 4H), 4.01 (m, 4H), 7.30 (s, 1H), 7.45 (m, 1H), 7.62 (s, 1H), 7.73 (s, 1H), 8.39 (s, 1H), 8.50 (br s, 1H).
[M+H]$^+$ 532.4.

EXAMPLE 101

2-{4-[2-(6-Fluoro-1H-indol-4-yl)-4-morpholin-4-yl-thieno[3,2-d]pyrimidin-6-ylmethyl]-piperazin-1-yl}-2-methyl-propan-1-ol Prepared using Suzuki coupling method A of Reference Example 2 to give a white solid (23 mg).
$\delta_H$ (400 MHz, CDCl$_3$) 0.89 (br s, 6H), 2.68 (br s, 8H), 3.51 (br s, 2H), 3.93 (m, 4H), 4.11 (m, 4H), 7.20 (m, 1H), 7.32 (m, 1H), 7.39 (s, 1H), 7.57 (s, 1H), 8.00 (m, 1H), 8.25 (br s, 1H).
[M+H]$^+$ 525.4.

EXAMPLE 102

4-Morpholin-4-yl-6-piperidin-1-ylmethyl-2-(2-trifluoromethyl-1H-indol-4-yl)-thieno[3,2-d]pyrimidine Prepared using Suzuki coupling method B of Reference Example 2 to give a white solid (34 mg).
$\delta_H$ (400 MHz, CDCl$_3$) 1.48-1.69 (m, 6H), 2.53 (br s, 4H), 3.83 (s, 2H), 3.94 (t, J=4.8, 4H), 4.11 (t, J=4.8, 4H), 7.39 (s, 1H), 7.46 (dd, J=8.0 and 7.6, 1H), 7.55 (d, J=8.0, 1H), 8.02 (s, 1H), 8.28 (d, J=7.6, 1H), 8.47 (br s, 1H).
[M+H]$^+$ 502.

EXAMPLE 103

6-[4-(2-Methoxy-ethyl)-piperidin-1-ylmethyl]-4-morpholin-4-yl-2-(2-trifluoromethyl-1H-indol-4-yl)-thieno[3,2-d]pyrimidine Prepared using Suzuki coupling method B of Reference Example 2 to give a yellow solid (68 mg).
$\delta_H$ (400 MHz, CDCl$_3$) 1.32-1.61 (m, 5H), 1.71-1.75 (m, 2H), 2.08-2.15 (m, 2H), 2.98-3.02 (m, 2H), 3.35 (s, 3H), 3.44 (t, J=6.4, 2H), 3.84 (s, 2H), 3.93 (t, J=4.8, 4H), 4.11 (t, J=4.8, 4H), 7.39 (s, 1H), 7.44-7.56 (m, 2H), 8.02 (s, 1H), 8.28 (d, J=8.4, 1H), 8.49 (br s, 1H).
[M+H]$^+$ 560.

EXAMPLE 104

4-Morpholin-4-yl-6-piperazin-1-ylmethyl-2-(2-trifluoromethyl-1H-indol-4-yl)-thieno[2,3-d]pyrimidine Prepared using Suzuki coupling method B of Reference Example 2 then Boc deprotection to give a pale yellow solid (111 mg).
$\delta_H$ (400 MHz, d$_6$-DMSO) 2.41 (br s, 4H), 2.72-2.76 (br m, 4H), 3.76 (s, 2H), 3.82 (t, J=4.6, 4H), 3.95 (t, J=4.6, 4H), 7.43 (t, J=8.4, 1H), 7.54 (s, 1H), 7.62 (d, J=8.4, 1H), 7.91 (s, 1H), 8.26 (d, J=8.4, 1H), 12.40 (br s, 1H).
[M+H]$^+$ 503.

EXAMPLE 105

4-Morpholin-4-yl-6-piperidin-1-ylmethyl-2-(6-trifluoromethyl-1H-indol-4-yl)-thieno[3,2-d]pyrimidine Prepared using Suzuki coupling method B of Reference Example 2 to give an off-white solid (92 mg).
$\delta_H$ (400 MHz, CDCl$_3$) 1.50-1.68 (m,6H), 2.53 (br s, 4H), 3.83 (s, 2H), 3.94 (t, J=4.8, 4H), 4.11 (t, J=4.8, 4H), 7.38 (s, 1H), 7.48 (t, J=2.8, 1H), 7.63 (br s, 1H), 7.78 (s, 1H), 8.46 (s, 1H), 8.56 (br s, 1H).
[M+H]$^+$ 502.

EXAMPLE 106

2-(5-Fluoro-1H-indol-4-yl)-4-morpholin-4-yl-6-piperazin-1-ylmethyl-thieno[2,3-d]pyrimidine Prepared using Suzuki coupling method B of Reference Example 2 then Boc deprotection to give a buff-coloured solid (59 mg).

$\delta_H$ (400 MHz, d$_6$-DMSO) 2.41 (br s, 4H), 2.72-2.75 (m, 4H), 3.74-3.78 (m, 6H), 3.87-3.90 (m, 4H), 6.71 (t, J=2.2, 1H), 7.01 (dd, J=11.2 and 8.8, 1H), 7.43-7.48 (m, 2H), 7.56 (s, 1H), 11.24 (br s, 1H).
[M+H]$^+$ 453.

EXAMPLE 107

4-(4-Morpholin-4-yl-6-piperazin-1-ylmethyl-thieno[2,3-d]pyrimidin-2-yl)-1H-indole-2-carbonitrile Prepared using Suzuki coupling method B of Reference Example 2 to give an off-white solid (30 mg).

$\delta_H$ (400 MHz, d$_6$-DMSO) 2.40 (br s, 4H), 2.70-2.73 (m,4H), 3.75 (s, 2H), 3.81-3.83 (m, 4H), 3.92-3.95 (m, 4H), 7.47 (t, J=8.0, 1H), 7.55 (s, 1H), 7.61 (d, J=8.0, 1H), 8.17 (d, J=0.8, 1H), 8.26 (dd, J=8.0 and 0.8, 1H).
[M+H]$^+$ 460.

EXAMPLE 108

4-(4-Morpholin-4-yl-6-piperazin-1-ylmethyl-thieno[2,3-d]pyrimidin-2-yl)-1H-indole-2-carboxylic acid amide Also isolated as a product from the reaction of Example 107. Obtained as an off-white solid (18 mg).

$\delta_H$ (400 MHz, d$_6$-DMSO) 2.41 (br s, 4H), 2.70-2.73 (m, 4H), 3.76 (s, 2H), 3.82 (t, J=4.8, 4H), 3.93 (t, J=4.8, 4H), 7.30 (t, J=8.0, 1H), 7.38 (br s, 1H), 7.54 (s, 1H), 7.55 (d, J=8.0, 1H), 8.05 (d, J=0.8, 1H), 8.12 (br s, 1H), 8.14 (dd, J=8.0 and 0.8, 1H).
[M+H]$^+$ 478.

EXAMPLE 109

1-Butoxy-3-{4-[2-(1H-indol-4-yl)-4-morpholin-4-yl-thieno[3,2-d]pyrimidin-6-ylmethyl]-piperazin-1-yl}-propan-2-ol To a stirred solution of 2-(1H-indol-4-yl)-4-morpholin-4-yl-6-piperazin-1-ylmethyl-thieno[3,2-d]pyrimidine (50 mg) in N,N-dimethylformamide (3 mL) at r.t. was added 0.1 M Na$_2$HPO$_4$ pH 6.8 buffer (0.5 mL) and butyl glycidyl ether (18 μL) and the resulting cloudy mixture was heated at 55° C. for 3 days with 2 extra equivalents of butyl glycidyl ether (18 μL) added during this time. The reaction mixture was partitioned between EtOAc (15 mL) and brine (15 mL), the organic layer was dried (Na$_2$SO$_4$), concentrated and the residue purified by flash chromatography (silica; 96:4 EtOAc/MeOH as eluent) to give an off-white solid (38 mg).

$\delta_H$ (400 MHz, CDCl$_3$) 0.81 (t, J=6.8, 3H), 1.21-1.53 (m, 4H), 2.35-2.69 (br m, 10H), 3.32-3.57 (m, 5H), 3.78 (s, 2H), 3.84 (t, J=4.8, 4H), 4.00 (t, J=4.8, 4H), 7.22-7.28 (m, 2H), 7.30 (s, 1H), 7.42 (d, J=8.0, 1H), 7.47 (br s, 1H), 8.11 (d, J=8.0, 1H), 8.18 (br s, 1H).
[M+H]$^+$ 565.

EXAMPLE 110

6-(cis-3,5-Dimethyl-piperazin-1-ylmethyl)-2-(6-fluoro-1H-indol-4-yl)-4-morpholin-4-yl-thieno[3,2-d]pyrimidine To a solution of toluene-4-sulfonic acid 2-[6-fluoro-1-(toluene-4-sulfonyl)-1H-indol-4-yl]-4-morpholin-4-yl-thieno[3,2-d]pyrimidin-6-ylmethyl ester (100 mg, 0.144 mmol) in DMF (1 mL) were added potassium carbonate (100 mg, 0.724 mmol) and (cis)-2,6-dimethyl-piperazine (33 mg, 0.289 mmol). The reaction mixture was stirred at RT for 2 h before water and DCM were added. The phases were separated using a hydrophobic frit and the organic phase was concentrated in vacuo. The resultant residue was dissolved in dioxane (1 mL) and IMS (1 mL), and an aqueous solution of NaOH (12 M, 1 mL, 12 mmol) was added. The mixture was stirred at RT for 3 h before a sat. aqueous solution of ammonium chloride and DCM were added.

The phases were separated using a hydrophobic frit and the organic phase was concentrated in vacuo. The resultant residue was purified by column chromatography to give the title compound as a white solid (33.0 mg, 48%).

[M+H]$^+$ 481.4

NMR $\delta_H$ (400 MHz, DMSO-d$_6$) 0.90 (s, 3H), 0.92 (s, 3H), 1.61 (t, J=10.5, 2H), 2.72-2.81 (m, 4H), 3.82 (m, 6H), 3.98 (m, 4H), 7.30 (m, 1H), 7.41-7.46 (m, 3H), 7.89 (dd, J=2.5, 11.5, 1H) and 11.28 (bs, 1H).

EXAMPLE 111

{1-[2-(6-Fluoro-1H-indol-4-yl)-4-morpholin-4-yl-thieno[3,2-d]pyrimidin-6-ylmethyl]-pyrrolidin-3-yl}-dimethyl-amine Prepared according to the method used in the preparation of 6-(cis-3,5-dimethyl-piperazin-1-ylmethyl)-2-(6-fluoro-1H-indol-4-yl)-4-morpholin-4-yl-thieno[3,2-d]pyrimidine using dimethyl-pyrrolidin-3-yl-amine in place of 2,6-dimethyl-piperazine. The title compound was obtained as a white solid (21.8 mg, 36%).

[M+H]$^+$ 481.3

NMR $\delta_H$ (400 MHz, DMSO-d$_6$) 1.58-1.70 (m, 1H), 1.83-1.94 (m, 1H), 2.09 (s, 6H), 2.41 (dd, J=6.5, 8.5, 1H), 2.58 (m, 1H), 2.67-2.83 (m, 3H), 3.82 (m, 4H), 3.95-4.00 (m, 6H), 7.30 (m, 1H), 7.41 (s, 1H), 7.44 (m, 2H), 7.90 (dd, J=2.5, 11.5, 1H) and 11.29 (bs, 1H).

EXAMPLE 112

2-(6-Fluoro-1H-indol-4-yl)-6-(3-methyl-piperazin-1-ylmethyl)-4-morpholin-4-yl-thieno[3,2-d]pyrimidine Prepared according to the method used in the preparation of 6-(cis-3,5-dimethyl-piperazin-1-ylmethyl)-2-(6-fluoro-1H-indol-4-yl)-4-morpholin-4-yl-thieno[3,2-d]pyrimidine, using 2-methyl-piperazine-1-carboxylic acid tert-butyl ester in place of 2,6-dimethyl-piperazine, followed by BOC-deprotection using TFA:DCM (1:1). The title compound was obtained as a white solid (19.8 mg, 33%).

[M+H]$^+$ 467.3

NMR $\delta_H$ (400 MHz, DMSO-d$_6$) 0.91 (d, J=6, 3H), 1.68 (t, J=10, 1H), 2.02 (m, 1H), 2.64-2.83 (m, 5H), 3.81 (m, 6H), 3.98 (m, 4H), 7.30 (m, 1H), 7.43 (m, 3H), 7.89 (dd, J=2.5, 11.5, 1H) and 11.28 (bs, 1H).

EXAMPLE 113

1-[2-(6-Fluoro-1H-indol-4-yl)-4-morpholin-4-yl-thieno[3,2-d]pyrimidin-6-ylmethyl]-piperidin-4-ylamine Prepared according to the method used in the preparation of 6-(cis-3,5-dimethyl-piperazin-1-ylmethyl)-2-(6-fluoro-1H-indol-4-yl)-4-morpholin-4-yl-thieno[3,2-d]pyrimidine, using piperidin-4-yl-carbamic acid tert-butyl ester in place of 2,6-dimethyl-piperazine, followed by BOC-deprotection using TFA:DCM (1:1). The title compound was obtained as a white solid (25 mg, 33%).
[M+H]$^+$ 467.3
NMR $\delta_H$ (400 MHz, DMSO-d$_6$) 1.22-1.34 (m, 2H), 1.69 (m, 2H), 2.10 (apparent t, J=11, 2H), 2.56 (m, 1H), 2.85 (m, 2H), 3.83 (m, 6H), 3.99 (m, 4H), 7.30 (m, 1H), 7.39-7.46 (m, 3H), 7.89 (dd, J=2.5, 11.5, 1H) and 11.28 (bs, 1H).

EXAMPLE 114

2-(6-Fluoro-1H-indol-4-yl)-4-morpholin-4-yl-6-(4-pyrrolidin-1-yl-piperidin-1-ylmethyl)-thieno[3,2-d]pyrimidine Prepared according to the method used in the preparation of 6-(cis-3,5-dimethyl-piperazin-1-ylmethyl)-2-(6-fluoro-1H-indol-4-yl)-4-morpholin-4-yl-thieno[3,2-d]pyrimidine, using 4-pyrrolidin-1-yl-piperidine in place of 2,6-dimethyl-piperazine. The title compound was obtained as a white solid (31.5 mg, 48%).
[M+H]$^+$ 521.3
NMR $\delta_H$ (400 MHz, DMSO-d$_6$) 1.39-1.47 (m, 2H), 1.65 (m, 4H), 1.80 (m, 2H), 1.95 (m, 1H), 2.10 (apparent t, J=11, 2H), 2.45 (m, 4H), 2.87 (m, 2H), 3.83 (m, 6H), 3.97 (m, 4H), 7.30 (m, 1H), 7.41 (s, 1H), 7.44 (m, 2H), 7.90 (dd, J=2.5, 11.5, 1H) and 11.29 (bs, 1H).

EXAMPLE 115

{1-[2-(5-Fluoro-1H-indol-4-yl)-4-morpholin-4-yl-thieno[3,2-d]pyrimidin-6-ylmethyl]-piperidin-4-yl}-dimethyl-amine Prepared by using Suzuki coupling method A of Reference Example 2. The title compound was obtained as a white solid (110 mg, 74%).
[M+H]$^+$ 495.3
NMR $\delta_H$ (400 MHz, DMSO-d$_6$) 1.40 (m, 1H), 1.72 (m, 2H), 2.00-2.11 (m, 4H), 2.09 (m, 6H), 2.95 (m, 2H), 3.78 (m, 4H), 3.83 (s, 2H), 3.92 (m, 4H), 6.67 (m, 1H), 6.98 (dd, J=2.5, 11, 1H), 7.37 (s, 1H), 7.42 (apparent t, J=2.5, 1H), 7.45 (m, 1H) and 11.23 (bs, 1H).

EXAMPLE 116

{1-[2-(6-Fluoro-1H-indol-4-yl)-4-morpholin-4-yl-thieno[3,2-d]pyrimidin-6-ylmethyl]-piperidin-4-yl}-dimethyl-amine Prepared by using Suzuki coupling method A of Reference Example 2. The title compound was obtained as a white solid (10 mg, 21%).
[M+H]$^+$ 495.3
NMR $\delta_H$ (400 MHz, DMSO-d$_6$) 1.40 (m, 1H), 1.72 (m, 2H), 1.97-2.11 (m, 4H), 2.18 (m, 6H), 2.95 (m, 2H), 3.78-3.85 (m, 6H), 3.98 (m, 4H), 7.30 (m, 1H), 7.41-7.47 (m, 3H), 7.89 (dd, J=2.5, 11.5, 1H) and 11.36 (bs, 1H).

EXAMPLE 117

2-{4-[2-(6-Fluoro-1H-indol-4-yl)-4-morpholin-4-yl-thieno[3,2-d]pyrimidin-6-ylmethyl]-piperazin-1-yl}-N,N-dimethyl-isobutyramide Prepared by using Suzuki coupling method B of Reference Example 2. The title compound was obtained as a colourless glass (48 mg, 30%).
[M+H]$^+$ 544.4
NMR $\delta_H$ (400 MHz, CDCl$_3$) 1.29 (s, 6H), 1.57 (m, 2H), 2.61 (m, 6H), 2.93 (m, 3H), 3.49 (m, 3H), 3.86 (m, 2H), 3.92 (m, 4H), 4.10 (m, 4H), 7.17 (dd, J=2.7, 9.4, 1H), 7.30 (dd, J=2.1, 2.7, 1H), 7.37-7.56 (m, 2H), 7.97 (dd, J=2.1, 11, 1H) and 8.32 (bs, 1H).

EXAMPLE 118

{1-[2-(6-Fluoro-1H-indol-4-yl)-4-morpholin-4-yl-thieno[3,2-d]pyrimidin-6-ylmethyl]-piperidin-3-yl}-dimethyl-amine Prepared by using Suzuki coupling method B of Reference Example 2. The title compound was obtained as a brown glass (61 mg, 54%).
[M+H]$^+$ 495.4
NMR $\delta_H$ (400 MHz, CDCl$_3$) 1.21-1.35 (m, 1H), 1.56-1.69 (m, 1H), 1.74-1.82 (m, 1H), 1.93-2.13 (m, 3H), 2.36 (m, 6H), 2.54 (m, 1H), 2.89 (m, 1H), 3.14 (m, 1H), 3.86 (s, 2H), 3.91 (m, 4H), 4.08 (m, 4H), 7.17 (dd, J=1.7, 9, 1H), 7.30 (apparent t, J=2.7, 1H), 7.35 (s, 1H), 7.54 (m, 1H), 7.97 (dd, J=2.4, 11.4, 1H) and 8.28 (bs, 1H).

EXAMPLE 119

2-(6-Fluoro-1H-indol-4-yl)-6-((S)-3-isopropyl-piperazin-1-ylmethyl)-4-morpholin-4-yl-thieno[3,2-d]pyrimidine Prepared by using Suzuki coupling method B of Reference Example 2 followed by BOC-deprotection using TFA:DCM (1:8). The title compound was obtained as a white solid (62 mg, 34%).
[M+H]$^+$ 495.2
NMR $\delta_H$ (400 MHz, CDCl$_3$) 0.92 (d, J=7, 3H), 0.96 (d, J=7, 3H), 1.62 (m, 1H), 1.94 (t, J=10.6, 1H), 2.17 (m, 1H), 2.57 (m, 1H), 2.88 (d, J=10.6, 1H), 2.90-2.99 (m, 2H), 3.06 (m, 1H), 3.84 (m, 2H), 3.91 (m, 4H), 4.08 (m, 4H), 7.17 (ddd, J=0.8, 2.2, 8.8, 1H), 7.30 (dd, J=2.2, 3.2, 1H), 7.36 (s, 1H), 7.54 (m, 1H), 7.97 (dd, J=2.2, 11, 1H) and 8.27 (bs, 1H).

EXAMPLEs 120-151

Compounds of the Invention Produced by Parallel Synthesis

Intermediates were prepared using the general methods described above. The following methods were adopted for the preparation of compounds 120 to 151 by parallel synthesis:
2-(1H-Indol-4-yl)-4-morpholin-4-yl-6-piperazin-1-ylmethyl-thieno[3,2-d]pyrimidine, alkylhalide and triethylamine were mixed together in DMF and stirred at 20-80° C. When the reaction was judged to be complete, the solvent was removed under reduced pressure, the residue dissolved in DMSO and purified by preparative HPLC. The chromatographic solvents were removed under reduced pressure to afford the product >85% purity.

Methanesulfonic acid 2-(1H-indol-4-yl)-4-morpholin-4-yl-thieno[3,2-d]pyrimidin-6-ylmethyl ester, amine and triethylamine were mixed together in DMF and stirred at room temperature. When the reaction was judged to be complete, the solvent was removed under reduced pressure, the residue dissolved in DMSO and purified by preparative HPLC. The chromatographic solvents were removed under reduced pressure to afford the product >85% purity.

120: 2-(1H-Indol-4-yl)-6-[4-(2-methoxy-ethyl)-piperazin-1-ylmethyl]-4-morpholin-4-yl-thieno[3,2-d]pyrimidine $[M+H]^+$ 493.

121: 3-{4-[2-(1H-Indol-4-yl)-4-morpholin-4-yl-thieno[3,2-d]pyrimidin-6-ylmethyl]-piperazin-1-yl}-propan-1-ol $[M+H]^+$ 493.

122: 3-{4-[2-(1H-Indol-4-yl)-4-morpholin-4-yl-thieno[3,2-d]pyrimidin-6-ylmethyl]-piperazin-1-yl}-propionitrile $[M+H]^+$ 488.

123: 2-{4-[2-(1H-Indol-4-yl)-4-morpholin-4-yl-thieno[3,2-d]pyrimidin-6-ylmethyl]-piperazin-1-yl}-acetamide $[M+H]^+$ 492.

124: 1-{4-[2-(1H-Indol-4-yl)-4-morpholin-4-yl-thieno[3,2-d]pyrimidin-6-ylmethyl]-piperazin-1-yl}-propan-2-ol $[M+H]^+$ 493.

125: 3-{4-[2-(1H-Indol-4-yl)-4-morpholin-4-yl-thieno[3,2-d]pyrimidin-6-ylmethyl]-piperazin-1-yl}-propionamide $[M+H]^+$ 506.

126: 6-(4-Cyclobutylmethyl-piperazin-1-ylmethyl)-2-(1H-indol-4-yl)-4-morpholin-4-yl-thieno[3,2-d]pyrimidine $[M+H]^+$ 503.

127: N-Cyclopropyl-2-{4-[2-(1H-indol-4-yl)-4-morpholin-4-yl-thieno[3,2-d]pyrimidin-6-ylmethyl]-piperazin-1-yl}-acetamide $[M+H]^+$ 532.

128: 6-[4-(2,6-Dichloro-pyridin-4-ylmethyl)-piperazin-1-ylmethyl]-2-(1H-indol-4-yl)-4-morpholin-4-yl-thieno[3,2-d]pyrimidine $[M+H]^+$ 594.

129: 2-(1H-Indol-4-yl)-4-morpholin-4-yl-6-(4-propyl-piperazin-1-ylmethyl)-thieno[3,2-d]pyrimidine $[M+H]^+$ 477.

130: 1-{4-[2-(1H-Indol-4-yl)-4-morpholin-4-yl-thieno[3,2-d]pyrimidin-6-ylmethyl]-piperazin-1-yl}-3,3-dimethyl-butan-2-one $[M+H]^+$ 533.

131: 2-(1H-Indol-4-yl)-6-(4-isobutyl-piperazin-1-ylmethyl)-4-morpholin-4-yl-thieno[3,2-d]pyrimidine $[M+H]^+$ 491.

132: 2-{4-[2-(1H-Indol-4-yl)-4-morpholin-4-yl-thieno[3,2-d]pyrimidin-6-ylmethyl]-piperazin-1-yl}-ethylamine $[M+H]^+$ 478.

133: Diethyl-(2-{4-[2-(1H-indol-4-yl)-4-morpholin-4-yl-thieno[3,2-d]pyrimidin-6-ylmethyl]-piperazin-1-yl}-ethyl)-amine $[M+H]^+$ 534.

134: 6-(4-Ethyl-piperazin-1-ylmethyl)-2-(1H-indol-4-yl)-4-morpholin-4-yl-thieno[3,2-d]pyrimidine $[M+H]^+$ 463.

135: 2-(1H-Indol-4-yl)-6-(4-methyl-piperidin-1-ylmethyl)-4-morpholin-4-yl-thieno[3,2-d]pyrimidine $[M+H]^+$ 448.

136: 2-(1H-Indol-4-yl)-6-(3-methyl-piperidin-1-ylmethyl)-4-morpholin-4-yl-thieno[3,2-d]pyrimidine $[M+H]^+$ 448.

137: 6-(3,5-Dimethyl-piperidin-1-ylmethyl)-2-(1H-indol-4-yl)-4-morpholin-4-yl-thieno[3,2-d]pyrimidine $[M+H]^+$ 462.

138: 6-(2-Ethyl-piperidin-1-ylmethyl)-2-(1H-indol-4-yl)-4-morpholin-4-yl-thieno[3,2-d]pyrimidine $[M+H]^+$ 462.

139: {1-[2-(1H-Indol-4-yl)-4-morpholin-4-yl-thieno[3,2-d]pyrimidin-6-ylmethyl]-piperidin-3-yl}-methanol $[M+H]^+$ 464.

140: 2-(1H-Indol-4-yl)-6-(2-methyl-piperidin-1-ylmethyl)-4-morpholin-4-yl-thieno[3,2-d]pyrimidine $[M+H]^+$ 448.

141: 2-(1H-Indol-4-yl)-4-morpholin-4-yl-6-[4-(3-piperidin-1-yl-propyl)-piperazin-1-ylmethyl]-thieno[3,2-d]pyrimidine

[M+H]+ 560.

142: 2-(1H-Indol-4-yl)-4-morpholin-4-yl-6-(4-pyridin-2-ylmethyl-piperazin-1-ylmethyl)-thieno[3,2-d]pyrimidine

[M+H]+ 526.

143: 4-{4-[2-(1H-Indol-4-yl)-4-morpholin-4-yl-thieno[3,2-d]pyrimidin-6-ylmethyl]-piperazin-1-yl}-butyronitrile

[M+H]+ 502.

144: 2-(1H-Indol-4-yl)-4-morpholin-4-yl-6-piperidin-1-ylmethyl-thieno[3,2-d]pyrimidine

[M+H]+ 434.

145: 2-(1H-Indol-4-yl)-6-(2-methyl-pyrrolidin-1-ylmethyl)-4-morpholin-4-yl-thieno[3,2-d]pyrimidine

[M+H]+ 434.

146: 2-(1H-Indol-4-yl)-4-morpholin-4-yl-6-(4-pyridin-2-yl-piperazin-1-ylmethyl)-thieno[3,2-d]pyrimidine

[M+H]+ 512.

147: {1-[2-(1H-Indol-4-yl)-4-morpholin-4-yl-thieno[3,2-d]pyrimidin-6-ylmethyl]-pyrrolidin-3-yl}-methanol

[M+H]+ 450.

148: 2-(1H-Indol-4-yl)-6-{4-[2-(1-methyl-pyrrolidin-2-yl)-ethyl]-piperazin-1-ylmethyl}-4-morpholin-4-yl-thieno[3,2-d]pyrimidine

[M+H]+ 546.

149: 2-(1H-Indol-4-yl)-4-morpholin-4-yl-6-[4-(2-piperidin-1-yl-ethyl)-piperazin-1-ylmethyl]-thieno[3,2-d]pyrimidine

[M+H]+ 546.

150: 2-(1H-Indol-4-yl)-4-morpholin-4-yl-6-[4-(2-pyrrolidin-1-yl-ethyl)-piperazin-1-ylmethyl]-thieno[3,2-d]pyrimidine

[M+H]+ 532.

151: 6-(4-Cyclopropylmethyl-piperazin-1-ylmethyl)-2-(1H-indol-4-yl)-4-morpholin-4-yl-thieno[3,2-d]pyrimidine

[M+H]+ 489.

EXAMPLE 152

6-(cis-3,5-Dimethyl-piperazin-1-ylmethyl)-2-(1H-indol-4-yl)-4-morpholin-4-yl-thieno[3,2-d]pyrimidine Prepared by using Suzuki coupling Method B of Example reference 2. The title compound was obtained as a tan solid (61.6 mg, 78%).

[M+H]+ 463.3

NMR $\delta_H$ (400 MHz, CDCl$_3$) 1.05 (d, J=6.8, 6H), 1.74 (apparent t, J=11.3, 2H), 2.88 (m, 2H), 3.00 (m, 2H), 3.82 (s, 2H), 3.91 (m, 4H), 4.09 (m, 4H), 7.29-7.34 (m, 2H), 7.37 (s, 1H), 7.49 (d, J=8.5, 1H), 7.54 (m, 1H), 8.18 (d, J=6.8, 1H) and 8.29 (bs, 1H).

EXAMPLE 153

6-(cis-3,5-Dimethyl-piperazin-1-ylmethyl)-2-(5-fluoro-1H-indol-4-yl)-4-morpholin-4-yl-thieno[3,2-d]pyrimidine Prepared by using Suzuki coupling Method B of Example reference 2. The title compound was obtained as a white solid (102 mg, 81%).

[M+H]+ 481.3

NMR $\delta_H$ (400 MHz, DMSO-d$_6$) 0.92 (d, J=6.3, 6H), 1.62 (apparent t, J=10.3, 2H), 2.78 (m, 4H), 3.77 (m, 4H), 3.82 (s, 2H), 3.93 (m, 4H), 6.66 (m, 1H), 7.00 (dd, J=8.8, 11.1, 1H), 7.37 (s, 1H), 7.42-7.47 (m, 2H) and 11.24 (bs, 1H).

EXAMPLE 154

{1-[2-(6-Fluoro-1H-indol-4-yl)-4-morpholin-4-yl-thieno[3,2-d]pyrimidin-6-ylmethyl]-piperidin-4-yl}-methyl-amine Prepared by using Suzuki coupling Method B of Example reference 2 followed by BOC-deprotection using TFA:DCM (1:4) The title compound was obtained as a yellow solid (14 mg, 20%).

[M+H]+ 481.2

NMR $\delta_H$ (400 MHz, CDCl$_3$) 1.46 (m, 2H), 1.91 (m, 2H), 2.19 (t, J=10.7, 2H), 2.38-2.47 (m, 4H), 2.96 (m, 2H), 3.84 (s, 2H), 3.91 (m, 4H), 4.08 (m, 4H), 7.17 (dd, J=2.1, 8.8, 1H), 7.29 (dd, J=2.6, 3.3, 1H), 7.34 (s, 1H), 7.53 (m, 1H), 7.97 (dd, J=2.1, 10.9, 1H) and 8.27 (bs, 1H).

EXAMPLE 155

2-(6-Fluoro-1H-indol-4-yl)-6-((R)-3-isopropyl-piperazin-1-ylmethyl)-4-morpholin-4-yl-thieno[3,2-d]pyrimidine Prepared by using Suzuki coupling Method B of Example reference 2 followed by BOC-deprotection using TFA:DCM (1:1) The title compound was obtained as a cream solid (78 mg, 79%).

[M+H]+ 495.2

NMR $\delta_H$ (400 MHz, CDCl$_3$) 0.91 (d, J=6.6, 3H), 0.95 (d, J=6.6, 3H), 1.55-1.65 (m, 1H), 1.93 (t, J=10.2, 1H), 2.15 (dt, J=3, 10.2, 1H), 2.54-2.59 (m, 1H), 2.85-2.99 (m, 3H), 3.05 (m, 1H), 3.82 (d, J=14.5, 1H), 3.86 (d, J=14.5, 1H), 3.91 (m, 4H), 4.08 (m, 4H), 7.17 (dd, J=1.9, 8.7, 1H), 7.30 (t, J=2.7, 1H), 7.36 (s, 1H), 7.53 (m, 1H), 7.96 (dd, J=2.7, 11.1, 1H) and 8.29 (bs, 1H).

EXAMPLE 156

Biological Testing

Compounds of the invention, prepared as described in the preceding Examples, were submitted to the following series of biological assays:

(i) PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. $IC_{50}$ values were subsequently determined using sigmoidal dose-response curve fit (variable slope). All of the compounds tested against the p110δ isoform of PI3K had an $IC_{50}$ against PI3K of 50 μM or less. Typically the $IC_{50}$ against PI3K was 5-500 nM.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 hours before reading at 544 nm excitation, 590 nm emission. $EC_{50}$ values were calculated using a sigmoidal dose response curve fit. All the compounds tested had an $EC_{50}$s of 50 uM or less in the range of cell lines utilized.

(iii) B Cell Proliferation Inhibition

Peripheral blood mononuclear cells (PBMCs) were isolated from whole blood and seeded at optimal density in a 96 well plate and incubated for 5 days in the presence of anti-IgM and test compounds. BrdU labelling solution was added on day 4 and cells were incubated overnight before an ELISA was performed to measure cell proliferation. $EC_{50}$ values were calculated using a sigmoidal dose-inhibition curve fit. Tested compounds typically showed an $EC_{50}$<50 μM.

EXAMPLE 157

Tablet Composition

Tablets, each weighing 0.15 g and containing 25 mg of a compound of the invention are manufactured as follows:

Composition for 10,000 tablets

Active compound (250 g)

Lactose (800 g)

Corn starch (415g)

Talc powder (30 g)

Magnesium stearate (5 g)

The active compound, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

EXAMPLE 158

Injectable Formulation

| Formulation A | |
|---|---|
| Active compound | 200 mg |
| Hydrochloric Acid Solution 0.1M or | 4.0 to 7.0 |
| Sodium Hydroxide Solution 0.1M q.s. to pH | |
| Sterile water q.s. to | 10 ml |

The compound of the invention is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
|---|---|
| Active Compound | 125 mg |
| Sterile, Pyrogen-free, pH 7 Phosphate Buffer, q.s. to | 25 ml |
| Active compound | 200 mg |
| Benzyl Alcohol | 0.10 g |
| Glycofurol 75 | 1.45 g |
| Water for injection q.s to | 3.00 ml |

The active compound is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE 159

Syrup Formulation

| | |
|---|---|
| Active compound | 250 mg |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is a thienopyrimidine of formula (Ia) or (Ib):

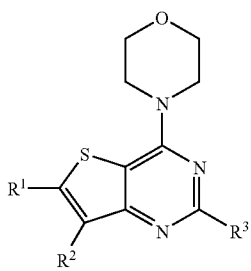

(Ia)

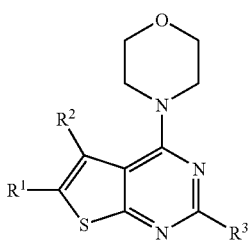

(Ib)

wherein
R¹ is a group of formula:

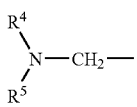

R² is H, halo or $C_1$-$C_6$ alkyl;
R³ is an indole group which is unsubstituted or substituted;
R⁴ and R⁵ form, together with the N atom to which they are attached, a group selected from piperazine, piperidine and pyrrolidine, which group is unsubstituted or substituted by one or more groups selected from $C_1$-$C_6$ alkyl, —S(O)$_2$R¹⁰, —S(O)$_2$-(alk)$_q$-NR¹¹R¹², oxo (═O), -alk-OR¹⁰, -(alk)$_q$-Het, a heterocyclyl group and —NR¹³R¹⁴;
or one of R⁴ and R⁵ is $C_1$-$C_6$ alkyl and the other is a piperazine, piperidine or pyrrolidine group, which group is unsubstituted or substituted;
R¹⁰ is H or $C_1$-$C_6$ alkyl which is unsubstituted;
R¹¹ and R¹² are each independently selected from H and $C_1$-$C_6$ alkyl which is unsubstituted, or
R¹¹ and R¹² together form, with the N atom to which they are attached, a 5- or 6-membered saturated heterocyclic group;
R¹³ and R¹⁴ are each independently selected from $C_1$-$C_6$ alkyl, —S(O)$_2$R¹⁰, alk-OR¹⁰, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof;
with the proviso that, in formula (Ia) only, when R² is H and R³ is unsubstituted indole, then —NR⁴R⁵ is other than (i) piperazine which is unsubstituted or substituted by one substituent selected from methyl, —S(O)$_2$ Me and —CH$_2$CH$_2$OH; and (ii) piperidine which is substituted by one substituent selected from —NMe$_2$, —N(Me)(CH$_2$CH$_2$OMe) and morpholino.

2. A compound which is a thienopyrimidine of formula (Ia'):

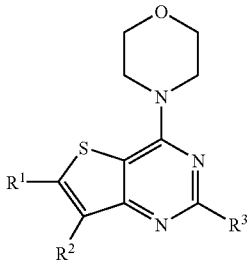

(Ia')

wherein
R¹ is a group of formula:

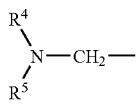

R² is halo or $C_1$-$C_6$ alkyl;
R³ is an indole group which is unsubstituted or substituted;
R⁴ and R⁵ form, together with the N atom to which they are attached, a group selected from piperazine, piperidine and pyrrolidine, which group is unsubstituted or substituted by one or more groups selected from $C_1$-$C_6$ alkyl, —S(O)$_2$R¹⁰, —S(O)$_2$-(alk)$_q$-NR¹¹R¹², oxo(═O), -alk-OR¹⁰, -(alk)$_q$-Het, a heterocyclyl group and —NR¹³R¹⁴;
or one of R⁴ and R⁵ is $C_1$-$C_6$ alkyl and the other is a piperazine, piperidine or pyrrolidine group, which group is unsubstituted or substituted;
R¹⁰ is H or $C_1$-$C_6$ alkyl which is unsubstituted;
R¹¹ and R¹² are each independently selected from H and $C_1$-$C_6$ alkyl which is unsubstituted, or
R¹¹ and R¹² together form, with the N atom to which they are attached, a 5- or 6-membered saturated heterocyclic group;
R¹³ and R¹⁴ are each independently selected from $C_1$-$C_6$ alkyl, —S(O)$_2$R¹⁰, alk-OR¹⁰, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof.

3. A compound which is a thienopyrimidine of formula (Ia"):

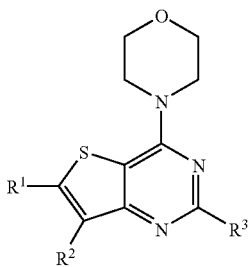

(Ia″)

wherein
R¹ is a group of formula:

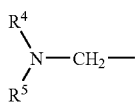

R² is H, halo or $C_1$-$C_6$ alkyl
R³ is an indole group which is substituted;
R⁴ and R⁵ form, together with the N atom to which they are attached, a group selected from piperazine, piperidine and pyrrolidine, which group is unsubstituted or substituted by one or more groups selected from $C_1$-$C_6$ alkyl, —S(O)₂R¹⁰, —S(O)₂-(alk)$_q$-NR¹¹R¹², oxo(=O), -(alk)-OR¹⁰, -(alk)$_q$-Het, a heterocyclyl group and —NR¹³R¹⁴;
or one of R⁴ and R⁵ is $C_1$-$C_6$ alkyl and the other is a piperazine, piperidine or pyrrolidine group, which group is unsubstituted or substituted;
R¹⁰ is H or $C_1$-$C_6$ alkyl which is unsubstituted;
R¹¹ and R¹² are each independently selected from H and $C_1$-$C_6$ alkyl which is unsubstituted, or R¹¹ and R¹² together form, with the N atom to which they are attached, a 5- or 6-membered saturated heterocyclic group;
R¹³ and R¹⁴ are each independently selected from $C_1$-$C_6$ alkyl, —S(O)₂R¹⁰, alk-OR¹⁰, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof.

4. A compound which is a thienopyrimidine of formula (Ia‴):

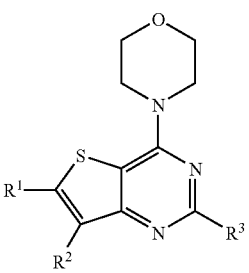

(Ia‴)

wherein
R¹ is a group of formula:

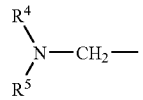

R² is H;
R³ is an unsubstituted indole group;
R⁴ and R⁵ form, together with the N atom to which they are attached, a group selected from:
  piperazine which is substituted by —S(O)₂-(alk)$_q$-NR¹¹R¹², $C_2$-$C_6$ alkyl, oxo (=O), -(alk)$_q$-Het, a heterocyclyl group or —NR¹³R¹⁴
  piperidine which is unsubstituted or substituted by —S(O)₂R¹⁰, —S(O)₂-(alk)$_q$-NR¹¹R¹², $C_1$-$C_6$ alkyl, oxo (=O), -alk-OR¹⁰, -(alk)$_q$-Het or a heterocyclyl group;
  pyrrolidine which is unsubstituted or substituted by —S(O)₂R¹⁰, —S(O)₂-(alk)$_q$-NR¹¹R¹², $C_1$-$C_6$ alkyl, oxo (=O), -alk-OR¹⁰, -(alk)$_q$-Het, a heterocyclyl group or —NR¹³R¹⁴
or one of R⁴ and R⁵ is $C_1$-$C_6$ alkyl and the other is a piperazine, piperidine or pyrrolidine group, which group is unsubstituted or substituted;
R¹⁰ is H or $C_1$-$C_6$ alkyl which is unsubstituted;
R¹¹ and R¹² are each independently selected from H and $C_1$-$C_6$ alkyl which is unsubstituted, or R¹¹ and R¹² together form, with the N atom to which they are attached, a 5- or 6-membered saturated heterocyclic group;
R¹³ and R¹⁴ are each independently selected from $C_1$-$C_6$ alkyl, —S(O)₂R¹⁰, alk-OR¹⁰, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof;
with the proviso that the thienopyrimidine is not selected from:
{1-[2-(1H-Indol-4-yl)-4-morpholin-4-yl-thieno[3,2-d]pyrimidin-6-ylmethyl]-piperidin-4-yl}-(2-methoxy-ethyl)-methyl-amine;
2-{4-[2-(1H-Indol-4-yl)-4-morpholin-4-yl-thieno[3,2-d]pyrimidin-6-ylmethyl]-piperazin-1-yl}-ethanol; and
{1-[2-(1H-Indol-4-yl)-4-morpholin-4-yl-thieno[3,2-d]pyrimidin-6-ylmethyl]-piperidin-4-yl}-dimethyl-amine.

5. A compound which is a thienopyrimidine of formula (Ib'):

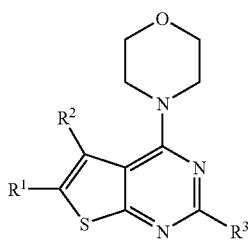

(Ib')

wherein
R¹ is a group of formula:

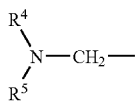

R² is H, halo or $C_1$-$C_6$ alkyl
R³ is an indole group which is unsubstituted or substituted;
R⁴ and R⁵ form, together with the N atom to which they are attached, a group selected from piperazine, piperidine and pyrrolidine, which group is unsubstituted or substituted by —S(O)₂R¹⁰, —S(O)₂-(alk)$_q$-NR¹¹R¹², $C_1$-$C_6$ alkyl, oxo (=O), -alk-OR¹⁰, -(alk)$_q$-Het, a heterocyclyl group or —NR¹³R¹⁴;
or one of R⁴ and R⁵ is $C_1$-$C_6$ alkyl and the other is a piperazine, piperidine or pyrrolidine group, which group is unsubstituted or substituted;
R¹⁰ is H or $C_1$-$C_6$ alkyl which is unsubstituted;
R¹¹ and R¹² are each independently selected from H and $C_1$-$C_6$ alkyl which is unsubstituted, or
R¹¹ and R¹² together form, with the N atom to which they are attached, a 5- or 6-membered saturated heterocyclic group;
R¹³ and R¹⁴ are each independently selected from $C_1$-$C_6$ alkyl, —S(O)₂R¹⁰, alk-OR¹⁰, -(alk)$_q$-Ph and -(alk)$_q$-Het;
Ph is phenyl;
q is 0 or 1;
Het is a thiazole, imidazole, pyrrole, pyridine or pyrimidine group, which group is unsubstituted or substituted; and
alk is $C_1$-$C_6$ alkylene;
or a pharmaceutically acceptable salt thereof.

6. A compound which is selected from:
2-(1H-Indol-4-yl)-4-morpholin-4-yl-6-[4-(3-morpholin-4-yl-propane-1-sulfonyl)-piperazin-1-ylmethyl]-thieno[3,2-d]pyrimidine;
(3-{4-[2-(1H-Indol-4-yl)-4-morpholin-4-yl-thieno[3,2-d]pyrimidin-6-ylmethyl]-piperazine-1-sulfonyl}-propyl)-dimethyl-amine;
2-(1H-Indol-4-yl)-6-(4-methyl-piperazin-1-ylmethyl)-4-morpholin-4-yl-thieno[2,3-d]pyrimidine;
2-(1H-Indol-4-yl)-6-(4-methanesulfonyl-piperazin-1-ylmethyl)-4-morpholin-4-yl-thieno[2,3-d]pyrimidine;
2-(7-Methyl-1H-indol-4-yl)-6-(4-methyl-piperazin-1-ylmethyl)-4-morpholin-4-yl-thieno[3,2-d]pyrimidine;
2-(1H-Indol-4-yl)-7-methyl-6-(4-methyl-piperazin-1-ylmethyl)-4-morpholin-4-yl-thieno[3,2-d]pyrimidine;
Benzyl-{1-[2-(1H-indol-4-yl)-4-morpholin-4-yl-thieno[3,2-d]pyrimidine-6-ylmethyl]-piperidin-4-yl}-(2-methoxy-ethyl)-amine;
2-(6-Methoxy-1H-indol-4-yl)-6-(4-methyl-piperazin-1-ylmethyl)-4-morpholin-4-yl-thieno[3,2-d]pyrimidine;
1-(2-hydroxy-ethyl)-4-[2-(1H-indol-4-yl)-4-morpholin-4-yl-thieno[3,2-d]pyrimidine-6-ylmethyl]-piperazin-2-one;
2-(1H-Indol-4-yl)-4-morpholin-4-yl-6-(4-thiazol-4-ylmethyl-piperazin-1-ylmethyl)-thieno[3,2-d]pyrimidine;
6-[4-(1H-Imidazol-2-ylmethyl)-piperazin-1-ylmethyl]-2-(1H-indol-4-yl)-4-morpholin-4-yl-thieno[3,2-d]pyrimidine;
2-(1H-Indol-4-yl)-4-morpholin-4-yl-6-(4-pyridin-2-ylmethyl-piperidin-1-ylmethyl)-thieno[3,2-d]pyrimidine;
2-(1H-Indol-4-yl)-4-morpholin-4-yl-6-(4-pyrimidin-2-yl-piperazin-1-ylmethyl)-thieno[3,2-d]pyrimidine;
1'-[2-(1H-Indol-4-yl)-4-morpholin-4-yl-thieno[3,2-d]pyrimidin-6-ylmethyl]-[1,4']bipiperidinyl;
2-(1H-indol-4-yl)-6-[4-(1-methyl-1H-imidazol-2-ylmethyl)-piperazin-1-ylmethyl]-4-morpholin-4-yl-thieno[3,2-d]pyrimidine;
[2-(1H-indol-4-yl)-4-morpholin-4-yl-thieno[3,2-d]pyrimidin-6-ylmethyl]-(1-methanesulphonyl-piperidin-4-yl)-methyl-amine;
N-{1-[2-(1H-Indol-4-yl)-4-morpholin-4-yl-thieno[3,2-d]pyrimidin-6-ylmethyl]-pyrrolidin-3-yl}-N-methyl-methanesulfonamide;
{1-[2-(1H-Indol-4-yl)-4-morpholin-4-yl-thieno[3,2-d]pyrimidin-6-ylmethyl]piperidin-4-yl}-(2-methoxy-ethyl)-thiazol-2-ylmethyl-amine;
N-{1-[2-(1H-Indol-4-yl)-4-morpholin-4-yl-thieno[3,2-d]pyrimidin-6-ylmethyl]-pyrrolidin-2-ylmethyl}-N-methyl-methanesulfonamide;
2-(2-Methyl-1H-indol-4-yl)-6-(4-methyl-piperazin-1-ylmethyl)-4-morpholin-4-yl-thieno[3,2-d]pyrimidine;
2-(6-Fluoro-1H-indol-4-yl)-6-(4-methyl-piperazin-1-ylmethyl)-4-morpholin-4-yl-thieno[3,2-d]pyrimidine;
4-[6-(4-Methyl-piperazin-1-ylmethyl)-4-morpholin-4-yl-thieno[3,2-d]pyrimidin-2-yl]-1H-indole-6-carbonitrile;
[2-(1H-Indol-4-yl)-4-morpholin-4-yl-thieno[3,2-d]pyrimidin-6-ylmethyl]-(1-methanesulfonyl-pyrrolidin-3-yl)-methyl-amine;
4-(4-Morpholin-4-yl-6-piperazin-1-ylmethyl-thieno[3,2-d]pyrimidin-2-yl)-1H-indole-6-sulfonic acid dimethylamide;
4-[6-(4-Cyclopropylmethyl-piperazin-1-ylmethyl)-4-morpholin-4-yl-thieno[3,2-d]pyrimidin-2-yl]-1H-indole-6-sulfonic acid dimethylamide;
2-{4-[2-(6-Dimethylsulfamoyl-1H-indol-4-yl)-4-morpholin-4-yl-thieno[3,2-d]pyri-midin-6-ylmethyl]-piperazin-1-yl}-isobutyramide;
4-{4-Morpholin-4-yl-6-[4-(2,2,2-trifluoro-ethyl)-piperazin-1-ylmethyl]-thieno[3,2-d]pyrimidin-2-yl}-1H-indole-6-sulfonic acid dimethylamide;
4-Morpholin-4-yl-6-piperazin-1-ylmethyl-2-(6-trifluoromethyl-1H-indol-4-yl)-thieno[3,2-d]pyrimidine;
6-(4-Cyclopropylmethyl-piperazin-1-ylmethyl)-4-morpholin-4-yl-2-(6-trifluoro-methyl-1H-indol-4-yl)-thieno[3,2-d]pyrimidine;
2-{4-[4-Morpholin-4-yl-2-(6-trifluoromethyl-1H-indol-4-yl)-thieno[3,2-d]pyri-midin-6-ylmethyl]-piperazin-1-yl}-isobutyramide;
4-Morpholin-4-yl-6-[4-(2,2,2-trifluoro-ethyl)-piperazin-1-ylmethyl]-2-(6-tri-fluoromethyl-1H-indol-4-yl)-thieno[3,2-d]pyrimidine;
4-Morpholin-4-yl-6-piperazin-1-ylmethyl-2-(2-trifluoromethyl-1H-indol-4-yl)-thieno[3,2-d]pyrimidine;

2-{4-[4-Morpholin-4-yl-2-(2-trifluoromethyl-1H-indol-4-yl)-thieno[3,2-d]pyrimidin-6-ylmethyl]-piperazin-1-yl}-isobutyramide;
6-(4-Cyclopropylmethyl-piperazin-1-ylmethyl)-4-morpholin-4-yl-2-(2-trifluoro-methyl-1H-indol-4-yl)-thieno[3,2-d]pyrimidine;
4-Morpholin-4-yl-6-[4-(2,2,2-trifluoro-ethyl)-piperazin-1-ylmethyl]-2-(2-tri-fluoromethyl-1H-indol-4-yl)-thieno[3,2-d]pyrimidine;
2-(6-Methanesulfonyl-1H-indol-4-yl)-4-morpholin-4-yl-6-piperazin-1-ylmethyl-thieno[3,2-d]pyrimidine;
6-(4-Cyclopropylmethyl-piperazin-1-ylmethyl)-2-(6-methanesulfonyl-1H-indol-4-yl)-4-morpholin-4-yl-thieno[3,2-d]pyrimidine;
2-{4-[2-(6-Methanesulfonyl-1H-indol-4-yl)-4-morpholin-4-yl-thieno[3,2-d]pyrimidin-6-ylmethyl]-piperazin-1-yl}-isobutyramide;
2-(6-Methanesulfonyl-1H-indol-4-yl)-4-morpholin-4-yl-6-[4-(2,2,2-trifluoro-ethyl)piperazin-1-ylmethyl]-thieno[3,2-d]pyrimidine;
2-{4-[2-(5-Fluoro-1H-indol-4-yl)-4-morpholin-4-yl-thieno[3,2-d]pyrimidin-6-ylmethyl]-piperazin-1-yl}-isobutyramide;
2-(5-Fluoro-1H-indol-4-yl)-4-morpholin-4-yl-6-[4-(2,2,2-trifluoro-ethyl)-piperazin-1-ylmethyl]-thieno[3,2-d]pyrimidine;
6-(4-Cyclopropylmethyl-piperazin-1-ylmethyl)-2-(5-fluoro-1H-indol-4-yl)-4-morpholin-4-yl-thieno[3,2-d]pyrimidine;
4-(4-Morpholin-4-yl-6-piperazin-1-ylmethyl-thieno[3,2-d]pyrimidin-2-yl)-1H-indole-6-carboxylic acid amide;
4-{6-[4-(1-Carbamoyl-1-methyl-ethyl)-piperazin-1-ylmethyl]-4-morpholin-4-yl-thieno[3,2-d]pyrimidin-2-yl}-1H-indole-6-carboxylic acid amide;
4-{4-Morpholin-4-yl-6-[4-(2,2,2-trifluoro-ethyl)-piperazin-1-ylmethyl]-thieno[3,2-d]pyrimidin-2-yl}-1H-indole-6-carboxylic acid amide;
4-[6-(4-Cyclopropylmethyl-piperazin-1-ylmethyl)-4-morpholin-4-yl-thieno[3,2-d]pyrimidin-2-yl]-1H-indole-6-carboxylic acid amide;
4-{4-Morpholin-4-yl-6-[4-(2,2,2-trifluoro-ethyl)-piperazin-1-ylmethyl]-thieno[3,2-d]pyrimidin-2-yl}-1H-indole-2-carbonitrile;
2-{4-[2-(2-Cyano-1H-indol-4-yl)-4-morpholin-4-yl-thieno[3,2-d]pyrimidin-6-ylmethyl]-piperazin-1-yl}-isobutyramide;
4-[6-(4-Cyclopropylmethyl-piperazin-1-ylmethyl)-4-morpholin-4-yl-thieno[3,2-d]pyrimidin-2-yl]-1H-indole-2-carbonitrile;
4-{4-Morpholin-4-yl-6-[4-(2,2,2-trifluoro-ethyl)-piperazin-1-ylmethyl]-thieno[3,2-d]pyrimidin-2-yl}-1H-indole-6-carbonitrile;
4-[6-(4-Cyclopropylmethyl-piperazin-1-ylmethyl)-4-morpholin-4-yl-thieno[3,2-d]pyrimidin-2-yl]-1H-indole-6-carbonitrile;
6-(4-Cyclopropylmethyl-piperazin-1-ylmethyl)-2-(6-fluoro-1H-indol-4-yl)-4-morpholin-4-yl-thieno[3,2-d]pyrimidine;
2-(6-Fluoro-1H-indol-4-yl)-4-morpholin-4-yl-6-[4-(2,2,2-trifluoro-ethyl)-piperazin-1-ylmethyl]-thieno[3,2-d]pyrimidine;
2-(6-Fluoro-1H-indol-4-yl)-4-morpholin-4-yl-6-piperazin-1-ylmethyl-thieno[3,2-d]pyrimidine;
2-(5-Fluoro-1H-indol-4-yl)-4-morpholin-4-yl-6-piperazin-1-ylmethyl-thieno[3,2-d]pyrimidine;
4-(4-Morpholin-4-yl-6-piperazin-1-ylmethyl-thieno[3,2-d]pyrimidin-2-yl)-1H-indole-6-carbonitrile;
4-[6-(4-Isopropyl-piperazin-1-ylmethyl)-4-morpholin-4-yl-thieno[3,2-d]pyrimidin-2-yl]-1H-indole-6-carbonitrile;
2-(6-Methanesulfonyl-1H-indol-4-yl)-4-morpholin-4-yl-6-piperidin-1-ylmethyl-thieno[3,2-d]pyrimidine;
2-(6-Methanesulfonyl-1H-indol-4-yl)-6-[4-(2-methoxy-ethyl)-piperidin-1-ylmethyl]-4-morpholin-4-yl-thieno[3,2-d]pyrimidine;
4-{6-[4-(2-Methoxy-ethyl)-piperidin-1-ylmethyl]-4-morpholin-4-yl-thieno[3,2-d]pyrimidin-2-yl}-1H-indole-6-carbonitrile;
4-{6-[4-(2-Methoxy-ethyl)-piperidin-1-ylmethyl]-4-morpholin-4-yl-thieno[3,2-d]pyrimidin-2-yl}-1H-indole-6-sulfonic acid dimethylamide;
2-(6-Methanesulfonyl-1H-indol-4-yl)-4-morpholin-4-yl-6-piperazin-1-ylmethyl-thieno[2,3-d]pyrimidine;
2-(5-Fluoro-1H-indol-4-yl)-6-[4-(2-methoxy-ethyl)-piperidin-1-ylmethyl]-4-morpholin-4-yl-thieno[3,2-d]pyrimidine;
4-{6-[4-(2-Methoxy-ethyl)-piperidin-1-ylmethyl]-4-morpholin-4-yl-thieno[3,2-d]pyrimidin-2-yl}-1H-indole-2-carbonitrile;
4-[6-(4-Methyl-piperazin-1-ylmethyl)-4-morpholin-4-yl-thieno[3,2-d]pyrimidin-2-yl]-1H-indole-6-carboxylic acid dimethylamide;
2-{4-[2-(6-Cyano-1H-indol-4-yl)-4-morpholin-4-yl-thieno[3,2-d]pyrimidin-6-ylmethyl]-piperazin-1-yl}-isobutyramide;
2-{4-[2-(6-Fluoro-1H-indol-4-yl)-4-morpholin-4-yl-thieno[3,2-d]pyrimidin-6-ylmethyl]-piperazin-1-yl}-isobutyramide;
2-(6-Fluoro-1H-indol-4-yl)-4-morpholin-4-yl-6-piperidin-1-ylmethyl-thieno[3,2-d]pyrimidine;
2-(6-Fluoro-1H-indol-4-yl)-6-[4-(2-methoxy-ethyl)-piperidin-1-ylmethyl]-4-morpholin-4-yl-thieno[3,2-d]pyrimidine;
4-(4-Morpholin-4-yl-6-piperidin-1-ylmethyl-thieno[3,2-d]pyrimidin-2-yl)-1H-indole-6-carbonitrile;
2-(6-Fluoro-1H-indol-4-yl)-4-morpholin-4-yl-6-piperazin-1-ylmethyl-thieno[2,3-d]pyrimidine;
2-{4-[2-(6-Fluoro-1H-indol-4-yl)-4-morpholin-4-yl-thieno[3,2-d]pyrimidin-6-ylmethyl]-piperazin-1-yl}-N-methyl-isobutyramide;
2-(6-Fluoro-1H-indol-4-yl)-6-[4-(2-methoxy-ethyl)-piperidin-1-ylmethyl]-7-methyl-4-morpholin-4-yl-thieno[3,2-d]pyrimidine;
4-{6-[4-(2-Methoxy-ethyl)-piperidin-1-ylmethyl]-7-methyl-4-morpholin-4-yl-thieno[3,2-d]pyrimidin-2-yl}-1H-indole-6-carbonitrile;
2-{4-[2-(6-Fluoro-1H-indol-4-yl)-7-methyl-4-morpholin-4-yl-thieno[3,2-d]pyrimidin-6-ylmethyl]-piperazin-1-yl}-isobutyramide;
2-(6-Methanesulfonyl-1H-indol-4-yl)-6-[4-(2-methoxy-ethyl)-piperidin-1-ylmethyl]-7-methyl-4-morpholin-4-yl-thieno[3,2-d]pyrimidine;
2-{4-[2-(6-Cyano-1H-indol-4-yl)-7-methyl-4-morpholin-4-yl-thieno[3,2-d]pyrimidin-6-ylmethyl]-piperazin-1-yl}-isobutyramide;
2-{4-[2-(6-Methanesulfonyl-1H-indol-4-yl)-7-methyl-4-morpholin-4-yl-thieno[3,2-d]pyrimidin-6-ylmethyl]-piperazin-1-yl}-isobutyramide;
2-{4-[2-(1H-Indol-4-yl)-4-morpholin-4-yl-thieno[3,2-d]pyrimidin-6-ylmethyl]-piperazin-1-yl}-2-methyl-1-pyrrolidin-1-yl-propan-1-one;
Cyclopropylmethyl-{1-[2-(1H-indol-4-yl)-4-morpholin-4-yl-thieno[3,2-d]pyrimidin-6-ylmethyl]-piperidin-4-yl}-(2-methoxy-ethyl)-amine;

2-(1H-Indol-4-yl)-6-(4-isopropyl-piperazin-1-ylmethyl)-4-morpholin4yl-thieno[3,2-d]pyrimidine;
2-(1H-Indol-4-yl)-6-(4-isopropyl-piperazin-1-ylmethyl)-4-morpholin-4-yl-thieno[2,3-d]pyrimidine;
6-[4-(2-Methoxy-ethyl)-piperidin-1-ylmethyl]-4-morpholin-4-yl-2-(6-trifluoromethyl-1H-indol-4-yl)-thieno[3,2-d]pyrimidine;
2-(1H-Indol-4-yl)-4-morpholin-4-yl-6-piperazin-1-ylmethyl-thieno[2,3-d]pyrimidine;
4-Morpholin-4-yl-6-piperazin-1-ylmethyl-2-(6-trifluoromethyl-1H-indol-4-yl)-thieno[2,3-d]pyrimidine;
2-{4-[2-(1H-Indol-4-yl)-4-morpholin-4-yl-thieno[2,3-d]pyrimidin-6-ylmethyl]-piperazin-1-yl}-ethanol;
4-[6-(4-Isopropyl-piperazin-1-ylmethyl)-4-morpholin-4-yl-thieno[2,3-d]pyrimidin-2-yl]-1H-indole-6-carbonitrile;
4-(4-Morpholin-4-yl-6-piperazin-1-ylmethyl-thieno[2,3-d]pyrimidin-2-yl)-1H-indole-6-carbonitrile;
4-(4-Morpholin-4-yl-6-piperidin-1-ylmethyl-thieno[3,2-d]pyrimidin-2-yl)-1H-indole-6-carboxylic acid amide;
4-(4-Morpholin-4-yl-6-piperidin-1-ylmethyl-thieno[3,2-d]pyrimidin-2-yl)-1H-indole-6-sulfonic acid dimethylamide;
4-{6-[4-(2-Methoxy-ethyl)-piperidin-1-ylmethyl]-4-morpholin-4-yl-thieno[3,2-d]pyrimidin-2-yl}-1H-indole-6-carboxylic acid amide;
4-(4-Morpholin-4-yl-6-piperazin-1-ylmethyl-thieno[2,3-d]pyrimidin-2-yl)-1H-indole-6-sulfonic acid dimethylamide;
4-(4-Morpholin-4-yl-6-piperazin-1-ylmethyl-thieno[2,3-d]pyrimidin-2-yl)-1H-indole-6-carboxylic acid amide;
2-{4-[2-(6-Methanesulfonyl-1H-indol-4-yl)-4-morpholin-4-yl-thieno[3,2-d]pyrimidin-6-ylmethyl]-piperazin-1-yl}-N-methyl-isobutyramide;
2-(5-Fluoro-1H-indol-4-yl)-4-morpholin-4-yl-6-piperidin-1-ylmethyl-thieno[3,2-d]pyrimidine;
4-(4-Morpholin-4-yl-6-piperidin-1-ylmethyl-thieno[3,2-d]pyrimidin-2-yl)-1H-indole-2-carbonitrile;
4-{6-[4-(2-Hydroxy-ethyl)-piperazin-1-ylmethyl]-4-morpholin-4-yl-thieno[3,2-d]pyrimidin-2-yl}-1H-indole-6-carbonitrile;
2-{4-[2-(6-Methanesulfonyl-1H-indol-4-yl)-4-morpholin-4-yl-thieno[3,2-d]pyrimidin-6-ylmethyl]-piperazin-1-yl}-ethanol;
4-{6-[4-(2-Hydroxy-1,1-dimethyl-ethyl)-piperazin-1-ylmethyl]-4-morpholin-4-yl-thieno[3,2-d]pyrimidin-2-yl}-1H-indole-6-carbonitrile;
2-{4-[2-(6-Fluoro-1H-indol-4-yl)-4-morpholin-4-yl-thieno[3,2-d]pyrimidin-6-ylmethyl]-piperazin-1-yl}-2-methyl-propan-1-ol;
4-Morpholin-4-yl-6-piperidin-1-ylmethyl-2-(2-trifluoromethyl-1H-indol-4-yl)-thieno[3,2-d]pyrimidine;
6-[4-(2-Methoxy-ethyl)-piperidin-1-ylmethyl]-4-morpholin-4-yl-2-(2-trifluoromethyl-1H-indol-4-yl)-thieno[3,2-d]pyrimidine;
4-Morpholin-4-yl-6-piperazin-1-ylmethyl-2-(2-trifluoromethyl-1H-indol-4-yl)-thieno[2,3-d]pyrimidine;
4-Morpholin-4-yl-6-piperidin-1-ylmethyl-2-(6-trifluoromethyl-1H-indol-4-yl)-thieno[3,2-d]pyrimidine;
2-(5-Fluoro-1H-indol-4-yl)-4-morpholin-4-yl-6-piperazin-1-ylmethyl-thieno[2,3-d]pyrimidine;
4-(4-Morpholin-4-yl-6-piperazin-1-ylmethyl-thieno[2,3-d]pyrimidin-2-yl)-1H-indole-2-carbonitrile;
4-(4-Morpholin-4-yl-6-piperazin-1-ylmethyl-thieno[2,3-d]pyrimidin-2-yl)-1H-indole-2-carboxylic acid amide;
1-Butoxy-3-{4-[2-(1H-indol-4-yl)-4-morpholin-4-yl-thieno[3,2-d]pyrimidin-6-ylmethyl]-piperazin-1-yl}-propan-2-ol;
6-(cis-3,5-Dimethyl-piperazin-1-ylmethyl)-2-(6-fluoro-1H-indol-4-yl)-4-morpholin-4-yl-thieno[3,2-d]pyrimidine;
{1-[2-(6-Fluoro-1H-indol-4-yl)-4-morpholin-4-yl-thieno[3,2-d]pyrimidin-6-ylmethyl]-pyrrolidin-3-yl}-dimethyl-amine;
2-(6-Fluoro-1H-indol-4-yl)-6-(3-methyl-piperazin-1-ylmethyl)-4-morpholin-4-yl-thieno[3,2-d]pyrimidine;
1-[2-(6-Fluoro-1H-indol-4-yl)-4-morpholin-4-yl-thieno[3,2-d]pyrimidin-6-ylmethyl]-piperidin-4-ylamine;
2-(6-Fluoro-1H-indol-4-yl)-4-morpholin-4-yl-6-(4-pyrrolidin-1-yl-piperidin-1-ylmethyl)-thieno[3,2-d]pyrimidine;
{1-[2-(5-Fluoro-1H-indol-4-yl)-4-morpholin-4-yl-thieno[3,2-d]pyrimidin-6-ylmethyl]-piperidin-4-yl}-dimethyl-amine;
{1-[2-(6-Fluoro-1H-indol-4-yl)-4-morpholin-4-yl-thieno[3,2-d]pyrimidin-6-ylmethyl]-piperidin-4-yl}-dimethyl-amine;
2-{4-[2-(6-Fluoro-1H-indol-4-yl)-4-morpholin-4-yl-thieno[3,2-d]pyrimidin-6-ylmethyl]-piperazin-1-yl}-N,N-dimethyl-isobutyramide;
{1-[2-(6-Fluoro-1H-indol-4-yl)-4-morpholin-4-yl-thieno[3,2-d]pyrimidin-6-ylmethyl]-piperidin-3-yl}-dimethyl-amine;
2-(6-Fluoro-1H-indol-4-yl)-6-((S)-3-isopropyl-piperazin-1-ylmethyl)-4-morpholin-4-yl-thieno[3,2-d]pyrimidine;
2-(1H-Indol-4-yl)-6-[4-(2-methoxy-ethyl)-piperazin-1-ylmethyl]-4-morpholin-4-yl-thieno[3,2-d]pyrimidine;
3-{4-[2-(1H-Indol-4-yl)-4-morpholin-4-yl-thieno[3,2-d]pyrimidin-6-ylmethyl]-piperazin-1-yl}-propan-1-ol;
3-{4-[2-(1H-Indol-4-yl)-4-morpholin-4-yl-thieno[3,2-d]pyrimidin-6-ylmethyl]-piperazin-1-yl}-propionitrile;
2-{4-[2-(1H-Indol-4-yl)-4-morpholin-4-yl-thieno[3,2-d]pyrimidin-6-ylmethyl]-piperazin-1-yl}-acetamide;
1-{4-[2-(1H-Indol-4-yl)-4-morpholin-4-yl-thieno[3,2-d]pyrimidin-6-ylmethyl]-piperazin-1-yl}-propan-2-ol;
3-{4-[2-(1H-Indol-4-yl)-4-morpholin-4-yl-thieno[3,2-d]pyrimidin-6-ylmethyl]-piperazin-1-yl}-propionamide;
6-(4-Cyclobutylmethyl-piperazin-1-ylmethyl)-2-(1H-indol-4-yl)-4-morpholin-4-yl-thieno[3,2-d]pyrimidine;
N-Cyclopropyl-2-{4-[2-(1H-indol-4-yl)-4-morpholin-4-yl-thieno[3,2-d]pyrimidin-6-ylmethyl]-piperazin-1-yl}-acetamide;
6-[4-(2,6-Dichloro-pyridin-4-ylmethyl)-piperazin-1-ylmethyl]-2-(1H-indol-4-yl)-4-morpholin-4-yl-thieno[3,2-d]pyrimidine;
2-(1H-Indol-4-yl)-4-morpholin-4-yl-6-(4-propyl-piperazin-1-ylmethyl)-thieno[3,2-d]pyrimidine;
1-{4-[2-(1H-Indol-4-yl)-4-morpholin-4-yl-thieno[3,2-d]pyrimidin-6-ylmethyl]-piperazin-1-yl}-3,3-dimethyl-butan-2-one;
2-(1H-Indol-4-yl)-6-(4-isobutyl-piperazin-1-ylmethyl)-4-morpholin-4-yl-thieno[3,2-d]pyrimidine;
2-{4-[2-(1H-Indol-4-yl)-4-morpholin-4-yl-thieno[3,2-d]pyrimidin-6-ylmethyl]-piperazin-1-yl}-ethylamine;
Diethyl-(2-{4-[2-(1H-indol-4-yl)-4-morpholin-4-yl-thieno[3,2-d]pyrimidin-6-ylmethyl]-piperazin-1-yl}-ethyl)-amine;
6-(4-Ethyl-piperazin-1-ylmethyl)-2-(1H-indol-4-yl)-4-morpholin-4-yl-thieno[3,2-d]pyrimidine;
2-(1H-Indol-4-yl)-6-(4-methyl-piperidin-1-ylmethyl)-4-morpholin-4-yl-thieno[3,2-d]pyrimidine;

2-(1H-Indol-4-yl)-6-(3-methyl-piperidin-1-ylmethyl)-4-morpholin-4-yl-thieno[3,2-d]pyrimidine;
6-(3,5-Dimethyl-piperidin-1-ylmethyl)-2-(1H-indol-4-yl)-4-morpholin-4-yl-thieno[3,2-d]pyrimidine;
6-(2-Ethyl-piperidin-1-ylmethyl)-2-(1H-indol-4-yl)-4-morpholin-4-yl-thieno[3,2-d]pyrimidine;
{1-[2-(1H-Indol-4-yl)-4-morpholin-4-yl-thieno[3,2-d]pyrimidin-6-ylmethyl]-piperidin-3-yl}-methanol;
2-(1H-Indol-4-yl)-6-(2-methyl-piperidin-1-ylmethyl)-4-morpholin-4-yl-thieno[3,2-d]pyrimidine;
2-(1H-Indol-4-yl)-4-morpholin-4-yl-6-[4-(3-piperidin-1-yl-propyl)-piperazin-1-ylmethyl]-thieno[3,2-d]pyrimidine;
2-(1H-Indol-4-yl)-4-morpholin-4-yl-6-(4-pyridin-2-ylmethyl-piperazin-1-ylmethyl)-thieno[3,2-d]pyrimidine;
4-{4-[2-(1H-Indol-4-yl)-4-morpholin-4-yl-thieno[3,2-d]pyrimidin-6-ylmethyl]-piperazin-1-yl}-butyronitrile;
2-(1H-Indol-4-yl)-4-morpholin-4-yl-6-piperidin-1-ylmethyl-thieno[3,2-d]pyrimidine;
2-(1H-Indol-4-yl)-6-(2-methyl-pyrrolidin-1-ylmethyl)-4-morpholin-4-yl-thieno[3,2-d]pyrimidine;
2-(1H-Indol-4-yl)-4-morpholin-4-yl-6-(4-pyridin-2-yl-piperazin-1-ylmethyl)-thieno[3,2-d]pyrimidine;
{1-[2-(1H-Indol-4-yl)-4-morpholin-4-yl-thieno[3,2-d]pyrimidin-6-ylmethyl]-pyrrolidin-3-yl}-methanol;
2-(1H-Indol-4-yl)-6-{4-[2-(1-methyl-pyrrolidin-2-yl)-ethyl]-piperazin-1-ylmethyl}-4-morpholin-4-yl-thieno[3,2-d]pyrimidine;
2-(1H-Indol-4-yl)-4-morpholin-4-yl-6-[4-(2-piperidin-1-yl-ethyl)-piperazin-1-ylmethyl]-thieno[3,2-d]pyrimidine;
2-(1H-Indol-4-yl)-4-morpholin-4-yl-6-[4-(2-pyrrolidin-1-yl-ethyl)-piperazin-1-ylmethyl]-thieno[3,2-d]pyrimidine;
6-(4-Cyclopropylmethyl-piperazin-1-ylmethyl)-2-(1H-indol-4-yl)-4-morpholin-4-yl-thieno[3,2-d]pyrimidine;
6-(cis-3,5-Dimethyl-piperazin-1-ylmethyl)-2-(1H-indol-4-yl)-4-morpholin-4-yl-thieno[3,2-d]pyrimidine;
6-(cis-3,5-Dimethyl-piperazin-1-ylmethyl)-2-(5-fluoro-1H-indol-4-yl)-4-morpholin-4-yl-thieno[3,2-d]pyrimidine;
{1-[2-(6-Fluoro-1H-indol-4-yl)-4-morpholin-4-yl-thieno[3,2-d]pyrimidin-6-ylmethyl]-piperidin-4-yl}-methylamine; and
2-(6-Fluoro-1H-indol-4-yl)-6-((R)-3-isopropyl-piperazin-1-ylmethyl)-4-morpholin-4-yl-thieno[3,2-d]pyrimidine;
and the pharmaceutically acceptable salts thereof.

7. A process for producing a compound as defined in claim 1, which process comprises treating a compound of formula (IIIa) or (IIIb):

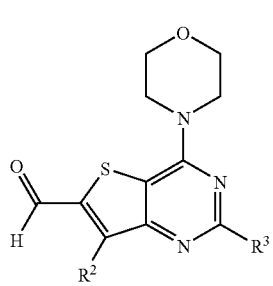

(IIIa)

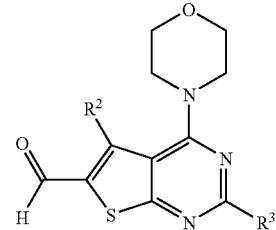

(IIIb)

wherein X, $R^2$ and $R^3$ are as defined in claim 1, with an amine of formula $NHR^4R^5$ in which $R^4$ and $R^5$ are as defined in claim 1, in the presence of a suitable reducing agent.

8. A process according to claim 7 which further comprises producing the compound of formula (IIIa) or (IIIb) by treating a compound of formula (IIIa) or (IIIb):

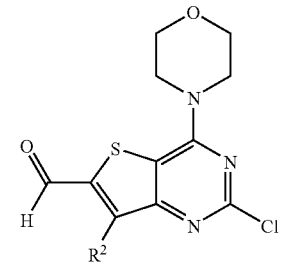

(IIa)

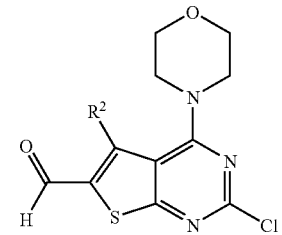

(IIb)

wherein $R^2$ is H, halo or $C_1$-$C_6$ alkyl, with a boronic acid or ester thereof of formula $R^3B(OR^{15})_2$, in which $R^3$ is an indole group which is unsubstituted or substituted, and each $R^{15}$ is H or $C_1$-$C_6$ alkyl or the two groups $OR^{15}$ form, together with the boron atom to which they are attached, a pinacolato boronate ester group, in the presence of a Pd catalyst.

9. A process for producing a compound as defined in claim 1, which process comprises treating a compound of formula (IVa) or (IVb):

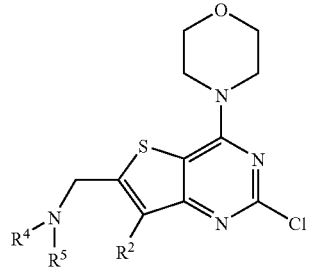

(IVa)

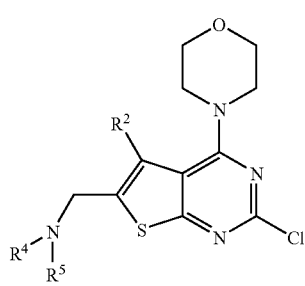

wherein $R^2$, $R^4$ and $R^5$ are as defined in claim 1, with a boronic acid or ester thereof of formula $R^3B(OR^{15})_2$ in which $R^3$ is as defined in claim 1 and each $R^{15}$ is H or $C_1$-$C_6$ alkyl or the two groups $OR^{15}$ form, together with the boron atom to which they are attached, a pinacolato boronate ester group, in the presence of a Pd catalyst.

10. A process according to claim 9 which further comprises producing the compound of formula (IVa) or (IVb) by treating a compound of formula (IIa) or (IIb):

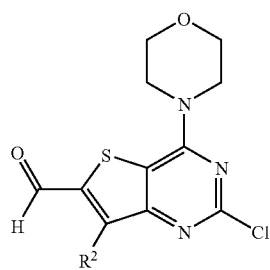

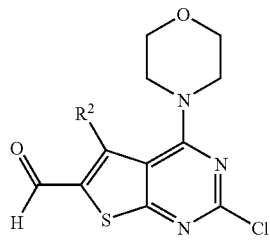

wherein $R^2$ is H, halo or $C_1$-$C_6$ alkyl, with an amine of formula $NHR^4R^5$ in which $R^4$ and $R^5$ form, together with the N atom to which they are attached, a group selected from piperazine, piperidine and pyrrolidine, which group is unsubstituted or substituted by one or more groups selected from $C_1$-$C_6$ alkyl, —$S(O)_2R^{10}$, —$S(O)_2$-(alk)$_q$-$NR^{11}R^{12}$, oxo(=O), -alk-$OR^{10}$, -(alk)$_q$-Het, a heterocyclyl group and —$NR^{13}R^{14}$; or one of $R^4$ and $R^5$ is $C_1$-$C_6$ alkyl and the other is a piperazine, piperidine or pyrrolidine group, which group is unsubstituted or substituted; $R^{10}$ is H or $C_1$-$C_6$ alkyl which is unsubstituted; $R^{11}$ and $R^{12}$ are each independently selected from H and $C_1$-$C_6$ alkyl which is unsubstituted, or $R^{11}$ and $R^{12}$ together form, with the N atom to which they are attached, a 5- or 6-membered saturated heterocyclic group; $R^{13}$ and $R^{14}$ are each independently selected from $C_1$-$C_6$ alkyl, —$S(O)_2R^{10}$, alk-$OR^{10}$, -(alk)$_q$-Ph and -(alk)$_q$-Het;

Ph is phenyl; q is 0 or 1; Het is a thiazole, imidazole, pyrrole, pyridine or pyrimidine group, which group is unsubstituted or substituted; and alk is $C_1$-$C_6$ alkylene, in the presence of a suitable reducing agent.

11. A process for producing a pharmaceutically acceptable salt as defined in claim 1, which process comprises treating a thienopyrimidine of formula (Ia) or (Ib):

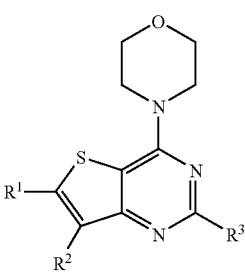

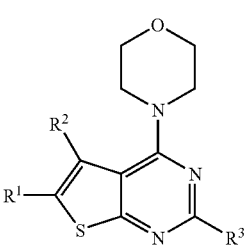

wherein $R^1$, $R^2$, and $R^3$ are as defined in claim 1, with a suitable acid in a suitable solvent.

12. A process according to claim 11, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

13. A process according to claim 11, wherein the acid is selected from methanesulphonic acid, benzenesulphonic acid, hydrochloric acid, phosphoric acid and sulphuric acid.

14. A pharmaceutical composition which comprises a pharmaceutically acceptable carrier or diluent and, as an active ingredient, a compound as claimed in claim 1.

15. A composition according to claim 14 which is formulated for oral administration.

16. A process for producing a pharmaceutical composition which process comprises combining a compound as defined in claim 1 with a pharmaceutically acceptable carrier.

* * * * *

UNITED STATES PATENT AND TRADEMARK OFFICE
CERTIFICATE OF CORRECTION

PATENT NO. : 8,252,792 B2
APPLICATION NO. : 12/298507
DATED : August 28, 2012
INVENTOR(S) : Baker et al.

It is certified that error appears in the above-identified patent and that said Letters Patent is hereby corrected as shown below:

In the Claims:

In Column 173, Line 30

Replace:
$-S(O)_2 \ _R{}^{10}, -S(O)_2-(alk)_q$

With:
$-S(O)_2 \ R^{10}, -S(O)_2-(alk)_q$

In Column 176, Line 44

Replace:
-1H-indole-6-sulfonic acid dimethylamide;

With:
-1*H*-indole-6-sulfonic acid dimethylamide;

In Column 176, Line 47

Replace:
-1H-indole-6-sulfonic acid dimethylamide

With:
-1*H*-indole-6-sulfonic acid dimethylamide

Signed and Sealed this
Eighth Day of October, 2013

Teresa Stanek Rea
*Deputy Director of the United States Patent and Trademark Office*

In Column 176, line 49

Replace:
1-1H-indol

With:
1-1*H*-indol

In Column 176, Line 53

Replace:
-1H-indole

With:
-1*H*-indole

In Column 176, Line 56

Replace:
-1H-indol

With:
-1*H*-indol

In Column 176, Line 58

Replace:
-1H-indol

With:
-1*H*-indol

In Column 176, Line 60

Replace:
-1H-indol

With:
-1*H*-indol

In Column 176, Line 64

Replace:
-1H-indol-4-yl)-theino[3,2-d]pyrimidine

With:
-1*H*-indol-4-yl)-theino[3,2-d]pyrimidine

In Column 176, Line 67

Replace:
-1H-indol

With:
-1*H*-indol

In Column 177, Line 1

Replace:
-1H-indol

With:
-1*H*-indol

In Column 177, Line 5

Replace:
-1H-indole-4-yl)-theino[3,2-d]pyrimidine

With:
-1*H*-indole-4-yl)-theino[3,2-d]pyrimidine

In Column 177, Line 8

Replace:
-1H-indol

With:
-1*H*-indol

CERTIFICATE OF CORRECTION (continued)
U.S. Pat. No. 8,252,792 B2

In Column 177, Line 10

Replace:
l-1H-indol

With:
1-1*H*-indol

In Column 177, Line 13

Replace:
-1H-indol

With:
-1*H*-indol

In Column 177, Line 15

Replace:
-1H-indol

With:
-1*H*-indol

In Column 177, Line 18

Replace:
1-1H-indol

With:
1-1*H*-indol

In Column 177, Line 21

Replace:
-1H-indol

With:
-1*H*-indol

CERTIFICATE OF CORRECTION (continued)
U.S. Pat. No. 8,252,792 B2

In Column 177, Line 24

Replace:
-1H-indol

With:
-1*H*-indol

In Column 177, Line 28

Replace:
-1H-indol

With:
-1*H*-indol

In Column 177, Line 31

Replace:
-1H-indole

With:
-1*H*-indole

In Column 177, Line 34

Replace:
1H-indole

With:
1*H*-indole

In Column 177, Line 36

Replace:
-1H-indole

With:
-1*H*-indole

In Column 177, Line 39

Replace:
-1H-indole

With:
-1*H*-indole

In Column 177, Line 42

Replace:
-1H-indole

With:
-1*H*-indole

In Column 177, Line 44

Replace:
-1H-indol

With:
-1*H*-indol

In Column 177, Line 48

Replace:
-1H-indole

With:
-1*H*-indole

In Column 177, Line 51

Replace:
-1H-indole

With
-1*H*-indole

In Column 177, Line 54

Replace:
-1H-indole

With:
-1*H*-indole

In Column 177, Line 57

Replace:
-1H-indol

With:
-1*H*-indol

In Column 177, Line 59

Replace:
-1H-indol

With:
-1*H*-indol

In Column 177, Line 64

Replace:
-1H-indol

With:
-1*H*-indol

In Column 180, Line 5

Replace:
-1H-indol

With:
-1*H*-indol

In Column 180, Line 7

Replace:
-1H-indol

With:
-1*H*-indol

In Column 180, Line 10

Replace:
-1H-indol

With:
-1*H*-indol

In Column 180, Line 12

Replace:
-1H-indol

With:
-1*H*-indol

In Column 180, line 14

Replace:
-1H-indol

With:
-1*H*-indol

In Column 180, Line 17

Replace:
-1H-indol

With:
-1*H*-indol

In Column 180, Line 20

Replace:
-1H-indol

With:
-1*H*-indol

In Column 180, Line 23

Replace:
-1H-indol

With:
-1*H*-indol

In Column 180, Line 25

Replace:
N,N-

With:
*N,N*-

In Column 180, Line 26

Replace:
-1H-indol

With:
-1*H*-indol

In Column 180, Line 29

Replace:
-1H-indol

With:
-1*H*-indol

In Column 180, Line 32

Replace:
(1H-indol-4-yl)

With:
(1*H*-Indol-4-yl)

In Column 180, Line 34

Replace:
(1H-Indol-4-yl)

With:
(1*H*-Indol-4-yl)

In Column 180, Line 38

Replace:
(1H-Indol-4-yl)

With:
(1*H*-Indol-4-yl)

In Column 180, Line 40

Replace:
(1H-Indol-4-yl)

With:
(1*H*-Indol-4-yl)

In Column 180, Line 42

Replace:
(1H-Indol-4-yl)

With:
(1*H*-Indol-4-yl)

CERTIFICATE OF CORRECTION (continued)
U.S. Pat. No. 8,252,792 B2

In Column 180, Line 44

Replace:
1H-indol

With:
1*H*-indol

In Column 180, Line 46

Replace:
1H-indol

With:
-1*H*-indol

In Column 180, Line 50

Replace:
1H-indol

With:
1*H*-indol

In Column 180, Line 52

Replace:
1H-Indol

With:
1*H*-Indol

In Column 180, Line 54

Replace:
1H-Indol

With:
1*H*-Indol

CERTIFICATE OF CORRECTION (continued)
U.S. Pat. No. 8,252,792 B2

In Column 180, Line 57

Replace:
1H-Indol

With:
1*H*-Indol

In Column 180, Line 59

Replace:
1H-Indol

With:
1*H*-Indol

In Column 180, Line 61

Replace:
1H-indol

With:
1*H*-indol

In Column 180, Line 64

Replace:
1H-indol

With:
1*H*-indol

In Column 180, Line 66

Replace:
1H-Indol

With:
1*H*-Indol

CERTIFICATE OF CORRECTION (continued)
U.S. Pat. No. 8,252,792 B2

In column 181, Line 1

Replace:
1H-Indol

With:
1*H*-Indol

In column 181, Line 3

Replace:
1H-indol

With:
1*H*-indol

In Column 181, Line 5

Replace:
1H-indol

With:
1*H*-indol

In Column 181, Line 7

Replace:
1H-Indol

With:
1*H*-Indol

In Column 181, Line 9

Replace:
1H-Indol

With:
1*H*-Indol

In Column 181, Line 11

Replace:
1H-Indol

With:
1*H*-Indol

In Column 181, Line 14

Replace:
1H-Indol

With:
1*H*-Indol

In Column 181, Line 16

Replace:
1H-Indol

With:
1*H*-Indol

In Column 181, Line 18

Replace:
1H-Indol

With:
1*H*-Indol

In Column 181, Line 20

Replace:
1H-Indol

With:
1*H*-Indol

CERTIFICATE OF CORRECTION (continued)
U.S. Pat. No. 8,252,792 B2

In Column 181, Line 22

Replace:
1H-Indol

With:
1*H*-Indol

In Column 181, Line 22

Replace:
1H-Indol

With:
1*H*-Indol

In Column 181, Line 26

Replace:
1H-Indol

With:
1*H*-Indol

In Column 181, Line 29

Replace:
1H-Indol

With:
1*H*-Indol

In Column 181, Line 32

Replace:
1H-Indol

With:
1*H*-Indol

CERTIFICATE OF CORRECTION (continued)
U.S. Pat. No. 8,252,792 B2

In Column 181, Line 35

Replace:
1H-indol

With:
1*H*-indol

In Column 182, Line 19

Replace:
(IIIa) or (IIIb)

With:
(IIa) or (IIb)